(12) United States Patent
Krishnan

(10) Patent No.: US 11,865,148 B2
(45) Date of Patent: *Jan. 9, 2024

(54) METHODS OF DELIVERING TRANSGENES TO THE EYE

(71) Applicant: Krystal Biotech, Inc., Pittsburgh, PA (US)

(72) Inventor: Suma Krishnan, Pittsburgh, PA (US)

(73) Assignee: Krystal Biotech, Inc., Pittsburgh, PA (US)

( * ) Notice: Subject to any disclaimer, the term of this patent is extended or adjusted under 35 U.S.C. 154(b) by 73 days.

This patent is subject to a terminal disclaimer.

(21) Appl. No.: 18/060,515

(22) Filed: Nov. 30, 2022

(65) Prior Publication Data

US 2023/0149486 A1 May 18, 2023

Related U.S. Application Data

(63) Continuation of application No. 17/529,161, filed on Nov. 17, 2021, now abandoned, which is a continuation of application No. 16/598,982, filed on Oct. 10, 2019, now Pat. No. 11,185,564, which is a continuation of application No. 16/177,153, filed on Oct. 31, 2018, now Pat. No. 10,441,614, which is a continuation of application No. 15/851,488, filed on Dec. 21, 2017, now Pat. No. 10,155,016, which is a continuation of application No. 15/393,151, filed on Dec. 28, 2016, now Pat. No. 9,877,990.

(60) Provisional application No. 62/320,316, filed on Apr. 8, 2016.

(51) Int. Cl.
| | |
|---|---|
| *A61K 35/763* | (2015.01) |
| *A61K 9/00* | (2006.01) |
| *A61K 38/17* | (2006.01) |
| *A61K 38/39* | (2006.01) |
| *A61K 48/00* | (2006.01) |
| *C07K 14/78* | (2006.01) |
| *C12N 9/02* | (2006.01) |
| *A61K 9/06* | (2006.01) |
| *A61K 47/38* | (2006.01) |

(52) U.S. Cl.
CPC .......... *A61K 35/763* (2013.01); *A61K 9/0014* (2013.01); *A61K 38/1748* (2013.01); *A61K 38/39* (2013.01); *A61K 48/005* (2013.01); *C07K 14/78* (2013.01); *C12N 9/0071* (2013.01); *C12Y 114/11004* (2013.01); *A61K 9/06* (2013.01); *A61K 47/38* (2013.01); *C12N 2710/16643* (2013.01)

(58) Field of Classification Search
CPC .............. A61K 35/763; A61K 38/1748; A61K 48/005; A61K 38/39; A61K 9/0014; A61K 9/06; A61K 47/38; C12N 9/0071; C12N 2710/16643; C12Y 114/11004; C07K 14/78

See application file for complete search history.

(56) References Cited

U.S. PATENT DOCUMENTS

| | | | |
|---|---|---|---|
| 5,658,724 A | 8/1997 | Deluca et al. | |
| 5,672,344 A | 9/1997 | Kelley et al. | |
| 5,998,174 A | 12/1999 | Glorioso et al. | |
| 6,106,826 A | 8/2000 | Brandt et al. | |
| 6,719,982 B1 | 4/2004 | Coffin et al. | |
| 6,846,670 B2 | 1/2005 | Schwartz et al. | |
| 6,887,490 B1 | 5/2005 | Jahoda et al. | |
| 7,531,167 B2 | 5/2009 | Glorioso et al. | |
| 9,314,505 B2 | 4/2016 | Wise et al. | |
| 9,877,990 B2 | 1/2018 | Krishnan et al. | |
| 10,155,016 B2 | 12/2018 | Krishnan et al. | |
| 10,174,341 B2 | 1/2019 | Glorioso et al. | |
| 10,441,614 B2 | 10/2019 | Krishnan et al. | |
| 10,525,090 B2 | 1/2020 | Krishnan et al. | |
| 11,185,564 B2 | 11/2021 | Krishnan et al. | |
| 2003/0082142 A1 | 5/2003 | Coffin et al. | |
| 2004/0253606 A1 | 12/2004 | Aziz et al. | |
| 2007/0066552 A1* | 3/2007 | Clarke ................ | A61K 9/0014 424/440 |
| 2008/0299182 A1 | 12/2008 | Zhang | |
| 2010/0081707 A1* | 4/2010 | Ali .......................... | A61P 27/02 604/151 |
| 2011/0212530 A1 | 9/2011 | Baltimore et al. | |

(Continued)

FOREIGN PATENT DOCUMENTS

| | | |
|---|---|---|
| CN | 102 212 559 | 4/2014 |
| EP | 3377637 | 9/2018 |

(Continued)

OTHER PUBLICATIONS

Wang JH, Roberts GE, Liu GS. Updates on Gene Therapy for Diabetic Retinopathy. Curr Diab Rep. May 16, 2020;20(7):22. (Year: 2020).*

(Continued)

*Primary Examiner* — Rachel B Gill
(74) *Attorney, Agent, or Firm* — MORRISON & FOERSTER LLP

(57) ABSTRACT

Provided herein are methods of delivering transgenes to an eye of a subject comprising the use of pharmaceutical compositions having one or more polynucleotides suitable for enhancing, increasing, augmenting, and/or supplementing the levels of the transgene in the eye. Also provided herein are methods of correcting vision loss in a subject in need thereof comprising the use of the pharmaceutical compositions described herein.

21 Claims, 17 Drawing Sheets
(7 of 17 Drawing Sheet(s) Filed in Color)
Specification includes a Sequence Listing.

(56) References Cited

U.S. PATENT DOCUMENTS

| | | | |
|---|---|---|---|
| 2013/0295076 A1 | 11/2013 | Kolattukudy et al. | |
| 2013/0331547 A1 | 12/2013 | Hall et al. | |
| 2014/0256798 A1 | 9/2014 | Osborn et al. | |
| 2014/0288155 A1 | 9/2014 | Hovnanian et al. | |
| 2014/0341877 A1 | 11/2014 | Kolattukudy | |
| 2015/0038556 A1 | 2/2015 | Heartlein et al. | |
| 2015/0352191 A1 | 12/2015 | South et al. | |
| 2016/0153000 A1* | 6/2016 | Glorioso | A61K 48/005 435/456 |
| 2016/0250267 A1* | 9/2016 | Uchida | C07K 14/005 424/93.2 |
| 2016/0324934 A1 | 11/2016 | Angel et al. | |
| 2017/0096684 A1 | 4/2017 | Alton et al. | |
| 2017/0290866 A1 | 10/2017 | Krishnan et al. | |
| 2017/0319693 A1* | 11/2017 | Koizumi | A61K 31/4409 |
| 2018/0353614 A1* | 12/2018 | Peters | C07K 16/40 |
| 2019/0160122 A1 | 5/2019 | Krishnan et al. | |
| 2019/0276845 A1 | 9/2019 | Glorioso et al. | |
| 2019/0328644 A1 | 10/2019 | Krishnan et al. | |
| 2020/0061209 A1* | 2/2020 | Bennett | A61K 9/0048 |
| 2020/0101123 A1 | 4/2020 | Krishnan et al. | |
| 2020/0199618 A1* | 6/2020 | Krisky | C12N 15/86 |
| 2021/0040172 A1* | 2/2021 | Cascio | A61P 25/00 |
| 2022/0273737 A1 | 9/2022 | Krishnan et al. | |

FOREIGN PATENT DOCUMENTS

| | | | | |
|---|---|---|---|---|
| WO | WO 1999/064094 | | 12/1999 | |
| WO | WO 2000/040734 | | 7/2000 | |
| WO | WO 2013/121202 | | 8/2013 | |
| WO | WO 2015/009952 | | 1/2015 | |
| WO | WO 2015/117021 | | 8/2015 | |
| WO | WO-2016191684 A1 * | 12/2016 | | A61K 48/00 |
| WO | WO 2017/165806 | | 9/2017 | |
| WO | WO 2017/165813 | | 9/2017 | |
| WO | WO 2017/176336 | | 10/2017 | |
| WO | WO 2019/200163 | | 10/2019 | |
| WO | WO 2019/210219 | | 10/2019 | |
| WO | WO 2020/006486 | | 1/2020 | |

OTHER PUBLICATIONS

Acland GM, Aguirre GD, Ray J, Zhang Q, Aleman TS, Cideciyan AV, Pearce-Kelling SE, Anand V, Zeng Y, Maguire AM, Jacobson SG, Hauswirth WW, Bennett J. Gene therapy restores vision in a canine model of childhood blindness. Nat Genet. May 2001;28(1):92-5. (Year: 2001).*

Pepose JS, Leib DA. Herpes simplex viral vectors for therapeutic gene delivery to ocular tissues. Recent breakthroughs in the molecular genetics of ocular diseases. Invest Ophthalmol Vis Sci. May 1994;35(6):2662-6. (Year: 1994).*

Liu X, Brandt CR, Gabelt BT, et al. Herpes simplex virus mediated gene transfer to primate ocular tissues. Exp Eye Res. 1999;69(4):385-395. (Year: 1999).*

Fraefel C, Mendes-Madeira A, Mabon O, Lefebvre A, Le Meur G, Ackermann M, Moullier P, Rolling F. In vivo gene transfer to the rat retina using herpes simplex virus type 1 (HSV-1)-based amplicon vectors. Gene Ther. Aug. 2005;12(16):1283-8. (Year: 2005).*

Spencer B, Agarwala S, Gentry L, Brandt CR. HSV-1 vector-delivered FGF2 to the retina is neuroprotective but does not preserve functional responses. Mol Ther. May 2001;3(5 Pt 1):746-56. (Year: 2001).*

Ali RR, Reichel MB, Hunt DM, Bhattacharya SS. Gene therapy for inherited retinal degeneration. Br J Ophthalmol. Sep. 1997;81(9):795-801. (Year: 1997).*

Peek R, Verjans GM, Meek B. Herpes simplex virus infection of the human eye induces a compartmentalized virus-specific B cell response. J Infect Dis. Dec. 1, 2002;186(11):1539-46. Epub Nov. 4, 2002. (Year: 2002).*

Messmer EM, Kenyon KR, Rittinger O, Janecke AR, Kampik A. Ocular manifestations of keratitis-ichthyosis-deafness (KID) syndrome. Ophthalmology. Feb. 2005;112(2):e1-6. (Year: 2005).*

Farasat S, Wei MH, Herman M, Liewehr DJ, Steinberg SM, Bale SJ, Fleckman P, Toro JR. Novel transglutaminase-1 mutations and genotype-phenotype investigations of 104 patients with autosomal recessive congenital ichthyosis in the USA. J Med Genet. Feb. 2009;46(2):103-11. Epub Oct. 23, 2008. (Year: 2008).*

Choate KA, Kinsella TM, Williams ML, Nolan GP, Khavari PA. Transglutaminase 1 delivery to lamellar ichthyosis keratinocytes. Hum Gene Ther. Dec. 1, 1996;7(18):2247-53. doi: 10.1089/hum. 1996.7.18-2247. PMID: 8953315. (Year: 1996).*

Mayr E, Koller U, Bauer JW. Chapter 23: Gene Therapy for the COL7A1 Gene. In: Gene Therapy—Tools and Potential Applications. Feb. 2013, doi: 10.5772/51926. (Year: 2013).*

Sabater AL, Tovar A, Gomez J, Parry T, Chen H, Agostini B, Krishnan S. Topical beremagene geperpavec (B-VEC) for the treatment of recurrent cicatrizing conjunctivitis in a patient with dystrophic epidermolysis bullosa. ARVO Annual Meeting, New Orleans, LA, USA, Apr. 23-27, 2023. (Year: 2023).*

Aldawsari et al., "Progress in Topical siRNA Delivery Approaches for Skin Disorders," Curr Pharm Des. (2015) 21(31): 4594-4605.

Andtbacka et al., "Talimogene Laherparepvec Improves Durable Response Rate in Patients With Advanced Melanoma," J Clin Oncol. (2015) 33(25): 2780-2788.

Armstrong, M. "Krystal gets more skin in the epidermolysis bullosa game." Vantage. Mar. 5, 2019.

Armstrong, M. "Krystal gets a flying start in epidermolysis bullosa gene therapy" Vantage. Oct. 17, 2018.

Bastian et al., "Herpes simplex virus type 1 immediate-early protein ICP22 is required for VICE domain formation during productive viral infection." J Viral. Mar. 2010;84(5):2384-94. doi: 10.1128/JVI.01686-09. Epub Dec. 23, 2009.

Boehmer et al., "Herpes Virus Replication," IUBMB Life (2003) 55(1):13-22.

Brehm et al., "Immunogenicity of herpes simplex virus type 1 mutants containing deletions in one or more alpha-genes: ICP4, ICP27, ICP22, and ICP0," Virology (1999) 256(2): 258-69.

Burton et al., "Gene delivery using herpes simplex virus vectors." DNA Cell Biol. Dec. 2002;21(12):915-936.

Chamorro et al., "Gene Editing for the Efficient Correction of a Recurrent COL7A1 Mutation in Recessive Dystrophic Epidermolysis Bullosa Keratinocytes", Molecular Therapy—Nucleic Acids, vol. 5, 2016, pp. 1-13.

Christiano AM. Collagen, type VII, alpha 1 (epidermolysis bullosa, dystrophic, dominant and recessive) [Homo sapiens]. NCBI Reference Sequence: NP_000085.1. Dep. Mar. 19, 1999.

Clinicaltrials.gov. NCT03536143: Topical Bercolagene Telserpavec (KB103) Gene Therapy to Restore Functional Collagen VII for the Treatment of Dystrophic Epidermolysis Bullosa (GEM-1). May 24, 2018.

Clinicaltrials.gov. NCT04047732: Topical KB105 Gene Therapy for the Treatment of TGM1-deficient Autosonnal Recessive Congenital Ichthyosis (ARCI). Aug. 7, 2019.

Clinicaltrials.gov. NCT04214002: The Natural History of Wounds in Patients with Dystrophic Epidermolysis Bullosa (DEB). Dec. 30, 2019.

Communication pursuant to Article 94(3) EPC for EP 16826873.8, dated Apr. 17, 2019, 7 pages.

Periphagen, Complaint in PeriphaGen v. Krystal Biotech, Filed May 1, 2020 in the Western District of Pennsylvania (96 pgs).

Deluca et al., "Isolation and Characterization of Deletion Mutants of Herpes Simplex Virus Type 1 in the Gene Encoding Immediate-Early Regulatory Protein ICP4", Journal Of Virology, (1985) 56(2): 558-570.

Di et al., "Phase I study protocol for ex vivo lentiviral gene therapy for the inherited skin disease, Netherton syndrome," Hum Gene Ther Clin Dev. (2013) 24(4):182-190.

Dingwell et al., "The Herpes Simplex Virus gE-gl Complex Facilitates Cell-to-Cell Spread and Binds to Components of Cell Junctions," J Virol. (1998) 72(11): 8933-8942.

Eming SA, Krieg T, Davidson JM. Gene therapy and wound healing. Clin Dermatol. Jan.-Feb. 2007;25(1):79-92.

Eming et al., "Gene transfer in tissue repair: status, challenges and future directions," Exp Opin Biol Ther (2004) 4(9): 1373-1386.

(56) References Cited

OTHER PUBLICATIONS

Final Office Action received for U.S. Appl. No. 15/393,151, dated Aug. 31, 2017, 13 pages.
Fink et al., "Gene therapy for pain: Results of a Phase I clinical trial," Ann Neurol (2011) 70(2):207-212.
Geller et al., "An efficient deletion mutant packaging system for defective herpes simplex virus vectors: potential applications to human gene therapy and neuronal physiology," Proc Natl Acad Sci U S A. (1990) 87(22): 8950-8954.
Georgiadis et al., "Lentiviral Engineered Fibroblasts Expressing Codon-Optimized COL7A1 Restore Anchoring Fibrils in RDEB", Journal of Investigative Dermatology, (2016) 136: 284-292.
Glorioso JC. "Herpes simplex viral vectors: late bloomers with big potential." Hum Gene Ther. (2014) 25(2): 83-91.
Goins et al. "Engineering HSV-1 Vectors for Gene Therapy," Methods Mol Biol (2014) 1144: 63-79.
Goins et al. "Generation of replication-competent and -defective HSV vectors," Cold Spring Harb Protoc. May 1, 2011;2011(5): 512; pdb.prot5615.
Gorell et al., "Gene therapy for skin diseases," Cold Spring Harb Perspect Med (2014) 4:a015149.
Goto et al., "Fibroblasts Show More Potential as Target Cells than Keratinocytes in COL7A1 Gene Therapy of Dystrophic Epidermolysis Bullosa", Journal of Investigative Dermatology, (2006) 126: 766-772.
Grant, Kyle, "Production and Purification of Highly Replication Defective Hsv-1 Based Gene Therapy Vectors", Doctoral Dissertation, University of Pittsburgh, 2008, 137 pages.
Gurevich et al. 759 "Successful in vivo COL7A1 gene delivery and correction of recessive dystrophic epidermolysis bullosa (RDEB) skin using an off the shelf HSV-1 vector (KB103)." J Invest Derm. vol. 138, Iss. 5 Supp. May 2018, p. S129. Available online Apr. 19, 2018.
Heikkinen et al., "Diremerization of human lysyl hydroxylase 3 (LH3) is mediated by the amino acids 541 547," Matrix Biology (2010) 30(1):27-33.
Hennig et al., "HEK293-based production platform for y-retroviral (self-inactivating) vectors: application for safe and efficient transfer of COL7A1 cDNA". Hum Gene Ther Clin Dev. Dec. 2014;25(4):218-28.
International Preliminary Report on Patentability received for PCT Patent Application No. PCT/US2016/068974, dated Oct. 18, 2018, 11 pages.
International Search Report and Written Opinion received for PCT Patent Application No. PCT/US2016/068974, dated May 18, 2017, 18 pages.
Invitation to Pay Additional Fee received for PCT Patent Application No. PCT/US2016/068974, dated Mar. 27, 2017, 8 pages.
Kim et al., "Microneedles for Drug and Vaccine Delivery", Advanced Drug Delivery Reviews, vol. 64, 2012, pp. 1547-1568.
Kohlhapp et al., Molecular Pathways: Mechanism of Action for Talimogene Laherparepvec, a New Oncolytic Virus Immunotherapy, Clinical Cancer Research (2015) 22(5):1048-1054.
Kopecki et al., "Commentary: New advances in the development of therapies for treating inherited skin fragility disorders," Wound Practice and Research (2015) 23(4): 184, Dec. 5, 2015.
Krisky et al., "Deletion of multiple immediate-early genes from herpes simplex virus reduces cytotoxicity and permits long-term gene expression in neurons," Gene Ther. (1998) 5(12):1593-603.
Krisky et al., "Development of herpes simplex virus replication-defective multigene vectors for combination gene therapy applications," Gene Ther (1998) 5(110):1517-1530.
Krystal Biotech, Inc. "Krystal Biotech Announces Settlement with PeriphaGen, Inc." Mar. 15, 2022, https://ir.krystalbio.com/node/8481/pdf. (Year: 2022).
Lachmann, R. "Herpes simplex virus-based vectors," Int J Exp Pathol. (2004) 85(4): 177-190.
Lewin et al., "Gene therapy for autosomal dominant disorders of keratin," J Investig Dermatol Symp Proc. (2005) 10(1): 47-61.
Lu et al., "Topical Application of Viral Vectors for Epidermal Gene Transfer", J Invest Dermatol. (1997) 108(5): 803-808.
Ma et al., "Efficacy of Herpes Simplex Virus Vector Encoding V the Human Preproenkephalin Gene for Treatment of Facial Pain in Mice," J aral Facial Pain Headachce (2016) 30(1):42-50.
Marconi et al., "HSV as a Vector in Vaccine Development and Gene Therapy." In: Madame Curie Bioscience Database [Internet]. Austin (TX): Landes Bioscience; 2000-2013. 30 pages.
Marconi et al., "Replication-defective herpes simplex virus vectors for gene transfer in vivo," Proc Natl Acad Sci USA (1996) 93:11319-11320.
Mayr et al., "Gene Therapy for the COL7A1 Gene", Chapter 23, Intech, 2013, pp. 561-589.
McGowan et al., "Keratin 17 n ull mice exhibit age- and strain-dependent alopecia," Genes & Dev (2002) 16:1412-1422.
Miezeiewski et al., "Role of adherens junction proteins in differential herpes simplex virus type 2 infectivity in communication-competent and -deficient cell lines," Intervirology. (2012) 55(6): 465-474.
Miyagawa et al., "Herpes simplex viral-vector design for efficient transfuction of nonneuronal cells without cytotoxcity," Proc Natl Acad Sci USA (2015) 112(13):E1632-E1641.
Miyagawa et al., "Deletion of the Virion Host Shut-off Gene Enhances Neuronal-Selective Transgene Expression from an HSV Vector Lacking Functional IE Genes," Mol Ther Methods Clin Dev. (2017) 6: 79-90.
Ng et al., "Fibroblast-Derived Dermal Matrix Drives Development of Aggressive Cutaneous Squamous Cell Carcinoma in Patients with Recessive Dystrophic Epidermolysis Bullosa", Cancer Research, vol. 72, No. 14, Jul. 15, 2012, pp. 3522-3534.
Non-Final Office Action received for U.S. Appl. No. 15/393,151, dated Apr. 14, 2017, 13 pages.
Non-Final Office Action received for U.S. Appl. No. 15/851,488, dated May 14, 2018, 10 pages.
Non-Final Office Action received for U.S. Appl. No. 16/177,153, dated May 9, 2019, 13 pages.
Notice of Allowance received for U.S. Appl. No. 15/393,151, dated Dec. 6, 2017, 11 pages.
Notice of Allowance received for U.S. Appl. No. 15/851,488, dated Oct. 29, 2018, 11 pages.
Notice of Allowance received for U.S. Appl. No. 16/177,153, dated Aug. 30, 2019, 10 pages.
Ortiz-Urda et al., "Injection of Genetically Engineered Fibroblasts Corrects Regenerated Human Epidermolysis Bullosa Skin Tissue", The Journal of Clinical Investigation, vol. 111, No. 2, Jan. 2003, pp. 251-255.
*Periphagen, Inc* v *Krystalbiotech, Inc et al.* Pennsylvania Western District Court Judge: Mark R Hornak Case #: 2:20-U cv-00646 Nature of Suit 890 ather Statutes—ather Statutory Actions Cause 18:1836(b) Civil Action to Protect Trade Secrets; Filed May 1, 2020. (Year: 2020).
Periphagen, Krystal Biotech Inc., Answer and Counterclaim in *PeriphaGen* v. *Krystal Biotech*, Filed Jun. 6, 2020 in the Western District of Pennsylvania (60 pgs).
Rahn et al., "Invasion of Herpes Simplex Virus Type 1 into Murine Epidermis: An Ex Vivo Infection Study," J Invest Dermatol. (2015) 135(12): 3009-3016.
Salam A. "Krystal's KB103 splits experts' thoughts on potential for HSV-1 risk in dystrophic epidermolysis bullosa patients, but final Phase I/II efficacy assured." Nov. 7, 2018. Biopharm Insight.
Salameh et al., "Early events in herpes simplex virus lifecycle with implications for an infection of lifetime," Open Virol J. (2012) 6:1-6.
Salmon-Ehr et al., "Implication of Interleukin-4 in Wound Healing", Laboratory Investigation, vol. 80, No. 8, Aug. 2000, pp. 1337-1343.
Samaniego et al., "Persistence and Expression of the Herpes Simplex Virus Genome in the Absence of Immediate-Early Proteins", Journal of Virology, (1998) 72(4); 3307-3320.
Samaniego et al., "The herpes simplex virus immediate-early protein ICP0 affects transcription from the viral genome and infected-cell survival in the absence of ICP4 and ICP27," J Virol. (1997) 71(6): 4614-4625.

(56) References Cited

OTHER PUBLICATIONS

Sankar et al., "A novel role for keratin 17 in coordinating oncogenic transformation and cellular adhersion in eqing sarcoma," Molecular and Cellular Biology (2013) 33(22):4448-4460.

Shen et al., "Herpes simplex virus 1 (HSV-1) for cancer treatment," Cancer Gene Therapy (2006) 13: 975-992.

Silva et al., "Herpes Virus Amplicon Vectors", Viruses, vol. 1, 2009, pp. 594-629.

Siprashvili et al., "Long-term type VII collagen restoration to human epidermolysis bullosa skin tissue," Hum Gene Ther. Oct. 2010;21(10):1299-310.

Stow et al., Isolation and characterization of a herpes simplex virus type 1 mutant containing a deletion within the gene encoding the immediate early polypeptide Vmw110. J Gen Viral. Dec. 1986;67 ( Pt 12):2571-85.

Sufiawati et al., "HIV-associated disruption of tight and adherens junctions of oral epithelial cells facilitates HSV-1 infection and spread," PLoS One. (2014) 9(2): e88803.

Sufiawati et al., "HIV-induced matrix metalloproteinase-9 activation through mitogen-activated protein kinase signalling promotes HSV-1 cell-to-cell spread in oral epithelial cells," J Gen Virol. (2018) 99(7): 937-947.

Theopold et al., "A novel replication-defective HSV-1 vector for regulatable gene delivery to wounds," Journal of the American College of Surgeons (2004) 199(3):57-58.

Uitto et al., "Progress toward Treatment and Cure of Epidermolysis Bullosa: Summary of the DEBRA International Research Symposium EB2015", Journal of Investigative Dermatology, vol. 136, 2016, pp. 352-358.

Wang et al., "Comparative Effectiveness of Antinociceptive Gene Therapies in Animal Models of Diabetic Neuropathic Pain", Gene Therapy, vol. 20, 2013, pp. 742-750.

Watanabe et al., "Properties of a Herpes Simplex Virus Multiple Immediate-early Gene-Deleted Recombinant as a Vaccine Vector", Virology, vol. 357, 2007, pp. 186-198.

Watt et al., "Lysyl Hydroxylase 3 Localizes to Epidermal Basement Membrane and Is Reduced in Patients with Recessive Dystrophic Epidermolysis Bullosa", Plos One, (2015) 10(9): e0137639.

Weiss et al., "The Role of Interleukin 10 in the Pathogenesis and Potential Treatment of Skin Diseases", Journal of the American Academy of Dermatology, vol. 50, No. 5, May 2004, pp. 657-675.

White et al., "Evaluation and optimization of the administration of a selectively replicating herpes simplex viral vector to the brain by convection-enhanced delivery," Cancer Gene Ther. May 2011;18(5):358-69. doi: 10.1038/ cgt.2011.2. Epub Mar. 4, 2011.

Wolfe et al., "Engineering Herpes Simplex Viral Vectors for Therapeutic Gene Transfer", Chapter 6, Gene and Cell Therapy, 2004, pp. 103-129.

Woodley et al., "Normal and Gene-Corrected Dystrophic Epidermolysis Bullosa Fibroblasts Alone Can Produce Type VII Collagen at the Basement Membrane Zone", The Journal of Investigative Dermatology, vol. 121, No. 5, Nov. 2003, pp. 1021-1028.

Woodley, et al., "Intradermal Injection of Lentiviral Vectors Corrects Regenerated Human Dystrophic Epidermolysis Bullosa Skin Tissue in Vivo", Molecular Therapy, vol. 10, No. 2, Aug. 2004, pp. 318-326.

Wu et al., "Prolonged gene expression and cell survival after infection by a herpes simplex virus mutant defective in the immediate-early genes encoding ICP4, ICP27, and ICP22," J Virol. (1996) 70(9): 6358-6369.

\* cited by examiner

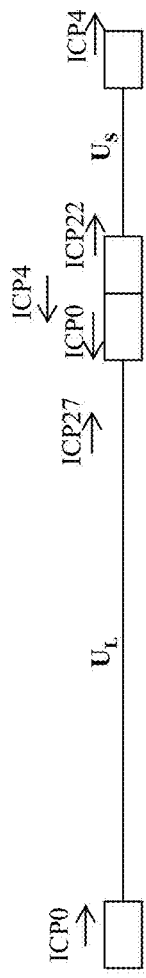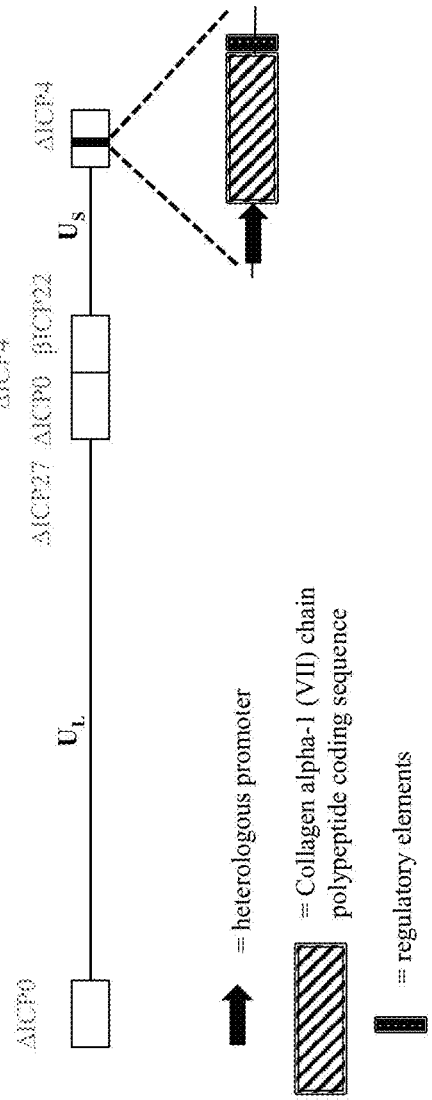

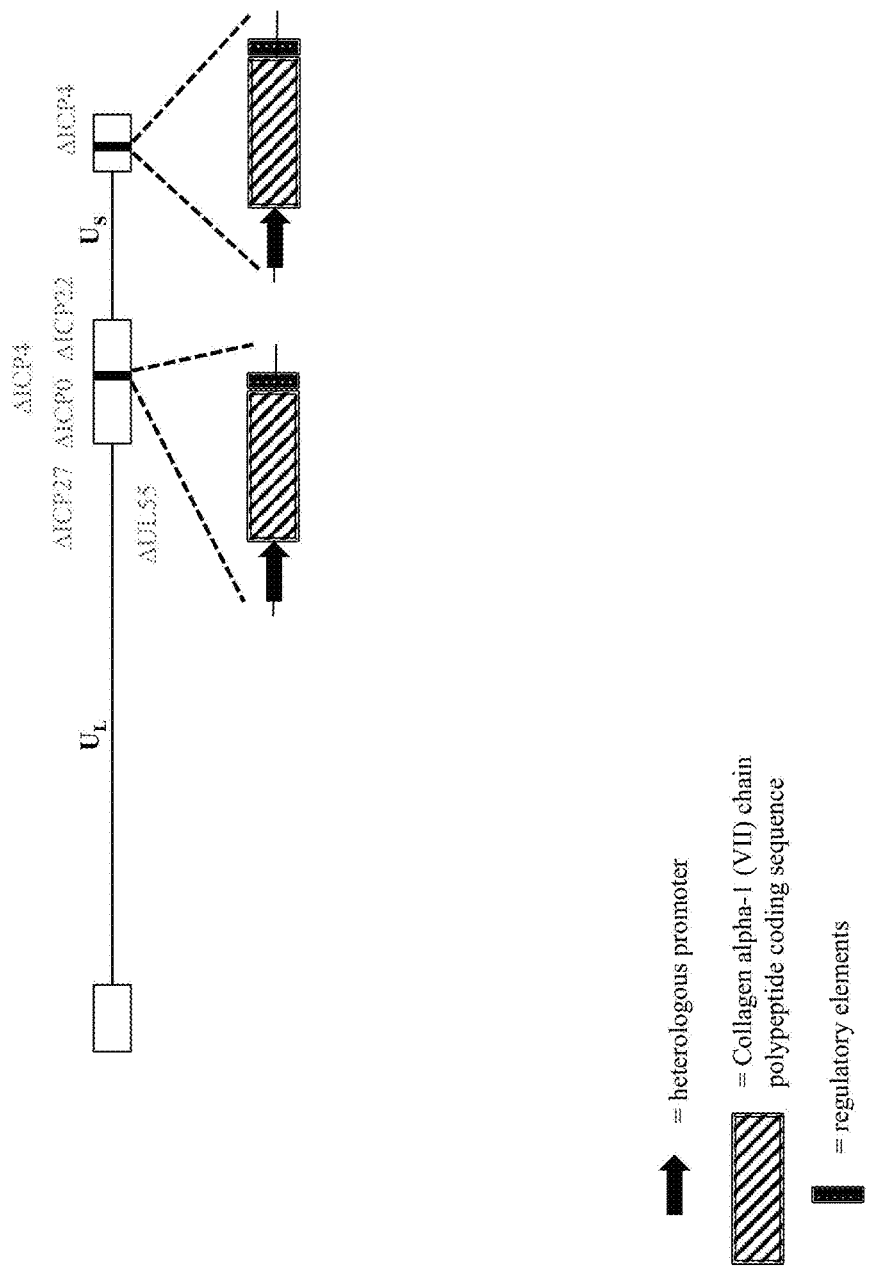

METHODS OF DELIVERING TRANSGENES TO THE EYE

CROSS REFERENCE TO RELATED APPLICATIONS

The present application is a continuation of U.S. patent application Ser. No. 17/529,161, filed Nov. 17, 2021, which is a continuation of U.S. patent application Ser. No. 16/598,982, filed Oct. 10, 2019, now issued as U.S. Pat. No. 11,185,564, which is a continuation of U.S. patent application Ser. No. 16/177,153, filed Oct. 31, 2018, now issued as U.S. Pat. No. 10,441,614, which is a continuation of U.S. patent application Ser. No. 15/851,488, filed Dec. 21, 2017, now issued as U.S. Pat. No. 10,155,016, which is a continuation of U.S. patent application Ser. No. 15/393,151, filed Dec. 28, 2016, now issued as U.S. Pat. No. 9,877,990, which claims the benefit of U.S. Provisional Patent Application Ser. No. 62/320,316, filed Apr. 8, 2016, each of which are incorporated herein by reference in its entirety.

SUBMISSION OF ELECTRONIC SEQUENCE LISTING

The content of the electronic Sequence Listing (file name: 761342000105SeqList.xml, date recorded: Nov. 30, 2022, size: 171,429 bytes) is herein incorporated by reference in its entirety.

FIELD OF THE INVENTION

The present disclosure relates, in part, to methods of use for delivering transgenes to the eye of a subject, including a subject having or at risk of developing vision loss.

BACKGROUND

A number of serious disease-related skin conditions are associated with one or more genetic disorders in patients suffering from these diseases. One such disease, epidermolysis bullosa (EB), is a group of genetic disorders that cause the skin and mucous membranes of an affected individual to blister and erode in response to minor injury or friction, such as scraping, rubbing, or scratching. Dystrophic epidermolysis bullosa (DEB) is one of the major forms of EB. The signs and symptoms of this condition vary widely among affected individuals, ranging from mild (blistering may only affect the hands, feet, knees, and elbows) to severe (widespread blistering and scarring, possibly leading to vision loss, disfigurement, and other serious, and sometimes fatal, medical conditions).

Dystrophic epidermolysis bullosa is classified into three major types. Autosomal dominant dystrophic epidermolysis bullosa (referred to as dominant dystrophic epidermolysis bullosa or DDEB) is typically the mildest form, with blistering often restricted to the hands, feet knees and elbows. The other two types of dystrophic epidermolysis bullosa, Hallopeau-Siemens type recessive dystrophic epidermolysis bullosa, and non-Hallopeau-Siemens type recessive epidermolysis bullosa (collectively referred to as recessive dystrophic epidermolysis bullosa or RDEB) are more severe. RDEB is most often characterized by extensive blistering and scarring of the skin and mucosal membranes. Blisters are routinely present over the whole body, including on mucous membranes (such as the lining of the mouth and digestive tract), and healing of these blisters results in extensive scarring. Damage to the mouth and esophagus can make it difficult to chew and swallow food, leading to chronic malnutrition and slow growth. Complications from extensive scarring can include fusion of the fingers and toes, joint deformities, and eye inflammation leading to vision loss. Additionally, patients suffering from RDEB have a high risk of developing squamous cell carcinoma, which can be unusually aggressive in this patient population, often becoming life-threatening. Although the three types of dystrophic epidermolysis bullosa differ in severity, they have many shared features, and are caused by the same genetic mutations.

Dystrophic epidermolysis bullosa is caused by mutations to the Col7a1 gene, which encodes the Collagen alpha-1 (VII) chain protein (Collagen 7). More than 240 distinct mutations to this gene have been identified in DEB patients. Additionally, a significant decrease in expression of the PLOD3 gene, which encodes the collagen modifying Lysyl hydroxylase 3 enzyme (LH3), has also been observed in dystrophic epidermolysis patients. Collagen alpha-1 (VII) chain protein functions to strengthen and stabilize the skin, while Lysyl hydroxylase 3 plays a critical role in the synthesis and secretion of functional Collagen alpha-1 (VII) chain protein. Briefly, Col7a1 transcripts are translated, and the resulting peptides are post-translationally modified by hydroxylating their proline residues (by prolyl hydroxylases) and their lysine residues (by lysyl hydroxylases, such as LH3). Hydroxylysine residues can then be glycosylated, and subsequently, three glycosylated peptides form a triple helix known as pro-collagen, and are secreted from the cell. The secreted pro-collagen can then associate in to higher-order structures, forming anchoring fibrils. The anchoring fibrils are then available to help organize, stabilize, and aid in adherence of the epithelial basement membrane. The epithelial basement membrane is responsible for anchoring the epithelium to the underlying loose connective tissue, and is essential for dermal-epidermal stability (dermoepidermal junction integrity). Mutations in the Col7a1 gene, and diminished levels of PLOD3 expression, impair the ability of Collagen alpha-1 (VII) chain protein to properly connect the epidermis to the dermis in dystrophic epidermolysis bullosa patients, leading to fragile skin.

Treatment options for epidermolysis bullosa patients are limited, and current care focuses on managing the symptoms of the disease, including providing medication to control pain and itching, administering oral antibiotics to stave off infections resulting from open wounds on the skin and mucosa, and surgical strategies to address scarring and deformities. Investigational methods for treating the underlying causes of epidermolysis bullosa include administering purified Collagen 7, fibroblasts containing Collagen 7, or viral vectors encoding Collagen 7, by intradermal injection. Because many DEB patients have multiple wounds spanning large areas of trauma-prone sites (such as the sacrum, hips, feet, lower back, and hands), any treatment involving intradermal injection would be extremely invasive, as these large wound areas would all need to be injected, likely repeatedly, although injection time intervals are unclear.

Thus there exists a clear need for less invasive/minimally invasive/non-invasive treatment options for epidermolysis bullosa patients that can address the deficiencies in the Collagen alpha-1 (VII) chain protein, as well as deficiencies in the Lysyl hydroxylase 3 protein, observed in this patient population.

All references cited herein, including patent applications, patent publications, non-patent literature, and UniProtKB/Swiss-Prot Accession numbers are herein incorporated by reference in their entirety, as if each individual reference were specifically and individually indicated to be incorporated by reference.

BRIEF SUMMARY

In order to meet these needs, the present disclosure relates, in part, to pharmaceutical compositions and methods of use for providing prophylactic, palliative, or therapeutic relief of a wound, disorder, or disease of the skin in a subject, especially in a subject having, or at risk of developing, one or more symptoms of epidermolysis bullosa. In particular, the present disclosure relates, in part, to a method of treating an individual by administering (e.g., topically or transdermally administering) a pharmaceutical composition comprising one or more polynucleotides encoding a Collagen alpha-1 (VII) chain polypeptide, a Lysyl hydroxylase 3 polypeptide, a Keratin type I cytoskeletal 17 polypeptide and/or a chimeric polypeptide thereof.

Accordingly, certain aspects of the present disclosure relate to a pharmaceutical composition comprising a virus comprising a vector, wherein the vector comprises one or more transgenes encoding a Collagen alpha-1 (VII) chain polypeptide, a Lysyl hydroxylase 3 polypeptide, or a chimeric polypeptide thereof, and a pharmaceutically acceptable carrier. In some embodiments, the virus is an adenovirus, adeno-associated virus, retrovirus, lentivirus, sendai virus, herpes simplex virus, vaccinia virus, or any hybrid virus thereof. In some embodiments, the virus is replication-defective. In some embodiments, the virus is a herpes simplex virus (HSV). In some embodiments, the herpes simplex virus is a herpes simplex type 1 virus, a herpes simplex type 2 virus, or any derivatives thereof. In some embodiments, the herpes simplex virus comprises a modified envelope. In some embodiments, the modified envelope alters the herpes simplex virus tissue tropism relative to a wild-type herpes simplex virus. In some embodiments, the modified envelope comprises a mutant herpes simplex virus glycoprotein. In some embodiments, the vector is an HSV-1 amplicon or an HSV-1 hybrid amplicon. In some embodiments, the HSV-1 hybrid amplicon is an HSV/AAV hybrid amplicon, an HSV/EBV hybrid amplicon, and HSV/EBV/RV hybrid amplicon, or an HSV/Sleeping Beauty hybrid amplicon. In some embodiments, the vector is a recombinant herpes simplex virus genome. In some embodiments, the recombinant herpes simplex virus genome is a recombinant HSV-1 genome, a recombinant HSV-2 genome, or any derivatives thereof. In some embodiments, the recombinant herpes simplex virus genome comprises an inactivating mutation in an immediate early herpes simplex virus gene. In some embodiments, the herpes simplex virus gene is ICP0, ICP4, ICP22, ICP27, ICP47, tk, UL41, or UL55. In some embodiments, the recombinant herpes simplex virus genome comprises an inactivating mutation in the ICP4, ICP27, and UL55 genes. In some embodiments, the recombinant herpes simplex virus genome comprises an inactivating mutation in the ICP4, ICP22, ICP27, ICP47, and UL55 genes. In some embodiments, the inactivating mutation in the ICP4, ICP27, and UL55 genes is a deletion of the coding sequence of the ICP4, ICP27, and UL55 genes. In some embodiments, the inactivating mutation in the ICP22 and ICP47 genes is a deletion in the promoter region of the ICP22 and ICP47 genes. In some embodiments, the recombinant herpes simplex virus genome comprises an inactivating mutation in the ICP4 and ICP22 genes. In some embodiment, the recombinant herpes simplex virus genome comprises an inactivating mutation in the ICP0 and ICP4 genes. In some embodiments, the recombinant herpes simplex virus genome comprises an inactivating mutation in the ICP0, ICP4, and ICP22 genes. In some embodiments, the recombinant herpes simplex virus genome comprises an inactivating mutation in the ICP0, ICP4, ICP22, and ICP27 genes. In some embodiments, the recombinant herpes simplex virus genome comprises an inactivating mutation in the ICP0, ICP4, ICP22, ICP27, and UL55 genes. In some embodiments, the inactivating mutation is a deletion of the coding sequence of the genes. In some embodiments, the recombinant herpes simplex virus genome further comprises an inactivating mutation in the ICP47 gene, an inactivating mutation in the UL41 gene, or an inactivation mutation in the ICP47 and UL41 genes. In some embodiments, the recombinant herpes simplex virus genome comprises the one or more transgenes within one or more viral gene loci. In some embodiments, the recombinant herpes simplex virus genome comprises the one or more transgenes within one or more of the ICP4 viral gene loci. In some embodiments, the recombinant herpes simplex virus genome comprises the one or more transgenes within the UL41 viral gene locus. In some embodiments, the vector is capable of replicating within a target cell when delivered into said target cell. In some embodiments, the pharmaceutically acceptable carrier is suitable for topical or transdermal administration. In some embodiments, the one or more transgenes comprises an miRNA binding site. In some embodiments, the one or more transgenes are operably linked to one or more heterologous promoters. In some embodiments, the one or more heterologous promoters are one or more of the human cytomegalovirus (HCMV) immediate early promoter, the elongation factor-1 (EF1) promoter, and/or any combinations thereof. In some embodiment, the vector comprises a transgene encoding a Collagen alpha-1 (VII) chain polypeptide. In some embodiments, the vector comprises two transgenes, wherein each transgene encodes a Collagen alpha-1 (VII) chain polypeptide. In some embodiments, the Collagen alpha-1 (VII) chain polypeptide has at least 80% sequence identity to the sequence of SEQ ID NO: 2. In some embodiments, the collagen alpha-1 (VII) chain polypeptide is a fragment, wherein the fragment has at least 100 consecutive amino acids of SEQ ID NO: 2. In some embodiments, the Collagen alpha-1 (VII) chain polypeptide enhances, increases, augments, and/or supplements anchoring fibril formation of a subject when the polypeptide is expressed in one or more target cells of the subject. In some embodiments, the Collagen alpha-1 (VII) chain polypeptide enhances, increases, augments, and/or supplements epithelial basement membrane organization and/or epithelial basement adherence of a subject when the polypeptide is expressed in one or more target cells of the subject. In some embodiments, the Lysyl hydroxylase 3 polypeptide has at least 80% sequence identity to the sequence of SEQ ID NO: 4. In some embodiments, the Lysyl hydroxylase 3 polypeptide is a fragment, wherein the fragment has at least 100 consecutive amino acids of SEQ ID NO: 4. In some embodiments, the Lysyl hydroxylase 3 polypeptide enhances, increases, augments, and/or supplements the formation of hydroxylysine residues on one or more collagen polypeptides of a subject when the Lysyl hydroxylase 3 polypeptide is expressed in one or more target cells of the subject. In some embodiments, the Lysyl hydroxylase 3 polypeptide enhances, increases, augments, and/or supplements anchoring fibril formation, epithelial basement membrane organization, and/or epithelial basement adherence of a subject when the polypeptide is expressed in one or more target cells of the subject. In some embodiments, the vector comprises at least a first transgene and a second transgene. In some embodiments, the first transgene encodes a Collagen alpha-1 (VII) chain polypeptide and the second transgene encodes a Lysyl hydroxylase 3 polypeptide. In some embodiments, the vector comprises a transgene that is polycistronic. In some embodiments, the polycistronic transgene encodes a Collagen alpha-1 (VII) chain polypeptide on a first open reading frame (ORF) and a Lysyl hydroxylase 3 polypeptide on a second open reading frame (ORF). In some embodiments, the first and second ORFs are separated by an internal ribosomal entry site (IRES). In some embodiments, the Collagen alpha-1 (VII) chain polypeptide and the Lysyl hydroxylase 3 polypeptide are at about an equimolar ratio when the polypeptides are expressed in one or more target cells of a subject. In some embodiments, the Collagen alpha-1 (VII) chain polypeptide and the Lysyl hydroxylase 3 polypeptide enhance, increase, augment, and/or supplement anchoring fibril formation, epithelial basement membrane organization, and/or epithelial basement adherence of a subject when the polypeptides are expressed in one or more target cells of the subject. In some embodiments, the chimeric polypeptide comprises a linker polypeptide between the Collagen alpha-1 (VII) chain polypeptide and the Lysyl hydroxylase 3 polypeptide. In some embodiments, the linker polypeptide is a T2A, P2A, E2A, or F2A linker polypeptide. In some embodiments, the linker polypeptide has at least 80% sequence identity to the sequence of SEQ ID NO: 6, SEQ ID NO: 8, SEQ ID NO: 10 or SEQ ID NO: 12. In some embodiments, the chimeric polypeptide has at least 80% sequence identity to the sequence of SEQ ID NO: 14, SEQ ID NO: 16, SEQ ID NO: 18, SEQ ID NO: 20, SEQ ID NO: 22, SEQ ID NO: 24, SEQ ID NO: 26 or SEQ ID NO: 28. In some embodiments, the chimeric polypeptide enhances, increases, augments, and/or supplements anchoring fibril formation, epithelial basement membrane organization, and/or epithelial basement adherence of a subject when the polypeptide is expressed in one or more target cells of the subject.

Other aspects of the present disclosure relate to a method of providing prophylactic, palliative, or therapeutic relief of a wound, disorder, or disease of the skin in a subject, the method comprising topically or transdermally administering a pharmaceutical composition capable of enhancing, increasing, augmenting, and/or supplementing the levels of a Collagen alpha-1 (VII) chain polypeptide and/or a Lysyl hydroxylase 3 polypeptide in one or more cells of the subject. In some embodiments, the pharmaceutical composition comprises a virus comprising a vector, wherein the vector comprises one or more transgenes encoding a Collagen alpha-1 (VII) chain polypeptide, a Lysyl hydroxylase 3 polypeptide, or a chimeric polypeptide thereof, and a pharmaceutically acceptable carrier. In some embodiments, the virus is an adenovirus, adeno-associated virus, retrovirus, lentivirus, sendai virus, herpes simplex virus, vaccinia virus, or any hybrid virus thereof. In some embodiments, the virus is replication-defective. In some embodiments, the virus is a herpes simplex virus (HSV). In some embodiments, the herpes simplex virus is a herpes simplex type 1 virus, a herpes simplex type 2 virus, or any derivatives thereof. In some embodiments, the herpes simplex virus comprises a modified envelope. In some embodiments, the modified envelope alters the herpes simplex virus tissue tropism relative to a wild-type herpes simplex virus. In some embodiments, the modified envelope comprises a mutant herpes simplex virus glycoprotein. In some embodiments, the vector is an HSV-1 amplicon or an HSV-1 hybrid amplicon. In some embodiments, the HSV-1 hybrid amplicon is an HSV/AAV hybrid amplicon, an HSV/EBV hybrid amplicon, and HSV/EBV/RV hybrid amplicon, or an HSV/Sleeping Beauty hybrid amplicon. In some embodiments, the vector is a recombinant herpes simplex virus genome. In some embodiments, the recombinant herpes simplex virus genome is a recombinant HSV-1 genome, a recombinant HSV-2 genome, or any derivatives thereof. In some embodiments, the recombinant herpes simplex virus genome comprises an inactivating mutation in an immediate early herpes simplex virus gene. In some embodiments, the herpes simplex virus gene is ICP0, ICP4, ICP22, ICP27, ICP47, tk, UL41, or UL55. In some embodiments, the recombinant herpes simplex virus genome comprises an inactivating mutation in the ICP4, ICP27, and UL55 genes. In some embodiments, the recombinant herpes simplex virus genome comprises an inactivating mutation in the ICP4, ICP22, ICP27, ICP47, and UL55 genes. In some embodiments, the inactivating mutation in the ICP4, ICP27, and UL55 genes is a deletion of the coding sequence of the ICP4, ICP27, and UL55 genes. In some embodiments, the inactivating mutation in the ICP22 and ICP47 genes is a deletion in the promoter region of the ICP22 and ICP47 genes. In some embodiments, the recombinant herpes simplex virus genome comprises an inactivating mutation in the ICP4 and ICP22 genes. In some embodiment, the recombinant herpes simplex virus genome comprises an inactivating mutation in the ICP0 and ICP4 genes. In some embodiments, the recombinant herpes simplex virus genome comprises an inactivating mutation in the ICP0, ICP4, and ICP22 genes. In some embodiments, the recombinant herpes simplex virus genome comprises an inactivating mutation in the ICP0, ICP4, ICP22, and ICP27 genes. In some embodiments, the recombinant herpes simplex virus genome comprises an inactivating mutation in the ICP0, ICP4, ICP22, ICP27, and UL55 genes. In some embodiments, the inactivating mutation is a deletion of the coding sequence of the genes. In some embodiments, the recombinant herpes simplex virus genome further comprises an inactivating mutation in the ICP47 gene, an inactivating mutation in the UL41 gene, or an inactivation mutation in the ICP47 and UL41 genes. In some embodiments, the recombinant herpes simplex virus genome comprises the one or more transgenes within one or more viral gene loci. In some embodiments, the recombinant herpes simplex virus genome comprises the one or more transgenes within one or more of the ICP4 viral gene loci. In some embodiments, the recombinant herpes simplex virus genome comprises the one or more transgenes within the UL41 viral gene locus. In some embodiments, the vector is capable of replicating within a target cell when delivered into said target cell. In some embodiments, the pharmaceutically acceptable carrier is suitable for topical or transdermal administration. In some embodiments, the one or more transgenes comprises an miRNA binding site. In some embodiments, the one or more transgenes are operably linked to one or more heterologous promoters. In some embodiments, the one or more heterologous promoters are one or more of the human cytomegalovirus (HCMV) immediate early promoter, the elongation factor-1 (EF1) promoter, and/or any combinations thereof. In some embodiments, the vector comprises a transgene encoding a Collagen alpha-1 (VII) chain polypeptide. In some embodiments, the vector comprises two transgenes, wherein each transgene encodes a Collagen alpha-1 (VII) chain polypeptide. In some embodiments, the Collagen alpha-1 (VII) chain polypeptide has at least 80% sequence identity to the sequence of SEQ ID NO: 2. In some embodiments, the collagen alpha-1 (VII) chain polypeptide is a fragment, wherein the fragment has at least 100 consecutive amino acids of SEQ ID NO: 2. In some embodiments, the Collagen alpha-1 (VII) chain polypeptide enhances, increases, augments, and/or supplements anchoring fibril formation of a subject when the polypeptide is expressed in one or more target cells of the subject. In some embodiments, the Collagen alpha-1 (VII) chain polypeptide enhances, increases, augments, and/or supplements epithelial basement membrane organization and/or epithelial basement adherence of a subject when the polypeptide is expressed in one or more target cells of the subject. In some embodiments, the Lysyl hydroxylase 3 polypeptide has at least 80% sequence identity to the sequence of SEQ ID NO: 4. In some embodiments, the Lysyl hydroxylase 3 polypeptide is a fragment, wherein the fragment has at least 100 consecutive amino acids of SEQ ID NO: 4. In some embodiments, the Lysyl hydroxylase 3 polypeptide enhances, increases, augments, and/or supplements the formation of hydroxylysine residues on one or more collagen polypeptides of a subject when the Lysyl hydroxylase 3 polypeptide is expressed in one or more target cells of the subject. In some embodiments, the Lysyl hydroxylase 3 polypeptide enhances, increases, augments, and/or supplements anchoring fibril formation, epithelial basement membrane organization, and/or epithelial basement adherence of a subject when the polypeptide is expressed in one or more target cells of the subject. In some embodiments, the vector comprises at least a first transgene and a second transgene. In some embodiments, the first transgene encodes a Collagen alpha-1 (VII) chain polypeptide and the second transgene encodes a Lysyl hydroxylase 3 polypeptide. In some embodiments, the vector comprises a transgene that is polycistronic. In some embodiments, the polycistronic transgene encodes a Collagen alpha-1 (VII) chain polypeptide on a first open reading frame (ORF) and a Lysyl hydroxylase 3 polypeptide on a second open reading frame (ORF). In some embodiments, the first and second ORFs are separated by an internal ribosomal entry site (IRES). In some embodiments, the Collagen alpha-1 (VII) chain polypeptide and the Lysyl hydroxylase 3 polypeptide are at about an equimolar ratio when the polypeptides are expressed in one or more target cells of a subject. In some embodiments, the Collagen alpha-1 (VII) chain polypeptide and the Lysyl hydroxylase 3 polypeptide enhance, increase, augment, and/or supplement anchoring fibril formation, epithelial basement membrane organization, and/or epithelial basement adherence of a subject when the polypeptides are expressed in one or more target cells of the subject. In some embodiments, the chimeric polypeptide comprises a linker polypeptide between the Collagen alpha-1 (VII) chain polypeptide and the Lysyl hydroxylase 3 polypeptide. In some embodiments, the linker polypeptide is a T2A, P2A, E2A, or F2A linker polypeptide. In some embodiments, the linker polypeptide has at least 80% sequence identity to the sequence of SEQ ID NO: 6, SEQ ID NO: 8, SEQ ID NO: 10 or SEQ ID NO: 12. In some embodiments, the chimeric polypeptide has at least 80% sequence identity to the sequence of SEQ ID NO: 14, SEQ ID NO: 16, SEQ ID NO: 18, SEQ ID NO: 20, SEQ ID NO: 22, SEQ ID NO: 24, SEQ ID NO: 26 or SEQ ID NO: 28. In some embodiments, the chimeric polypeptide enhances, increases, augments, and/or supplements anchoring fibril formation, epithelial basement membrane organization, and/or epithelial basement adherence of a subject when the polypeptide is expressed in one or more target cells of the subject. In some embodiments, the pharmaceutical composition is administered one, two three, four, five or more times per day. In some embodiments, the pharmaceutical composition is administered to one or more affected and/or unaffected areas of the subject. In some embodiments, the disease or disorder of the skin is one or more of epidermolysis bullosa, skin cancer, psoriasis, lichen planus, lupus, rosacea, eczema, cutaneous candidiasis, cellulitis, impetigo, decubitus ulcers, erysipelas, ichthyosis vulgaris, dermatomyositis, acrodermatitis, stasis dermatitis, nethertons syndrome, epidermolysis bullosa simplex (LAMB3 gene), autosomal recessive congenital ichthyosis, xeroderma pigmentosa, and pemphigoid.

Other aspects of the present disclosure relate to an isolated chimeric polypeptide, wherein the isolated chimeric polypeptide comprises a Collagen alpha-1 (VII) chain polypeptide, a Lysyl hydroxylase 3 polypeptide, and a linker polypeptide, wherein the Collagen alpha-1 (VII) chain polypeptide and the Lysyl hydroxylase 3 polypeptide are separated by the linker polypeptide, to polynucleotides encoding the same, to vectors comprising the polynucleotides, and to host cells comprising the vectors. In some embodiments, the vector is an HSV-1 amplicon or an HSV-1 hybrid amplicon. In some embodiments, the HSV-1 hybrid amplicon is an HSV/AAV hybrid amplicon, an HSV/EBV hybrid amplicon, and HSV/EBV/RV hybrid amplicon, or an HSV/Sleeping Beauty hybrid amplicon. In some embodiments, the vector is a recombinant herpes simplex virus genome. In some embodiments, the recombinant herpes simplex virus genome is a recombinant HSV-1 genome, a recombinant HSV-2 genome, or any derivatives thereof. In some embodiments, the recombinant herpes simplex virus genome comprises an inactivating mutation in an immediate early herpes simplex virus gene. In some embodiments, the herpes simplex virus gene is ICP0, ICP4, ICP22, ICP27, ICP47, tk, UL41, or UL55. In some embodiments, the recombinant herpes simplex virus genome comprises an inactivating mutation in the ICP4, ICP27, and UL55 genes. In some embodiments, the recombinant herpes simplex virus genome comprises an inactivating mutation in the ICP4, ICP22, ICP27, ICP47, and UL55 genes. In some embodiments, the inactivating mutation in the ICP4, ICP27, and UL55 genes is a deletion of the coding sequence of the ICP4, ICP27, and UL55 genes. In some embodiments, the inactivating mutation in the ICP22 and ICP47 genes is a deletion in the promoter region of the ICP22 and ICP47 genes. In some embodiments, the recombinant herpes simplex virus genome comprises an inactivating mutation in the ICP4 and ICP22 genes. In some embodiment, the recombinant herpes simplex virus genome comprises an inactivating mutation in the ICP0 and ICP4 genes. In some embodiments, the recombinant herpes simplex virus genome comprises an inactivating mutation in the ICP0, ICP4, and ICP22 genes. In some embodiments, the recombinant herpes simplex virus genome comprises an inactivating mutation in the ICP0, ICP4, ICP22, and ICP27 genes. In some embodiments, the recombinant herpes simplex virus genome comprises an inactivating mutation in the ICP0, ICP4, ICP22, ICP27, and UL55 genes. In some embodiments, the inactivating mutation is a deletion of the coding sequence of the genes. In some embodiments, the recombinant herpes simplex virus genome further comprises an inactivating mutation in the ICP47 gene, an inactivating mutation in the UL41 gene, or an inactivation mutation in the ICP47 and UL41 genes. In some embodiments, the recombinant herpes simplex virus genome comprises the polynucleotide within one or more viral gene loci. In some embodiments, the recombinant herpes simplex virus genome comprises the polynucleotide within one or more of the ICP4 viral gene loci. In some embodiments, the recombinant herpes simplex virus genome comprises the polynucleotide within the UL41 viral gene locus.

Other aspects of the present disclosure relate to a vector comprising one or more polynucleotides encoding a Collagen alpha-1 (VII) chain polypeptide, a Lysyl hydroxylase 3 polypeptide, a Keratin type I cytoskeletal 17 polypeptide, or any combinations thereof, wherein the vector is a recombinant herpes simplex virus genome, and to host cells comprising the vector. In some embodiments, the recombinant herpes simplex virus genome is a recombinant HSV-1 genome, a recombinant HSV-2 genome, or any derivatives thereof. In some embodiments, the recombinant herpes simplex virus genome comprises an inactivating mutation in an immediate early herpes simplex virus gene. In some embodiments, the herpes simplex virus gene is ICP0, ICP4, ICP22, ICP27, ICP47, tk, UL41, or UL55. In some embodiments, the recombinant herpes simplex virus genome comprises an inactivating mutation in the ICP4, ICP27, and UL55 genes. In some embodiments, the recombinant herpes simplex virus genome comprises an inactivating mutation in the ICP4, ICP22, ICP27, ICP47, and UL55 genes. In some embodiments, the inactivating mutation in the ICP4, ICP27, and UL55 genes is a deletion of the coding sequence of the ICP4, ICP27, and UL55 genes. In some embodiments, the inactivating mutation in the ICP22 and ICP47 genes is a deletion in the promoter region of the ICP22 and ICP47 genes. In some embodiments, the recombinant herpes simplex virus genome comprises an inactivating mutation in the ICP4 and ICP22 genes. In some embodiment, the recombinant herpes simplex virus genome comprises an inactivating mutation in the ICP0 and ICP4 genes. In some embodiments, the recombinant herpes simplex virus genome comprises an inactivating mutation in the ICP0, ICP4, and ICP22 genes. In some embodiments, the recombinant herpes simplex virus genome comprises an inactivating mutation in the ICP0, ICP4, ICP22, and ICP27 genes. In some embodiments, the recombinant herpes simplex virus genome comprises an inactivating mutation in the ICP0, ICP4, ICP22, ICP27, and UL55 genes. In some embodiments, the inactivating mutation is a deletion of the coding sequence of the genes. In some embodiments, the recombinant herpes simplex virus genome further comprises an inactivating mutation in the ICP47 gene, an inactivating mutation in the UL41 gene, or an inactivation mutation in the ICP47 and UL41 genes. In some embodiments, the recombinant herpes simplex virus genome comprises the one or more polynucleotides within one or more viral gene loci. In some embodiments, the recombinant herpes simplex virus genome comprises the one or more polynucleotides within one or more of the ICP4 viral gene loci. In some embodiments, the recombinant herpes simplex virus genome comprises the one or more polynucleotides within the UL41 viral gene locus. In some embodiments, the vector comprises one polynucleotide encoding a Collagen alpha-1 (VII) chain polypeptide. In some embodiments, the vector comprises two polynucleotides encoding a Collagen alpha-1 (VII) chain polypeptide.

Other aspects of the present disclosure relate to methods of collecting a herpes simplex virus, wherein a vector of interest is packaged within said herpes simplex virus. In some embodiments the method comprises the steps of contacting a host cell with a vector encoding a helper virus, contacting said host cell with a HSV-1 amplicon or HSV-1 hybrid amplicon comprising one or more polynucleotides described herein, and collecting the Herpes simplex virus generated by said host cell. In some embodiments, the method comprises the steps of contacting a complementing host cell with a recombinant herpes simplex virus genome vector comprising one or more polynucleotides described herein, and collecting the herpes simplex virus generated by said complementing host cell. In some embodiments, the collected herpes simplex virus is a herpes simplex type 1 virus, a herpes simplex type 2 virus, or any derivatives thereof.

Other aspects of the present disclosure relate to a kit comprising a pharmaceutical composition described herein and instructions for administering the pharmaceutical composition.

Other aspects of the present disclosure relate to relate to a pharmaceutical composition comprising a virus comprising a vector, wherein the vector comprises one or more transgenes encoding a Collagen alpha-1 (VII) chain polypeptide, a Lysyl hydroxylase 3 polypeptide, a Keratin type I cytoskeletal 17 polypeptide, or a chimeric polypeptide thereof, and a pharmaceutically acceptable carrier. In some embodiments, the virus is an adenovirus, adeno-associated virus, retrovirus, lentivirus, sendai virus, herpes simplex virus, vaccinia virus, or any hybrid virus thereof. In some embodiments, the virus is replication-defective. In some embodiments, the virus is a herpes simplex virus (HSV). In some embodiments, the herpes simplex virus is a herpes simplex type 1 virus, a herpes simplex type 2 virus, or any derivatives thereof. In some embodiments, the vector is an HSV-1 amplicon or an HSV-1 hybrid amplicon. In some embodiments, the HSV-1 hybrid amplicon is an HSV/AAV hybrid amplicon, an HSV/EBV hybrid amplicon, and HSV/EBV/RV hybrid amplicon, or an HSV/Sleeping Beauty hybrid amplicon. In some embodiments, the vector is a recombinant herpes simplex virus genome. In some embodiments, the recombinant herpes simplex virus genome is a recombinant HSV-1 genome, a recombinant HSV-2 genome, or any derivatives thereof. In some embodiments, the recombinant herpes simplex virus genome comprises an inactivating mutation in an immediate early herpes simplex virus gene. In some embodiments, the herpes simplex virus gene is ICP0, ICP4, ICP22, ICP27, ICP47, tk, UL41, or UL55. In some embodiments, the recombinant herpes simplex virus genome comprises an inactivating mutation in the ICP4, ICP27, and UL55 genes. In some embodiments, the recombinant herpes simplex virus genome comprises an inactivating mutation in the ICP4, ICP22, ICP27, ICP47, and UL55 genes. In some embodiments, the inactivating mutation in the ICP4, ICP27, and UL55 genes is a deletion of the coding sequence of the ICP4, ICP27, and UL55 genes. In some embodiments, the inactivating mutation in the ICP22 and ICP47 genes is a deletion in the promoter region of the ICP22 and ICP47 genes. In some embodiments, the recombinant herpes simplex virus genome comprises an inactivating mutation in the ICP4 and ICP22 genes. In some embodiment, the recombinant herpes simplex virus genome comprises an inactivating mutation in the ICP0 and ICP4 genes. In some embodiments, the recombinant herpes simplex virus genome comprises an inactivating mutation in the ICP0, ICP4, and ICP22 genes. In some embodiments, the recombinant herpes simplex virus genome comprises an inactivating mutation in the ICP0, ICP4, ICP22, and ICP27 genes. In some embodiments, the recombinant herpes simplex virus genome comprises an inactivating mutation in the ICP0, ICP4, ICP22, ICP27, and UL55 genes. In some embodiments, the inactivating mutation is a deletion of the coding sequence of the genes. In some embodiments, the recombinant herpes simplex virus genome further comprises an inactivating mutation in the ICP47 gene, an inactivating mutation in the UL41 gene, or an inactivation mutation in the ICP47 and UL41 genes. In some embodiments, the recombinant herpes simplex virus genome comprises the one or more transgenes within one or more viral gene loci. In some embodiments, the recombinant herpes simplex virus genome comprises the one or more transgenes within one or more of the ICP4 viral gene loci. In some embodiments, the recombinant herpes simplex virus genome comprises the one or more transgenes within the UL41 viral gene locus. In some embodiments, the vector is capable of replicating within a target cell when delivered into said target cell. In some embodiments, the pharmaceutically acceptable carrier is suitable for topical or transdermal administration. In some embodiments, the pharmaceutically acceptable carrier is suitable for subcutaneous or intradermal administration. In some embodiments, the one or more transgenes comprises an miRNA binding site. In some embodiment, the vector comprises a transgene encoding a Collagen alpha-1 (VII) chain polypeptide. In some embodiment, the vector comprises a transgene encoding a Lysyl hydroxylase 3 polypeptide. In some embodiment, the vector comprises a transgene encoding a Keratin type I cytoskeletal 17 polypeptide. In some embodiments, the vector comprises two transgenes, wherein each transgene encodes a Collagen alpha-1 (VII) chain polypeptide. In some embodiments, the Collagen alpha-1 (VII) chain polypeptide has at least 80% sequence identity to the sequence of SEQ ID NO: 2. In some embodiments, the collagen alpha-1 (VII) chain polypeptide is a fragment, wherein the fragment has at least 100 consecutive amino acids of SEQ ID NO: 2. In some embodiments, the Collagen alpha-1 (VII) chain polypeptide enhances, increases, augments, and/or supplements anchoring fibril formation of a subject when the polypeptide is expressed in one or more target cells of the subject. In some embodiments, the Collagen alpha-1 (VII) chain polypeptide enhances, increases, augments, and/or supplements epithelial basement membrane organization and/or epithelial basement adherence of a subject when the polypeptide is expressed in one or more target cells of the subject. In some embodiments, the Lysyl hydroxylase 3 polypeptide has at least 80% sequence identity to the sequence of SEQ ID NO: 4. In some embodiments, the Lysyl hydroxylase 3 polypeptide is a fragment, wherein the fragment has at least 100 consecutive amino acids of SEQ ID NO: 4. In some embodiments, the Lysyl hydroxylase 3 polypeptide enhances, increases, augments, and/or supplements the formation of hydroxylysine residues on one or more collagen polypeptides of a subject when the Lysyl hydroxylase 3 polypeptide is expressed in one or more target cells of the subject. In some embodiments, the Lysyl hydroxylase 3 polypeptide enhances, increases, augments, and/or supplements anchoring fibril formation, epithelial basement membrane organization, and/or epithelial basement adherence of a subject when the polypeptide is expressed in one or more target cells of the subject. In some embodiments, the Keratin type I cytoskeletal 17 polypeptide has at least 80% sequence identity to the sequence of SEQ ID NO: In some embodiments, the Keratin type I cytoskeletal 17 polypeptide is a fragment, wherein the fragment has at least 100 consecutive amino acids of SEQ ID NO: 30. In some embodiments, the Keratin type I cytoskeletal 17 polypeptide enhances, increases, augments, and/or supplements wound healing in a subject. In some embodiments, the vector comprises at least a first transgene and a second transgene. In some embodiments, the first transgene and the second transgene each encode a Collagen alpha-1 (VII) chain polypeptide. In some embodiments, the first transgene encodes a Collagen alpha-1 (VII) chain polypeptide and the second transgene encodes a Lysyl hydroxylase 3 polypeptide. In some embodiments, the first transgene encodes a Collagen alpha-1 (VII) chain polypeptide and the second transgene encodes a Keratin type I cytoskeletal 17 polypeptide. In some embodiments, the first transgene encodes a Lysyl hydroxylase 3 polypeptide and the second transgene encodes a Keratin type I cytoskeletal 17 polypeptide. In some embodiments, the vector comprises at least a first transgene, a second transgene, and a third transgene. In some embodiments, the first transgene encodes a Collagen alpha-1 (VII) chain polypeptide, the second transgene encodes a Lysyl hydroxylase 3 polypeptide, and the third transgene encodes a Keratin type I cytoskeletal 17 polypeptide.

Other aspects of the present disclosure relate to a method of providing prophylactic, palliative, or therapeutic relief of a wound, disorder, or disease of the skin in a subject, the method comprising administering to the subject a pharmaceutical composition comprising a vector, wherein the vector is a recombinant herpes simplex virus genome, and wherein the pharmaceutical composition is capable of enhancing, increasing, augmenting, and/or supplementing the levels of a Collagen alpha-1 (VII) chain polypeptide and/or a Lysyl hydroxylase 3 polypeptide and/or a Keratin type I cytoskeletal 17 polypeptide in one or more cells of the subject. In some embodiments, the pharmaceutical composition comprises a virus comprising the vector, wherein the vector comprises one or more transgenes encoding a Collagen alpha-1 (VII) chain polypeptide, a Lysyl hydroxylase 3 polypeptide, a Keratin type I cytoskeletal 17 polypeptide, or a chimeric polypeptide thereof, and a pharmaceutically acceptable carrier. In some embodiments, the virus is an adenovirus, adeno-associated virus, retrovirus, lentivirus, sendai virus, herpes simplex virus, vaccinia virus, or any hybrid virus thereof. In some embodiments, the virus is replication-defective. In some embodiments, the virus is a herpes simplex virus (HSV). In some embodiments, the herpes simplex virus is a herpes simplex type 1 virus, a herpes simplex type 2 virus, or any derivatives thereof. In some embodiments, the recombinant herpes simplex virus genome is a recombinant HSV-1 genome, a recombinant HSV-2 genome, or any derivatives thereof. In some embodiments, the recombinant herpes simplex virus genome comprises an inactivating mutation in an immediate early herpes simplex virus gene. In some embodiments, the herpes simplex virus gene is ICP0, ICP4, ICP22, ICP27, ICP47, tk, UL41, or UL55. In some embodiments, the recombinant herpes simplex virus genome comprises an inactivating mutation in the ICP4, ICP27, and UL55 genes. In some embodiments, the recombinant herpes simplex virus genome comprises an inactivating mutation in the ICP4, ICP22, ICP27, ICP47, and UL55 genes. In some embodiments, the inactivating mutation in the ICP4, ICP27, and UL55 genes is a deletion of the coding sequence of the ICP4, ICP27, and UL55 genes. In some embodiments, the inactivating mutation in the ICP22 and ICP47 genes is a deletion in the promoter region of the ICP22 and ICP47 genes. In some embodiments, the recombinant herpes simplex virus genome comprises an inactivating mutation in the ICP4 and ICP22 genes. In some embodiment, the recombinant herpes simplex virus genome comprises an inactivating mutation in the ICP0 and ICP4 genes. In some embodiments, the recombinant herpes simplex virus genome comprises an inactivating mutation in the ICP0, ICP4, and ICP22 genes. In some embodiments, the recombinant herpes simplex virus genome comprises an inactivating mutation in the ICP0, ICP4, ICP22, and ICP27 genes. In some embodiments, the recombinant herpes simplex virus genome comprises an inactivating mutation in the ICP0, ICP4, ICP22, ICP27, and UL55 genes. In some embodiments, the inactivating mutation is a deletion of the coding sequence of the genes. In some embodiments, the recombinant herpes simplex virus genome further comprises an inactivating mutation in the ICP47 gene, an inactivating mutation in the UL41 gene, or an inactivation mutation in the ICP47 and UL41 genes. In some embodiments, the recombinant herpes simplex virus genome comprises the one or more transgenes within one or more viral gene loci. In some embodiments, the recombinant herpes simplex virus genome comprises the one or more transgenes within one or more of the ICP4 viral gene loci. In some embodiments, the recombinant herpes simplex virus genome comprises the one or more transgenes within the UL41 viral gene locus. In some embodiments, the vector is capable of replicating within a target cell when delivered into said target cell. In some embodiments, the pharmaceutically acceptable carrier is suitable for topical or transdermal administration. In some embodiments, the pharmaceutically acceptable carrier is suitable for subcutaneous or intradermal administration. In some embodiments, the one or more transgenes comprises an miRNA binding site. In some embodiments, the vector comprises a transgene encoding a Collagen alpha-1 (VII) chain polypeptide. In some embodiments, the vector comprises a transgene encoding a Lysyl hydroxylase 3 polypeptide. In some embodiments, the vector comprises a transgene encoding a Keratin type I cytoskeletal 17 polypeptide. In some embodiments, the Collagen alpha-1 (VII) chain polypeptide has at least 80% sequence identity to the sequence of SEQ ID NO: 2. In some embodiments, the collagen alpha-1 (VII) chain polypeptide is a fragment, wherein the fragment has at least 100 consecutive amino acids of SEQ ID NO: 2. In some embodiments, the Collagen alpha-1 (VII) chain polypeptide enhances, increases, augments, and/or supplements anchoring fibril formation of a subject when the polypeptide is expressed in one or more target cells of the subject. In some embodiments, the Collagen alpha-1 (VII) chain polypeptide enhances, increases, augments, and/or supplements epithelial basement membrane organization and/or epithelial basement adherence of a subject when the polypeptide is expressed in one or more target cells of the subject. In some embodiments, the Lysyl hydroxylase 3 polypeptide has at least 80% sequence identity to the sequence of SEQ ID NO: 4. In some embodiments, the Lysyl hydroxylase 3 polypeptide is a fragment, wherein the fragment has at least 100 consecutive amino acids of SEQ ID NO: 4. In some embodiments, the Lysyl hydroxylase 3 polypeptide enhances, increases, augments, and/or supplements the formation of hydroxylysine residues on one or more collagen polypeptides of a subject when the Lysyl hydroxylase 3 polypeptide is expressed in one or more target cells of the subject. In some embodiments, the Lysyl hydroxylase 3 polypeptide enhances, increases, augments, and/or supplements anchoring fibril formation, epithelial basement membrane organization, and/or epithelial basement adherence of a subject when the polypeptide is expressed in one or more target cells of the subject. In some embodiments, the Keratin type I cytoskeletal 17 polypeptide has at least 80% sequence identity to the sequence of SEQ ID NO: 30. In some embodiments, the Keratin type I cytoskeletal 17 polypeptide is a fragment, wherein the fragment has at least 100 consecutive amino acids of SEQ ID NO: 30. In some embodiments, the Keratin type I cytoskeletal 17 polypeptide enhances, increases, augments, and/or supplements wound healing in a subject. In some embodiments, the vector comprises at least a first transgene and a second transgene. In some embodiments, the first transgene and the second transgene each encode a Collagen alpha-1 (VII) chain polypeptide. In some embodiments, the first transgene encodes a Collagen alpha-1 (VII) chain polypeptide and the second transgene encodes a Lysyl hydroxylase 3 polypeptide. In some embodiments, the first transgene encodes a Collagen alpha-1 (VII) chain polypeptide and the second transgene encodes a Keratin type I cytoskeletal 17 polypeptide. In some embodiments, the first transgene encodes a Lysyl hydroxylase 3 polypeptide and the second transgene encodes a Keratin type I cytoskeletal 17 polypeptide. In some embodiments, the vector comprises at least a first transgene, a second transgene, and a third transgene. In some embodiments, the first transgene encodes a Collagen alpha-1 (VII) chain polypeptide, the second transgene encodes a Lysyl hydroxylase 3 polypeptide, and the third transgene encodes a Keratin type I cytoskeletal 17 polypeptide. In some embodiments, the pharmaceutical composition is administered topically or transdermally to the subject. In some embodiments, the pharmaceutical composition is administered subcutaneously or intradermally to the subject. In some embodiments, the pharmaceutical composition is administered one, two three, four, five or more times per day. In some embodiments, the pharmaceutical composition is administered to one or more affected and/or unaffected areas of the subject. In some embodiments, the disease or disorder of the skin is one or more of epidermolysis bullosa, skin cancer, psoriasis, lichen planus, lupus, rosacea, eczema, cutaneous candidiasis, cellulitis, impetigo, decubitus ulcers, erysipelas, ichthyosis vulgaris, dermatomyositis, acrodermatitis, stasis dermatitis, nethertons syndrome, epidermolysis bullosa simplex (LAMB3 gene), autosomal recessive congenital ichthyosis, xeroderma pigmentosa, and pemphigoid.

BRIEF DESCRIPTION OF THE DRAWINGS

The patent or application file contains at least one drawing executed in color. Copies of this patent or patent application publication with color drawings will be provided by the Office upon request and payment of the necessary fee.

FIGS. 1A-F show schematics of wild-type and modified herpes simplex virus genomes. FIG. 1A shows a wild-type herpes simplex virus genome. FIG. 1B shows a modified herpes simplex virus genome comprising a transgene encoding a Collagen alpha-1 (VII) chain polypeptide. FIG. 1C shows a modified herpes simplex virus genome comprising two transgenes, one encoding a Collagen alpha-1 (VII) chain polypeptide and the other encoding a Lysyl hydroxylase 3 polypeptide, with the transgenes encoded on the same strand of DNA. FIG. 1D shows a modified herpes simplex virus genome comprising two transgenes, one encoding a Collagen alpha-1 (VII) chain polypeptide and the other encoding a Lysyl hydroxylase 3 polypeptide, with the transgenes encoded on opposite strands of DNA in an antisense orientation. FIG. 1E shows a modified herpes simplex virus genome comprising a transgene that is polycistronic, encoding a Collagen alpha-1 (VII) chain polypeptide and a Lysyl hydroxylase 3 polypeptide separated by an internal ribosomal entry site (IRES). FIG. 1F shows a modified herpes simplex virus genome comprising a transgene encoding a chimeric polypeptide comprising a Collagen alpha-1 (VII) chain polypeptide, a linker polypeptide, and a Lysyl hydroxylase 3 polypeptide.

FIGS. 2A-G show additional schematics of wild-type and modified herpes simplex virus genomes. FIG. 2A shows a wild-type herpes simplex virus genome. FIG. 2B shows a modified herpes simplex virus genome comprising deletions of the coding sequences of ICP4 (both copies), ICP27, and UL55 and deletions of the promoter sequences of ICP22 and ICP47, with two transgenes encoding Collagen alpha-1 (VII) chain polypeptides integrated at the ICP4 loci. FIG. 2C shows a modified herpes simplex virus genome comprising deletions of the coding sequences of ICP4 (both copies) and ICP22, with two transgenes encoding Collagen alpha-1 (VII) chain polypeptides integrated at the ICP4 loci. FIG. 2D shows a modified herpes simplex virus genome comprising deletions of the coding sequences of ICP0 and ICP4 (both copies), with two transgenes encoding Collagen alpha-1 (VII) chain polypeptides integrated at the ICP4 loci. FIG. 2E shows a modified herpes simplex virus genome comprising deletions of the coding sequences of ICP0, ICP4 (both copies), and ICP22, with two transgenes encoding Collagen alpha-1 (VII) chain polypeptides integrated at the ICP4 loci. FIG. 2F shows a modified herpes simplex virus genome comprising deletions of the coding sequences of ICP0, ICP4 (both copies), ICP22, and ICP27, with two transgenes encoding Collagen alpha-1 (VII) chain polypeptides integrated at the ICP4 loci. FIG. 2G shows a modified herpes simplex virus genome comprising deletions of the coding sequences of ICP0, ICP4 (both copies), ICP22, ICP27, and UL55, with two transgenes encoding Collagen alpha-1 (VII) chain polypeptides integrated at the ICP4 loci.

FIG. 5A shows human Col7 protein expression in uninfected normal and RDEB fibroblasts, as well as fibroblasts infected with KB103 at the indicated multiplicity of infection (MOI). FIG. shows human Col7 protein expression in uninfected normal and RDEB keratinocytes, as well as keratinocytes infected with KB103 at the indicated multiplicity of infection (MOI). Human GAPDH protein expression is shown as a loading control.

DETAILED DESCRIPTION

Figure 1C:
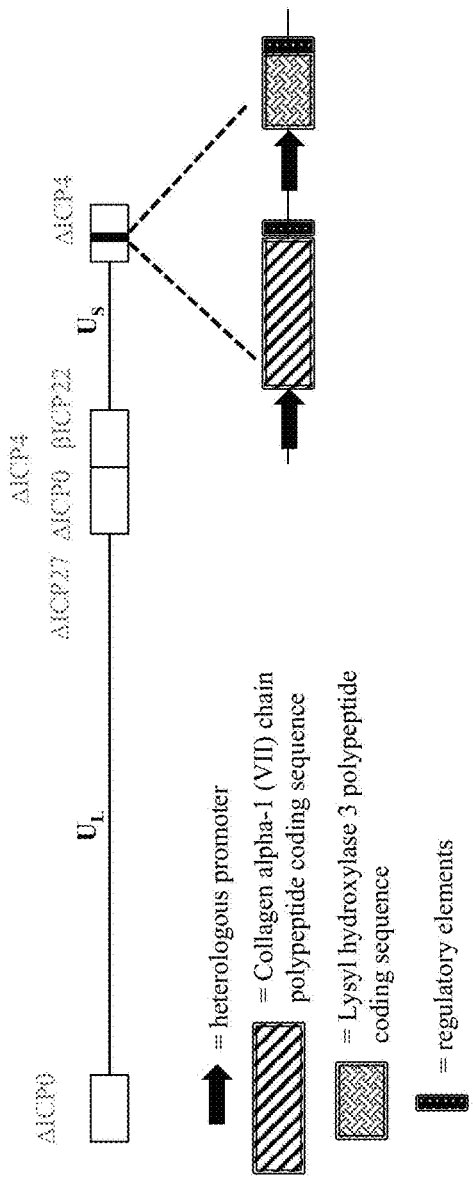

The present disclosure relates, in part, to pharmaceutical compositions comprising one or more polynucleotides encoding a Collagen alpha-1 (VII) chain polypeptide, a Lysyl hydroxylase 3 polypeptide, a Keratin type I cytoskeletal 17 polypeptide, and/or a chimeric polypeptide thereof. In some embodiments, the pharmaceutical composition comprises a vector, wherein the vector comprises one or more transgenes encoding a Collagen alpha-1 (VII) chain polypeptide, a Lysyl hydroxylase 3 polypeptide, a Keratin type I cytoskeletal 17 polypeptide, and/or a chimeric polypeptide thereof. In some embodiments, the vector comprises one or more transgenes suitable for enhancing, increasing, augmenting, and/or supplementing the levels of Collagen alpha-1 (VII) chain polypeptide and/or Lysyl hydroxylase 3 polypeptide and/or Keratin type I cytoskeletal 17 polypeptide in one or more cells of a subject. The present disclosure also relates, in part, to methods of providing prophylactic, palliative, or therapeutic relief of a wound, disorder, or disease of the skin (e.g. dystrophic epidermolysis bullosa) in a subject by administering (e.g., topically or transdermally administering) a pharmaceutical composition described herein.

The following description sets forth exemplary methods, parameters, and the like. It should be recognized, however, that such description is not intended as a limitation on the scope of the present disclosure but is instead provided as a description of exemplary embodiments.

General Techniques

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al. eds., (2003)); the series *Methods in Enzymology* (Academic Press, Inc.): *PCR 2: A Practical Approach* (M. J. MacPherson, B. D. Hames and G. R. Taylor eds. (1995)), Harlow and Lane, eds. (1988); *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney), ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Gene Transfer Vectors for Mammalian Cells* (J. M. Miller and M. P. Calos, eds., 1987); *PCR: The Polymerase Chain Reaction*, (Mullis et al., eds., 1994); *Short Protocols in Molecular Biology* (Wiley and Sons, 1999).

Definitions

Before describing the invention in detail, it is to be understood that this invention is not limited to particular compositions or biological systems, which can, of course, vary. It is also to be understood that the terminology used herein is for the purpose of describing particular embodiments only, and is not intended to be limiting.

As used herein, the singular forms "a", "an" and "the" include plural referents unless the content clearly dictates otherwise. Thus, for example, reference to "a molecule" optionally includes a combination of two or more such molecules, and the like.

As used herein, the term "about" refers to the usual error range for the respective value readily known to the skilled person in this technical field. Reference to "about" a value or parameter herein includes (and describes) embodiments that are directed to that value or parameter per se.

As used herein, the terms "polynucleotide", "nucleic acid sequence", "nucleic acid", and variations thereof shall be generic to polydeoxyribonucleotides (containing 2-deoxy-D-ribose), to polyribonucleotides (containing D-ribose), to any other type of polynucleotide that is an N-glycoside of a purine or pyrimidine base, and to other polymers containing non-nucleotidic backbones, provided that the polymers contain nucleobases in a configuration that allows for base pairing and base stacking, as found in DNA and RNA. Thus, these terms include known types of nucleic acid sequence modifications, for example, substitution of one or more of the naturally occurring nucleotides with an analog, and inter-nucleotide modifications.

As used herein, a nucleic acid is "operatively linked" or "operably linked" when it is placed into a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous.

As used herein, the term "vector" refers to discrete elements that are used to introduce heterologous nucleic acids into cells for either expression or replication thereof. An expression vector includes vectors capable of expressing nucleic acids that are operatively linked with regulatory sequences, such as promoter regions, that are capable of effecting expression of such nucleic acids. Thus, an expression vector may refer to a DNA or RNA construct, such as a plasmid, a phage, recombinant virus or other vector that, upon introduction into an appropriate host cell, results in expression of the nucleic acids. Appropriate expression vectors are well known to those of skill in the art and include those that are replicable in eukaryotic cells and those that remain episomal or those which integrate into the host cell genome.

As used herein, an "open reading frame" or "ORF" refers to a continuous stretch of nucleic acids, either DNA or RNA, that encode a protein or polypeptide. Typically, the nucleic acids comprise a translation start signal or initiation codon, such as ATG or AUG, and a termination codon.

As used herein, an "internal ribosome entry site" or "IRES" refers to a nucleotide sequence that allows for translation initiation in the middle, e.g. after the first start codon, of an mRNA sequence.

As used herein, an "untranslated region" or "UTR" refers to unstranslated nucleic acids at the 5' and/or 3' ends of an open reading frame. The inclusion of one or more UTRs in a polynucleotide may affect post-transcriptional regulation, mRNA stability, and/or translation of the polynucleotide.

As used herein, the term "transgene" refers to a polynucleotide that is capable of being transcribed into RNA and translated and/or expressed under appropriate conditions, after being introduced into a cell. In some aspects, it confers a desired property to a cell into which it was introduced, or otherwise leads to a desired therapeutic or diagnostic outcome.

As used herein, the terms "polypeptide," "protein," and "peptide" are used interchangeably and may refer to a polymer of two or more amino acids.

As used herein, a "subject", "host", or an "individual" refers to any animal classified as a mammal, including humans, domestic and farm animals, and zoo, sports, or pet animals, such as dogs, horses, cats, cows, as well as animals used in research, such as mice and rats, etc. In some embodiments, the mammal is human.

As used herein, "topical administration" or "topically administering" refers to the delivery of a composition to a subject by contacting, directly or otherwise, a formulation comprising the composition to all or a portion of the skin of a subject. The term encompasses several routes of administration including, but not limited to, topical and transdermal. Topical administration is used as a means to deliver a composition to the epidermis or dermis of a subject, or to specific strata thereof.

As used herein, an "effective amount" is at least the minimum amount required to effect a measurable improvement or prevention of one or more symptoms of a particular disorder. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, delaying the progression of the disease, and/or prolonging survival. An effective amount can be administered in one or more administrations.

Pharmaceutical Compositions

Polynucleotides

In one aspect, provided herein is a pharmaceutical composition comprising one or more polynucleotides encoding a Collagen alpha-1 (VII) chain (Col7) polypeptide, a Lysyl hydroxylase 3 (LH3) polypeptide, a Keratin type I cytoskeletal 17 (KRT17) polypeptide, and/or a chimeric polypeptide thereof. In some embodiments, the pharmaceutical composition comprises one or more polynucleotides encoding a Collagen alpha-1 (VII) chain polypeptide. In some embodiments, the pharmaceutical composition comprises one or more polynucleotides encoding a Lysyl hydroxylase 3 polypeptide. In some embodiments, the pharmaceutical composition comprises one or more polynucleotides encoding a Keratin type I cytoskeletal 17 polypeptide. In some embodiments, the pharmaceutical composition comprises one or more polynucleotides encoding a chimeric polypeptide. In some embodiments, the pharmaceutical composition comprises one or more polynucleotides encoding a Collagen alpha-1 (VII) chain polypeptide and a Lysyl hydroxylase 3 polypeptide. In some embodiments, the pharmaceutical composition comprises one or more polynucleotides encoding a Collagen alpha-1 (VII) chain polypeptide and a Keratin type I cytoskeletal 17 polypeptide. In some embodiments, the pharmaceutical composition comprises one or more polynucleotides encoding a Lysyl hydroxylase 3 polypeptide and a Keratin type I cytoskeletal 17 polypeptide. In some embodiments, the pharmaceutical composition comprises one or more polynucleotides encoding a Collagen alpha-1 (VII) chain polypeptide, a Lysyl hydroxylase 3 polypeptide, and a Keratin type I cytoskeletal 17 polypeptide.

In some embodiments, the pharmaceutical composition comprises a vector, wherein the vector encodes one or more transgenes comprising a polynucleotide described herein. In some embodiments, the pharmaceutical composition comprises a vector, wherein the vector comprises one or more transgenes encoding a Collagen alpha-1 (VII) chain polypeptide, a Lysyl hydroxylase 3 polypeptide, a Keratin type I cytoskeletal 17 polypeptide, and/or a chimeric polypeptide thereof. In some embodiments, the vector comprises one or more transgenes encoding a Collagen alpha-1 (VII) chain polypeptide. In some embodiments, the vector comprises one or more transgenes encoding a Lysyl hydroxylase 3 polypeptide. In some embodiments, the vector comprises one or more transgenes encoding a Keratin type I cytoskeletal 17 polypeptide. In some embodiments, the vector comprises one or more transgenes encoding a chimeric polypeptide. In some embodiments, the vector comprises one or more transgenes encoding a Collagen alpha-1 (VII) chain polypeptide and one or more transgenes encoding a Lysyl hydroxylase 3 polypeptide. In some embodiments, the vector comprises one or more transgenes encoding a Collagen alpha-1 (VII) chain polypeptide and one or more transgenes encoding a Keratin type I cytoskeletal 17 polypeptide. In some embodiments, the vector comprises one or more transgenes encoding a Lysyl hydroxylase 3 polypeptide and one or more transgenes encoding a Keratin type I cytoskeletal 17 polypeptide. In some embodiments, the vector comprises one or more transgenes encoding a Collagen alpha-1 (VII) chain polypeptide, one or more transgenes encoding a Lysyl hydroxylase 3 polypeptide, and one or more transgenes encoding a Keratin type I cytoskeletal 17 polypeptide.

In some embodiments, the pharmaceutical composition comprises a synthetic RNA, wherein the synthetic RNA encodes one or more transgenes comprising a polynucleotide described herein. In some embodiments, the pharmaceutical composition comprises a synthetic RNA, wherein the synthetic RNA comprises one or more transgenes encoding a Collagen alpha-1 (VII) chain polypeptide, a Lysyl hydroxylase 3 polypeptide, a Keratin type I cytoskeletal 17 polypeptide, and/or a chimeric polypeptide thereof. In some embodiments, the synthetic RNA comprises one or more transgenes encoding a Collagen alpha-1 (VII) chain polypeptide. In some embodiments, the synthetic RNA comprises one or more transgenes encoding a Lysyl hydroxylase 3 polypeptide. In some embodiments, the synthetic RNA comprises one or more transgenes encoding a Keratin type I cytoskeletal 17 polypeptide. In some embodiments, the synthetic RNA comprises one or more transgenes encoding a chimeric polypeptide. In some embodiments, the synthetic RNA comprises one or more transgenes encoding a Collagen alpha-1 (VII) chain polypeptide and one or more transgenes encoding a Lysyl hydroxylase 3 polypeptide. In some embodiments, the synthetic RNA comprises one or more transgenes encoding a Collagen alpha-1 (VII) chain polypeptide and one or more transgenes encoding a Keratin type I cytoskeletal 17 polypeptide. In some embodiments, the synthetic RNA comprises one or more transgenes encoding a Lysyl hydroxylase 3 polypeptide and one or more transgenes encoding a Keratin type I cytoskeletal 17 polypeptide. In some embodiments, the synthetic RNA comprises one or more transgenes encoding a Collagen alpha-1 (VII) chain polypeptide, one or more transgenes encoding a Lysyl hydroxylase 3 polypeptide, and one or more transgenes encoding a Keratin type I cytoskeletal 17 polypeptide.

Collagen Alpha-1 (VII) Chain

In some aspects, a polynucleotide of the present disclosure encodes a Collagen alpha-1 (VII) chain polypeptide. An example of a polynucleotide that encodes a Collagen alpha-1 (VII) chain polypeptide is SEQ ID NO: 1. Polynucleotides of the present disclosure also include polynucleotides having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 1.

In some embodiments, a polynucleotide encoding a Collagen alpha-1 (VII) chain polypeptide is a polynucleotide that encodes an N-terminal truncation, a C-terminal truncation, or a fragment of a Collagen alpha-1 (VII) chain polypeptide. Polynucleotides encoding an N-terminal truncation, a C-terminal truncation, or a fragment of a Collagen alpha-1 (VII) chain polypeptide include polynucleotides that have at least 25, at least 50, at least 75, at least 100, at least 125, at least 150, at least 175, at least 200, at least 250, at least 300, or at least 350, at least 500, at least 1000, at least 2500, at least 5000, at least 7500, but fewer than 8835, consecutive nucleotides of SEQ ID NO: 1.

In some embodiments, a polynucleotide encoding a Collagen alpha-1 (VII) chain polypeptide is a polynucleotide that encodes a polypeptide having an amino acid sequence of SEQ ID NO: 2. In some embodiments, a polynucleotide encoding a Collagen alpha-1 (VII) chain polypeptide is a polynucleotide that encodes a polypeptide having an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 2. In some embodiments, the present disclosure relates to polynucleotides that encode polypeptides that are homologs of the *H. sapiens* Collagen alpha-1 (VII) chain polypeptide. Methods of identifying polypeptides that are homologs of a polypeptide of interest are well known to one of skill in the art.

In some embodiments, a polynucleotide encoding a Collagen alpha-1 (VII) chain polypeptide is a polynucleotide that encodes N-terminal truncations, C-terminal truncations, or fragments of the amino acid sequence of SEQ ID NO: 2. N-terminal truncations, C-terminal truncations, or fragments may comprise at least 10, at least 12, at least 14, at least 16, at least 18, at least 20, at least 30, at least 40, at least 50, at least 75, at least 100, at least 250, at least 500, at least 750, at least 1000, at least 1500, at least 2000, or at least 2500, but fewer than 2944, consecutive amino acids of SEQ ID NO: 2.

In some embodiments, the polynucleotide encoding a Collagen alpha-1 (VII) chain polypeptide expresses the Collagen alpha-1 (VII) chain polypeptide when the polynucleotide is delivered into one or more target cells of a subject. In some embodiments, expression of the Collagen alpha-1 (VII) chain polypeptide enhances, increases, augments, and/or supplements the levels of a Collagen alpha-1 chain polypeptide in one or more target cells. In some embodiments, expression of the Collagen alpha-1 (VII) chain polypeptide enhances, increases, augments, and/or supplements the function of a Collagen alpha-1 chain polypeptide in one or more target cells. In some embodiments, expression of the Collagen alpha-1 (VII) chain polypeptide enhances, increases, augments, and/or supplements the activity of a Collagen alpha-1 chain polypeptide in one or more target cells. In some embodiments, expression of the Collagen alpha-1 (VII) chain polypeptide enhances, increases, augments, and/or supplements anchoring fibril formation of the subject. In some embodiments, expression of the Collagen alpha-1 (VII) chain polypeptide enhances, increases, augments, and/or supplements epithelial basement membrane organization and/or epithelial basement adherence of the subject. In some embodiments, expression of the Collagen alpha-1 (VII) chain polypeptide enhances, increases, augments, and/or supplements dermoepidermal junction integrity of the subject.

Lysyl Hydroxylase 3

In some aspects, a polynucleotide of the present disclosure encodes a Lysyl hydroxylase 3 polypeptide. An example of a polynucleotide that encodes a Lysyl hydroxylase 3 polypeptide is SEQ ID NO: 3. Polynucleotides of the present disclosure also include polynucleotides having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 3.

In some embodiments, a polynucleotide encoding a Lysyl hydroxylase 3 polypeptide is a polynucleotide that encodes an N-terminal truncation, a C-terminal truncation, or a fragment of a Lysyl hydroxylase 3 polypeptide. Polynucleotides encoding an N-terminal truncation, a C-terminal truncation, or a fragment of a Lysyl hydroxylase 3 polypeptide include polynucleotides that have at least 25, at least 50, at least 75, at least 100, at least 125, at least 150, at least 175, at least 200, at least 250, at least 300, at least 350, at least 500, at least 750, at least 1000, at least 1500, or at least 2000, but fewer than 2217, consecutive nucleotides of SEQ ID NO: 3.

In some embodiments, a polynucleotide encoding a Lysyl hydroxylase 3 polypeptide is a polynucleotide that encodes a polypeptide having an amino acid sequence of SEQ ID NO: 4. In some embodiments, a polynucleotide encoding a Lysyl hydroxylase 3 polypeptide is a polynucleotide that encodes a polypeptide having an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 4. In some embodiments, the present disclosure relates to polynucleotides encoding polypeptides that are homologs of the *H. sapiens* Lysyl hydroxylase 3 polypeptide. Methods of identifying polypeptides that are homologs of a polypeptide of interest are well known to one of skill in the art.

In some embodiments, a polynucleotide encoding a Lysyl hydroxylase 3 polypeptide is a polynucleotide that encodes N-terminal truncations, C-terminal truncations, or fragments of the amino acid sequence of SEQ ID NO: 4. N-terminal truncations, C-terminal truncations, or fragments may comprise at least 10, at least 12, at least 14, at least 16, at least 18, at least 20, at least 30, at least 40, at least 50, at least 75, at least 100, at least 200, at least 300, at least 400, at least 500, at least 600, or at least 700, but fewer than 738, consecutive amino acids of SEQ ID NO: 4.

In some embodiments, the polynucleotide encoding a Lysyl hydroxylase 3 polypeptide expresses the Lysyl hydroxylase 3 polypeptide when the polynucleotide is delivered into one or more target cells of a subject. In some embodiments, expression of the Lysyl hydroxylase 3 polypeptide enhances, increases, augments, and/or supplements the levels of a Lysyl hydroxylase 3 polypeptide in one or more target cells. In some embodiments, expression of the Lysyl hydroxylase 3 polypeptide enhances, increases, augments, and/or supplements the function of a Lysyl hydroxylase 3 polypeptide in one or more target cells. In some embodiments, expression of the Lysyl hydroxylase 3 polypeptide enhances, increases, augments, and/or supplements the activity of a Lysyl hydroxylase 3 polypeptide in one or more target cells. In some embodiments, expression of the Lysyl hydroxylase 3 polypeptide enhances, increases, augments, and/or supplements the formation of hydroxylysine residues on one or more collagen polypeptides of the subject. In some embodiments, expression of the Lysyl hydroxylase 3 polypeptide enhances, increases, augments, and/or supplements anchoring fibril formation of the subject. In some embodiments, expression of the Lysyl hydroxylase 3 polypeptide enhances, increases, augments, and/or supplements epithelial basement membrane organization and/or epithelial basement adherence of the subject. In some embodiments, expression of the Lysyl hydroxylase 3 polypeptide enhances, increases, augments, and/or supplements dermoepidermal junction integrity of the subject.

In some embodiments, the polynucleotide encoding a Collagen alpha-1 (VII) chain polypeptide and the polynucleotide encoding a Lysyl hydroxylase 3 polypeptide are delivered to the same cell of a subject. In some embodiments, the polynucleotide encoding a Collagen alpha-1 chain (VII) polypeptide and the polynucleotide encoding a Lysyl hydroxylase 3 polypeptide express the Collagen alpha-1 (VII) chain polypeptide and the Lysyl hydroxylase 3 polypeptide when the polynucleotides are delivered into the same cell of a subject. In some embodiments, the polynucleotide encoding a Collagen alpha-1 (VII) chain polypeptide and the polynucleotide encoding a Lysyl hydroxylase 3 polypeptide express the Collagen alpha-1 (VII) chain polypeptide and Lysyl hydroxylase 3 polypeptide at equimolar ratios.

Keratin Type I Cytoskeletal 17

In some aspects, a polynucleotide of the present disclosure encodes a Keratin type I cytoskeletal 17 polypeptide. An example of a polynucleotide that encodes a Keratin type I cytoskeletal 17 polypeptide is SEQ ID NO: 29. Polynucleotides of the present disclosure also include polynucleotides having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 29.

In some embodiments, a polynucleotide encoding a Keratin type I cytoskeletal 17 polypeptide is a polynucleotide that encodes an N-terminal truncation, a C-terminal truncation, or a fragment of a Keratin type I cytoskeletal 17 polypeptide. Polynucleotides encoding an N-terminal truncation, a C-terminal truncation, or a fragment of a Collagen alpha-1 (VII) chain polypeptide include polynucleotides that have at least 25, at least 50, at least 75, at least 100, at least 125, at least 150, at least 175, at least 200, at least 250, at least 300, or at least 350, at least 500, at least 1000, at least 1250, but fewer than 1299, consecutive nucleotides of SEQ ID NO: 29.

In some embodiments, a polynucleotide encoding a Keratin type I cytoskeletal 17 polypeptide is a polynucleotide that encodes a polypeptide having an amino acid sequence of SEQ ID NO: 30. In some embodiments, a polynucleotide encoding a Keratin type I cytoskeletal 17 polypeptide is a polynucleotide that encodes a polypeptide having an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 30. In some embodiments, the present disclosure relates to polynucleotides that encode polypeptides that are homologs of the *H. sapiens* Keratin type I cytoskeletal 17 polypeptide. Methods of identifying polypeptides that are homologs of a polypeptide of interest are well known to one of skill in the art.

In some embodiments, a polynucleotide encoding a Keratin type I cytoskeletal 17 polypeptide is a polynucleotide that encodes N-terminal truncations, C-terminal truncations, or fragments of the amino acid sequence of SEQ ID NO: 30. N-terminal truncations, C-terminal truncations, or fragments may comprise at least 10, at least 12, at least 14, at least 16, at least 18, at least 20, at least 30, at least 40, at least 50, at least 75, at least 100, at least 150, at least 200, at least 250, at least 300, at least 350, at least 400, at least 425, but fewer than 432, consecutive amino acids of SEQ ID NO: 30.

In some embodiments, the polynucleotide encoding a Keratin type I cytoskeletal 17 polypeptide expresses the Keratin type I cytoskeletal 17 polypeptide when the polynucleotide is delivered into one or more target cells of a subject. In some embodiments, expression of the Keratin type I cytoskeletal 17 polypeptide enhances, increases, augments, and/or supplements the levels of a Keratin type I cytoskeletal 17 polypeptide in one or more target cells. In some embodiments, expression of the Keratin type I cytoskeletal 17 polypeptide enhances, increases, augments, and/or supplements the function of a Keratin type I cytoskeletal 17 polypeptide in one or more target cells. In some embodiments, expression of the Keratin type I cytoskeletal 17 polypeptide enhances, increases, augments, and/or supplements the activity of a Keratin type I cytoskeletal 17 polypeptide in one or more target cells. In some embodiments, expression of the Keratin type I cytoskeletal 17 polypeptide enhances, increases, augments, and/or supplements wound healing in the subject.

Chimeric Polypeptide Comprising Linker

In some embodiments, a polynucleotide of the present disclosure encodes a chimeric polypeptide comprising a Collagen alpha-1 (VII) chain polypeptide and a Lysyl hydroxylase 3 polypeptide. In some embodiments, the polynucleotide encoding a chimeric polypeptide further comprises a polynucleotide encoding a linker polypeptide. In some embodiments, the polynucleotide encoding a linker polypeptide is a polynucleotide encoding a cleavable linker polypeptide. Examples of polynucleotides encoding cleavable linker polypeptides may include, but are not limited to, polynucleotides encoding a T2A, P2A, E2A, or F2A linker polypeptide. In some embodiments, the polynucleotide encoding a linker polypeptide is a polynucleotide encoding a T2A linker polypeptide. In some embodiments, the polynucleotide encoding a linker polypeptide is a polynucleotide encoding a P2A linker polypeptide. In some embodiments, the polynucleotide encoding a linker polypeptide is a polynucleotide encoding an E2A linker polypeptide. In some embodiments, the polynucleotide encoding a linker polypeptide is a polynucleotide encoding an F2A linker polypeptide.

In some aspects, a polynucleotide of the present disclosure encodes a linker polypeptide. Examples of polynucleotides that encode linker polypeptides are SEQ ID NO: 5, SEQ ID NO: 7, SEQ ID NO: 9, and SEQ ID NO: 11. Polynucleotides of the present disclosure also include polynucleotides having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 5, SEQ ID NO: 7, SEQ ID NO: 9, or SEQ ID NO: 11.

In some embodiments, a polynucleotide encoding a linker polypeptide is a polynucleotide that encodes an N-terminal truncation, a C-terminal truncation, or a fragment of a linker polypeptide. Polynucleotides encoding an N-terminal truncation, a C-terminal truncation, or a fragment of a linker polypeptide include polynucleotides that have at least 5, at least 10, at least 15, at least 20, at least 25, at least 30, at least 35, at least 40, at least 45, at least 50, at least or at least 60, but fewer than 66, consecutive nucleotides of SEQ ID NO: 5, SEQ ID NO: 7, SEQ ID NO: 9, or SEQ ID NO: 11.

In some embodiments, a polynucleotide encoding a linker polypeptide is a polynucleotide that encodes a polypeptide having an amino acid sequence of SEQ ID NO: 6, SEQ ID NO: 8, SEQ ID NO: 10 or SEQ ID NO: 12. In some embodiments, a polynucleotide encoding a linker polypeptide is a polynucleotide that encodes a polypeptide having an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 6, SEQ ID NO: 8, SEQ ID NO: 10, or SEQ ID NO: 12.

In some embodiments, a polynucleotide encoding a linker polypeptide is a polynucleotide that encodes N-terminal truncations, C-terminal truncations, or fragments of the amino acid sequence of SEQ ID NO: 6, SEQ ID NO: 8, SEQ ID NO: 10, or SEQ ID NO: 12. N-terminal truncations, C-terminal truncations, or fragments may comprise at least 4, at least 6, at least 8, at least 10, at least 12, at least 14, at least 16, at least 18, or at least 20, but fewer than 22, consecutive amino acids of SEQ ID NO: 6, SEQ ID NO: 8, SEQ ID NO: 10, or SEQ ID NO: 12.

In some embodiments, the polynucleotide encoding a linker polypeptide further comprises a polynucleotide encoding one or more furin cleavage sites. In some embodiments, the polynucleotide encoding one or more furin cleavage sites encode an amino acid sequence that is the same or substantially similar to the sequence of the canonical furin cleavage site (Arg-X-(Arg/Lys)-Arg). In some embodiments, the one or more furin cleavage sites are encoded upstream of the linker polypeptide. In some embodiments, the one or more furin cleavage sites are encoded downstream of the linker polypeptide. In some embodiments, the one or more furin cleavage sites are encoded upstream of a T2A linker polypeptide. In some embodiments, the one or more furin cleavage sites are encoded downstream of a T2A linker polypeptide. In some embodiments, the one or more furin cleavage sites are encoded upstream of a P2A linker polypeptide. In some embodiments, the one or more furin cleavage sites are encoded downstream of a P2A linker polypeptide. In some embodiments, the one or more furin cleavage sites are encoded upstream of an E2A linker polypeptide. In some embodiments, the one or more furin cleavage sites are encoded downstream of an E2A linker polypeptide. In some embodiments, the one or more furin cleavage sites are encoded upstream of an F2A linker polypeptide. In some embodiments, the one or more furin cleavage sites are encoded downstream of an F2A linker polypeptide.

In some embodiments, the polynucleotide encoding a chimeric polypeptide encodes a chimeric polypeptide comprising a Collagen alpha-1 (VII) chain polypeptide, a linker polypeptide, and a Lysyl hydroxylase 3 polypeptide. In some embodiments, the polynucleotide encoding a chimeric polypeptide comprises, from 5' to 3', a polynucleotide encoding a Collagen alpha-1 (VII) chain polypeptide, a polynucleotide encoding a linker polypeptide, and a polynucleotide encoding a Lysyl hydroxylase 3 polypeptide. In some embodiments, the polynucleotide encoding a chimeric polypeptide comprises, from 5' to 3', a polynucleotide encoding a Lysyl hydroxylase 3 polypeptide, a polynucleotide encoding a linker polypeptide, and a polynucleotide encoding a Collagen alpha-1 (VII) chain polypeptide.

Examples of polynucleotides encoding chimeric polypeptides comprising a Collagen alpha-1 (VII) chain polypeptide, a linker polypeptide, and a Lysyl hydroxylase 3 polypeptide are SEQ ID NO: 13, SEQ ID NO: 15, SEQ ID NO: 17, SEQ ID NO: 19, SEQ ID NO: 21, SEQ ID NO: 23, SEQ ID NO: 25, and SEQ ID NO: 27. Polynucleotides of the present disclosure also include polynucleotides having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 13, SEQ ID NO: 15, SEQ ID NO: 17, SEQ ID NO: 19, SEQ ID NO: 21, SEQ ID NO: 23, SEQ ID NO: 25, or SEQ ID NO: 27.

In some embodiments, a polynucleotide encoding a chimeric polypeptide is a polynucleotide that encodes an N-terminal truncation, a C-terminal truncation, or a fragment of a chimeric polypeptide. Polynucleotides encoding an N-terminal truncation, a C-terminal truncation, or a fragment of a chimeric polypeptide include polynucleotides that have at least 25, at least 50, at least 75, at least 100, at least 125, at least 150, at least 175, at least 200, at least 250, at least 300, at least 350, at least 400, at least 450, at least 500, at least 550, at least 600, at least 650, at least 700, at least 750, at least 800, at least 850, at least 900, at least 950, at least 1000, at least 2000, at least 3000, at least 4000, at least 5000, at least 6000, at least 7000, at least 8000, at least 9000, or at least 10000, but fewer than 11121, consecutive nucleotides of SEQ ID NO: 13, SEQ ID NO: 15, SEQ ID NO: 17, SEQ ID NO: 19, SEQ ID NO: 21, SEQ ID NO: 23, SEQ ID NO: 25, or SEQ ID NO: 27.

In some embodiments, a polynucleotide encoding a chimeric polypeptide comprising a Collagen alpha-1 (VII) chain polypeptide, a linker polypeptide, and a Lysyl hydroxylase 3 polypeptide is a polynucleotide that encodes a polypeptide having an amino acid sequence of SEQ ID NO: 14, SEQ ID NO: 16, SEQ ID NO: 18, SEQ ID NO: 20, SEQ ID NO: 22, SEQ ID NO: 24, SEQ ID NO: 26 or SEQ ID NO: 28. In some embodiments, a polynucleotide encoding a chimeric polypeptide comprising a Collagen alpha-1 (VII) chain polypeptide, a linker polypeptide, and a Lysyl hydroxylase 3 polypeptide is a polynucleotide that encodes a polypeptide having an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 14, SEQ ID NO: 16, SEQ ID NO: 18, SEQ ID NO: 20, SEQ ID NO: 22, SEQ ID NO: 24, SEQ ID NO: 26 or SEQ ID NO: 28.

In some embodiments, a polynucleotide encoding a chimeric polypeptide comprising a Collagen alpha-1 (VII) chain polypeptide, a linker polypeptide, and a Lysyl hydroxylase 3 polypeptide is a polynucleotide that encodes N-terminal truncations, C-terminal truncations, or fragments of the amino acid sequence of SEQ ID NO: 14, SEQ ID NO: 16, SEQ ID NO: 18, SEQ ID NO: 20, SEQ ID NO: 22, SEQ ID NO: 24, SEQ ID NO: 26 or SEQ ID NO: 28. N-terminal truncations, C-terminal truncations, or fragments may comprise at least 25, at least 50, at least 75, at least 100, at least 125, at least 150, at least 175, at least 200, at least 250, at least 300, at least 350, at least 400, at least 450, at least 500, at least 550, at least 600, at least 650, at least 700, at least 750, at least 800, at least 850, at least 900, at least 950, at least 1000, at least 1250, at least 1500, at least 1750, at least 2000, at least 2250, at least 2500, at least 2750, at least 3000, at least 3250, or at least 3500, but fewer than 3706, consecutive amino acids of SEQ ID NO: 14, SEQ ID NO: 16, SEQ ID NO: 18, SEQ ID NO: 20, SEQ ID NO: 22, SEQ ID NO: 24, SEQ ID NO: 26 or SEQ ID NO: 28.

In some embodiments, the polynucleotide encoding a chimeric polypeptide expresses the chimeric polypeptide when the polynucleotide is delivered into one or more target cells of a subject. In some embodiments, the chimeric polypeptide is cleaved after being expressed in one or more target cells. In some embodiments, the chimeric polypeptide is cleaved within the linker polypeptide when expressed in one or more target cells. In some embodiments, the chimeric polypeptide is cleaved into two polypeptides, one comprising the Collagen alpha-1 (VII) chain polypeptide and the other comprising the Lysyl hydroxylase 3 polypeptide. In some embodiments, expression of the chimeric polypeptide enhances, increases, augments, and/or supplements the levels of a Collagen alpha-1 chain polypeptide and/or a Lysyl hydroxylase 3 polypeptide in one or more target cells. In some embodiments, expression of the chimeric polypeptide enhances, increases, augments, and/or supplements the function of a Collagen alpha-1 chain polypeptide and/or a Lysyl hydroxylase 3 polypeptide in one or more target cells. In some embodiments, expression of the chimeric polypeptide enhances, increases, augments, and/or supplements the activity of a Collagen alpha-1 chain polypeptide and/or a Lysyl hydroxylase 3 polypeptide in one or more target cells. In some embodiments, expression of the chimeric polypeptide enhances, increases, augments, and/or supplements the formation of hydroxylysine residues on one or more collagen polypeptides of the subject. In some embodiments, expression of the chimeric polypeptide enhances, increases, augments, and/or supplements anchoring fibril formation of the subject. In some embodiments, expression of the chimeric polypeptide enhances, increases, augments, and/or supplements epithelial basement membrane organization and/or epithelial basement adherence of the subject. In some embodiments, expression of the chimeric polypeptide enhances, increases, augments, and/or supplements dermoepidermal junction integrity of the subject.

Polynucleotides of the present disclosure may be codon-optimized. In some embodiments, polynucleotides of the present disclosure are codon-optimized for human cells. In some embodiments, polynucleotides of the present disclosure are codon-optimized for mouse cells. In some embodiments, polynucleotides of the present disclosure are codon-optimized for rat cells. In some embodiments, polynucleotides of the present disclosure are codon-optimized for hamster cells. In some embodiments, polynucleotides of the present disclosure are codon-optimized for canine cells. In some embodiments, polynucleotides of the present disclosure are codon-optimized for yeast cells. In some embodiments, polynucleotides of the present disclosure are codon-optimized for bacterial cells. Polynucleotides of the present disclosure may be DNA polynucleotides, RNA polynucleotides, or a combination of one or more DNA polynucleotides and one or more RNA polynucleotides.

Vectors

In some aspects, the present disclosure relates to vectors, preferably expression vectors, containing one or more polynucleotides described herein. In some embodiments, the vectors are DNA vectors. Generally, vectors suitable to maintain, propagate, or express polynucleotides to produce one or more polypeptides in a subject may be used. Examples of suitable vectors include, but are not limited to, plasmids, cosmids, episomes, transposons, and viral vectors (e.g., adenoviral, vaccinia viral, Sindbis-viral, measles, herpes viral, lentiviral, retroviral, adeno-associated viral vectors, etc.). In some embodiments, the vector is capable of autonomous replication in a host cell. In some embodiments, the vector is incapable of autonomous replication in a host cell. In some embodiments, the vector is capable of integrating into a host DNA. Methods for making vectors containing one or more polynucleotides of interest are well known to one of skill in the art.

In some embodiments, the vector is a herpes simplex virus vector. In some embodiments, the herpes simplex virus vector is a herpes virus amplicon vector. Herpes virus amplicon vectors, including structural features and methods of making the vectors, are generally known in the art (de Silva S. and Bowers W. "Herpes Virus Amplicon Vectors". Viruses 2009, 1, 594-629). In some embodiments, the vector is an HSV-1 amplicon. In some embodiments, the vector is an HSV-1 hybrid amplicon. Examples of HSV-1 hybrid amplicons may include, but are not limited to, HSV/AAV hybrid amplicons, HSV/EBV hybrid amplicons, HSV/EBV/RV hybrid amplicons, and HSV/Sleeping Beauty hybrid amplicons. In some embodiments, the vector is an HSV/AAV hybrid amplicon. In some embodiments, the vector is an HSV/EBV hybrid amplicon. In some embodiments, the vector is an HSV/EBV/RV hybrid amplicon. In some embodiments, the vector is an HSV/Sleeping Beauty hybrid amplicons.

In some embodiments, the herpes simplex virus vector is a recombinant herpes simplex virus genome. In some embodiments, the recombinant herpes simplex virus genome has been engineered to decrease or eliminate expression of one or more toxic herpes simplex virus genes. Methods of engineering recombinant herpes simplex virus genomes are generally described in WO2015/009952. In some embodiments, the recombinant herpes simplex virus genome comprises an inactivating mutation. Examples of inactivating mutations may include, but are not limited to, deletions, insertions, point mutations, and rearrangements. In some embodiments, the recombinant herpes simplex virus genome comprises an inactivating mutation in at least one, at least two, at least three, at least four, at least five, at least six, at least seven, or all eight of the ICP0, ICP4, ICP22, ICP27, ICP47, tk, UL41 and UL55 herpes simplex virus genes. In some embodiments, the recombinant herpes simplex virus genome comprises an inactivating mutation in the ICP0 gene. In some embodiments, the recombinant herpes simplex virus genome comprises an inactivating mutation in the ICP4 (one or both copies) gene. In some embodiments, the recombinant herpes simplex virus genome comprises an inactivating mutation in the ICP22 gene. In some embodiments, the recombinant herpes simplex virus genome comprises an inactivating mutation in the ICP27 gene. In some embodiments, the recombinant herpes simplex virus genome comprises an inactivating mutation in the ICP47 gene. In some embodiments, the recombinant herpes simplex virus genome comprises an inactivating mutation in the UL41 gene. In some embodiments, the recombinant herpes simplex virus genome comprises an inactivating mutation in the UL55 gene. In some embodiments, the recombinant herpes simplex virus genome is a recombinant HSV-1 genome, a recombinant HSV-2 genome, or any derivatives thereof. In some embodiments, the recombinant herpes simplex virus genome is a recombinant HSV-1 genome. In some embodiments, the recombinant herpes simplex virus genome is a recombinant HSV-2 genome.

In some embodiments, the recombinant herpes simplex virus genome comprises an inactivating mutation in the ICP4 (one or both copies), ICP27, and UL55 genes. In some embodiments, the recombinant herpes simplex virus genome comprises an inactivating mutation in the ICP4 (one or both copies), ICP22, ICP27, ICP47, and UL55 genes. In some embodiments, the inactivating mutation in the ICP4 (one or both copies), ICP27, and/or UL55 genes is a deletion of the coding sequence of the ICP4 (one or both copies), ICP27, and/or UL55 genes. In some embodiments, the inactivating mutation in the ICP22 and ICP47 genes is a deletion in the promoter region of the ICP22 and ICP47 genes (e.g., the ICP22 and ICP47 coding sequences are intact but are not transcriptionally active). In some embodiments, the recombinant herpes simplex virus genome comprises a deletion in the coding sequence of the ICP4 (one or both copies), ICP27, and UL55 genes and a deletion in the promoter region of the ICP22 and ICP47 genes. In some embodiments, the recombinant herpes simplex virus genome further comprises an inactivating mutation in the UL41 gene. In some embodiments, the recombinant herpes simplex virus genome is a recombinant HSV-1 genome, a recombinant HSV-2 genome, or any derivatives thereof. In some embodiments, the recombinant herpes simplex virus genome is a recombinant HSV-1 genome. In some embodiments, the recombinant herpes simplex virus genome is a recombinant HSV-2 genome.

In some embodiments, the recombinant herpes simplex virus genome comprises an inactivating mutation in the ICP4 (one or both copies) and ICP22 genes. In some embodiments, the recombinant herpes simplex virus genome comprises an inactivating mutation in the ICP0 and ICP4 (one or both copies) genes. In some embodiments, the recombinant herpes simplex virus genome comprises an inactivating mutation in the ICP0, ICP4 (one or both copies), and ICP22 genes. In some embodiments, the recombinant herpes simplex virus genome comprises an inactivating mutation in the ICP0, ICP4 (one or both copies), ICP22, and ICP27 genes. In some embodiments, the recombinant herpes simplex virus genome comprises an inactivating mutation in the ICP0, ICP4 (one or both copies), ICP22, ICP27 and UL55 genes. In some embodiments, the inactivating mutation in the ICP0, ICP4 (one or both copies), ICP22, ICP27 and/or UL55 genes comprises a deletion of the coding sequence of the ICP0, ICP4 (one or both copies), ICP22, ICP27 and/or UL55 genes. In some embodiments, the recombinant herpes simplex virus genome comprises a deletion in the coding sequence of the ICP0, ICP4 (one or both copies), ICP22, ICP27, and UL55 genes. In some embodiments, the recombinant herpes simplex virus genome further comprises an inactivating mutation in the ICP47 gene. In some embodiments, the recombinant herpes simplex virus genome further comprises an inactivating mutation in the UL41 gene. In some embodiments, the recombinant herpes simplex virus genome further comprises an inactivating mutation in the ICP47 gene and the UL41 gene. In some embodiments, the recombinant herpes simplex virus genome is a recombinant HSV-1 genome, a recombinant HSV-2 genome, or any derivatives thereof. In some embodiments, the recombinant herpes simplex virus genome is a recombinant HSV-1 genome. In some embodiments, the recombinant herpes simplex virus genome is a recombinant HSV-2 genome.

In some embodiments, the recombinant herpes simplex virus genome comprises an inactivating mutation in the ICP4 (one or both copies), ICP22, and ICP27 genes. In some embodiments, the recombinant herpes simplex virus genome comprises an inactivating mutation in the ICP4 (one or both copies), ICP22, ICP27, ICP47, and UL55 genes. In some embodiments, the recombinant herpes simplex virus genome comprises an inactivating mutation in the ICP0, ICP4 (one or both copies), ICP22, and ICP27 genes. In some embodiments, the recombinant herpes simplex virus genome is a recombinant HSV-1 genome, a recombinant HSV-2 genome, or any derivatives thereof. In some embodiments, the recombinant herpes simplex virus genome is a recombinant HSV-1 genome. In some embodiments, the recombinant herpes simplex virus genome is a recombinant HSV-2 genome.

In some embodiments, a recombinant herpes simplex virus genome comprises one or more polynucleotides of the present disclosure within one, two, three, four, five, six, seven or more viral gene loci. Examples of suitable viral loci may include, without limitation, the ICP0, ICP4, ICP22, ICP27, ICP47, tk, UL41 and UL55 herpes simplex viral gene loci. In some embodiments, a recombinant herpes simplex virus genome comprises one or more polynucleotide of the present disclosure within one or more of the viral ICP4 gene loci (e.g., a recombinant virus carrying a polynucleotide encoding Col7 in one or both of the ICP4 loci, a recombinant virus carrying a polynucleotide encoding LH3 in one or both of the ICP4 loci, a recombinant virus carrying a polynucleotide encoding KRT17 in one or both of the ICP4 loci, a recombinant virus carrying a polynucleotide encoding Col7 in one of the ICP4 loci and a polynucleotide encoding KRT17 in the other ICP4 loci, a recombinant virus carrying a polynucleotide encoding Col7 in one of the ICP4 loci and a polynucleotide encoding LH3 in the other ICP4 loci, a recombinant virus carrying a polynucleotide encoding LH3 in one of the ICP4 loci and a polynucleotide encoding KRT17 in the other ICP4 loci, etc.). In some embodiments, a recombinant herpes simplex virus genome comprises one or more polynucleotide of the present disclosure within the viral UL41 gene locus. In some embodiments, a recombinant herpes simplex virus genome comprises one or more polynucleotide of the present disclosure within the viral ICP47 gene locus. In some embodiments, a recombinant herpes simplex virus genome comprises one or more polynucleotides of the present disclosure within one or more of the viral ICP4 gene loci, and one or more polynucleotide of the present disclosure within the viral UL41 gene locus (e.g., a recombinant virus carrying a polynucleotide encoding Col7 in one or both of the ICP4 loci and a polynucleotide encoding LH3 in the UL41 locus, a recombinant virus carrying a polynucleotide encoding Col7 in one or both of the ICP4 loci and a polynucleotide encoding Col7 in the UL41 locus, a recombinant virus carrying a polynucleotide encoding Col7 in one or both of the ICP4 loci and a polynucleotide encoding KRT17 in the UL41 locus, a recombinant virus carrying a polynucleotide encoding LH3 in one or both of the ICP4 loci and a polynucleotide encoding LH3 in the UL41 locus, a recombinant virus carrying a polynucleotide encoding LH3 in one or both of the ICP4 loci and a polynucleotide encoding Col7 in the UL41 locus, a recombinant virus carrying a polynucleotide encoding LH3 in one or both of the ICP4 loci and a polynucleotide encoding KRT17 in the UL41 locus, a recombinant virus carrying a polynucleotide encoding KRT17 in one or both of the ICP4 loci and a polynucleotide encoding LH3 in the UL41 locus, a recombinant virus carrying a polynucleotide encoding KRT17 in one or both of the ICP4 loci and a polynucleotide encoding Col7 in the UL41 locus, a recombinant virus carrying a polynucleotide encoding KRT17 in one or both of the ICP4 loci and a polynucleotide encoding KRT17 in the UL41 locus, etc.).

A vector may include a polynucleotide of the present disclosure in a form suitable for expression of the polynucleotide in a host cell. Expression vectors may include one or more regulatory sequences operatively linked to the polynucleotide to be expressed. The term "regulatory sequence" includes promoters, enhancers and other expression control elements (e.g., polyadenylation signals). Examples of suitable enhancers may include, but are not limited to, enhancer sequences from mammalian genes (such as globin, elastase, albumin, α-fetoprotein, insulin and the like), and enhancer sequences from a eukaryotic cell virus (such as SV40 enhancer on the late side of the replication origin (bp 100-270), the cytomegalovirus early promoter enhancer, the polyoma enhancer on the late side of the replication origin, adenovirus enhancers, and the like). Examples of promoters suitable for transcription in mammalian host cells may include, but are not limited to, promoters obtained from the genomes of viruses (such as polyoma virus, fowlpox virus, adenovirus (such as Adenovirus 2), bovine papilloma virus, avian sarcoma virus, cytomegalovirus, a retrovirus, hepatitis-B virus, Simian Virus 40 (SV40), and the like), or from heterologous mammalian promoters (such as the actin promoter, an immunoglobulin promoter, from heat-shock promoters, and the like), provided such promoters are compatible with the host cells. In some embodiments, polynucleotides of the present disclosure are operably linked to one or more heterologous promoters. In some embodiments, the one or more heterologous promoters are one or more of the human cytomegalovirus (HCMV) immediate early promoter, the elongation factor-1 (EF1) promoter, and/or any combinations thereof. In some embodiments, the one or more heterologous promoters are one or more of constitutive promoters, tissue-specific promoters, temporal promoters, spatial promoters, inducible promoters and repressible promoters. Regulatory sequences may include those which direct constitutive expression of a nucleotide sequence, as well as tissue-specific regulatory and/or inducible sequences. The design of the expression vector can depend on such factors as the host cell to be contacted with a polynucleotide of the present disclosure, the level of expression of protein desired, and the like. The expression vectors of the present disclosure can be introduced into host cells to thereby produce proteins or polypeptides (e.g., Collagen alpha-1 (VII) chain polypeptides, Lysyl hydroxylase 3 polypeptides, Keratin type I cytoskeletal 17 polypeptides, chimeric polypeptides, and the like) encoded by polynucleotides as described herein.

In some embodiments, a vector of the present disclosure comprises one or more transgenes comprising one or more polynucleotide described herein. The one or more transgenes may be inserted in any orientation in the vector. If the vector comprises two or more transgenes (e.g., two or more, three or more, etc.), the transgenes may be inserted in the same orientation or opposite orientations to one another. Without wishing to be bound be theory, incorporating two transgenes into a vector in an antisense orientation may help to avoid read-through and ensure proper expression of each transgene. In some embodiments, the vector comprises one or more transgenes encoding a polypeptide selected from the group consisting of a Collagen alpha-1 (VII) chain polypeptide, a Lysyl hydroxylase 3 polypeptide, a Keratin type I cytoskeletal 17 polypeptide, and/or chimeric polypeptides thereof. In some embodiments, the vector comprises a single transgene encoding a Collagen alpa-1 (VII) chain polypeptide. In some embodiments, the vector comprises two transgenes each encoding a Collagen alpa-1 (VII) chain polypeptide. In some embodiments, the vector comprises three transgenes each encoding a Collagen alpa-1 (VII) chain polypeptide. In some embodiments, the vector comprises a single transgene encoding a Lysyl hydroxylase 3 polypeptide. In some embodiments, the vector comprises two transgenes each encoding a Lysyl hydroxylase 3 polypeptide. In some embodiments, the vector comprises three transgenes each encoding a Lysyl hydroxylase 3 polypeptide. In some embodiments, the vector comprises a single transgene encoding a Keratin type I cytoskeletal 17 polypeptide. In some embodiments, the vector comprises two transgenes each encoding a Keratin type I cytoskeletal 17 polypeptide. In some embodiments, the vector comprises three transgenes each encoding a Keratin type I cytoskeletal 17 polypeptide. In some embodiments, the vector comprises a single transgene encoding a chimeric polypeptide comprising a Collagen alpha-1 (VII) chain polypeptide, a Lysyl hydroxylase 3 polypeptide, and/or a Keratin type I cytoskeletal 17 polypeptide.

In some embodiments, the vector comprises at least two transgenes (e.g. two, three, four, five, six, seven or more transgenes). In some embodiments, the at least first transgene encodes a Collagen alpha-1 (VII) chain polypeptide and the at least second transgene encodes a Lysyl hydroxylase 3 polypeptide. In some embodiments, the at least first transgene encodes a Lysyl hydroxylase 3 polypeptide and the at least second transgene encodes a Collagen alpha-1 (VII) chain polypeptide. In some embodiments, the at least first transgene encodes a Collagen alpha-1 (VII) chain polypeptide and the at least second transgene encodes a Keratin type I cytoskeletal 17 polypeptide. In some embodiments, the at least first transgene encodes a Keratin type I cytoskeletal 17 polypeptide and the at least second transgene encodes a Collagen alpha-1 (VII) chain polypeptide. In some embodiments, the at least first transgene encodes a Lysyl hydroxylase 3 polypeptide and the at least second transgene encodes a Keratin type I cytoskeletal 17 polypeptide. In some embodiments, the at least first transgene encodes a Keratin type I cytoskeletal 17 polypeptide and the at least second transgene encodes a Lysyl hydroxylase 3 polypeptide. In some embodiments, the at least first transgene encodes a Collagen alpha-1 (VII) chain polypeptide and the at least second transgene encodes a chimeric polypeptide comprising a Collagen alpha-1 (VII) chain polypeptide, a Lysyl hydroxylase 3 polypeptide, and/or a Keratin type I cytoskeletal 17 polypeptide. In some embodiments, the at least first transgene encodes a Lysyl hydroxylase 3 polypeptide and the at least second transgene encodes a chimeric polypeptide comprising a Collagen alpha-1 (VII) chain polypeptide, a Lysyl hydroxylase 3 polypeptide, and/or a Keratin type I cytoskeletal 17 polypeptide. In some embodiments, the at least first transgene encodes a Keratin type I cytoskeletal 17 polypeptide and the at least second transgene encodes a chimeric polypeptide comprising a Collagen alpha-1 (VII) chain polypeptide, a Lysyl hydroxylase 3 polypeptide, and/or a Keratin type I cytoskeletal 17 polypeptide.

In some embodiments, the vector comprises at least three transgenes (e.g. three, four, five, six, seven or more transgenes). In some embodiments, the at least first transgene encodes a Collagen alpha-1 (VII) chain polypeptide, the at least second transgene encodes a Lysyl hydroxylase 3 polypeptide, and the at least third transgene encodes a Keratin type I cytoskeletal 17 polypeptide.

In some embodiments, the vector comprises a transgene that is polycistronic. In some embodiments, the polycistronic transgene encodes a Collagen alpha-1 (VII) chain polypeptide on a first open reading frame (ORF) and a Lysyl hydroxylase 3 polypeptide on a second open reading frame (ORF). In some embodiments, the polycistronic transgene encodes a Lysyl hydroxylase 3 polypeptide on a first open reading frame (ORF) and a Collagen alpha-1 (VII) chain polypeptide on a second open reading frame (ORF). In some embodiments, the polycistronic transgene encodes a Collagen alpha-1 (VII) chain polypeptide on a first open reading frame (ORF) and a keratin type I cytoskeletal 17 polypeptide on a second open reading frame (ORF). In some embodiments, the polycistronic transgene encodes a Keratin type I cytoskeletal polypeptide on a first open reading frame (ORF) and a Collagen alpha-1 (VII) chain polypeptide on a second open reading frame (ORF). In some embodiments, the polycistronic transgene encodes a Lysyl hydroxylase 3 polypeptide on a first open reading frame (ORF) and a keratin type I cytoskeletal 17 polypeptide on a second open reading frame (ORF). In some embodiments, the polycistronic transgene encodes a Keratin type I cytoskeletal polypeptide on a first open reading frame (ORF) and a Lysyl hydroxylase 3 polypeptide on a second open reading frame (ORF).

In some embodiments, the polycistronic transgene encodes a Collagen alpha-1 (VII) chain polypeptide on a first open reading frame (ORF) and a chimeric polypeptide comprising a Collagen alpha-1 (VII) chain polypeptide, a Lysyl hydroxylase 3 polypeptide, and/or a Keratin type I cytoskeletal 17 polypeptide on a second open reading frame (ORF). In some embodiments, the polycistronic transgene encodes a Lysyl hydroxylase 3 polypeptide on a first open reading frame (ORF) and a chimeric polypeptide comprising a Collagen alpha-1 (VII) chain polypeptide, a Lysyl hydroxylase 3 polypeptide, and/or a Keratin type I cytoskeletal 17 polypeptide on a second open reading frame (ORF). In some embodiments, the polycistronic transgene encodes a Keratin type I cytoskeletal 17 polypeptide on a first open reading frame (ORF) and a chimeric polypeptide comprising a Collagen alpha-1 (VII) chain polypeptide, a Lysyl hydroxylase 3 polypeptide, and/or a Keratin type I cytoskeletal 17 polypeptide on a second open reading frame (ORF). In some embodiments, the first and second ORFs are separated by an internal ribosomal entry site (IRES).

In some embodiments, the polycistronic transgene encodes a Collagen alpha-1 (VII) chain polypeptide on a first open reading frame (ORF), a Keratin type I cytoskeletal 17 polypeptide on a second open reading frame (ORF), and a Lysyl hydroxylase 3 polypeptide on a third open reading frame (ORF). In some embodiments, the polycistronic transgene encodes a Collagen alpha-1 (VII) chain polypeptide on a first open reading frame (ORF), a Lysyl hydroxylase 3 polypeptide on a second open reading frame (ORF), and a Keratin type I cytoskeletal 17 polypeptide on a third open reading frame (ORF). In some embodiments, the polycistronic transgene encodes a Lysyl hydroxylase 3 polypeptide on a first open reading frame (ORF), a Collagen alpha-1 (VII) chain polypeptide on a second open reading frame (ORF), and a Keratin type I cytoskeletal 17 polypeptide on a third open reading frame (ORF). In some embodiments, the polycistronic transgene encodes a Lysyl hydroxylase 3 polypeptide on a first open reading frame (ORF), a Keratin type I cytoskeletal 17 polypeptide on a second open reading frame (ORF), and a Collagen alpha-1 (VII) chain polypeptide on a third open reading frame (ORF). In some embodiments, the polycistronic transgene encodes a Keratin type I cytoskeletal 17 polypeptide on a first open reading frame (ORF), a Lysyl hydroxylase 3 polypeptide on a second open reading frame (ORF), and a Collagen alpha-1 (VII) chain polypeptide on a third open reading frame (ORF). In some embodiments, the polycistronic transgene encodes a Keratin type I cytoskeletal 17 polypeptide on a first open reading frame (ORF), a Collagen alpha-1 (VII) chain polypeptide on a second open reading frame (ORF), and a Lysyl hydroxylase 3 polypeptide on a third open reading frame (ORF). In some embodiments, the first, second, and third ORFs are separated by an internal ribosomal entry site (IRES).

Examples of suitable IRES's may include, but are not limited to, a virally-derived IRES (e.g. an IRES derived from a poliovirus, rhinovirus, encephalomyocarditis virus, foot-and-mouth disease virus, hepatitis C virus, classic swine fever virus, rous sarcoma virus, human immunodeficiency virus, cricket paralysis virus, Kaposi's sarcoma-associated herpesvirus, etc.) and a cellular mRNA-derived IRES (e.g. an IRES derived from growth factor mRNAs, such as fibroblast growth factor 2, platelet-derived growth factor B, and vascular endothelial growth factor, an IRES derived from transcription factor mRNAs, such as antennapedia, ultrapithoraxm, and NF-κB repressing factor, an IRES derived from oncogene mRNAs, such as c-myc, pim-1, and protein kinase p58$^{PITSLRE}$ etc.).

Vectors of the present disclosure may further encode additional coding and non-coding sequences. Examples of additional coding and non-coding sequences may include, but are not limited to, sequences encoding additional polypeptide tags, introns, 5' and 3' UTRs, and the like. Examples of suitable polypeptide tags may include, but are not limited to, any combination of purification tags, such as his-tags, flag-tags, maltose binding protein and glutathione-S-transferase tags, detection tags, such as tags that may be detected photometrically (e.g., red fluorescent protein, etc.) and tags that have a detectable enzymatic activity (e.g., alkaline phosphatase, etc.), tags containing secretory sequences, leader sequences, and/or stabilizing sequences, protease cleavage sites (e.g., furin cleavage sites, TEV cleavage sites, Thrombin cleavage sites), and the like. In some embodiments, the 5' and/or 3'UTRs increase the stability, localization, and/or translational efficiency of the polynucleotides. In some embodiments, the 5' and/or 3'UTRs are modified to increase the stability, localization, and/or translational efficiency of the one or more polynucleotides. In some embodiments, the 5' and/or 3'UTRs improve the level and/or duration of protein expression. In some embodiments, the 5' and/or 3'UTRs include elements (e.g., one or more miRNA binding sites, etc.) that may block or reduce off-target transgene expression (e.g., inhibiting expression in specific cell types (e.g., neuronal cells), at specific times in the cell cycle, at specific developmental stages, etc.). In some embodiments, the 5' and/or 3'UTRs include elements (e.g., one or more miRNA binding sites, etc.) that may enhance transgene expression in specific cell types.

Synthetic RNA Polynucleotides

In some aspects, the present disclosure relates to synthetic RNAs, in particular synthetic mRNAs, containing one or more polynucleotides described herein. In some embodiments, the synthetic mRNA polynucleotides comprise a 5'-cap structure. Examples of 5'-cap structures may include, but are not limited to, cap-0, cap-1, cap-2, and cap-3 structures, and derivatives thereof. In some embodiments, the synthetic mRNA polynucleotides comprise a 3'-poly(A) tail. In some embodiments, the synthetic mRNA polynucleotides comprise one or more 5' and/or 3' UTRs flanking the one or more coding sequences contained within the synthetic mRNA polynucleotides. In some embodiments, the 5' and/or 3' UTRs increase the stability, localization, and/or translational efficiency of the synthetic mRNA polynucleotides. In some embodiments, the 5' and/or 3' UTRs are modified to increase the stability, localization, and/or translational efficiency of the synthetic mRNA polynucleotides. In some embodiments, the 5' and/or 3' UTRs improve the level and/or duration of protein expression. In some embodiments, the 5' and/or 3' UTRs are modified to improve the level and/or duration of protein expression. In some embodiments, the 5' and/or 3'UTRs include elements (e.g., miRNA binding sites, etc.) that may limit off-target expression (e.g., inhibiting expression in specific cell types (e.g., neuronal cells), at specific times in the cell cycle, at specific developmental stages, etc.). In some embodiments, the 5' UTRs comprise a Kozak sequence. In some embodiments, the Kozak sequence is the same or substantially similar to the Kozak consensus sequence. Methods for making synthetic mRNA polynucleotides containing one or more polynucleotides of interest are well known to one of skill in the art.

In some aspects, the synthetic mRNA polynucleotides of the present disclosure comprise one or more modified ribonucleotides. Examples of modified ribonucleotides may include, but are not limited to, 2-thiouridine, 5-azauridine, pseudouridine, 4-thiouridine, 5-methyluridine, 5-aminouridine, 5-hydroxyuridine, 5-methyl-5-azauridine, 5-amino-5-azauridine, 5-methylpseudouridine, 5-aminopseudouridine, 5-hydroxypseudouridine, 4-thio-5-azauridine, 4-thiopseudouridine, 4-thio-5-methyluridine, 4-thio-4-thio-5-hydroxyuridine, 4-thio-5-methyl-5-azauridine, 4-thio-5-amino-5-azauridine, 4-thio-5-hydroxy-5-azauridine, 4-thio-5-methylpseudouridine, 4-thio-5-aminopseudouridine, 4-thio-5-hydroxypseudouridine, 2-thiocytidine, 5-azacytidine, pseudoisocytidine, N4-methylcytidine, N4-aminocytidine, N4-hydroxycytidine, 5-methylcytidine, 5-aminocytidine, 5-hydroxycytidine, 5-methyl-5-azacytidine, 5-amino-5-azacytidine, 5-hydroxy-5-azacytidine, 5-methylpseudoisocytidine, 5-aminopseudoisocytidine, 5-hydroxypseudoisocytidine, N4-methyl-5-azacytidine, N4-methylpseudoisocytidine, 2-thio-5-azacytidine, 2-thiopseudoisocytidine, 2-thio-N4-methylcytidine, 2-thio-N4-aminocytidine, 2-thio-N4-hydroxycytidine, 2-thio-5-methylcytidine, 2-thio-5-aminocytidine, 2-thio-5-hydroxycytidine, 2-thio-5-methyl-5-azacytidine, 2-thio-5-amino-5-azacytidine, 2-thio-5-hydroxy-5-azacytidine, 2-thio-5-methylpseudoisocytidine, 2-thio-5-aminopseudoisocytidine, 2-thio-5-hydroxypseudoisocytidine, 2-thio-N4-methyl-5-azacytidine, 2-thio-N4-methylpseudoisocytidine, N4-methyl-5-methylcytidine, N4-methyl-5-aminocytidine, N4-methyl-N4-methyl-5-methyl-5-azacytidine, N4-methyl-5-amino-5-azacytidine, N4-methyl-5-hydroxy-5-azacytidine, N4-methyl-5-methylpseudoisocytidine, N4-methyl-5-aminopseudoisocytidine, N4-methyl-5-hydroxypseudoisocytidine, N4-amino-5-azacytidine, N4-aminopseudoisocytidine, N4-amino-5-methylcytidine, N4-amino-5-aminocytidine, N4-amino-5-hydroxycytidine, N4-amino-5-methyl-5-azacytidine, N4-amino-5-amino-5-azacytidine, N4-amino-5-hydroxy-5-azacytidine, N4-amino-5-methylpseudoisocytidine, N4-amino-5-aminopseudoisocytidine, N4-amino-5-hydroxypseudoisocytidine, N4-hydroxy-5-azacytidine, N4-hydroxypseudoisocytidine, N4-hydroxy-5-methylcytidine, N4-hydroxy-5-aminocytidine, N4-hydroxy-5-hydroxycytidine, N4-hydroxy-5-methyl-5-azacytidine, N4-hydroxy-5-amino-5-azacytidine, N4-hydroxy-5-hydroxy-5-azacytidine, N4-hydroxy-5-methylpseudoisocytidine, N4-hydroxy-5-aminopseudoisocytidine, N4-hydroxy-5-hydroxypseudoisocytidine, 2-thio-N4-methyl-5-methylcytidine, 2-thio-N4-methyl-5-aminocytidine, 2-thio-N4-methyl-5-hydroxycytidine, 2-thio-N4-methyl-5-methyl-5-azacytidine, 2-thio-N4-methyl-5-amino-5-azacytidine, 2-thio-N4-methyl-5-hydroxy-5-azacytidine, 2-thio-N4-methyl-5-methylpseudoisocytidine, 2-thio-N4-methyl-5-aminopseudoisocytidine, 2-thio-N4-methyl-5-hydroxypseudoisocytidine, 2-thio-N4-amino-5-azacytidine, 2-thio-N4-aminopseudoisocytidine, 2-thio-N4-amino-5-methylcytidine, 2-thio-N4-amino-5-aminocytidine, 2-thio-N4-amino-5-hydroxycytidine, 2-thio-N4-amino-5-methyl-5-azacytidine, 2-thio-N4-amino-5-amino-5-azacytidine, 2-thio-N4-amino-5-hydroxy-5-azacytidine, 2-thio-N4-amino-5-methylpseudoisocytidine, 2-thio-N4-amino-5-aminopseudoisocytidine, 2-thio-N4-amino-5-hydroxpseudoisocytidine, 2-thio-N4-hydroxy-5-azacytidine, 2-thio-N4-hydroxypseudoisocytidine, 2-thio-N4-hydroxy-5-methylcytidine, N4-hydroxy-5-aminocytidine, 2-thio-N4-hydroxy-5-hydroxycytidine, 2-thio-N4-hydroxy-5-methyl-5-azacytidine, 2-thio-N4-hydroxy-5-amino-5-azacytidine, 2-thio-N4-hydroxy-5-hydroxy-5-azacytidine, 2-thio-N4-hydroxy-5-methylpseudoisocytidine, 2-thio-N4-hydroxy-5-aminopseudoisocytidine, 2-thio-N4-hydroxy-5-hydroxypseudoisocytidine, N6-methyladenosine, N6-aminoadenosine, N6-hydroxyadenosine, 7-deazaadenosine, 8-azaadenosine, N6-methyl-7-deazaadenosine, N6-methyl-8-azaadenosine, 7-deaza-8-azaadenosine, N6-methyl-7-deaza-8-azaadenosine, N6-amino-7-deazaadenosine, N6-amino-8-azaadenosine, N6-amino-7-deaza-8-azaadenosine, N6-hydroxyadenosine, N6-hydroxy-7-deazaadenosine, N6-hydroxy-8-azaadenosine, N6-hydroxy-7-deaza-8-azaadenosine, 6-thioguanosine, 7-deazaguanosine, 8-azaguanosine, 6-thio-7-deazaguanosine, 6-thio-8-azaguanosine, 7-deaza-8-azaguanosine, and 6-thio-7-deaza-8-azaguanosine.

In some embodiments, a polynucleotide encoding a Collagen alpha-1 (VII) chain polypeptide and a polynucleotide encoding a Lysyl hydroxylase 3 polypeptide are contained within two separate synthetic mRNA polynucleotides. In some embodiments, a polynucleotide encoding a Collagen alpha-1 (VII) chain polypeptide and a polynucleotide encoding a Keratin type I cytoskeletal 17 polypeptide are contained within two separate synthetic mRNA polynucleotides. In some embodiments, a polynucleotide encoding a Lysyl hydroxylase 3 polypeptide and a polynucleotide encoding a Keratin type I cytoskeletal 17 polypeptide are contained within two separate synthetic mRNA polynucleotides. In some embodiments, a polynucleotide encoding a Collagen alpha-1 (VII) chain polypeptide, a polynucleotide encoding a Lysyl hydroxylase 3 polypeptide, and a polynucleotide encoding a Keratin type I cytoskeletal 17 polypeptide are contained within three separate synthetic mRNA polynucleotides.

In some embodiments, a polynucleotide encoding a Collagen alpha-1 (VII) chain polypeptide, a polynucleotide encoding a Lysyl hydroxylase 3 polypeptide, and/or a polynucleotide encoding a Keratin type I cytoskeletal 17 polypeptide is a single contiguous polynucleotide contained within a single synthetic mRNA polynucleotide. In some embodiments, the single contiguous polynucleotide encodes a Collagen alpha-1 (VII) chain polypeptide on a first open reading frame (ORF) and a Lysyl hydroxylase 3 polypeptide on a second open reading frame (ORF) in a single synthetic mRNA. In some embodiments, the single contiguous polynucleotide encodes a Lysyl hydroxylase 3 polypeptide on a first open reading frame (ORF) and a Collagen alpha-1 (VII) chain polypeptide on a second open reading frame (ORF) in a single synthetic mRNA. In some embodiments, the single contiguous polynucleotide encodes a Collagen alpha-1 (VII) chain polypeptide on a first open reading frame (ORF) and a keratin type I cytoskeletal 17 polypeptide on a second open reading frame (ORF) in a single synthetic mRNA. In some embodiments, the single contiguous polynucleotide encodes a Keratin type I cytoskeletal polypeptide on a first open reading frame (ORF) and a Collagen alpha-1 (VII) chain polypeptide on a second open reading frame (ORF) in a single synthetic mRNA. In some embodiments, the single contiguous polynucleotide encodes a Lysyl hydroxylase 3 polypeptide on a first open reading frame (ORF) and a keratin type I cytoskeletal 17 polypeptide on a second open reading frame (ORF) in a single synthetic mRNA. In some embodiments, the single contiguous polynucleotide encodes a Keratin type I cytoskeletal polypeptide on a first open reading frame (ORF) and a Lysyl hydroxylase 3 polypeptide on a second open reading frame (ORF) in a single synthetic mRNA. In some embodiments, the single contiguous polynucleotide encodes a Collagen alpha-1 (VII) chain polypeptide on a first open reading frame (ORF) and a chimeric polypeptide comprising a Collagen alpha-1 (VII) chain polypeptide, a Lysyl hydroxylase 3 polypeptide, and/or a Keratin type I cytoskeletal 17 polypeptide on a second open reading frame (ORF) in a single synthetic mRNA. In some embodiments, the single contiguous polynucleotide encodes a Lysyl hydroxylase 3 polypeptide on a first open reading frame (ORF) and a chimeric polypeptide comprising a Collagen alpha-1 (VII) chain polypeptide, a Lysyl hydroxylase 3 polypeptide, and/or a Keratin type I cytoskeletal 17 polypeptide on a second open reading frame (ORF) in a single synthetic mRNA. In some embodiments, the single contiguous polynucleotide encodes a Keratin type I cytoskeletal 17 polypeptide on a first open reading frame (ORF) and a chimeric polypeptide comprising a Collagen alpha-1 (VII) chain polypeptide, a Lysyl hydroxylase 3 polypeptide, and/or a Keratin type I cytoskeletal 17 polypeptide on a second open reading frame (ORF) in a single synthetic mRNA. In some embodiments, the two ORFs are separated by an IRES.

In some embodiments, the single contiguous polynucleotide encodes a Collagen alpha-1 (VII) chain polypeptide on a first open reading frame (ORF), a Keratin type I cytoskeletal 17 polypeptide on a second open reading frame (ORF), and a Lysyl hydroxylase 3 polypeptide on a third open reading frame (ORF) in a single synthetic mRNA. In some embodiments, the single contiguous polynucleotide encodes a Collagen alpha-1 (VII) chain polypeptide on a first open reading frame (ORF), a Lysyl hydroxylase 3 polypeptide on a second open reading frame (ORF), and a Keratin type I cytoskeletal 17 polypeptide on a third open reading frame (ORF) in a single synthetic mRNA. In some embodiments, the single contiguous polynucleotide encodes a Lysyl hydroxylase 3 polypeptide on a first open reading frame (ORF), a Collagen alpha-1 (VII) chain polypeptide on a second open reading frame (ORF), and a Keratin type I cytoskeletal 17 polypeptide on a third open reading frame (ORF) in a single synthetic mRNA. In some embodiments, the single contiguous polynucleotide encodes a Lysyl hydroxylase 3 polypeptide on a first open reading frame (ORF), a Keratin type I cytoskeletal 17 polypeptide on a second open reading frame (ORF), and a Collagen alpha-1 (VII) chain polypeptide on a third open reading frame (ORF) in a single synthetic mRNA. In some embodiments, the single contiguous polynucleotide encodes a Keratin type I cytoskeletal 17 polypeptide on a first open reading frame (ORF), a Lysyl hydroxylase 3 polypeptide on a second open reading frame (ORF), and a Collagen alpha-1 (VII) chain polypeptide on a third open reading frame (ORF) in a single synthetic mRNA. In some embodiments, the single contiguous polynucleotide encodes a Keratin type I cytoskeletal 17 polypeptide on a first open reading frame (ORF), a Collagen alpha-1 (VII) chain polypeptide on a second open reading frame (ORF), and a Lysyl hydroxylase 3 polypeptide on a third open reading frame (ORF) in a single synthetic mRNA. In some embodiments, the first, second, and third ORFs are separated by an internal ribosomal entry site (IRES).

Examples of suitable IRES's may include, but are not limited to, a virally-derived IRES (e.g. an IRES derived from a poliovirus, rhinovirus, encephalomyocarditis virus, foot-and-mouth disease virus, hepatitis C virus, classic swine fever virus, rous sarcoma virus, human immunodeficiency virus, cricket paralysis virus, Kaposi's sarcoma-associated herpesvirus, etc.) and a cellular mRNA-derived IRES (e.g. an IRES derived from growth factor mRNAs, such as fibroblast growth factor 2, platelet-derived growth factor B, and vascular endothelial growth factor, an IRES derived from transcription factor mRNAs, such as antennapedia, ultrapithoraxm, and NF-κB repressing factor, an IRES derived from oncogene mRNAs, such as c-myc, pim-1, and protein kinase p58$^{PITSLRE}$ etc.).

In some embodiments, a polynucleotide encoding any of the chimeric polypeptides comprising a Collagen alpha-1 (VII) chain polypeptide, a Lysyl hydroxylase 3 polypeptide, and/or a Keratin type I cytoskeletal 17 polypeptide described herein is encoded on a single ORF within a synthetic mRNA polynucleotide.

Synthetic mRNA polynucleotides of the present disclosure may further encode additional coding sequences. Examples of additional coding sequences may include, but are not limited to, sequences encoding additional polypeptide tags. Examples of suitable polypeptide tags may include, but are not limited to, any combination of purification tags, such as his-tags, flag-tags, maltose binding protein and glutathione-S-transferase tags, detection tags, such as tags that may be detected photometrically (e.g., red fluorescent protein, etc.) and tags that have a detectable enzymatic activity (e.g., alkaline phosphatase, etc.), tags containing secretory sequences, leader sequences, and/or stabilizing sequences, protease cleavage sites (such as furin cleavage sites), and the like.

Delivery Vehicle

Certain aspects of the present disclosure relate to a pharmaceutical composition comprising a delivery vehicle comprising one or more polynucleotides described herein. In some embodiments, the delivery vehicle is suitable for delivering one or more polynucleotides into one or more target cells.

In some embodiments, the delivery vehicle is a virus. Examples of viral delivery vehicles may include, but are not limited to, adenovirus, adeno-associated virus, retrovirus, lentivirus, sendai virus, herpes simplex virus, vaccinia virus, or any hybrid virus thereof. In some embodiments, the virus is replication-defective. In some embodiments, the virus is replication-competent. In some embodiments, the virus has been modified to alter its tissue tropism relative to the tissue tropism of an unmodified, wild-type virus. Methods for producing a virus comprising one or more polynucleotides are well known to one of skill in the art.

In some embodiments, the viral delivery vehicle is a herpes simplex virus. Herpes simplex virus delivery vehicles may be produced by a process disclosed, for example, in WO2015/009952. In some embodiments, the herpes simplex virus comprises a modified envelope. In some embodiments, the modified envelope comprises one or more (e.g., one, two, three, four or more) mutant herpes simplex virus glycoproteins. Examples of herpes simplex virus glycoproteins may include, but are not limited to, the glycoproteins gB, gD, gH, and gL. In some embodiments, the modified envelope alters the herpes simplex virus tissue tropism relative to a wild-type herpes simplex virus. In some embodiments, the herpes simplex virus is a herpes simplex type 1 virus, a herpes simplex type 2 virus, of any derivatives thereof. In some embodiments, the virus is a herpes simplex type 1 virus. In some embodiments, the virus is a herpes simplex type 2 virus.

In some embodiments, the delivery vehicle is a non-viral delivery vehicle. In some embodiments, the non-viral delivery vehicle is a chemical-based delivery vehicle (a chemical-based delivery reagent). Examples of chemical-based delivery vehicles may include, but are not limited to, calcium phosphate, dendrimers, liposomes (cationic liposomes, non-cationic liposome, and mixtures), exosomes, charged lipids, and cationic polymers (such as DEAE-dextran, polyethylenimine, and the like). In some embodiments, the non-viral delivery vehicle is a non-chemical delivery vehicle. Examples of non-chemical delivery vehicles may include, but are not limited to, electroporation, nucleofection, sonoporation, optical transfection, and particle-based vehicles (such as a gene gun, magnet-assisted transfection, impalefection, particle bombardment, and the like). In some embodiments, the non-viral delivery vehicle is a dendrimer, liposome, exosome, charged lipid or cationic polymer. In some embodiments, the non-viral delivery vehicle is a dendrimer. In some embodiments, the non-viral delivery vehicle is a liposome. In some embodiments, the non-viral delivery vehicle is an exosome. In some embodiments, the non-viral delivery vehicle is a charged lipid. In some embodiments, the non-viral delivery vehicle is a cationic polymer. Methods for producing one or more polynucleotides of interest in a complex with a non-viral delivery vehicle are well known to one of skill in the art.

Pharmaceutically Acceptable Carrier

Certain aspects of the present disclosure relates to a pharmaceutical composition comprising a pharmaceutically acceptable carrier. In some embodiments, the pharmaceutically acceptable carrier is a carrier sufficient for topical and/or transdermal administration/application. In some embodiments, the pharmaceutically acceptable carrier is a carrier sufficient for subcutaneous and/or intradermal administration/application. In some embodiments, the pharmaceutically acceptable carrier is minimally invasive or non-invasive. Pharmaceutically acceptable carriers are generally nontoxic to recipients at the dosages and concentrations employed, and may include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; polyols such as glycerol (e.g., formulations including 10% glycerol); salt-forming counter-ions such as sodium; metal complexes (e.g. Zn-protein complexes); and/or non-ionic surfactants such as polyethylene glycol (PEG). A thorough discussion of pharmaceutically acceptable carriers is available in REMINGTON'S PHARMACEUTICAL SCIENCES (Mack Pub. Co., N. J. 1991).

In some embodiments, the pharmaceutically acceptable carrier is suitable for topical or transdermal applications/administrations. Examples of carriers suitable for use in a topical or transdermal application/administration may include, but are not limited to, ointments, pastes, creams, suspensions, emulsions, fatty ointments, gels, powders, lotions, solutions, sprays, patches, microneedle arrays, and inhalants. In some embodiments, the pharmaceutically acceptable carrier comprises one or more of an ointment, paste, cream, suspension, emulsion, fatty ointment, gel, powder, lotion, solution, spray, and an inhalant. In some embodiments, the pharmaceutically acceptable carrier comprises an ointment. In some embodiments, the pharmaceutically acceptable carrier comprises a paste. In some embodiments, the pharmaceutically acceptable carrier comprises a cream. In some embodiments, the pharmaceutically acceptable carrier comprises a suspension. In some embodiments, the pharmaceutically acceptable carrier comprises an emulsion. In some embodiments, the pharmaceutically acceptable carrier comprises a gel. In some embodiments, the pharmaceutically acceptable carrier comprises a powder. In some embodiments, the pharmaceutically acceptable carrier comprises a lotion. In some embodiments, the pharmaceutically acceptable carrier comprises a solution. In some embodiments, the pharmaceutically acceptable carrier comprises a spray. In some embodiments, the pharmaceutically acceptable carrier comprises an inhalant. In some embodiments, the pharmaceutical carrier comprises a patch (e.g. a patch that adheres to the skin). In some embodiments, the pharmaceutically acceptable carrier comprises a microneedle array. Methods for making and using microneedle arrays suitable for pharmaceutical composition delivery are generally known in the art (Kim Y. et al. "Microneedles for drug and vaccine delivery". *Advanced Drug Delivery Reviews* 2012, 64 (14): 1547-68).

In some embodiments, the pharmaceutically acceptable carrier comprises a combination of two, three, four, five or more different pharmaceutically acceptable carriers suitable for topical or transdermal applications/administrations.

In some embodiments, the pharmaceutically acceptable carrier further comprises one or more additional components. Examples of additional components may include, but are not limited to, binding agents (e.g., pregelatinised maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); wetting agents (e.g., sodium lauryl sulphate, etc.); salt solutions; alcohols; polyethylene glycols; gelatin; lactose; amylase; magnesium stearate; talc; silicic acid; viscous paraffin; hydroxymethylcellulose; polyvinylpyrrolidone; sweetenings; flavorings; perfuming agents; colorants; moisturizers; sunscreens; antibacterial agents; agents able to stabilize polynucleotides or prevent their degradation, and the like.

Pharmaceutical compositions and formulations as described herein may be prepared by mixing the delivery vehicle comprising one or more polynucleotides described herein with one or more pharmaceutically acceptable carriers. The formulations to be used for in vivo administration are generally sterile. Sterility may be readily accomplished, e.g., by filtration through sterile filtration membranes.

Methods of Treatment

The present disclosure relates, in part, to pharmaceutical compositions and methods of use for providing prophylactic, palliative, or therapeutic relief of a wound, disorder, or disease of the skin in a subject. Examples of diseases or disorders of the skin may include, but are not limited to, epidermolysis bullosa, skin cancer, psoriasis, lichen planus, lupus, rosacea, eczema, cutaneous candidiasis, cellulitis, impetigo, decubitus ulcers, erysipelas, ichthyosis vulgaris, dermatomyositis, acrodermatitis, stasis dermatitis, nethertons syndrome, epidermolysis bullosa simplex (LAMB3 gene), autosomal recessive congenital ichthyosis, xeroderma pigmentosa, and pemphigoid. In some embodiments, the disease or disorder of the skin is epidermolysis bullosa. In some embodiments, a subject has, or at risk of developing, one or more symptoms of epidermolysis bullosa.

The polynucleotides and pharmaceutical compositions described herein are useful for providing prophylactic, palliative, or therapeutic relief of a wound, disorder, or disease of the skin in a subject, including the treatment of one or more symptoms of epidermolysis bullosa (e.g., recessive dystrophic epidermolysis bullosa, dominant dystrophic epidermolysis bullosa, etc.). Pharmaceutical compositions of the present disclosure may be administered by any suitable method known in the art, including, without limitation, by oral administration, sublinguall administration, buccal administration, topical administration, rectal administration, via inhalation, transdermal administration, subcutaneous injection, intradermal injection, intravenous (IV) injection, intra-arterial injection, intramuscular injection, intracardiac injection, intraosseous injection, intraperitoneal injection, transmucosal administration, vaginal administration, intravitreal administration, intra-articular administration, periarticular administration, local administration, epicutaneous administration, or any combinations thereof. The pharmaceutical compositions may be delivered to an individual via a variety of routes, including, but not limited to, subcutaneous, intradermal, topical, transdermal, and transmucosal administrations. The present disclosure thus also encompasses methods of delivering any of the polynucleotides or pharmaceutical compositions described herein to an individual (such as an individual having, or at risk of developing, epidermolysis bullosa).

In some embodiments, there is provided prophylactic, palliative, or therapeutic relief of a wound, disorder, or disease of the skin in a subject comprising administering an effective amount of a pharmaceutical composition capable of enhancing, increasing, augmenting, and/or supplementing the levels of a Collagen alpha-1 chain polypeptide and/or a Lysyl hydroxylase 3 polypeptide and/or Keratin type I cytoskeletal 17 polypeptide in one or more cells of the subject. In some embodiments, the pharmaceutical composition is administered intradermally and/or subcutaneously. In some embodiments, the pharmaceutical composition is administered topically and/or trandermally. In some embodiments, there is provided prophylactic, palliative, or therapeutic relief of a wound, disorder, or disease of the skin in a subject comprising topically administering an effective amount of a pharmaceutical composition capable of enhancing, increasing, augmenting, and/or supplementing the levels of a Collagen alpha-1 chain polypeptide and/or a Lysyl hydroxylase 3 polypeptide and/or a Keratin type I cytoskeletal 17 polypeptide in one or more cells of the subject. The pharmaceutical composition may be any pharmaceutical composition described herein. In some embodiments, the individual is suffering from epidermolysis bullosa. In some embodiments, the individual is suffering from dystrophic epidermolysis bullosa. In some embodiments, the individual is suffering from dominant dystrophic epidermolysis bullosa. In some embodiments, the individual is suffering from recessive dystrophic epidermolysis bullosa. In some embodiments, the pharmaceutical composition is administered one, two, three, four, five or more times per day. In some embodiments, the pharmaceutical composition is administered to one or more affected areas of an individual. In some embodiments, the pharmaceutical composition is administered to one or more unaffected areas of the individual.

In some embodiments, a pharmaceutical composition described herein may be used to treat or alleviate one or more symptoms of epidermolysis bullosa. Symptoms of epidermolysis bullosa (e.g., recessive dystrophic epidermolysis bullosa, dominant dystrophic epidermolysis bullosa, etc.) may include, but are not limited to blisters on the skin (especially blisters on the hands, feet, knees, and elbows), blisters on the mucosa, scarring of the skin, scarring of the mucosa, skin erosion, deformity of fingernails and/or toenails, loss of fingernails and/or toenails, internal blistering (including on the vocal chords, esophagus, and upper airway), thickening of the skin (especially thickening of the skin on the palms and the soles of the feet), blistering of the scalp, scarring of the scalp, hair loss (scarring alopecia), thin-appearing skin, atrophic scarring, milia, dental conditions (such as tooth decay and poorly formed enamel), joint deformities, fusion of the fingers and toes, and dysphagia.

In some embodiments, there is provided a method of therapeutically treating an individual suffering from epidermolysis bullosa comprising administering an effective amount of a pharmaceutical composition capable of enhancing, increasing, augmenting, and/or supplementing the levels of a Collagen alpha-1 chain polypeptide and/or a Lysyl hydroxylase 3 polypeptide and/or a Keratin type I cytoskeletal 17 polypeptide in one or more cells of the individual. In some embodiments, the pharmaceutical composition is administered intradermally and/or subcutaneously. In some embodiments, the pharmaceutical composition is administered topically and/or trandermally. In some embodiments, there is provided a method of therapeutically treating an individual suffering from epidermolysis bullosa comprising topically administering an effective amount of a pharmaceutical composition capable of enhancing, increasing, augmenting, and/or supplementing the levels of a Collagen alpha-1 chain polypeptide and/or a Lysyl hydroxylase 3 polypeptide and/or Keratin type I cytoskeletal 17 polypeptide in one or more cells of the individual. The pharmaceutical composition may be any pharmaceutical composition described herein. In some embodiments, the individual is suffering from dystrophic epidermolysis bullosa. In some embodiments, the individual is suffering from dominant dystrophic epidermolysis bullosa. In some embodiments, the individual is suffering from recessive dystrophic epidermolysis bullosa. In some embodiments, the pharmaceutical composition is administered one, two, three, four, five or more times per day. In some embodiments, the pharmaceutical composition is administered to one or more affected areas of an individual. In some embodiments, the pharmaceutical composition is administered to one or more unaffected areas of the individual.

In some embodiments, there is provided a method of prophylactically treating an individual suffering from epidermolysis bullosa comprising administering an effective amount of a pharmaceutical composition capable of enhancing, increasing, augmenting, and/or supplementing the levels of a Collagen alpha-1 chain polypeptide and/or a Lysyl hydroxylase 3 polypeptide and/or Keratin type I cytoskeletal 17 polypeptide in one or more cells of the individual. In some embodiments, the pharmaceutical composition is administered intradermally and/or subcutaneously. In some embodiments, the pharmaceutical composition is administered topically and/or trandermally. In some embodiments, there is provided a method of prophylactically treating an individual suffering from epidermolysis bullosa comprising topically administering an effective amount of a pharmaceutical composition capable of enhancing, increasing, augmenting, and/or supplementing the levels of a Collagen alpha-1 chain polypeptide and/or a Lysyl hydroxylase 3 polypeptide and/or Keratin type I cytoskeletal 17 polypeptide in one or more cells of the individual. The pharmaceutical composition may be any pharmaceutical composition described herein. In some embodiments, the individual is suffering from dystrophic epidermolysis bullosa. In some embodiments, the individual is suffering from dominant dystrophic epidermolysis bullosa. In some embodiments, the individual is suffering from recessive dystrophic epidermolysis bullosa. In some embodiments, the pharmaceutical composition is administered one, two, three, four, five or more times per day. In some embodiments, the pharmaceutical composition is administered to one or more affected areas of an individual. In some embodiments, the pharmaceutical composition is administered to one or more unaffected areas of the individual.

In some embodiments, there is provided a method of prophylactically treating an individual at risk of developing epidermolysis bullosa comprising administering an effective amount of a pharmaceutical composition capable of enhancing, increasing, augmenting, and/or supplementing the levels of a Collagen alpha-1 chain polypeptide and/or a Lysyl hydroxylase 3 polypeptide and/or Keratin type I cytoskeletal 17 polypeptide in one or more cells of the individual. In some embodiments, the pharmaceutical composition is administered intradermally and/or subcutaneously. In some embodiments, the pharmaceutical composition is administered topically and/or trandermally. In some embodiments, there is provided a method of prophylactically treating an individual at risk of developing epidermolysis bullosa comprising topically administering an effective amount of a pharmaceutical composition capable of enhancing, increasing, augmenting, and/or supplementing the levels of a Collagen alpha-1 chain polypeptide and/or a Lysyl hydroxylase 3 polypeptide and/or Keratin type I cytoskeletal 17 polypeptide in one or more cells of the individual. The pharmaceutical composition may be any pharmaceutical composition described herein. In some embodiments, the individual is at risk of developing dystrophic epidermolysis bullosa. In some embodiments, the individual is at risk of developing dominant dystrophic epidermolysis bullosa. In some embodiments, the individual is at risk of developing recessive dystrophic epidermolysis bullosa. In some embodiments, the pharmaceutical composition is administered one, two, three, four, five or more times per day. In some embodiments, the pharmaceutical composition is administered to one or more affected areas of an individual. In some embodiments, the pharmaceutical composition is administered to one or more unaffected areas of the individual.

In some embodiments, administering to an individual an effective amount of any of the pharmaceutical compositions described herein enhances, increases, augments, and/or supplements the levels of a Collagen alpha-1 chain polypeptide and/or a Lysyl hydroxylase 3 polypeptide and/or Keratin type I cytoskeletal 17 polypeptide in one or more cells of the individual. In some embodiments, administering to an individual an effective amount of any of the pharmaceutical compositions described herein enhances, increases, augments, and/or supplements the function of a Collagen alpha-1 chain polypeptide and/or a Lysyl hydroxylase 3 polypeptide and/or a Keratin type I cytoskeletal 17 polypeptide in one or more cells of the individual. In some embodiments, administering to an individual an effective amount of any of the pharmaceutical compositions described herein enhances, increases, augments, and/or supplements the activity of a Collagen alpha-1 chain polypeptide and/or a Lysyl hydroxylase 3 polypeptide and/or Keratin type I cytoskeletal 17 polypeptide in one or more cells of the individual.

In some embodiments, administering to an individual an effective amount of any of the pharmaceutical compositions described herein enhances, increases, augments, and/or supplements anchoring fibril formation of the individual. In some embodiments, administering to an individual an effective amount of any of the pharmaceutical compositions described herein enhances, increases, augments, and/or supplements epithelial basement membrane organization of the individual. In some embodiments, administering to an individual an effective amount of any of the pharmaceutical compositions described herein enhances, increases, augments, and/or supplements epithelial basement adherence of the individual. In some embodiments, administering to an individual an effective amount of any of the pharmaceutical compositions described herein enhances, increases, augments, and/or supplements dermoepidermal junction integrity of the individual. In some embodiments, administering to an individual an effective amount of any of the pharmaceutical compositions described herein enhances, increases, augments, and/or supplements wound healing in the individual. Without wishing to be bound by theory, it is believed that increasing, augmenting, and/or supplementing the levels of a Collagen alpha-1 (VII) chain polypeptide in one or more cells of an individual, by administering one or more of the pharmaceutical compositions described herein, will allow for increased production and secretion of functional Collagen alpha-1 (VII) chain protein in the individual. Without wishing to be bound by theory, it is believed that increasing, augmenting, and/or supplementing the levels of a Lysyl hydroxylase 3 polypeptide in one or more cells of an individual, by administering one or more of the pharmaceutical compositions described herein, will increase the post-translation modification of Collagen alpha-1 (VII) chain polypeptides, enhancing production and/or secretion of functional Collagen alpha-1 (VII) chain protein in the individual. Without wishing to be bound by theory, it is further believed that increasing, augmenting, and/or supplementing the levels of a Collagen alpha-1 (VII) chain polypeptide and a Lysyl hydroxylase 3 polypeptide in the same cell of an individual, by administering one or more of the pharmaceutical compositions described herein (be it by contacting a cell with two separate polynucleotides expressing the polypeptides, by contacting a cell with a single contiguous polynucleotide separately expressing the two polypeptides, or by contacting a cell with a single contiguous polynucleotide expressing a chimeric polypeptide), will have an additive effect on enhancing the production and secretion of functional Collagen alpha-1 (VII) chain protein. Without wishing to be bound by theory, it is believed that increased production and secretion of functional Collagen alpha-1 (VII) chain protein will allow for improved anchoring fibril formation, helping organize, stabilize, and aid in the adherence of the epithelial basement membrane in the individual. Without wishing to be bound by theory, it is believed that ultimately, this will lead to increased dermal-epidermal stability for those suffering from epidermolysis bullosa, treating existing wounds, and preventing or delaying reformation of wounds in the treated areas.

Isolated Polynucleotides and Polypeptides

Certain aspects of the present disclosure relate to isolated polynucleotides comprising a polynucleotide encoding a Collagen alpha-1 (VII) chain polypeptide. Other aspects of the present disclosure relate to isolated polynucleotides comprising a polynucleotide encoding a Lysyl hydroxylase 3 polypeptide. Other aspects of the present disclosure relate to isolated polynucleotides comprising a polynucleotide encoding a Keratin type I cytoskeletal 17 polypeptide.

Other aspects of the present disclosure relate to isolated polynucleotides comprising a polynucleotide encoding a Collagen alpha-1 (VII) chain polypeptide and a polynucleotide encoding a Lysyl hydroxylase 3 polypeptide separated by a polynucleotide encoding a linker polypeptide. In some embodiments, the isolated polynucleotide encodes a chimeric polypeptide comprising a Collagen alpha-1 (VII) chain polypeptide, a linker polypeptide, and a Lysyl hydroxylase 3 polypeptide.

In some embodiments, the polynucleotide encoding a linker polypeptide further comprises a polynucleotide encoding one or more furin cleavage sites. In some embodiments, the one or more furin cleavage sites are encoded upstream of the linker polypeptide. In some embodiments, the one or more furin cleavage sites are encoded downstream of the linker polypeptide. In some embodiments, the one or more furin cleavage sites are encoded upstream of a T2A linker polypeptide. In some embodiments, the one or more furin cleavage sites are encoded downstream of a T2A linker polypeptide. In some embodiments, the one or more furin cleavage sites are encoded upstream of a P2A linker polypeptide. In some embodiments, the one or more furin cleavage sites are encoded downstream of a P2A linker polypeptide. In some embodiments, the one or more furin cleavage sites are encoded upstream of an E2A linker polypeptide. In some embodiments, the one or more furin cleavage sites are encoded downstream of an E2A linker polypeptide. In some embodiments, the one or more furin cleavage sites are encoded upstream of an F2A linker polypeptide. In some embodiments, the one or more furin cleavage sites are encoded downstream of an F2A linker polypeptide.

An example of a polynucleotide encoding a Collagen alpha-1 (VII) chain polypeptide is SEQ ID NO: 1. Polynucleotides encoding a Collagen alpha-1 (VII) chain polypeptide also include polynucleotides having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 1.

An example of a polynucleotide encoding a Lysyl hydroxylase 3 polypeptide is SEQ ID NO: 3. Polynucleotides encoding a Lysyl hydroxylase 3 polypeptide also include polynucleotides having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 3.

An example of a polynucleotide encoding a Keratin type I cytoskeletal 17 polypeptide is SEQ ID NO: 29. Polynucleotides encoding a Keratin type I cytoskeletal 17 polypeptide also include polynucleotides having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 29.

Examples of polynucleotides encoding linker polypeptides are SEQ ID NO: 5, SEQ ID NO: 7, SEQ ID NO: 9, and SEQ ID NO: 11. Polynucleotides encoding linker polypeptides also include polynucleotides having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 5, SEQ ID NO: 7, SEQ ID NO: 9, or SEQ ID NO: 11.

Examples of polynucleotides that encode chimeric polypeptides comprising a Collagen alpha-1 (VII) chain polypeptide, a linker polypeptide, and a Lysyl hydroxylase 3 polypeptide are SEQ ID NO: 13, SEQ ID NO: 15, SEQ ID NO: 17, SEQ ID NO: 19, SEQ ID NO: 21, SEQ ID NO: 23, SEQ ID NO: 25, and SEQ ID NO: 27. Polynucleotides that encode chimeric polypeptides also include polynucleotides having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 13, SEQ ID NO: 15, SEQ ID NO: 17, SEQ ID NO: 19, SEQ ID NO: 21, SEQ ID NO: 23, SEQ ID NO: 25, or SEQ ID NO: 27.

Further aspects of the present disclosure relate to one or more (e.g., one or more, two or more, three or more, etc.) isolated polynucleotides described herein contained within a vector. In some embodiments, the vector is an adenoviral vector, an adeno-associated viral vector, a retroviral vector, a lentiviral vector, a herpes simplex viral vector, a vaccinia viral vector, or any hybrid viral vector thereof. In some embodiments, the vector is a herpes simplex viral vector. In some embodiments, the vector comprises one or more (e.g., one or more, two or more, three or more, four or more, five or more, etc.) transgenes.

In some embodiments, the herpes simplex virus vector is a herpes virus amplicon vector. In some embodiments, the vector is an HSV-1 amplicon. In some embodiments, the vector is an HSV-1 hybrid amplicon. Examples of HSV-1 hybrid amplicons may include, but are not limited to, HSV/AAV hybrid amplicons, HSV/EBV hybrid amplicons, HSV/EBV/RV hybrid amplicons, and HSV/Sleeping Beauty hybrid amplicons. In some embodiments, the vector is an HSV/AAV hybrid amplicon. In some embodiments, the vector is an HSV/EBV hybrid amplicon. In some embodiments, the vector is an HSV/EBV/RV hybrid amplicon. In some embodiments, the vector is an HSV/Sleeping Beauty hybrid amplicons. Further aspects of the present disclosure relate to a method of producing a viral delivery vehicle containing one or more polynucleotides described herein. In some embodiments, the method comprises contacting a host cell with one or more viral vectors containing one or more isolated polynucleotides described herein, and collecting the viral delivery vehicle generated by the host cell. Methods of culturing cells and contacting cells with one or more viral vectors of interest (e.g. by transduction or transfection) are well known to one of skill in the art.

In some embodiments, the herpes simplex virus vector is a recombinant herpes simplex virus genome. In some embodiments, the recombinant herpes simplex virus genome has been engineered to decrease or eliminate expression of one or more toxic herpes simplex virus genes. In some embodiments, the recombinant herpes simplex virus genome comprises an inactivating mutation. Examples of inactivating mutations may include, but are not limited to, deletions (e.g., deletion of the coding sequence of a gene or deletion of one or more of the gene's transcriptional regulatory elements), insertions, point mutations, and rearrangements. In some embodiments, the recombinant herpes simplex virus genome comprises an inactivating mutation in one or more immediate early genes. In some embodiments, the recombinant herpes simplex virus genome comprises an inactivating mutation in at least one, at least two, at least three, at least four, at least five, at least six, at least seven, or all eight of the ICP0, ICP4, ICP22, ICP27, ICP47, tk, UL41 and UL55 herpes simplex virus genes. In some embodiments, the recombinant herpes simplex virus genome comprises an inactivating mutation is in the ICP0 gene. In some embodiments, the recombinant herpes simplex virus genome comprises an inactivating mutation is in the ICP4 gene. In some embodiments, the recombinant herpes simplex virus genome comprises an inactivating mutation is in the ICP22 gene. In some embodiments, the recombinant herpes simplex virus genome comprises an inactivating mutation is in the ICP27 gene. In some embodiments, the recombinant herpes simplex virus genome comprises an inactivating mutation is in the ICP4, ICP22, and ICP27 genes. In some embodiments, the recombinant herpes simplex virus genome comprises an inactivating mutation in the ICP4, ICP27, and UL55 genes. In some embodiments, the recombinant herpes simplex virus genome comprises an inactivating mutation in the ICP4, ICP22, ICP27, ICP47, and UL55 genes. In some embodiments, the recombinant herpes simplex virus genome comprises an inactivating mutation is in the ICP0, ICP4, ICP22, and ICP27 genes. In some embodiments, the recombinant herpes simplex virus genome is a recombinant HSV-1 genome, a recombinant HSV-2 genome, or any derivatives thereof. In some embodiments, the recombinant herpes simplex virus genome is a recombinant HSV-1 genome. In some embodiments, the recombinant herpes simplex virus genome is a recombinant HSV-2 genome.

In some embodiments, an isolated recombinant herpes simplex virus genome comprises one or more (e.g., one or more, two or more, three or more, four or more, five or more, etc.) polynucleotides (e.g., transgenes) of the present disclosure within one, two, three, four, five, six, seven or more viral gene loci. Examples of suitable viral loci may include, without limitation, the ICP0, ICP4, ICP22, ICP27, ICP47, tk, UL41 and UL55 herpes simplex viral gene loci. In some embodiments, an isolated recombinant herpes simplex virus genome comprises one or more polynucleotide of the present disclosure within one or more of the viral ICP4 gene loci (e.g., a recombinant virus carrying a polynucleotide encoding Col7 in one or both of the ICP4 loci, a recombinant virus carrying a polynucleotide encoding LH3 in one or both of the ICP4 loci, a recombinant virus carrying a polynucleotide encoding KRT17 in one or both of the ICP4 loci, a recombinant virus carrying a polynucleotide encoding Col7 in one of the ICP4 loci and a polynucleotide encoding KRT17 in the other ICP4 loci, a recombinant virus carrying a polynucleotide encoding Col7 in one of the ICP4 loci and a polynucleotide encoding LH3 in the other ICP4 loci, a recombinant virus carrying a polynucleotide encoding LH3 in one of the ICP4 loci and a polynucleotide encoding KRT17 in the other ICP4 loci, etc.). In some embodiments, an isolated recombinant herpes simplex virus genome comprises one or more polynucleotide of the present disclosure within the viral UL41 gene locus. In some embodiments, an isolated recombinant herpes simplex virus genome comprises one or more polynucleotide of the present disclosure within the viral ICP47 gene locus. In some embodiments, an isolated recombinant herpes simplex virus genome comprises one or more polynucleotides of the present disclosure within one or more of the viral ICP4 gene loci, and one or more polynucleotide of the present disclosure within the viral UL41 gene locus (e.g., a recombinant virus carrying a polynucleotide encoding Col7 in one or both of the ICP4 loci and a polynucleotide encoding LH3 in the UL41 locus, a recombinant virus carrying a polynucleotide encoding Col7 in one or both of the ICP4 loci and a polynucleotide encoding Col7 in the UL41 locus, a recombinant virus carrying a polynucleotide encoding Col7 in one or both of the ICP4 loci and a polynucleotide encoding KRT17 in the UL41 locus, a recombinant virus carrying a polynucleotide encoding LH3 in one or both of the ICP4 loci and a polynucleotide encoding LH3 in the UL41 locus, a recombinant virus carrying a polynucleotide encoding LH3 in one or both of the ICP4 loci and a polynucleotide encoding Col7 in the UL41 locus, a recombinant virus carrying a polynucleotide encoding LH3 in one or both of the ICP4 loci and a polynucleotide encoding KRT17 in the UL41 locus, a recombinant virus carrying a polynucleotide encoding KRT17 in one or both of the ICP4 loci and a polynucleotide encoding LH3 in the UL41 locus, a recombinant virus carrying a polynucleotide encoding KRT17 in one or both of the ICP4 loci and a polynucleotide encoding Col7 in the UL41 locus, a recombinant virus carrying a polynucleotide encoding KRT17 in one or both of the ICP4 loci and a polynucleotide encoding KRT17 in the UL41 locus, etc.).

In some aspects, the isolated polynucleotides described herein are contained within a synthetic mRNA. In some embodiments, the synthetic mRNA comprises one or more modified ribonucleotides.

Certain aspects of the present disclosure relate to isolated polypeptides comprising a Collagen alpha-1 (VII) chain polypeptide. Other aspects of the present disclosure relate to isolated polypeptides comprising a Lysyl hydroxylase 3 polypeptide. Other aspects of the present disclosure relate to isolated polypeptides comprising a Keratin type I cytoskeletal 17 polypeptide.

Other aspects of the present disclosure relate to isolated chimeric polypeptides comprising a Collagen alpha-1 (VII) chain polypeptide and a Lysyl hydroxylase 3 polypeptide separated by a linker polypeptide.

In some embodiments, the linker polypeptide further comprises one or more furin cleavage sites. In some embodiments, the amino acid sequence of the furin cleavage site is the same or substantially similar to the sequence of the canonical furin cleavage site (Arg-X-(Arg/Lys)-Arg). In some embodiments, the one or more furin cleavage sites are at the N-terminus of the linker polypeptide. In some embodiments, the one or more furin cleavage sites are at the C-terminus of the linker polypeptide. In some embodiments, the linker polypeptide comprises, from N-terminus to C-terminus, one or more furin cleavage sites and a T2A linker polypeptide. In some embodiments, the linker polypeptide comprises, from N-terminus to C-terminus, a T2A linker polypeptide and one or more furin cleavage sites. In some embodiments, the linker polypeptide comprises, from N-terminus to C-terminus, one or more furin cleavage sites and a P2A linker polypeptide. In some embodiments, the linker polypeptide comprises, from N-terminus to C-terminus, a P2A linker polypeptide and one or more furin cleavage sites. In some embodiments, the linker polypeptide comprises, from N-terminus to C-terminus, one or more furin cleavage sites and an E2A linker polypeptide. In some embodiments, the linker polypeptide comprises, from N-terminus to C-terminus, an E2A linker polypeptide and one or more furin cleavage sites. In some embodiments, the linker polypeptide comprises, from N-terminus to C-terminus, one or more furin cleavage sites and an F2A linker polypeptide. In some embodiments, the linker polypeptide comprises, from N-terminus to C-terminus, an F2A linker polypeptide and one or more furin cleavage sites.

In some aspects, the isolated polypeptide comprising a Collagen alpha-1 (VII) chain polypeptide comprises the amino acid sequence of SEQ ID NO: 2. Isolated polypeptides may also comprise a Collagen alpha-1 (VII) chain polypeptide containing an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 2.

In some aspects, the isolated polypeptide comprising a Lysyl hydroxylase 3 polypeptide comprises the amino acid sequence of SEQ ID NO: 4. Isolated polypeptides may also comprise a Lysyl hydroxylase 3 polypeptide containing an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 4.

In some aspects, the isolated polypeptide comprising a Keratin type I cytoskeletal 17 polypeptide comprises the amino acid sequence of SEQ ID NO: 30. Isolated polypeptides may also comprise a Keratin type I cytoskeletal 17 polypeptide containing an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 30.

In some aspects, the chimeric polypeptide comprises a Collagen alpha-1 (VII) chain polypeptide containing the amino acid sequence of SEQ ID NO: 2. Chimeric polypeptides may also comprise a Collagen alpha-1 (VII) chain polypeptide containing an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 2.

In some aspects, the chimeric polypeptide comprises a Lysyl hydroxylase 3 polypeptide containing the amino acid sequence of SEQ ID NO: 4. Chimeric polypeptides may also comprise a Lysyl hydroxylase 3 polypeptide containing an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 4.

In some aspects, the chimeric polypeptide comprises a linker polypeptide containing the amino acid sequence of SEQ ID NO: 6, SEQ ID NO: 8, SEQ ID NO: 10 or SEQ ID NO: 12. Chimeric polypeptides may also comprise a linker polypeptide containing an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 6, SEQ ID NO: 8, SEQ ID NO: 10 or SEQ ID NO: 12.

In some aspects, the chimeric polypeptide is the amino acid sequence of SEQ ID NO: 14, SEQ ID NO: 16, SEQ ID NO: 18, SEQ ID NO: 20, SEQ ID NO: 22, SEQ ID NO: 24, SEQ ID NO: 26 or SEQ ID NO: 28. Chimeric polypeptides may also be an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 14, SEQ ID NO: 16, SEQ ID NO: 18, SEQ ID NO: 20, SEQ ID NO: 22, SEQ ID NO: 24, SEQ ID NO: 26 or SEQ ID NO: 28.

Host Cells

Certain aspects of the present disclosure relate to one or more host cells comprising a vector comprising a polynucleotide described herein. In some embodiments, the vector is any of the isolated recombinant herpes simplex virus vectors described herein. In some embodiments, the host cells are bacterial cells (e.g., *E. coli* cells, etc.). In some embodiments, the host cells are fungal cells (e.g., *S. cerevisiae* cells, etc.). In some embodiments, the host cells are insect cells (e.g., S2 cells, etc.). In some embodiments, the host cells are mammalian cells. In some embodiments, the host cells are cells from a cell line. Examples of suitable host cells or cell lines may include, but are not limited to, 293, HeLa, SH-Sy5y, Hep G2, CACO-2, A549, L929, 3T3, K562, CHO-K1, MDCK, HUVEC, Vero, N20, COS-7, PSN1, VCaP, CHO cells, and the like. In some embodiments, the vector is an adenoviral vector, an adeno-associated viral vector, a retroviral vector, a lentiviral vector, a herpes simplex viral vector, a vaccinia viral vector, or any hybrid viral vectors thereof. In some embodiments, the vector is a herpes simplex viral vector. In some embodiments, the vector is an HSV-1 amplicon or HSV-1 hybrid amplicon. In some embodiments, the host cells comprise a helper virus. In some embodiments, the host cells comprising a helper virus are contacted with a vector described herein. In some embodiments, contacting a host cell comprising a helper virus with an HSV-1 amplicon or HSV-1 hybrid amplicon described herein results in the production of a virus comprising one or more vectors described herein. In some embodiments, the virus is collected from the supernatant of the contacted host cell. Methods of generating virus by contacting host cells comprising a helper virus with an HSV-1 amplicon or HSV-1/hybrid amplicon are known in the art. In some embodiments, the host cell is a complementing host cell. In some embodiments, the complementing host cell expresses one or more genes that are inactivated in any of the viral vectors described herein. In some embodiments, the complementing host cell is contacted with a recombinant herpes simplex virus genome described herein.

In some embodiments, contacting a complementing host cell with a recombinant herpes simplex virus genome described herein results in the production of a virus comprising one or more vectors described herein. In some embodiments, the virus is collected from the supernatant of the contacted host cell. Methods of generating virus by contacting complementing host cells with a recombinant herpes simplex virus are generally described in WO2015/009952.

Articles of Manufacture or Kits

Certain aspects of the present disclosure relate to an article of manufacture or a kit comprising a pharmaceutical composition described herein. In some embodiments, the article of manufacture or kit comprises a package insert comprising instructions for administering the pharmaceutical composition to provide prophylactic, palliative, or therapeutic relief of a wound, disorder, or disease of the skin in a subject.

In some embodiments, the delivery vehicle comprising one or more polynucleotides described herein and pharmaceutically acceptable carrier are in the same container or separate containers. Suitable containers include, for example, bottles, vials, bags and syringes. The container may be formed from a variety of materials such as glass, plastic (such as polyvinyl chloride or polyolefin), or metal alloy (such as stainless steel or hastelloy). In some embodiments, the container comprises a label on, or associated with the container, wherein the label indicates directions for use. The article of manufacture or kit may further include other materials desirable from a commercial and user standpoint, including other buffers, diluents, filters, and the like.

ENUMERATED EMBODIMENTS

Embodiment 1: A pharmaceutical composition comprising:
a) a virus comprising a vector, wherein the vector comprises one or more transgenes encoding a polypeptide selected from the group consisting of a Collagen alpha-1 (VII) chain polypeptide, a Lysyl hydroxylase 3 polypeptide, and a chimeric polypeptide thereof; and
b) a pharmaceutically acceptable carrier.

Embodiment 2: The pharmaceutical composition of embodiment 1, wherein the virus is an adenovirus, adeno-associated virus, retrovirus, lentivirus, sendai virus, herpes simplex virus, vaccinia virus, or any hybrid virus thereof.

Embodiment 3: The pharmaceutical composition of embodiment 1, wherein the virus is a herpes simplex virus (HSV).

Embodiment 4: The pharmaceutical composition of any of embodiments 1 to 3, wherein the virus is replication-defective.

Embodiment 5: The pharmaceutical composition of embodiment 3, wherein the herpes simplex virus is a herpes simplex type 1 virus, a herpes simplex type 2 virus, or any derivatives thereof.

Embodiment 6: The pharmaceutical composition of embodiment 3, wherein the herpes simplex virus comprises a modified envelope.

Embodiment 7: The pharmaceutical composition of embodiment 6, wherein the modified envelope alters the herpes simplex virus tissue tropism relative to a wild-type herpes simplex virus.

Embodiment 8: The pharmaceutical composition of embodiment 6, wherein the modified envelope comprises a mutant herpes simplex virus glycoprotein.

Embodiment 9: The pharmaceutical composition of embodiment 1, wherein the vector is an HSV-1 amplicon or an HSV-1 hybrid amplicon.

Embodiment 10: The pharmaceutical composition of embodiment 9, wherein the HSV-1 hybrid amplicon is an HSV/AAV hybrid amplicon, an HSV/EBV hybrid amplicon, and HSV/EBV/RV hybrid amplicon, or an HSV/Sleeping Beauty hybrid amplicon.

Embodiment 11: The pharmaceutical composition of embodiment 1, wherein the vector is a recombinant herpes simplex virus genome.

Embodiment 12: The pharmaceutical composition of embodiment 11, wherein the recombinant herpes simplex virus genome is a recombinant HSV-1 genome, a recombinant HSV-2 genome, or any derivatives thereof.

Embodiment 13: The pharmaceutical composition of embodiment 11 or 12, wherein the recombinant herpes simplex virus genome comprises an inactivating mutation in an immediate early herpes simplex virus gene.

Embodiment 14: The pharmaceutical composition of embodiment 13, wherein the herpes simplex virus gene is selected from the group consisting of ICP0, ICP4, ICP22, ICP27, ICP47, tk, UL41, and UL55.

Embodiment 15: The pharmaceutical composition of any of embodiments 11 to 14, wherein the recombinant herpes simplex virus genome comprises an inactivating mutation in the ICP4 and ICP22 genes.

Embodiment 16: The pharmaceutical composition of any of embodiments 11 to 14, wherein the recombinant herpes simplex virus genome comprises an inactivating mutation in the ICP0 and ICP4 genes.

Embodiment 17: The pharmaceutical composition of embodiment 15 or embodiment 16, wherein the recombinant herpes simplex virus genome comprises an inactivating mutation in the ICP0, ICP4, and ICP22 genes.

Embodiment 18: The pharmaceutical composition of any of embodiments 15 to 17, wherein the recombinant herpes simplex virus genome comprises an inactivating mutation in the ICP0, ICP4, ICP22, and ICP27 genes.

Embodiment 19: The pharmaceutical composition of any of embodiments 15 to 18, wherein the recombinant herpes simplex virus genome comprises an inactivating mutation in the ICP0, ICP4, ICP22, ICP27, and UL55 genes.

Embodiment 20: The pharmaceutical composition of any of embodiments 15 to 18, wherein the inactivating mutation is a deletion of the coding sequence of the genes.

Embodiment 21: The pharmaceutical composition of any of embodiments 15 to 20, further comprising an inactivating mutation in the ICP47 gene.

Embodiment 22: The pharmaceutical composition of any of embodiments 11 to 21, further comprising an inactivating mutation in the UL41 gene.

Embodiment 23: The pharmaceutical composition of any of embodiments 11 to 22, wherein the recombinant herpes simplex virus genome comprises the one or more transgenes within one or more viral gene loci.

Embodiment 24: The pharmaceutical composition of any of embodiments 11 to 23, wherein the recombinant herpes simplex virus genome comprises the one or more transgenes within one or more of the ICP4 viral gene loci.

Embodiment 25: The pharmaceutical composition of any of embodiments 11 to 24, wherein the recombinant herpes simplex virus genome comprises the one or more transgenes within the UL41 viral gene locus.

Embodiment 26: The pharmaceutical composition of embodiment 1, wherein the vector is capable of replicating within a target cell when delivered into said target cell.

Embodiment 27: The pharmaceutical composition of embodiment 1, wherein the pharmaceutically acceptable carrier is suitable for topical or transdermal administration.

Embodiment 28: The pharmaceutical composition of embodiment 1, wherein the one or more transgenes comprises an miRNA binding site.

Embodiment 29: The pharmaceutical composition of embodiment 1, wherein the one or more transgenes are operably linked to one or more heterologous promoters.

Embodiment 30: The pharmaceutical composition of embodiment 29, wherein the one or more heterologous promoters are selected from the group consisting of the human cytomegalovirus (HCMV) immediate early promoter, the elongation factor-1 (EF1) promoter, and any combinations thereof.

Embodiment 31: The pharmaceutical composition of embodiment 1, wherein the vector comprises a transgene encoding a Collagen alpha-1 (VII) chain polypeptide.

Embodiment 32: The pharmaceutical composition of embodiment 1, wherein the vector comprises two transgenes, wherein each transgene encodes a Collagen alpha-1 (VII) chain polypeptide.

Embodiment 33: The pharmaceutical composition of embodiment 1, wherein the Collagen alpha-1 (VII) chain polypeptide has at least 80% sequence identity to the sequence of SEQ ID NO: 2.

Embodiment 34: The pharmaceutical composition of embodiment 1, wherein the collagen alpha-1 (VII) chain polypeptide is a fragment, wherein the fragment has at least 100 consecutive amino acids of SEQ ID NO: 2.

Embodiment 35: The pharmaceutical composition of embodiment 1, wherein the Collagen alpha-1 (VII) chain polypeptide enhances, increases, augments, and/or supplements anchoring fibril formation of a subject when the polypeptide is expressed in one or more target cells of the subject.

Embodiment 36: The pharmaceutical composition of embodiment 1, wherein the Collagen alpha-1 (VII) chain polypeptide enhances, increases, augments, and/or supplements epithelial basement membrane organization and/or epithelial basement adherence of a subject when the polypeptide is expressed in one or more target cells of the subject.

Embodiment 37: The pharmaceutical composition of embodiment 1, wherein the Lysyl hydroxylase 3 polypeptide has at least 80% sequence identity to the sequence of SEQ ID NO: 4.

Embodiment 38: The pharmaceutical composition of embodiment 1, wherein the Lysyl hydroxylase 3 polypeptide is a fragment, wherein the fragment has at least 100 consecutive amino acids of SEQ ID NO: 4.

Embodiment 39: The pharmaceutical composition of embodiment 1, wherein the Lysyl hydroxylase 3 polypeptide enhances, increases, augments, and/or supplements the formation of hydroxylysine residues on one or more collagen polypeptides of a subject when the Lysyl hydroxylase 3 polypeptide is expressed in one or more target cells of the subject.

Embodiment 40: The pharmaceutical composition of embodiment 1, wherein the Lysyl hydroxylase 3 polypeptide enhances, increases, augments, and/or supplements anchoring fibril formation, epithelial basement membrane organization, and/or epithelial basement adherence of a subject when the polypeptide is expressed in one or more target cells of the subject.

Embodiment 41: The pharmaceutical composition of embodiment 1, wherein the vector comprises at least a first transgene and a second transgene.

Embodiment 42: The pharmaceutical composition of embodiment 41, wherein the first transgene encodes a Collagen alpha-1 (VII) chain polypeptide and the second transgene encodes a Lysyl hydroxylase 3 polypeptide.

Embodiment 43: The pharmaceutical composition of embodiment 1, wherein the vector comprises a transgene that is polycistronic.

Embodiment 44: The pharmaceutical composition of embodiment 43, wherein the polycistronic transgene encodes a Collagen alpha-1 (VII) chain polypeptide on a first open reading frame (ORF) and a Lysyl hydroxylase 3 polypeptide on a second open reading frame (ORF).

Embodiment 45: The pharmaceutical composition of embodiment 44, wherein the first and second ORFs are separated by an internal ribosomal entry site (IRES).

Embodiment 46: The pharmaceutical composition of any of embodiments 42 to 45, wherein the Collagen alpha-1 (VII) chain polypeptide and the Lysyl hydroxylase 3 polypeptide are at about an equimolar ratio when the polypeptides are expressed in one or more target cells of a subject.

Embodiment 47: The pharmaceutical composition of any of embodiments 42 to 45, wherein the Collagen alpha-1 (VII) chain polypeptide and the Lysyl hydroxylase 3 polypeptide enhance, increase, augment, and/or supplement anchoring fibril formation, epithelial basement membrane organization, and/or epithelial basement adherence of a subject when the polypeptides are expressed in one or more target cells of the subject.

Embodiment 48: The pharmaceutical composition of embodiment 1, wherein the chimeric polypeptide comprises a linker polypeptide between the Collagen alpha-1 (VII) chain polypeptide and the Lysyl hydroxylase 3 polypeptide.

Embodiment 49: The pharmaceutical composition of embodiment 48, wherein the linker polypeptide is a T2A, P2A, E2A, or F2A linker polypeptide.

Embodiment 50: The pharmaceutical composition of embodiment 48 or 49, wherein the linker polypeptide has at least 80% sequence identity to the sequence of SEQ ID NO: 6, SEQ ID NO: 8, SEQ ID NO: 10 or SEQ ID NO: 12.

Embodiment 51: The pharmaceutical composition of any of embodiments 48 to 50, wherein the chimeric polypeptide has at least 80% sequence identity to the sequence of SEQ ID NO: 14, SEQ ID NO: 16, SEQ ID NO: 18, SEQ ID NO: 20, SEQ ID NO: 22, SEQ ID NO: 24, SEQ ID NO: 26 or SEQ ID NO: 28.

Embodiment 52: The pharmaceutical composition of any of embodiments 48 to 51, wherein the chimeric polypeptide enhances, increases, augments, and/or supplements anchoring fibril formation, epithelial basement membrane organization, and/or epithelial basement adherence of a subject when the polypeptide is expressed in one or more target cells of the subject.

Embodiment 53: A method of providing prophylactic, palliative, or therapeutic relief of a wound, disorder, or disease of the skin in a subject, the method comprising topically or transdermally administering a pharmaceutical composition capable of enhancing, increasing, augmenting, and/or supplementing the levels of a Collagen alpha-1 (VII) chain polypeptide and/or a Lysyl hydroxylase 3 polypeptide in one or more cells of the subject.

Embodiment 54: The method of embodiment 53, wherein the pharmaceutical composition comprises:
  a) a virus comprising a vector, wherein the vector comprises one or more transgenes encoding a polypeptide selected from the group consisting of a Collagen alpha-1 (VII) chain polypeptide, a Lysyl hydroxylase 3 polypeptide, and a chimeric polypeptide thereof; and
  b) a pharmaceutically acceptable carrier.

Embodiment 55: The method of embodiment 54, wherein the virus is an adenovirus, adeno-associated virus, retrovirus, lentivirus, sendai virus, herpes simplex virus, vaccinia virus, or any hybrid virus thereof.

Embodiment 56: The method of embodiment 54, wherein the virus is a herpes simplex virus (HSV).

Embodiment 57: The method of any of embodiments 54 to 56, wherein the virus is replication-defective.

Embodiment 58: The method of embodiment 56, wherein the herpes simplex virus is a herpes simplex type 1 virus, a herpes simplex type 2 virus, or any derivatives thereof.

Embodiment 59: The method of embodiment 56, wherein the herpes simplex virus comprises a modified envelope.

Embodiment 60: The method of embodiment 59, wherein the modified envelope alters the herpes simplex virus tissue tropism relative to a wild-type herpes simplex virus.

Embodiment 61: The method of embodiment 59, wherein the modified envelope comprises a mutant herpes simplex virus glycoprotein.

Embodiment 62: The method of embodiment 54, wherein the vector is an HSV-1 amplicon or an HSV-1 hybrid amplicon.

Embodiment 63: The method of embodiment 62, wherein the HSV-1 hybrid amplicon is an HSV/AAV hybrid amplicon, an HSV/EBV hybrid amplicon, and HSV/EBV/RV hybrid amplicon, or an HSV/Sleeping Beauty hybrid amplicon.

Embodiment 64: The method of embodiment 54, wherein the vector is a recombinant herpes simplex virus genome.

Embodiment 65: The method of embodiment 64, wherein the recombinant herpes simplex virus genome is a recombinant HSV-1 genome, a recombinant HSV-2 genome, or any derivatives thereof.

Embodiment 66: The method of embodiment 64 or 65, wherein the recombinant herpes simplex virus genome comprises an inactivating mutation in an immediate early herpes simplex virus gene.

Embodiment 67: The method of embodiment 66, wherein the herpes simplex virus gene is selected from the group consisting of ICP0, ICP4, ICP22, ICP27, ICP47, tk, UL41, and UL55.

Embodiment 68: The method of any of embodiments 64 to 67, wherein the recombinant herpes simplex virus genome comprises an inactivating mutation in the ICP4 and ICP22 genes.

Embodiment 69: The method of any of embodiments 64 to 67, wherein the recombinant herpes simplex virus genome comprises an inactivating mutation in the ICP0 and ICP4 genes.

Embodiment 70: The method of embodiment 68 or 69, wherein the recombinant herpes simplex virus genome comprises an inactivating mutation in the ICP0, ICP4, and ICP22 genes.

Embodiment 71: The method of any of embodiments 68 to 70, wherein the recombinant herpes simplex virus genome comprises an inactivating mutation in the ICP0, ICP4, ICP22, and ICP27 genes.

Embodiment 72: The method of any of embodiments 68 to 71, wherein the recombinant herpes simplex virus genome comprises an inactivating mutation in the ICP0, ICP4, ICP22, ICP27, and UL55 genes.

Embodiment 73: The method of any of embodiments 68 to 72, wherein the inactivating mutation is a deletion of the coding sequence of the genes.

Embodiment 74: The method of any of embodiments 68 to 73, further comprising an inactivating mutation in the ICP47 gene.

Embodiment 75: The method of any of embodiments 64 to 74, further comprising an inactivating mutation in the UL41 gene.

Embodiment 76: The method of any of embodiments 64 to 75, wherein the recombinant herpes simplex virus genome comprises the one or more transgenes within one or more viral gene loci.

Embodiment 77: The method of any of embodiments 64 to 76, wherein the recombinant herpes simplex virus genome comprises the one or more transgenes within one or more of the ICP4 viral gene loci.

Embodiment 78: The method of any of embodiments 64 to 77, wherein the recombinant herpes simplex virus genome comprises the one or more transgenes within the UL41 viral gene locus.

Embodiment 79: The method of embodiment 54, wherein the vector is capable of replicating within a target cell when delivered into said target cell.

Embodiment 80: The method of embodiment 54, wherein the pharmaceutically acceptable carrier is suitable for topical or transdermal administration.

Embodiment 81: The method of embodiment 54, wherein the one or more transgenes comprises an miRNA binding site.

Embodiment 82: The method of embodiment 54, wherein the one or more transgenes are operably linked to one or more heterologous promoters.

Embodiment 83: The method of embodiment 82, wherein the one or more heterologous promoters are selected from the group consisting of the human cytomegalovirus (HCMV) immediate early promoter, the elongation factor-1 (EF1) promoter, and any combinations thereof.

Embodiment 84: The method of embodiment 54, wherein the vector comprises a transgene encoding a Collagen alpha-1 (VII) chain polypeptide.

Embodiment 85: The method of embodiment 54, wherein the vector comprises two transgenes, wherein each transgene encodes a Collagen alpha-1 (VII) chain polypeptide.

Embodiment 86: The method of embodiment 54, wherein the Collagen alpha-1 (VII) chain polypeptide has at least 80% sequence identity to the sequence of SEQ ID NO: 2.

Embodiment 87: The method of embodiment 54, wherein the Collagen alpha-1 (VII) chain polypeptide is a fragment, wherein the fragment has at least 100 consecutive amino acids of SEQ ID NO: 2.

Embodiment 88: The method of embodiment 54, wherein the Collagen alpha-1 (VII) chain polypeptide enhances, increases, augments, and/or supplements anchoring fibril formation of a subject when the polypeptide is expressed in one or more target cells of the subject.

Embodiment 89: The method of embodiment 54, wherein the Collagen alpha-1 (VII) chain polypeptide enhances, increases, augments, and/or supplements epithelial basement membrane organization and/or epithelial basement adherence of a subject when the polypeptide is expressed in one or more target cells of the subject.

Embodiment 90: The method of embodiment 54, wherein the Lysyl hydroxylase 3 polypeptide has at least 80% sequence identity to the sequence of SEQ ID NO: 4.

Embodiment 91: The method of embodiment 54, wherein the Lysyl hydroxylase 3 polypeptide is a fragment, wherein the fragment has at least 100 consecutive amino acids of SEQ ID NO: 4.

Embodiment 92: The method of embodiment 54, wherein the Lysyl hydroxylase 3 polypeptide enhances, increases, augments, and/or supplements the formation of hydroxylysine residues on one or more collagen polypeptides of a subject when the Lysyl hydroxylase 3 polypeptide is expressed in one or more target cells of the subject.

Embodiment 93: The method of embodiment 54, wherein the Lysyl hydroxylase 3 polypeptide enhances, increases, augments, and/or supplements anchoring fibril formation, epithelial basement membrane organization, and/or epithelial basement adherence of a subject when the polypeptide is expressed in one or more target cells of the subject.

Embodiment 94: The method of embodiment 54, wherein the vector comprises at least a first transgene and a second transgene.

Embodiment 95: The method of embodiment 94, wherein the first transgene encodes a Collagen alpha-1 (VII) chain polypeptide and the second transgene encodes a Lysyl hydroxylase 3 polypeptide.

Embodiment 96: The method of embodiment 54, wherein the vector comprises a transgene that is polycistronic.

Embodiment 97: The method of embodiment 96, wherein the polycistronic transgene encodes a Collagen alpha-1 (VII) chain polypeptide on a first open reading frame (ORF) and a Lysyl hydroxylase 3 polypeptide on a second open reading frame (ORF).

Embodiment 98: The method of embodiment 97, wherein the first and second ORFs are separated by an internal ribosomal entry site (IRES).

Embodiment 99: The method of any of embodiments 95 to 98, wherein the Collagen alpha-1 (VII) chain polypeptide and the Lysyl hydroxylase 3 polypeptide are at about an equimolar ratio when the polypeptides are expressed in one or more target cells of a subject.

Embodiment 100: The method of any of embodiments 95 to 98, wherein the Collagen alpha-1 (VII) chain polypeptide and the Lysyl hydroxylase 3 polypeptide enhance, increase, augment, and/or supplement anchoring fibril formation, epithelial basement membrane organization, and/or epithelial basement adherence of a subject when the polypeptides are expressed in one or more target cells of the subject.

Embodiment 101: The method of embodiment 54, wherein the chimeric polypeptide comprises a linker polypeptide between the Collagen alpha-1 (VII) chain polypeptide and the Lysyl hydroxylase 3 polypeptide.

Embodiment 102: The method of embodiment 101, wherein the linker polypeptide is a T2A, P2A, E2A, or F2A linker polypeptide.

Embodiment 103: The method of embodiment 101 or 102, wherein the linker polypeptide has at least 80% sequence identity to the sequence of SEQ ID NO: 6, SEQ ID NO: 8, SEQ ID NO: 10 or SEQ ID NO: 12.

Embodiment 104: The method of any of embodiments 101 to 103, wherein the chimeric polypeptide has at least 80% sequence identity to the sequence of SEQ ID NO: 14, SEQ ID NO: 16, SEQ ID NO: 18, SEQ ID NO: 20, SEQ ID NO: 22, SEQ ID NO: 24, SEQ ID NO: 26 or SEQ ID NO: 28.

Embodiment 105: The method of any of embodiments 101 to 104, wherein the chimeric polypeptide enhances, increases, augments, and/or supplements anchoring fibril formation, epithelial basement membrane organization, and/ or epithelial basement adherence of a subject when the polypeptide is expressed in one or more target cells of the subject.

Embodiment 106: The method of embodiment 53, wherein the pharmaceutical composition is administered one, two three, four, five or more times per day.

Embodiment 107: The method of embodiment 53, wherein the pharmaceutical composition is administered to one or more affected and/or unaffected areas of the subject.

Embodiment 108: The method of embodiment 53, wherein the disease or disorder of the skin is one or more of epidermolysis bullosa, skin cancer, psoriasis, lichen planus, lupus, rosacea, eczema, cutaneous candidiasis, cellulitis, impetigo, decubitus ulcers, erysipelas, ichthyosis vulgaris, dermatomyositis, acrodermatitis, stasis dermatitis, nethertons syndrome, epidermolysis bullosa simplex (LAMB3 gene), autosomal recessive congenital ichthyosis, xeroderma pigmentosa, and pemphigoid.

Embodiment 109: An isolated chimeric polypeptide, wherein the isolated chimeric polypeptide comprises;
  a) a Collagen alpha-1 (VII) chain polypeptide;
  b) a Lysyl hydroxylase 3 polypeptide; and
  c) a linker polypeptide;
    wherein the Collagen alpha-1 (VII) chain polypeptide and the Lysyl hydroxylase 3 polypeptide are separated by the linker polypeptide.

Embodiment 110: The isolated chimeric polypeptide of embodiment 109, wherein the Collagen alpha-1 (VII) chain polypeptide has at least 80% sequence identity to the sequence of SEQ ID NO: 2.

Embodiment 111: The isolated chimeric polypeptide of embodiment 109, wherein the Lysyl hydroxylase 3 polypeptide has at least 80% sequence identity to the sequence of SEQ ID NO: 4.

Embodiment 112: The isolated chimeric polypeptide of embodiment 109, wherein the linker polypeptide has at least 80% sequence identity to the sequence of SEQ ID NO: 6, SEQ ID NO: 8, SEQ ID NO: 10 or SEQ ID NO: 12.

Embodiment 113: The isolated chimeric polypeptide of any of embodiments 109 to 112, wherein the isolated chimeric polypeptide has at least 80% sequence identity to the sequence of SEQ ID NO: 14, SEQ ID NO: 16, SEQ ID NO: 18, SEQ ID NO: 20, SEQ ID NO: 22, SEQ ID NO: 24, SEQ ID NO: 26 or SEQ ID NO: 28.

Embodiment 114: A polynucleotide encoding the chimeric polypeptide of any of embodiments 109 to 113.

Embodiment 115: A vector comprising the polynucleotide of embodiment 114.

Embodiment 116: The vector of embodiment 115, wherein the vector is an HSV-1 amplicon or an HSV-1 hybrid amplicon.

Embodiment 117: The vector of embodiment 116 wherein the HSV-1 hybrid amplicon is an HSV/AAV hybrid amplicon, an HSV/EBV hybrid amplicon, and HSV/EBV/RV hybrid amplicon, or an HSV/Sleeping Beauty hybrid amplicon.

Embodiment 118: The vector of embodiment 115, wherein the vector is a recombinant herpes simplex virus genome.

Embodiment 119: The vector of embodiment 118, wherein the recombinant herpes simplex virus genome is a recombinant HSV-1 genome, a recombinant HSV-2 genome, or any derivatives thereof.

Embodiment 120: The vector of embodiment 118 or 119, wherein the recombinant herpes simplex virus genome comprises an inactivating mutation in an immediate early herpes simplex virus gene.

Embodiment 121: The vector of embodiment 120, wherein the herpes simplex virus gene is selected from the group consisting of ICP0, ICP4, ICP22, ICP27, ICP47, tk, UL41, and UL55.

Embodiment 122: The vector of any of embodiments 118 to 121, wherein the recombinant herpes simplex virus genome comprises an inactivating mutation in the ICP4 and ICP22 genes.

Embodiment 123: The vector of any of embodiments 118 to 121, wherein the recombinant herpes simplex virus genome comprises an inactivating mutation in the ICP0 and ICP4 genes.

Embodiment 124: The vector of embodiment 122 or 123, wherein the recombinant herpes simplex virus genome comprises an inactivating mutation in the ICP0, ICP4, and ICP22 genes.

Embodiment 125: The vector of any of embodiments 122 to 124, wherein the recombinant herpes simplex virus genome comprises an inactivating mutation in the ICP0, ICP4, ICP22, and ICP27 genes.

Embodiment 126: The vector of any of embodiments 122 to 125, wherein the recombinant herpes simplex virus genome comprises an inactivating mutation in the ICP0, ICP4, ICP22, ICP27, and UL55 genes.

Embodiment 127: The vector of any of embodiments 122 to 126, wherein the inactivating mutation is a deletion of the coding sequence of the genes.

Embodiment 128: The vector of any of embodiments 122 to 127, further comprising an inactivating mutation in the ICP47 gene.

Embodiment 129: The vector of any of embodiments 118 to 128, further comprising an inactivating mutation in the UL41 gene.

Embodiment 130: The vector of any of embodiments 118 to 129, wherein the recombinant herpes simplex virus genome comprises the polynucleotide within one or more viral gene loci.

Embodiment 131: The vector of any of embodiments 118 to130, wherein the recombinant herpes simplex virus genome comprises the polynucleotide within one or more of the ICP4 viral gene loci.

Embodiment 132: The vector of any of embodiments 118 to131, wherein the recombinant herpes simplex virus genome comprises the polynucleotide within the UL41 viral gene locus.

Embodiment 133: A vector comprising one or more polynucleotides encoding a Collagen alpha-1 (VII) chain polypeptide, a Lysyl hydroxylase 3 polypeptide, a Keratin type I cytoskeletal 17 polypeptide, or any combinations thereof, wherein the vector is a recombinant herpes simplex virus genome.

Embodiment 134: The vector of embodiment 133, wherein the recombinant herpes simplex virus genome is a recombinant HSV-1 genome, a recombinant HSV-2 genome, or any derivatives thereof.

Embodiment 135: The vector of embodiment 133 or 134, wherein the recombinant herpes simplex virus genome comprises an inactivating mutation in an immediate early herpes simplex virus gene.

Embodiment 136: The vector of embodiment 135, wherein the herpes simplex virus gene is selected from the group consisting of ICP0, ICP4, ICP22, ICP27, ICP47, tk, UL41, and UL55.

Embodiment 137: The vector of any of embodiments 133 to 136, wherein the recombinant herpes simplex virus genome comprises an inactivating mutation in the ICP4 and ICP22 genes.

Embodiment 138: The vector of any of embodiments 133 to 136, wherein the recombinant herpes simplex virus genome comprises an inactivating mutation in the ICP0 and ICP4 genes.

Embodiment 139: The vector of embodiment 137 or 138, wherein the recombinant herpes simplex virus genome comprises an inactivating mutation in the ICP0, ICP4, and ICP22 genes.

Embodiment 140: The vector of any of embodiments 137 to 139, wherein the recombinant herpes simplex virus genome comprises an inactivating mutation in the ICP0, ICP4, ICP22, and ICP27 genes.

Embodiment 141: The vector of any of embodiments 137 to 140, wherein the recombinant herpes simplex virus genome comprises an inactivating mutation in the ICP0, ICP4, ICP22, ICP27, and UL55 genes.

Embodiment 142: The vector of any of embodiments 137 to 141, wherein the inactivating mutation is a deletion of the coding sequence of the genes.

Embodiment 143: The vector of any of embodiments 137 to 142, further comprising an inactivating mutation in the ICP47 gene.

Embodiment 144: The vector of any of embodiments 133 to 143, further comprising an inactivating mutation in the UL41 gene.

Embodiment 145: The vector of any of embodiments 133 to 144, wherein the recombinant herpes simplex virus genome comprises the one or more polynucleotides within one or more viral gene loci.

Embodiment 146: The vector of any of embodiments 133 to 145, wherein the recombinant herpes simplex virus genome comprises the one or more polynucleotides within one or more of the ICP4 viral gene loci.

Embodiment 147: The vector of any of embodiments 133 to 146, wherein the recombinant herpes simplex virus genome comprises the one or more polynucleotides within the UL41 viral gene locus.

Embodiment 148: The vector of any of embodiments 133 to 147, wherein the vector comprises one polynucleotide encoding a Collagen alpha-1 (VII) chain polypeptide.

Embodiment 149: The vector of any of embodiments 133 to 147, wherein the vector comprises two polynucleotides encoding a Collagen alpha-1 (VII) chain polypeptide.

Embodiment 150: A host cell comprising the vector of any of embodiments 115 to 149.

Embodiment 151: A method of collecting a herpes simplex virus, wherein a vector of interest is packaged within said herpes simplex virus, the method comprising;
a) contacting a host cell with a vector encoding a helper virus;
b) contacting said host cell with a vector of any of embodiments 115 to 117; and
c) collecting the Herpes simplex virus generated by said host cell.

Embodiment 152: A method of collecting a herpes simplex virus, wherein a vector of interest is packaged within said herpes simplex virus, the method comprising;
a) contacting a complementing host cell with a vector of any of embodiments 118 to 149; and
b) collecting the herpes simplex virus generated by said complementing host cell.

Embodiment 153: The method of embodiment 151 or 152, wherein the herpes simplex virus is a herpes simplex type 1 virus, a herpes simplex type 2 virus, or any derivatives thereof.

Embodiment 154: A kit comprising:
a) the pharmaceutical composition of any of embodiments 1 to 52; and
b) instructions for administering the pharmaceutical composition.

Embodiment 155: A pharmaceutical composition comprising:
a) a virus comprising a vector, wherein the vector comprises one or more transgenes encoding a polypeptide selected from the group consisting of a Collagen alpha-1 (VII) chain polypeptide, a Lysyl hydroxylase 3 polypeptide, a Keratin type I cytoskeletal 17 polypeptide, and a chimeric polypeptide thereof; and
b) a pharmaceutically acceptable carrier.

Embodiment 156: The pharmaceutical composition of embodiment 155, wherein the virus is an adenovirus, adeno-associated virus, retrovirus, lentivirus, sendai virus, herpes simplex virus, vaccinia virus, or any hybrid virus thereof.

Embodiment 157: The pharmaceutical composition of embodiment 155, wherein the virus is a herpes simplex virus (HSV).

Embodiment 158: The pharmaceutical composition of any of embodiments 155 to 157, wherein the virus is replication-defective.

Embodiment 159: The pharmaceutical composition of any of embodiments 155 to 158, wherein the herpes simplex virus is a herpes simplex type 1 virus, a herpes simplex type 2 virus, or any derivatives thereof.

Embodiment 160: The pharmaceutical composition of any of embodiments 155 to 159, wherein the vector is an HSV-1 amplicon or an HSV-1 hybrid amplicon.

Embodiment 161: The pharmaceutical composition of embodiment 160, wherein the HSV-1 hybrid amplicon is an HSV/AAV hybrid amplicon, an HSV/EBV hybrid amplicon, and HSV/EBV/RV hybrid amplicon, or an HSV/Sleeping Beauty hybrid amplicon.

Embodiment 162: The pharmaceutical composition of any of embodiments 155 to 159, wherein the vector is a recombinant herpes simplex virus genome.

Embodiment 163: The pharmaceutical composition of embodiment 162, wherein the recombinant herpes simplex virus genome is a recombinant HSV-1 genome, a recombinant HSV-2 genome, or any derivatives thereof.

Embodiment 164: The pharmaceutical composition of embodiment 162 or 163, wherein the recombinant herpes simplex virus genome comprises an inactivating mutation in an immediate early herpes simplex virus gene.

Embodiment 165: The pharmaceutical composition of embodiment 164, wherein the herpes simplex virus gene is selected from the group consisting of ICP0, ICP4, ICP22, ICP27, ICP47, tk, UL41, and UL55.

Embodiment 166: The pharmaceutical composition of any of embodiments 162 to 165, wherein the recombinant herpes simplex virus genome comprises an inactivating mutation in the ICP4 and ICP22 genes.

Embodiment 167: The pharmaceutical composition of any of embodiments 162 to 165, wherein the recombinant herpes simplex virus genome comprises an inactivating mutation in the ICP0 and ICP4 genes.

Embodiment 168: The pharmaceutical composition of embodiment 166 or 167, wherein the recombinant herpes simplex virus genome comprises an inactivating mutation in the ICP0, ICP4, and ICP22 genes.

Embodiment 169: The pharmaceutical composition of any of embodiments 166 to 168, wherein the recombinant herpes simplex virus genome comprises an inactivating mutation in the ICP0, ICP4, ICP22, and ICP27 genes.

Embodiment 170: The pharmaceutical composition of any of embodiments 166 to 169, wherein the recombinant herpes simplex virus genome comprises an inactivating mutation in the ICP0, ICP4, ICP22, ICP27, and UL55 genes.

Embodiment 171: The pharmaceutical composition of any of embodiments 166 to 170, wherein the inactivating mutation is a deletion of the coding sequence of the genes.

Embodiment 172: The pharmaceutical composition of any of embodiments 166 to 171, further comprising an inactivating mutation in the ICP47 gene.

Embodiment 173: The pharmaceutical composition of any of embodiments 162 to 172, further comprising an inactivating mutation in the UL41 gene.

Embodiment 174: The pharmaceutical composition of any of embodiments 162 to 173, wherein the recombinant herpes simplex virus genome comprises the one or more transgenes within one or more viral gene loci.

Embodiment 175: The pharmaceutical composition of any of embodiments 162 to 174, wherein the recombinant herpes simplex virus genome comprises the one or more transgenes within one or more of the ICP4 viral gene loci.

Embodiment 176: The pharmaceutical composition of any of embodiments 162 to 175, wherein the recombinant herpes simplex virus genome comprises the one or more transgenes within the UL41 viral gene locus.

Embodiment 177: The pharmaceutical composition of embodiment 155, wherein the vector is capable of replicating within a target cell when delivered into said target cell.

Embodiment 178: The pharmaceutical composition of embodiment 155, wherein the pharmaceutically acceptable carrier is suitable for topical or transdermal administration.

Embodiment 179: The pharmaceutical composition of embodiment 155, wherein the pharmaceutically acceptable carrier is suitable for subcutaneous or intradermal administration.

Embodiment 180: The pharmaceutical composition of embodiment 155, wherein the one or more transgenes comprises an miRNA binding site.

Embodiment 181: The pharmaceutical composition of any of embodiments 155 to 180, wherein the vector comprises a transgene encoding a Collagen alpha-1 (VII) chain polypeptide.

Embodiment 182: The pharmaceutical composition of any of embodiments 155 to 180, wherein the vector comprises a transgene encoding a Lysyl hydroxylase 3 polypeptide.

Embodiment 183: The pharmaceutical composition of any of embodiments 155 to 180, wherein the vector comprises a transgene encoding a Keratin type I cytoskeletal 17 polypeptide.

Embodiment 184: The pharmaceutical composition of any of embodiments 155 to 180, wherein the Collagen alpha-1 (VII) chain polypeptide has at least 80% sequence identity to the sequence of SEQ ID NO: 2.

Embodiment 185: The pharmaceutical composition of any of embodiments 155 to 180, wherein the Collagen alpha-1 (VII) chain polypeptide is a fragment, wherein the fragment has at least 100 consecutive amino acids of SEQ ID NO: 2.

Embodiment 186: The pharmaceutical composition of any of embodiments 155 to 180, wherein the Collagen alpha-1 (VII) chain polypeptide enhances, increases, augments, and/or supplements anchoring fibril formation of a subject when the polypeptide is expressed in one or more target cells of the subject.

Embodiment 187: The pharmaceutical composition of any of embodiments 155 to 180, wherein the Collagen alpha-1 (VII) chain polypeptide enhances, increases, augments, and/or supplements epithelial basement membrane organization and/or epithelial basement adherence of a subject when the polypeptide is expressed in one or more target cells of the subject.

Embodiment 188: The pharmaceutical composition of any of embodiments 155 to 180, wherein the Lysyl hydroxylase 3 polypeptide has at least 80% sequence identity to the sequence of SEQ ID NO: 4.

Embodiment 189: The pharmaceutical composition of any of embodiments 155 to 180, wherein the Lysyl hydroxylase 3 polypeptide is a fragment, wherein the fragment has at least 100 consecutive amino acids of SEQ ID NO: 4.

Embodiment 190: The pharmaceutical composition of any of embodiments 155 to 180, wherein the Lysyl hydroxylase 3 polypeptide enhances, increases, augments, and/or supplements the formation of hydroxylysine residues on one or more collagen polypeptides of a subject when the Lysyl hydroxylase 3 polypeptide is expressed in one or more target cells of the subject.

Embodiment 191: The pharmaceutical composition of any of embodiments 155 to 180, wherein the Lysyl hydroxylase 3 polypeptide enhances, increases, augments, and/or supplements anchoring fibril formation, epithelial basement membrane organization, and/or epithelial basement adherence of a subject when the polypeptide is expressed in one or more target cells of the subject.

Embodiment 192: The pharmaceutical composition of any of embodiments 155 to 180, wherein the Keratin type I cytoskeletal 17 polypeptide has at least 80% sequence identity to the sequence of SEQ ID NO: 30.

Embodiment 193: The pharmaceutical composition of any of embodiments 155 to 180, wherein the Keratin type I cytoskeletal 17 polypeptide is a fragment, wherein the fragment has at least 100 consecutive amino acids of SEQ ID NO: 30.

Embodiment 194: The pharmaceutical composition of any of embodiments 155 to 180, wherein the Keratin type I cytoskeletal 17 polypeptide enhances, increases, augments, and/or supplements wound healing in a subject.

Embodiment 195: The pharmaceutical composition of any of embodiments 155 to 194, wherein the vector comprises at least a first transgene and a second transgene.

Embodiment 196: The pharmaceutical composition of embodiment 195, wherein the first transgene and the second transgene each encode a Collagen alpha-1 (VII) chain polypeptide.

Embodiment 197: The pharmaceutical composition of embodiment 195, wherein the first transgene encodes a Collagen alpha-1 (VII) chain polypeptide and the second transgene encodes a Lysyl hydroxylase 3 polypeptide.

Embodiment 198: The pharmaceutical composition of embodiment 195, wherein the first transgene encodes a Collagen alpha-1 (VII) chain polypeptide and the second transgene encodes a Keratin type I cytoskeletal 17 polypeptide.

Embodiment 199: The pharmaceutical composition of embodiment 195, wherein the first transgene encodes a Lysyl hydroxylase 3 polypeptide and the second transgene encodes a Keratin type I cytoskeletal 17 polypeptide.

Embodiment 200: The pharmaceutical composition of embodiment 155, wherein the vector comprises at least a first transgene, a second transgene, and a third transgene.

Embodiment 201: The pharmaceutical composition of embodiment 200, wherein the first transgene encodes a Collagen alpha-1 (VII) chain polypeptide, the second transgene encodes a Lysyl hydroxylase 3 polypeptide, and the third transgene encodes a Keratin type I cytoskeletal 17 polypeptide.

Embodiment 202: A method of providing prophylactic, palliative, or therapeutic relief of a wound, disorder, or disease of the skin in a subject, the method comprising administering to the subject a pharmaceutical composition comprising a vector, wherein the vector is a recombinant herpes simplex virus genome, and wherein the pharmaceutical composition is capable of enhancing, increasing, augmenting, and/or supplementing the levels of a Collagen alpha-1 (VII) chain polypeptide and/or a Lysyl hydroxylase 3 polypeptide and/or a Keratin type I cytoskeletal 17 polypeptide in one or more cells of the subject.

Embodiment 203: The method of embodiment 202, wherein the pharmaceutical composition comprises:
a) a virus comprising the vector, wherein the vector comprises one or more transgenes encoding a polypeptide selected from the group consisting of a Collagen alpha-1 (VII) chain polypeptide, a Lysyl hydroxylase 3 polypeptide, a Keratin type I cytoskeletal 17 polypeptide, and a chimeric polypeptide thereof; and
b) a pharmaceutically acceptable carrier.

Embodiment 204: The method of embodiment 203, wherein the virus is an adenovirus, adeno-associated virus, retrovirus, lentivirus, sendai virus, herpes simplex virus, vaccinia virus, or any hybrid virus thereof.

Embodiment 205: The method of embodiment 203, wherein the virus is a herpes simplex virus (HSV).

Embodiment 206: The method of any of embodiments 203 to 205, wherein the virus is replication-defective.

Embodiment 207: The method of any of embodiment 203 to 206, wherein the herpes simplex virus is a herpes simplex type 1 virus, a herpes simplex type 2 virus, or any derivatives thereof.

Embodiment 208: The method of any of embodiments 202 to 207, wherein the recombinant herpes simplex virus genome is a recombinant HSV-1 genome, a recombinant HSV-2 genome, or any derivatives thereof.

Embodiment 209: The method of embodiment 202 to 208, wherein the recombinant herpes simplex virus genome comprises an inactivating mutation in an immediate early herpes simplex virus gene.

Embodiment 210: The method of embodiment 209, wherein the herpes simplex virus gene is selected from the group consisting of ICP0, ICP4, ICP22, ICP27, ICP47, tk, UL41, and UL55.

Embodiment 211: The method of any of embodiments 202 to 210, wherein the recombinant herpes simplex virus genome comprises an inactivating mutation in the ICP4 and ICP22 genes.

Embodiment 212: The method of any of embodiments 202 to 210, wherein the recombinant herpes simplex virus genome comprises an inactivating mutation in the ICP0 and ICP4 genes.

Embodiment 213: The method of embodiment 211 or 212, wherein the recombinant herpes simplex virus genome comprises an inactivating mutation in the ICP0, ICP4, and ICP22 genes.

Embodiment 214: The method of any of embodiments 211 to 213, wherein the recombinant herpes simplex virus genome comprises an inactivating mutation in the ICP0, ICP4, ICP22, and ICP27 genes.

Embodiment 215: The method of any of embodiments 211 to 214, wherein the recombinant herpes simplex virus genome comprises an inactivating mutation in the ICP0, ICP4, ICP22, ICP27, and UL55 genes.

Embodiment 216: The method of any of embodiments 211 to 215, wherein the inactivating mutation is a deletion of the coding sequence of the genes.

Embodiment 217: The method of any of embodiments 211 to 216, further comprising an inactivating mutation in the ICP47 gene.

Embodiment 218: The method of any of embodiments 202 to 217, further comprising an inactivating mutation in the UL41 gene.

Embodiment 219: The method of any of embodiments 202 to 218, wherein the recombinant herpes simplex virus genome comprises the one or more transgenes within one or more viral gene loci.

Embodiment 220: The method of any of embodiments 202 to 219, wherein the recombinant herpes simplex virus genome comprises the one or more transgenes within one or more of the ICP4 viral gene loci.

Embodiment 221: The method of any of embodiments 202 to 220, wherein the recombinant herpes simplex virus genome comprises the one or more transgenes within the UL41 viral gene locus.

Embodiment 222: The method of embodiment 202, wherein the vector is capable of replicating within a target cell when delivered into said target cell.

Embodiment 223: The method of embodiment 203, wherein the pharmaceutically acceptable carrier is suitable for topical or transdermal administration.

Embodiment 224: The method of embodiment 203, wherein the pharmaceutically acceptable carrier is suitable for subcutaneous or intradermal administration.

Embodiment 225: The method of embodiment 203, wherein the one or more transgenes comprises an miRNA binding site.

Embodiment 226: The method of any of embodiments 202 to 225, wherein the vector comprises a transgene encoding a Collagen alpha-1 (VII) chain polypeptide.

Embodiment 227: The method of any of embodiments 202 to 225, wherein the vector comprises a transgene encoding a Lysyl hydroxylase 3 polypeptide.

Embodiment 228: The method of any of embodiments 202 to 225, wherein the vector comprises a transgene encoding a Keratin type I cytoskeletal 17 polypeptide.

Embodiment 229: The method of any of embodiments 202 to 225, wherein the Collagen alpha-1 (VII) chain polypeptide has at least 80% sequence identity to the sequence of SEQ ID NO: 2.

Embodiment 230: The method of any of embodiments 202 to 225, wherein the Collagen alpha-1 (VII) chain polypeptide is a fragment, wherein the fragment has at least 100 consecutive amino acids of SEQ ID NO: 2.

Embodiment 231: The method of any of embodiments 202 to 225, wherein the Collagen alpha-1 (VII) chain polypeptide enhances, increases, augments, and/or supplements anchoring fibril formation of a subject when the polypeptide is expressed in one or more target cells of the subject.

Embodiment 232: The method of any of embodiments 202 to 225, wherein the Collagen alpha-1 (VII) chain polypeptide enhances, increases, augments, and/or supplements epithelial basement membrane organization and/or epithelial basement adherence of a subject when the polypeptide is expressed in one or more target cells of the subject.

Embodiment 233: The method of any of embodiments 202 to 225, wherein the Lysyl hydroxylase 3 polypeptide has at least 80% sequence identity to the sequence of SEQ ID NO: 4.

Embodiment 234: The method of any of embodiments 202 to 225, wherein the Lysyl hydroxylase 3 polypeptide is a fragment, wherein the fragment has at least 100 consecutive amino acids of SEQ ID NO: 4.

Embodiment 235: The method of any of embodiments 202 to 225, wherein the Lysyl hydroxylase 3 polypeptide enhances, increases, augments, and/or supplements the formation of hydroxylysine residues on one or more collagen polypeptides of a subject when the Lysyl hydroxylase 3 polypeptide is expressed in one or more target cells of the subject.

Embodiment 236: The method of any of embodiments 202 to 225, wherein the Lysyl hydroxylase 3 polypeptide enhances, increases, augments, and/or supplements anchoring fibril formation, epithelial basement membrane organization, and/or epithelial basement adherence of a subject when the polypeptide is expressed in one or more target cells of the subject.

Embodiment 237: The method of any of embodiments 202 to 225, wherein the Keratin type I cytoskeletal 17 polypeptide has at least 80% sequence identity to the sequence of SEQ ID NO: 30.

Embodiment 238: The method of any of embodiments 202 to 225, wherein the Keratin type I cytoskeletal 17 polypeptide is a fragment, wherein the fragment has at least 100 consecutive amino acids of SEQ ID NO: 30.

Embodiment 239: The method of any of embodiments 202 to 225, wherein the Keratin type I cytoskeletal 17 polypeptide enhances, increases, augments, and/or supplements wound healing in a subject.

Embodiment 240: The method of any of embodiments 202 to 239, wherein the vector comprises at least a first transgene and a second transgene.

Embodiment 241: The method of embodiment 240, wherein the first transgene and the second transgene each encode a Collagen alpha-1 (VII) chain polypeptide.

Embodiment 242: The method of embodiment 240, wherein the first transgene encodes a Collagen alpha-1 (VII) chain polypeptide and the second transgene encodes a Lysyl hydroxylase 3 polypeptide.

Embodiment 243: The method of embodiment 240, wherein the first transgene encodes a Collagen alpha-1 (VII) chain polypeptide and the second transgene encodes a Keratin type I cytoskeletal 17 polypeptide.

Embodiment 244: The method of embodiment 240, wherein the first transgene encodes a Lysyl hydroxylase 3 polypeptide and the second transgene encodes a Keratin type I cytoskeletal 17 polypeptide.

Embodiment 245: The method of any of embodiments 202 to 239, wherein the vector comprises at least a first transgene, a second transgene, and a third transgene.

Embodiment 246: The method of embodiment 245, wherein the first transgene encodes a Collagen alpha-1 (VII) chain polypeptide, the second transgene encodes a Lysyl hydroxylase 3 polypeptide, and the third transgene encodes a Keratin type I cytoskeletal 17 polypeptide.

Embodiment 247: The method of any of embodiments 202 to 246, wherein the pharmaceutical composition is administered topically or transdermally to the subject.

Embodiment 248: The method of any of embodiments 202 to 246, wherein the pharmaceutical composition is administered subcutaneously or intradermally to the subject.

Embodiment 249: The method of any of embodiments 202 to 248, wherein the pharmaceutical composition is administered one, two three, four, five or more times per day.

Embodiment 250: The method of any of embodiments 202 to 249, wherein the pharmaceutical composition is administered to one or more affected and/or unaffected areas of the subject.

Embodiment 251: The method of any of embodiments 202 to 250, wherein the disease or disorder of the skin is one or more of epidermolysis bullosa, skin cancer, psoriasis, lichen planus, lupus, rosacea, eczema, cutaneous candidiasis, cellulitis, impetigo, decubitus ulcers, erysipelas, ichthyosis vulgaris, dermatomyositis, acrodermatitis, stasis dermatitis, nethertons syndrome, epidermolysis bullosa simplex (LAMB3 gene), autosomal recessive congenital ichthyosis, xeroderma pigmentosa, and pemphigoid.

The specification is considered to be sufficient to enable one skilled in the art to practice the invention. Various modifications of the invention in addition to those shown and described herein will become apparent to those skilled in the art from the foregoing description and fall within the scope of the appended claims.

EXAMPLES

The present disclosure will be more fully understood by reference to the following example. It should not, however, be construed as limiting the scope of the present disclosure. It is understood that the examples and embodiments described herein are for illustrative purposes only and that various modifications or changes in light thereof will be suggested to persons skilled in the art and are to be included within the spirit and purview of this application and scope of the appended claims.

Figure 1D:
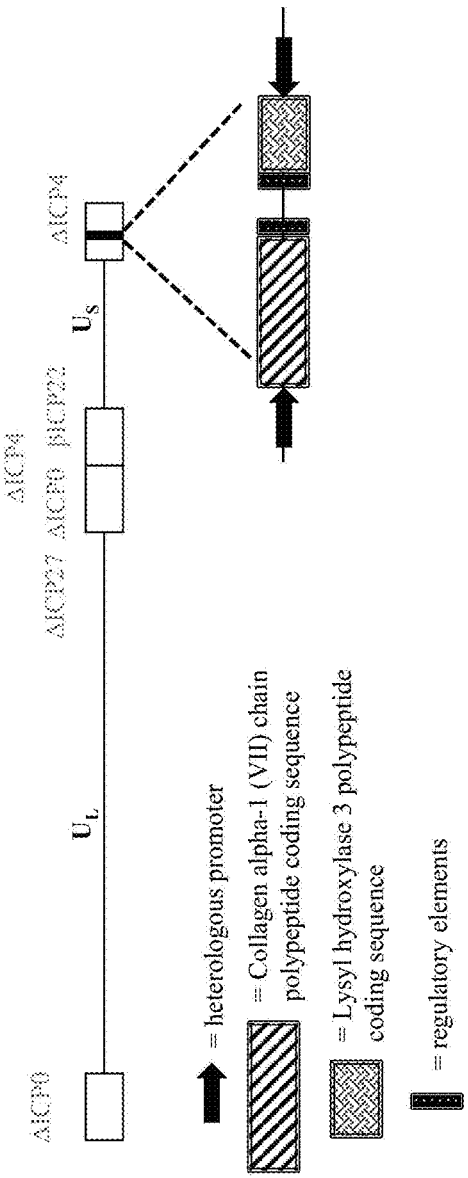

Example 1: Generating Modified Herpes Simplex Virus Vectors, and Producing/Isolating Virus Containing the Vectors To make modified herpes simplex virus genome vectors capable of expressing one or more transgenes in a target mammalian cell, a herpes simplex virus genome (FIG. 1A) is modified to inactivate the immediate early genes ICP0, ICP4, and ICP27, while the immediate early gene ICP22 is modified to include a heterologous, inducible promoter. This decreases the toxicity of the genome in mammalian cells. Next, a cassette is inserted into the modified herpes virus genome by restriction cloning. The cassette contains a heterologous promoter capable of expressing a transgene in a target mammalian cell. The promoter is operably linked to the nucleic acid sequence encoding a Collagen alpha-1 (VII) chain polypeptide, as well as downstream regulatory elements (FIG. 1B) ensuring proper production of the mRNA. Alternatively, the cassette includes two transgenes, each of which has its own heterologous promoter operably linked to the nucleic acid encoding either a Collagen alpha-1 (VII) chain polypeptide or a Lysyl hydroxylase 3 polypeptide. The transgenes are encoded either on the same strand of DNA (FIG. 1C), or on opposite strands of DNA in an antisense orientation (FIG. 1D). Linking each transgene with its own promoter and regulatory elements allows for independent expression of each coding sequence on separate mRNA transcripts. Expressing the transgenes from distinct promoters allows for the ability to operably link the coding sequences to different promoter types, which can drive expression of the transgenes at different levels, at different times in the cell cycle, in different cell types, or under the control of different inducers or repressors.

Figure 1E:
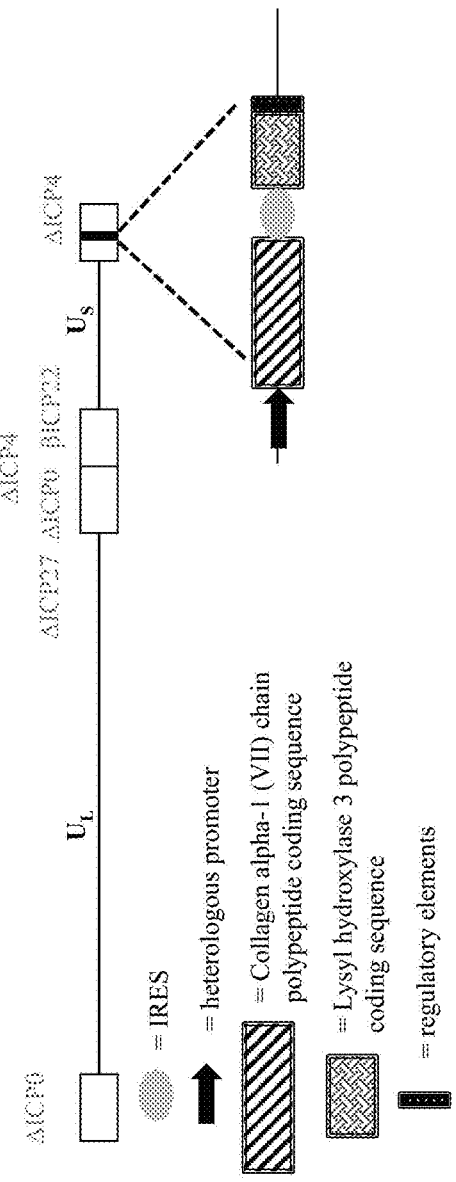
Figure 1F:
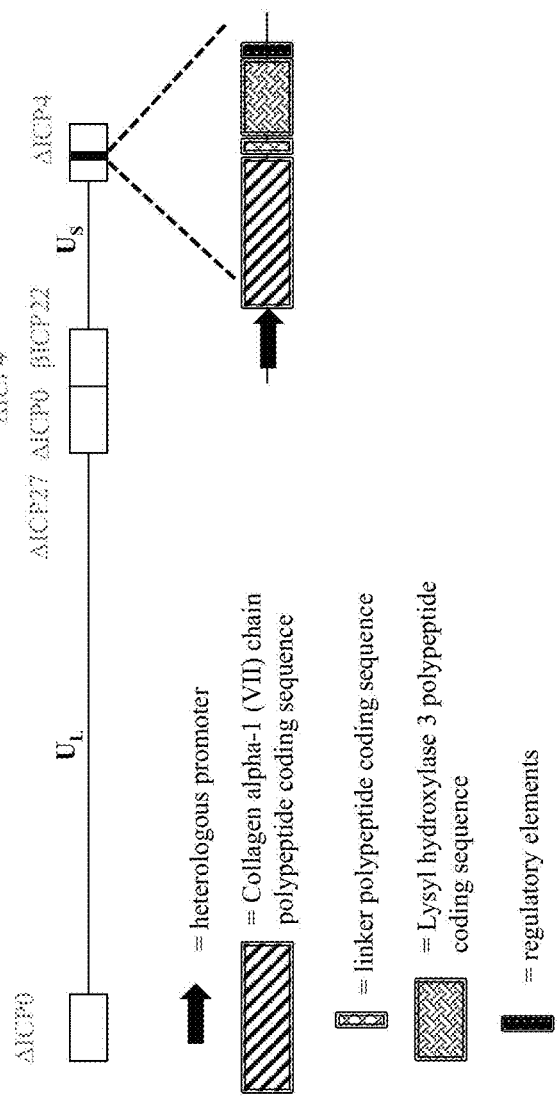

A modified herpes virus genome is also constructed that includes a cassette expressing a single mRNA encoding a Collagen alpha-1 (VII) chain polypeptide and a Lysyl hydroxylase 3 polypeptide separated by an internal ribosomal entry site (FIG. 1E). This allows for approximately equimolar production of each polypeptide when expressed in a target cell. Finally, a modified herpes virus genome is constructed that includes a cassette expressing a chimeric polypeptide. This chimeric polypeptide includes, from N-terminus to C-terminus, a Collagen alpha-1 (VII) chain polypeptide, a cleavable peptide linker, and a Lysyl hydroxylase 3 polypeptide (FIG. 1F).

Figure 2A:
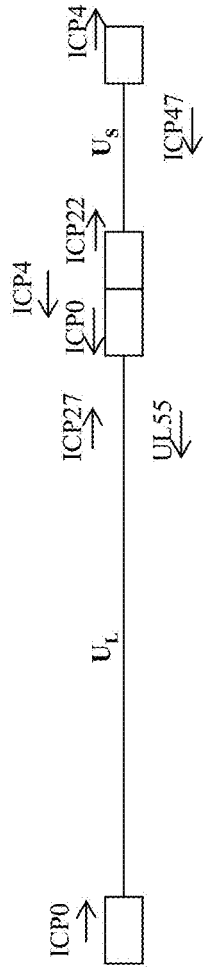

Additional modified herpes virus genomes are constructed that include two cassettes, each expressing Collagen alpha-1 (VII) chain polypeptides, where each cassette is inserted into a copy of the ICP4 gene locus (FIGS. 2B-2G) of the wild-type herpes simplex virus genome (FIG. 2A). These additional recombinant herpes virus genomes are constructed with various combinations of herpes virus gene deletions/modifications.

Figure 2B:
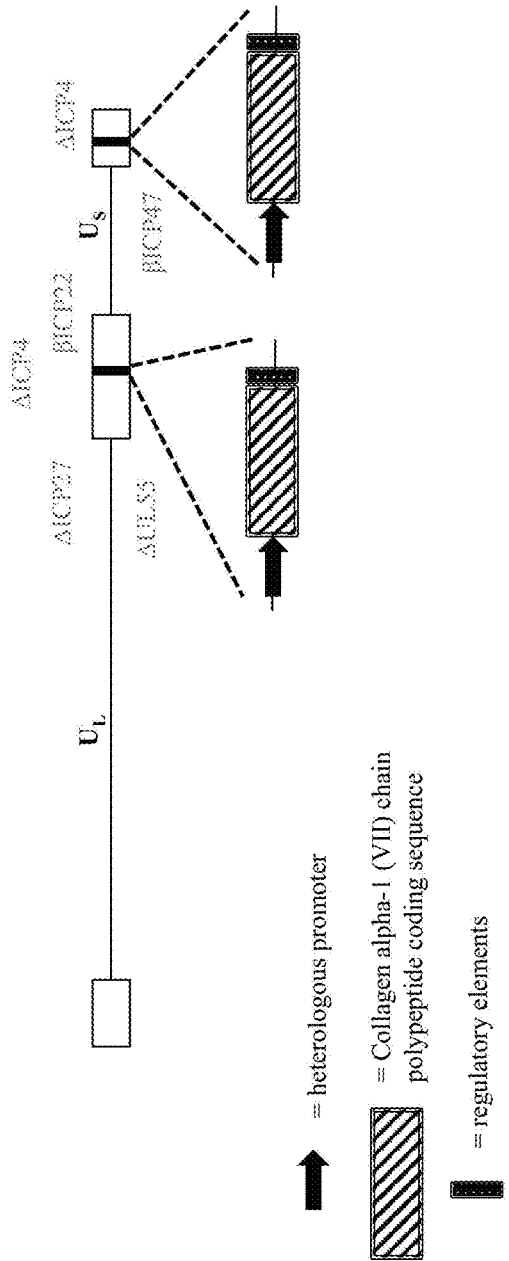
Figure 2C:
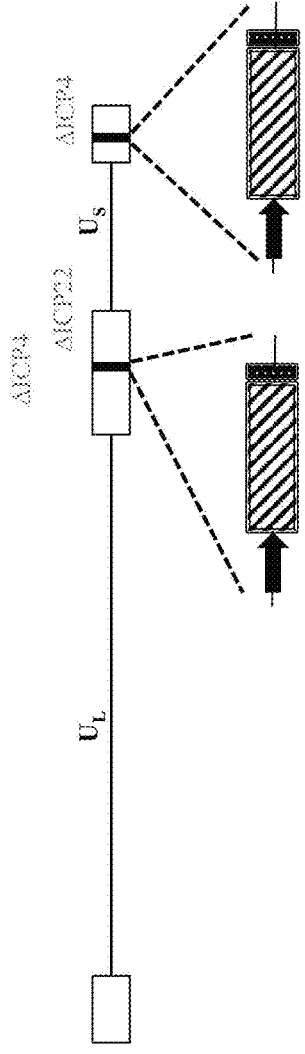
Figure 2D:
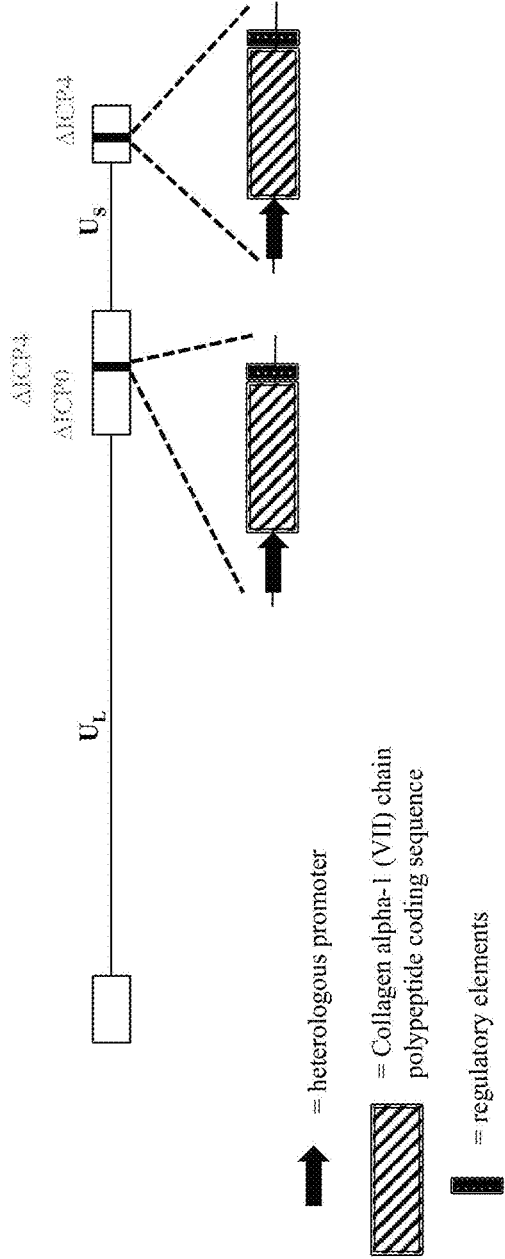
Figure 2E:
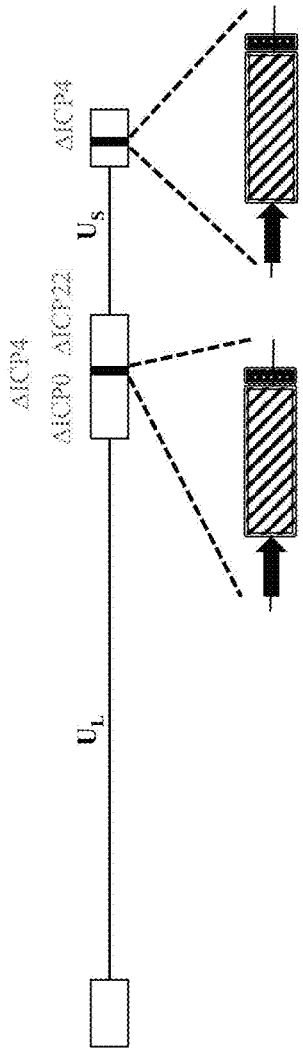
Figure 2F:
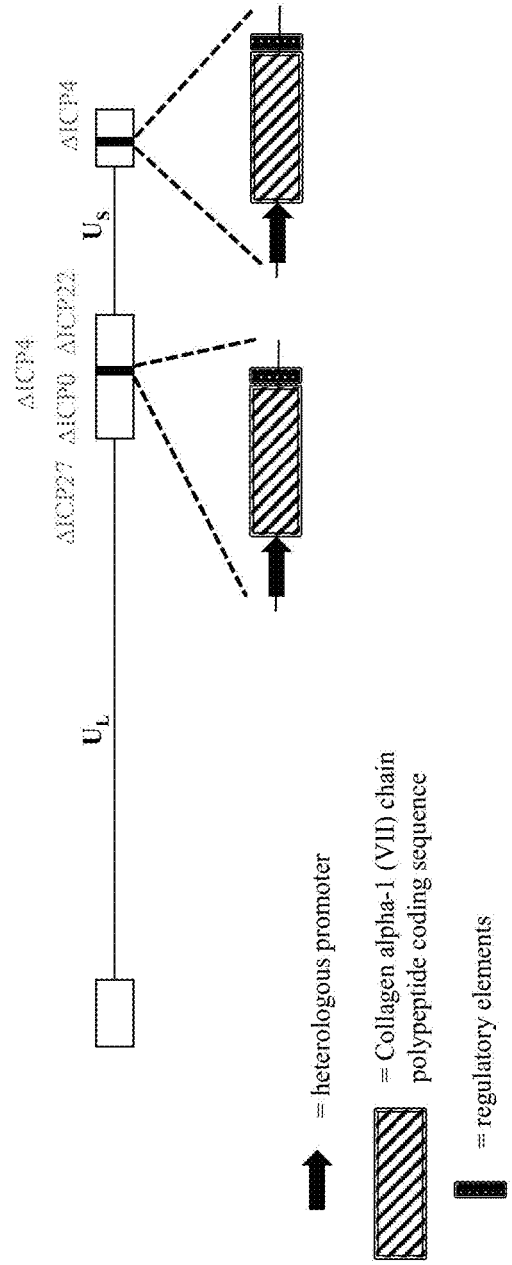

A recombinant herpes virus genome is constructed which contains deletions of the coding sequences of both copies of the ICP4 gene, as well as deletions of the coding sequences of the ICP27 and UL55 genes. These recombinant viruses are further modified to contain inactivating mutations in the promoter regions of the ICP22 and ICP47 genes such that the ICP22 and ICP47 genes are not expressed with normal kinetics (FIG. 2B).

Further recombinant herpes simplex viruses are constructed which incorporate expression cassettes for Collagen alpha-1 (VII) chain polypeptides into both loci of the herpes ICP4 genes. These recombinant viruses include: viruses containing deletions of the coding sequences of the ICP22 gene and both copies of the ICP4 gene (FIG. 2C); deletions of the coding sequences of the ICP0 gene and both copies of the ICP4 gene (FIG. 2D); deletions of the coding sequences of the ICP0 and ICP22 genes, and both copies of the ICP4 gene (FIG. 2E); deletions of the coding sequences of the ICP0, ICP22, and ICP27 genes, and both copies of the ICP4 gene (FIG. 2F); and deletions of the coding sequences of the ICP0, ICP22, ICP27, and UL55 genes, and both copies of the ICP4 gene (FIG. 2G). Additional vectors are constructed based upon the vectors shown in FIGS. 2C-2G which further comprise one or more transgenes encoding one or more additional effectors (e.g., LH3, KRT17) in the ICP0 and/or UL41 loci.

These modified herpes simplex virus genome vectors are transfected into engineered Vero cells that are modified to express herpes virus genes. These engineered Vero cells secrete replication-defective herpes simplex virus with the modified genomes packaged within into the supernatant. The supernatant is then collected, concentrated, and sterile filtered through a 5 μm filter.

Example 2: Rescuing Col7 Expression with Replication Defective HSV-1

The following example describes the construction of a replication defective herpes simplex type-1 virus modified to express the human COL7A1 gene, and use of such a viral vector to rescue several defects observed in cells isolated from RDEB patients.

Methods
Cells and Cell Culture

Normal and RDEB human dermal fibroblasts and keratinocytes were isolated as described previously (NG, Y. Z. et al. (2012) *Cancer Res.* 72: 3522-3534; Rheinwald, J. G. and Green, H. (1975) *Cell* 6: 331-42). Cells were cultured according to standard techniques. Construction of KB103

The KB103 vector was generated from D3GFP, a replication-defective HSV-1 vector backbone harboring GFP in place of the viral ICP4. The sequence of the GFP in D3GFP was replaced with the coding sequence of human COL7A1 using a transfer plasmid by cloning COL7A1 into the EcoRI site of the ICP4 recombination plasmid pSASB3. A mixed transfection/infection of the COL7A1 containing transfer plasmid and D3GFP vector was performed on VeroD cells. Resulting plaques which did not express GFP were isolated and tested by western blot for Col7 protein expression.

Virus Purification

KB103 virus was purified according to standard techniques (See Diefenbach, R. and Fraefel, C. Herpes Simplex Virus. New York: Humana Press, 2014).

Viral Infections

Cells were seeded in duplicates or triplicates in six-well plates at approximately 50% confluency one day prior to viral infection. An additional well was seeded in parallel for cell counting and MOI determination. 24 hours after cell seeding, cells from one well were trypsinized and counted to calculate the MOI, and viral stocks were thawed and diluted in cell culture medium to achieve the desired MOI. Culture medium was aspirated from each well to be infected, and 500 μL of KB103-containing medium (or control medium) was added to each well. Plates were incubated at 37° C. with 5-7.5% $CO_2$ for 1.5-2 hours with intermittent rocking every 15-20 minutes, then 1.5-2 mL of complete cell culture medium was added to each well, and the plates were incubated for 24-72 hours at 37° C. After incubation, the cells and supernatants were harvested and processed for analysis.

mRNA Quantification

Col7 transcripts were amplified from RNA isolated from primary RDEB keratinocytes after infection using a SYBR PCR assay (Sybr Select Master Mix, Life Technologies) according to the manufacturer's protocol. Col7 transcript levels were normalized to (3-actin transcript levels.

Western Blot Analysis

Cell lysates were generated from cells 48 hours post-infection, and western blots were carried out according to standard techniques using the following antibodies: rabbit anti-human Col7 polyclonal antibody (Sigma, Cat. #HPA042420), mouse anti-human GAPDH antibody (Santa Cruz Biotechnology, Cat. #sc-365062), rabbit anti-LH3 antibody (Protein Tech, Cat. #11027-1-AP), and mouse anti-TSP1 antibody (Santa Cruz Biotechnology, Cat. #sc-59887).

Immunofluorescence

Cells were plated on cover slips prior to infection, fixed 48 hours post-infection, and stained with a primary rabbit anti-human Col7 polyclonal antibody (Sigma, Cat. #HPA042420), washed, and further stained with a fluorescently labelled anti-rabbit secondary antibody (Invitrogen, Cat. 3 A11012). Cell nuclei were stained with DAPI using standard techniques.

Cellular Adhesion 96-well plates were coated with 10, 20, or 50 μg/mL rat tail Collagen 1 (Marathon Laboratory Supply) or human fibronectin (Sigma-Aldrich) in 100 μL reaction volume at 4° C. overnight, then washed with PBS, and blocked with PBS+0.1% BSA for 1 hour at 37° C. Mock (control) infected or KB103 infected RDEB keratinocytes ($2.4*10^4$ cells in 100 μL of DMEM/HamF12+0.1% BSA) were added to the plates and incubated at 37° C. for 40-90 minutes. Wells were washed three times with PBS to remove any unbound cells, and adherent cells were fixed with PFE for 20 minutes. The fixed cells were then treated with 70% ethanol, stained with crystal violet, resolved in 100% ethanol, and were quantified by measuring absorbance at 630 nm.

Skin Equivalent (SE) Organotypic Cultures

A skin equivalent organotypic culture composed of RDEB fibroblasts and keratinocytes was used to evaluate the expression of Col7 at the basement membrane zone (BMZ). Briefly, RDEB fibroblasts ($2*10^5$ cells per well) were embedded in fibrin gel matrix in six-well plates and incubated in DMEM+10% serum containing ascorbic acid and aprotinin for 24 hours at 37° C. and 5% $CO_2$. RDEB keratinocytes ($1*10^6$ cells per well) were then seeded on the matrix, grown to confluence in DMEM/F-12 keratinocyte medium containing 50 mg/mL of ascorbic acid, and raised at the air-liquid interface. Two days post raising, KB103 virus was added to the cultures (at an MOI of 3) and incubated for 1.5 hours. Following incubation, cultures were washed and incubated for 5-14 days to favor stratification and differentiation into an epithelium. Skin equivalents (SEs) were manually detached from the plates and embedded in optimal cutting temperature compound, frozen in liquid nitrogen, and cut into 6 mm sections for immunofluorescence staining with a monoclonal anti-Col7 antibody.

Results

KB103 Pharmacology in Normal and RDEB Cells

A number of ex vivo approaches have been undertaken to deliver the human COL7A1 gene to primary cells isolated from RDEB patients in an attempt to correct Col7 deficiencies (Ortiz-Urda, S. et al. (2003) *J Clin. Invest.* 111(2) 251-5; Woodley, D. T. et al. (2003) *J Invest. Dematol.* 121(5) 1021-8). Although successful in achieving durable correction of key disease features, an ex vivo gene delivery strategy for treating epidermolysis bullosa has a number of key disadvantages, including high cost, poor graft takes, surgical debridement, complex bandaging and wound care, and the high potential for post-surgical infection. An attractive alternate route for gene therapy is the use of viral or non-viral vectors to deliver gene products. However, non-viral vectors using plasmid DNA suffer from very low gene transfer efficiency when injected or topically administered, while the most widely used viral vectors in human gene therapy trials (retroviral vectors) do not infect non-dividing cells. This is problematic for gene delivery to the skin, as manipulation of the tissue (such as wounding) to create an adequate population of dividing cells would be required for retroviral gene therapy. Large-capacity adenoviral vectors can deliver genome-sized transcription units and survive in transduced cells for long periods of time, but the toxicity and immunogenicity of adenoviral particles, as well as the requirements for helper virus during vector production, remain as significant hurdles for their use in human gene therapy strategies. While replication-defective HSV vectors have been employed as delivery vehicles in a number of pre-clinical studies, no pre-clinical evidence supporting the use of HSV-based viral vectors for epidermolysis bullosa or other dermatological applications has been reported.

Figure 3:
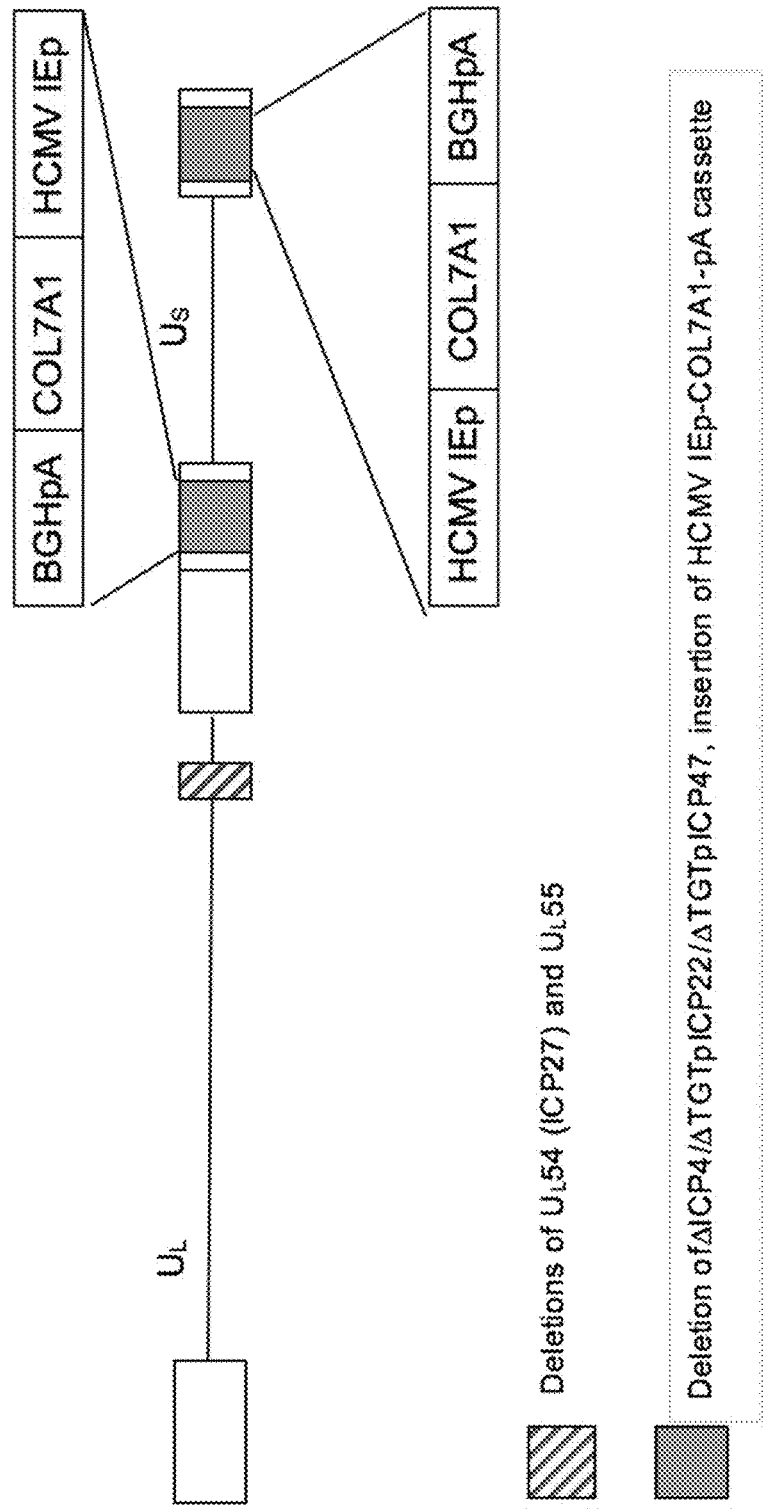
FIG. 3 shows a schematic of "KB103", a replication-defective herpes simplex type-1 virus (HSV-1) carrying a human collagen 7 (COL7A1) expression cassette.

To this end, a replication defective herpes simplex type-1 virus (HSV-1) encoding the human COL7A1 gene was developed as a novel vector useful for gene therapy treatment of DEB patients. An HSV-1 virus was modified to harbor complete deletions of the viral ICP4, ICP27, and UL55 genes, with the ICP4 deletion resulting in the removal of the upstream promoter sequences driving the transcription of the immediate early viral genes ICP22 and ICP47. The virus was further modified to include a human cytomegalovirus (HCMV) immediate early promoter-driven human COL7A1 expression cassette encoded within both copies of the deleted ICP4 loci, resulting in a replication-defective HSV-1 vector, termed KB103, suitable for delivering human COL7A1 to target cells (FIG. 3).

To test the ability of KB103 to deliver and express Col7 in human cells, and to rescue Col7 deficiencies in RDEB patients, patient-derived human dermal fibroblasts and keratinocytes were isolated from healthy individuals, as well as individuals suffering from RDEB, and these primary cells were infected with KB103 at various MOIs. 24-72 hours post infection, COL7A1 gene expression was measured by real-time PCR in transduced cells, while Col7 protein expression was analyzed in parallel by both western blot and immunofluorescence analysis.

Figure 4A:
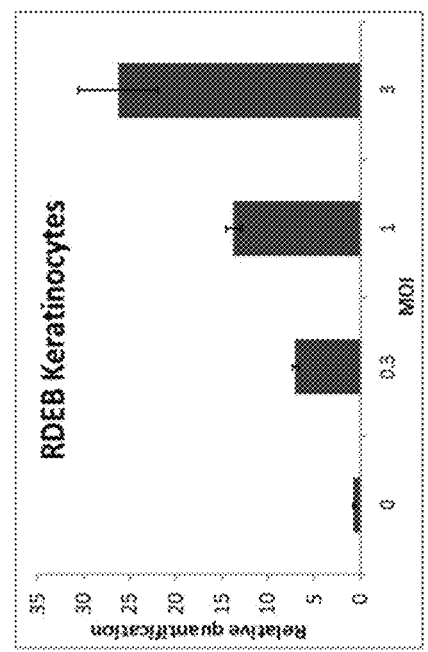
FIGS. 4A-4B show dose-dependent increases in COLT transcript levels from KB103-infected RDEB human dermal keratinocytes (FIG. 4A) and RDEB human dermal fibroblasts (FIG. 4B). Transcripts were quantified relative to (3-actin levels and normalized to expression in uninfected cells.
Figure 4B:
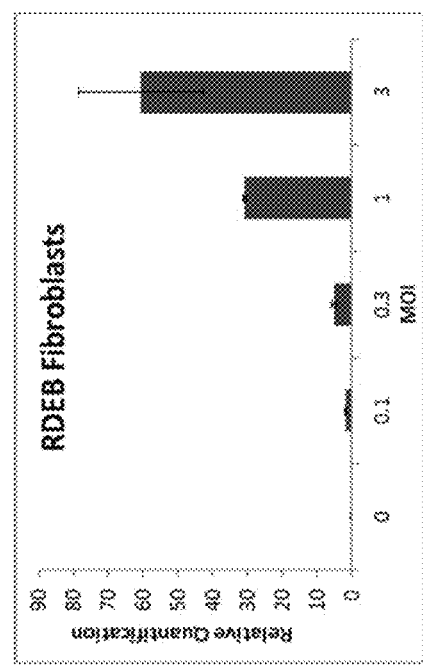

Dose-dependent increases in COL7A1 gene expression were observed in RDEB keratinocytes (FIG. 4A) and fibroblasts (FIG. 4B) infected with KB103. KB103 infection increased COL7A1 gene expression by approximately 7.5 fold, 12.5 fold, and 25 fold in RDEB keratinocytes infected at an MOI of 0.3, 1, and 3, respectively (FIG. 4A). Surprisingly, even more drastic changes in COL7A1 gene expression was observed in infected RDEB fibroblasts. While infections at an MOI of 0.1 and 0.3 showed moderate increases in COL7A1 gene expression, an approximate 30 fold increase in COL7A1 gene expression was measured for RDEB fibroblasts infected at an MOI of 1, while a 60 fold increase was observed in this cell type infected at an MOI of 3. This data showed that COL7A1 gene expression was massively upregulated in RDEB primary cells after infection with KB103.

Figure 5A:
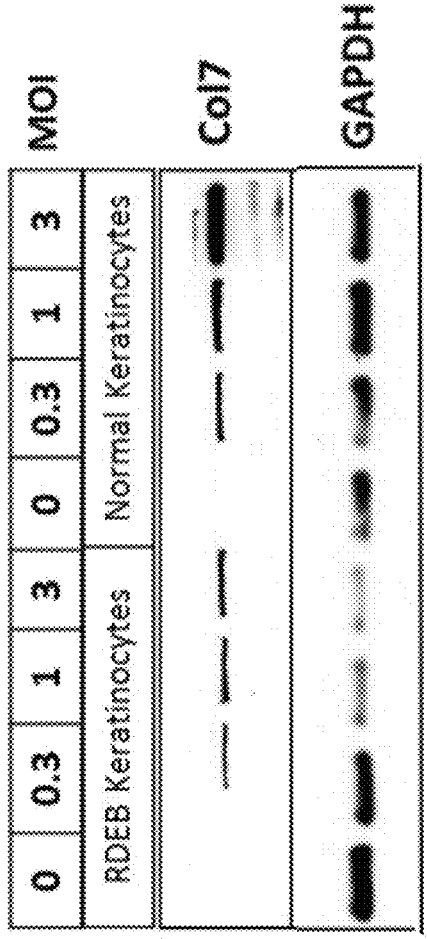
FIGS. 5A-5B show human Col7 protein expression detected in KB103-infected cells.
Figure 5B:
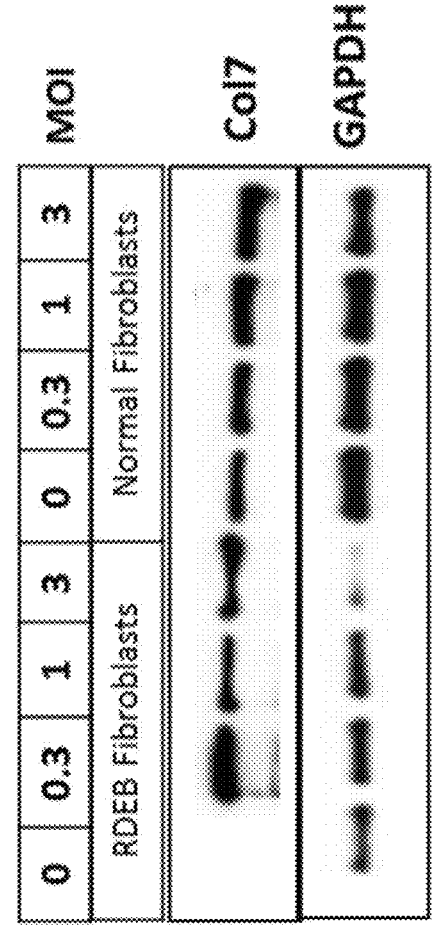

Consequently, robust Col7 protein expression was also observed in cells infected with KB103. Col7 protein expression was detected in both normal and RDEB keratinocytes (FIG. 5A) and fibroblasts (FIG. 5B) 48 hours after infection with KB103 at an MOI of 0.3, 1, and 3, with an apparent dose-dependent increase in Col7 protein expression observed at higher viral titers. Expression of Col7 was observed in both the supernatants and cell lysates from infected cells. Surprisingly, RDEB fibroblasts infected at an MOI of 0.3 showed higher levels of Col7 than was observed in uninfected normal fibroblasts (FIG. 5B), suggesting complete rescue of Col7 expression in RDEB fibroblasts using KB103, even at low viral titers. No obvious effects on cell morphology using high viral doses (MOI of 3) were observed. Additionally, no negative impacts on fibroblast or keratinocyte cell proliferation using high doses of KB103 were indicated in these experiments, as determined by GAPDH expression.

Figure 6:
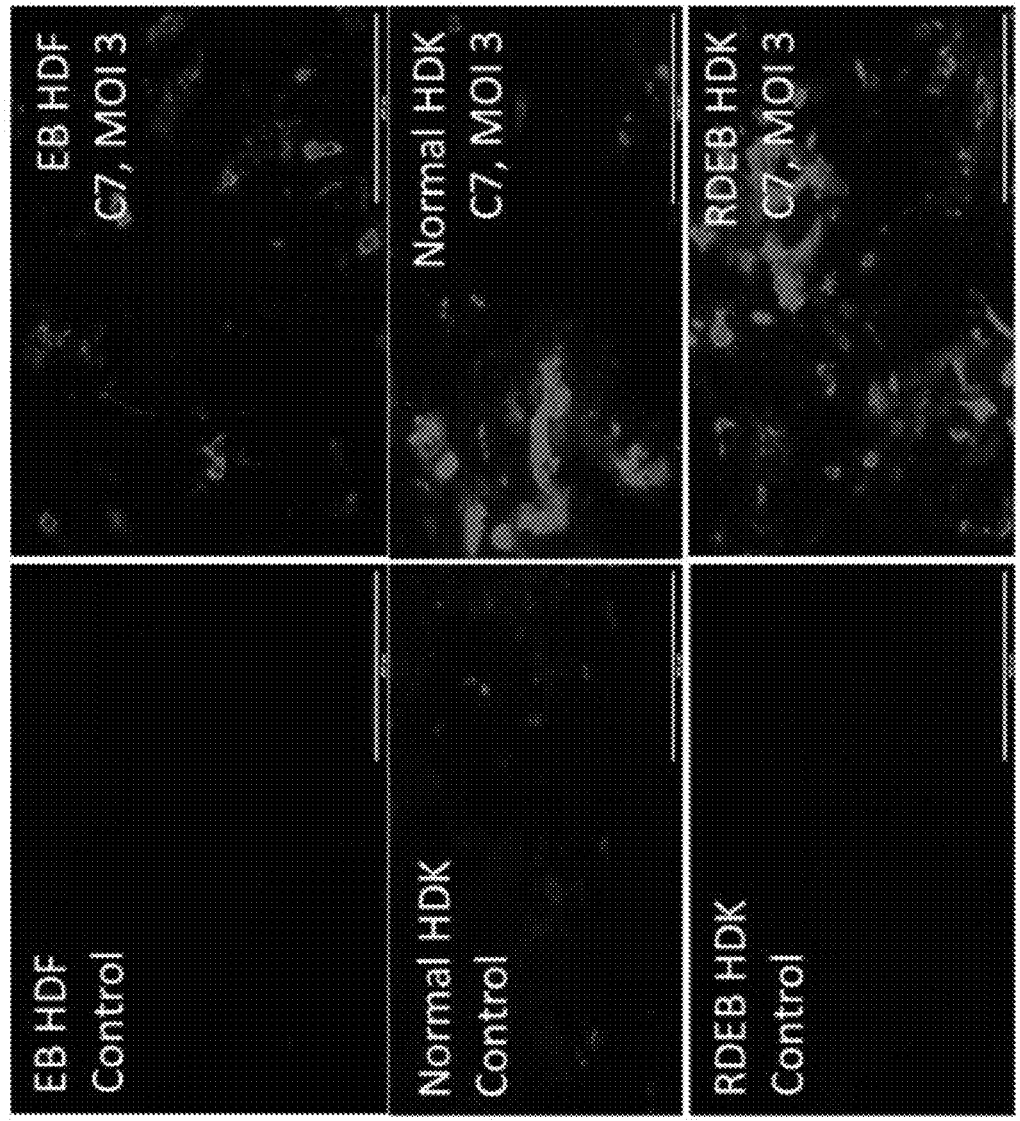
FIG. 6 shows human COL7A1 protein expression in uninfected (control) or KB103 infected (C7, MOI 3) RDEB human dermal fibroblasts (EB HDF), normal human dermal keratinocytes (Normal HDK), and RDEB human dermal keratinocytes (RDEB HDK), as assessed by immunofluorescence.
Figure 7:
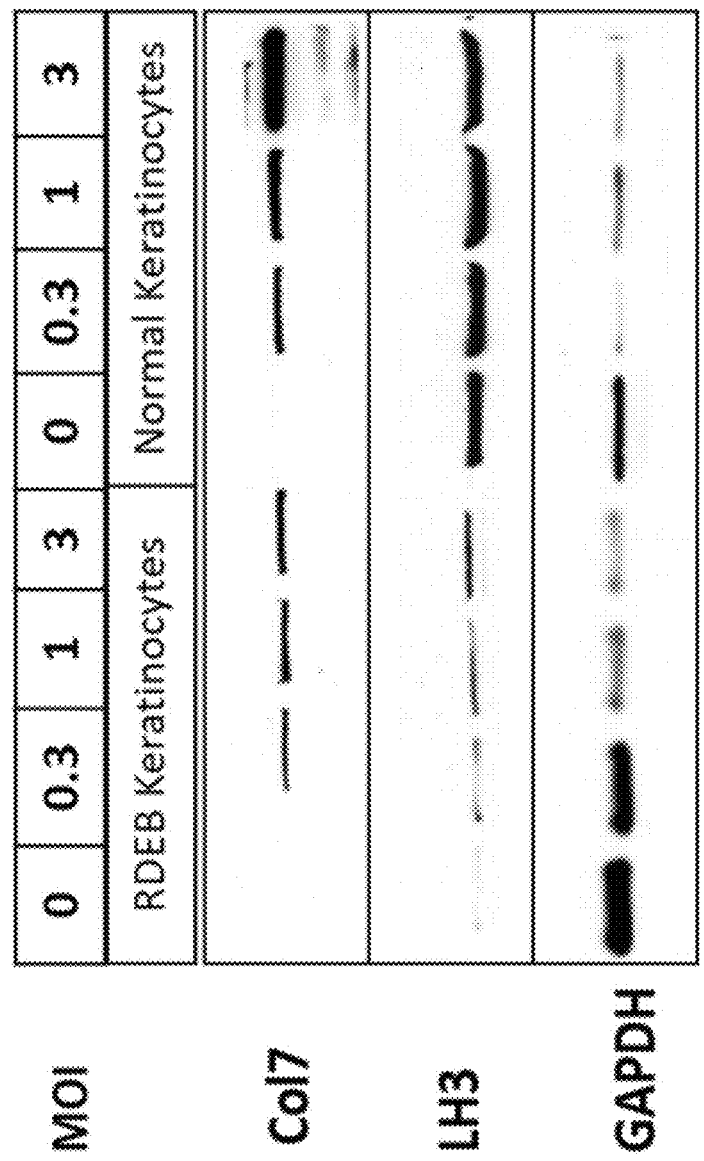
FIG. 7 shows human Col7 and LH3 protein expression in uninfected normal and RDEB human dermal keratinocytes, as well as keratinocytes infected with KB103 at the indicated MOI. Human GAPDH protein expression is shown as a loading control.

In agreement with the above experiments, a robust and dose-dependent increase in Col7 protein expression was confirmed in normal and RDEB cells infected with KB103, as demonstrated by immunofluorescent detection of Col7 protein expression (FIG. 6). As expected, no Col7 protein was detected in uninfected RDEB human dermal fibroblasts or keratinocytes; limited Col7 protein was detected in uninfected normal keratinocytes and fibroblasts. However, infection with KB103 was capable of rescuing Col7 protein expression in RDEB fibroblasts and keratinocytes at or above the levels observed in uninfected normal cells. Furthermore, infection efficiency of KB103 (at an MOI of 3) was calculated to be >95% based on an assessment of three or more independent panels for each infected replicate, showing that KB103 efficiently delivered and expressed the COL7A1 expression cassette. Taken together, this data suggested that KB103 was capable of delivering and expressing COL7A1 in normal and RDEB primary cells, and that KB103 was well tolerated by both human dermal fibroblasts and keratinocytes. Functional assessment of KB103 in RDEB cells The functionality of the human Col7 protein expressed from KB103 was next investigated in human dermal fibroblasts and keratinocytes. First, the effect of Col7 expression on the levels of lysyl hydroxylase 3 was tested in KB103-infected cells. LH3 is required for the deposition and organization of extracellular matrix, and it has been reported that LH3 levels are reduced in RDEB skin (Watt, S. A. et al. (2015) PLoS One 10(9): p. e0137639). Little to no LH3 was observed in uninfected RDEB keratinocytes relative to normal keratinocytes (FIG. 7, lanes 1 vs. 5), in agreement with previous studies. However, unexpectedly, a dose-dependent increase in LH3 levels, concomitant with increased Col7 protein expression, was observed in RDEB keratinocytes infected with KB103 (FIG. 7), suggesting that KB103 was capable of rescuing not only Col7 protein expression, but also LH3 expression in RDEB cells.

Figure 8:
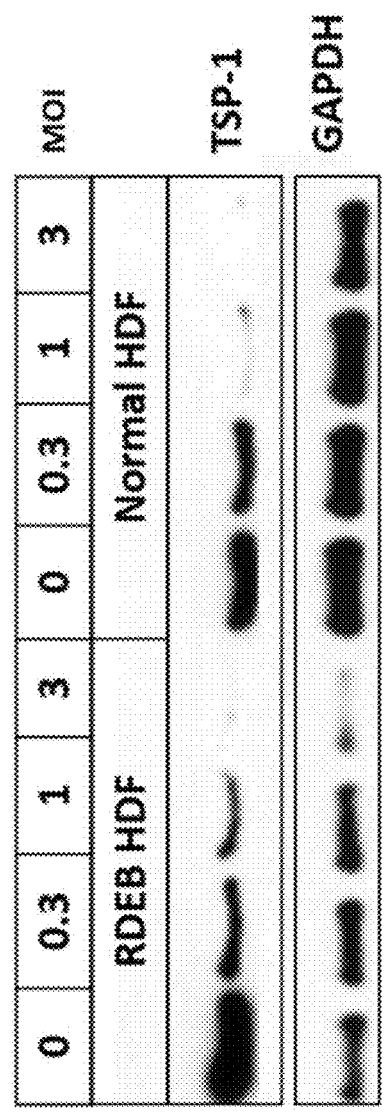
FIG. 8 shows human TSP-1 protein expression in uninfected normal and RDEB human dermal fibroblasts, as well as fibroblasts infected with KB103 at the indicated MOI. Human GAPDH protein expression is shown as a loading control.

Next, the effect of Col7 expression on TSP-1 levels was tested. TSP-1 is a negative regulator of angiogenesis, and has been reported to be increased in RDEB fibroblasts (Ng, Y. Z. et al. (2012) Cancer Res. 72(14): p. 3522-34). In agreement with previous studies, higher levels of TSP-1 were observed in uninfected RDEB vs. normal human dermal fibroblasts (FIG. 8, lanes 1 and 4). Surprisingly, TSP-1 protein expression was robustly inhibited upon infection of either normal or RDEB fibroblasts infected with KB103 (FIG. 8). This data suggested that KB103 may not only increase Col7 and LH3 levels in infected cells, but may also promote angiogenesis by inhibiting the negative regulator TSP-1.

Figure 9A:
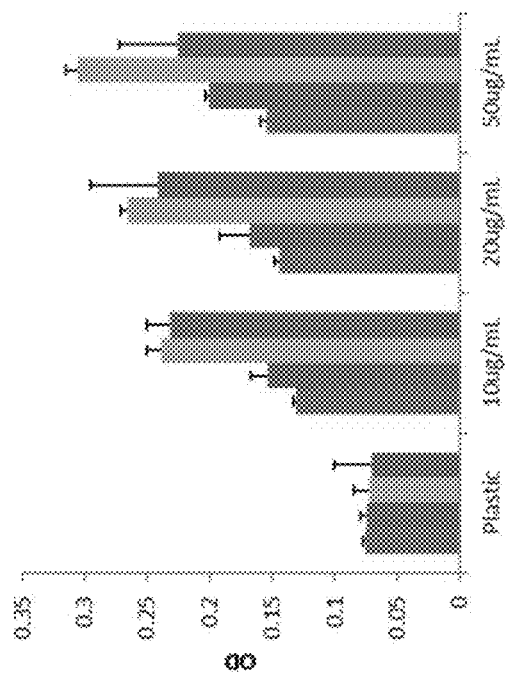
FIGS. 9A-9B show cellular adhesion of uninfected (control) RDEB human dermal keratinocytes, and keratinocytes infected with KB103 at the indicated MOIs, to wells treated with increasing concentration of rat tail Collagen 1 (FIG. 9A) and human Fibronectin (FIG. 9B)
Figure 9B:
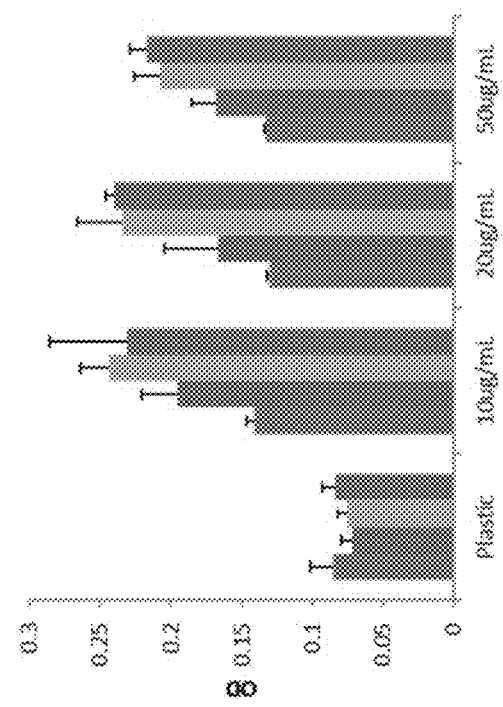

Finally, the ability of KB103 to increase cellular adherence of RDEB keratinocytes to either Collagen 1 or Fibronectin was tested. A dose-dependent increase in cellular adherence to both Collagen 1 and Fibronectin was observed in RDEB keratinocytes infected with KB103 at various MOIs (FIGS. 9A and 9B). Infection of RDEB keratinocytes at all MOIs tested showed higher adhesion to wells treated with all concentrations of both substrates relative to uninfected (control) cells. Taken together, this data indicated that the human Col7 protein expressed from KB103 was functional in the transduced cells. Functionality of this protein was indicated by its ability to increase LH3 protein levels, decrease TSP-1 protein levels, and improve cellular adherence to both Collagen 1 and Fibronectin relative to mock-infected samples.

KB103 Pharmacology and Toxicity in RDEB Organotypic Cultures

Figure 10:
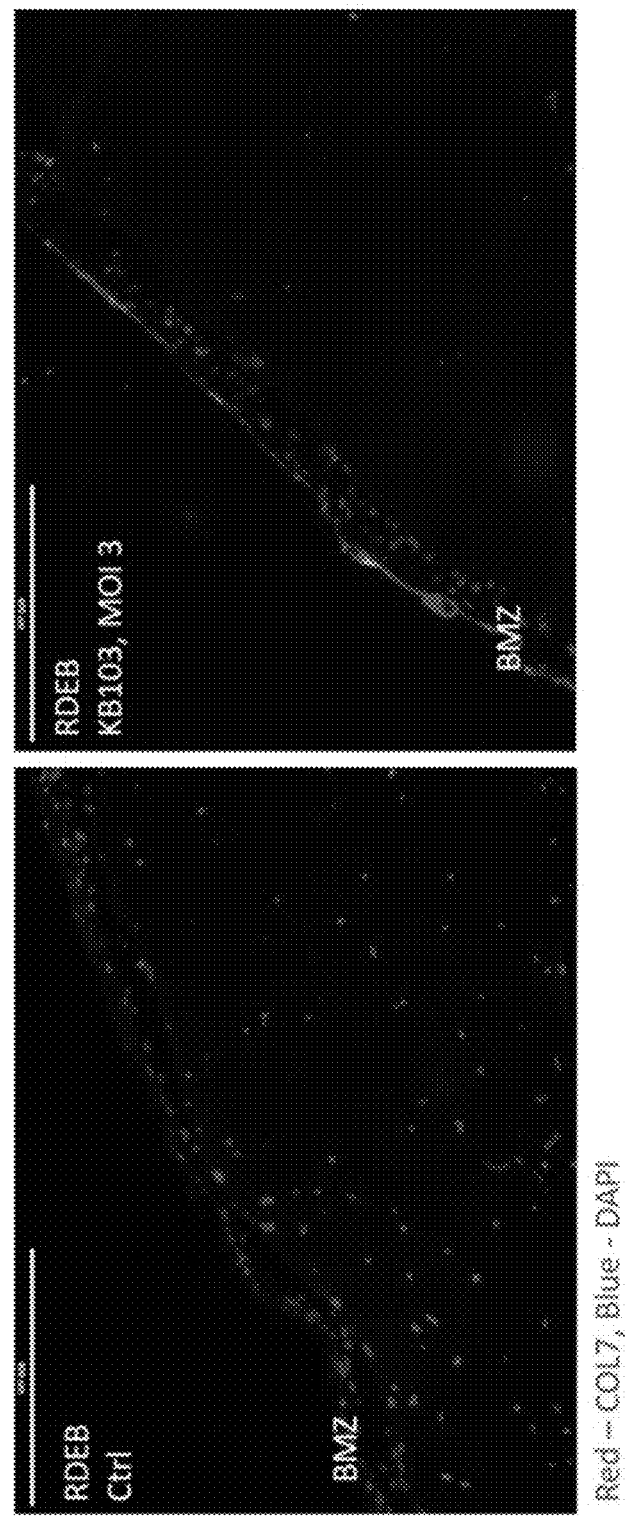
FIG. 10 shows Col7 deposition at the basement membrane zone (BMZ) in KB103 infected skin-equivalent organotypic cultures by immunofluorescence.

A skin equivalent (SE) organotypic culture composed of RDEB fibroblasts and keratinocytes was used to evaluate the expression of Col7 protein expressed from KB103 at the Basement Membrane Zone (BMZ). RDEB fibroblasts and keratinocytes were mock infected or infected with KB103 at an MOI of 3, and incubated for 5 days to favor stratification and differentiation into epithelium. The resulting skin equivalents (SEs) were isolated, sectioned, and stained for immunofluorescence to detect Col7 protein expression. Col7 expression was detected in these organotypic cultures from cells infected with KB103, and the initiation of Col7 protein deposition at the BMZ was observed relative to mock-infected controls (FIG. 10). This data suggested that not only could KB103 deliver COL7A1 and express Col7 protein efficiently, but the Col7 protein began to organize in organotypic cultures similar to the pattern of organization expected for Col7 protein in vivo.

Taken as whole, these experiments revealed, for the first time, that a replication-defective HSV-1 vector may be employed as a vehicle for delivering a COL7A1 expression cassette into primary cells isolated from epidermolysis bullosa patients. Moreover, these data revealed that Col7 protein could be expressed at high levels from this expression cassette in two different human cell types from healthy individuals, as well as individuals suffering from a dermatological disorder. Finally, the Col7 protein was shown to be functional, as it was capable of increasing expression of LH3, decreasing expression of TSP-1, increasing cellular adherence to Collagen 1 and Fibronectin, and could organize in organotypic cultures in a pattern similar to the organization of Col7 in vivo. Without wishing to be bound by theory, the data presented herein suggests that KB103 and other HSV-1 vectors may be useful as novel in vivo treatment strategies for epidermolysis bullosa and/or other dermatological applications.

Example 3: In Vivo Col7 Expression Using Replication Defective HSV-1

The following example describes the use of a replication defective herpes simplex type-1 virus (modified to contain a human COL7A1 transgene) as a delivery vehicle for expression of human Col7 protein in vivo.

Methods

Construction and Purification of KB 103

The KB103 virus was constructed and purified as described in Example 2 above. Viral infections KB103 virus was delivered to wild-type Balb/c or skhl-elite mice by intradermal injection as follows: each animal was injected once at 2-4 sites within the flank region of the animal with $1 \times 10^8$ plaque forming units (PFU) of virus/site in a volume of 50 µL. Animals were sacrificed 48 hours post KB103 administration, and the inject sites were harvested and processed for either real time qPCR or immunofluorescence analysis.

For qPCR analysis, skin tissue was dissected down to the fascia using a 6 mm punch biopsy tool. The biopsy was bisected into two pieces, and each piece was snap frozen using liquid nitrogen. Total RNA and DNA were isolated from one half of the biopsy using the Qiagen AllPrep DNA/RNA kit.

For immunofluorescence analysis, a circular area approximately one cm in diameter was excised from skin at the injection site, cut in half, and mounted in OCT so that the central portion of the circular area was facing upward. The prepared samples were freeze plunged into liquid nitrogen cooled isopentane, and stored at −80° C.

mRNA Quantification

Col7 transcripts were amplified from RNA isolated from mouse dermal tissue after KB103 injection using a 2-step protocol: 1) cDNA synthesis was carried out using the superscript III First Strand Synthesis kit (Thermofisher, Cat. #18-080-051), and 2) qPCR amplification was performed using the Quantitect Probe PCR kit (Qiagen, Cat. #204345) according to the manufacturer's protocol. 100 ng of cDNA was used in each reaction. Col7 transcript levels were normalized to GAPDH transcript levels.

Genome Copy Quantification

The copy number of KB103 viral genomes in the KB103 injected mice was quantified by qPCR amplification using the Quantitect Probe PCR kit (Qiagen Cat. #204345). 100 ng of mouse genomic DNA was used in each reaction, and mouse genomic GAPDH was used as a control.

Immunofluorescence

Tissue sections from mice injected with KB103 were fixed, and subsequently stained with a primary rabbit anti-human Col7 polyclonal antibody (Sigma, Cat. #HPA042420), washed, and further stained with a fluorescently labelled anti-rabbit secondary antibody (Invitrogen, Cat. 3 A11012). Cell nuclei were stained with DAPI using standard techniques.

Results

Figure 11:
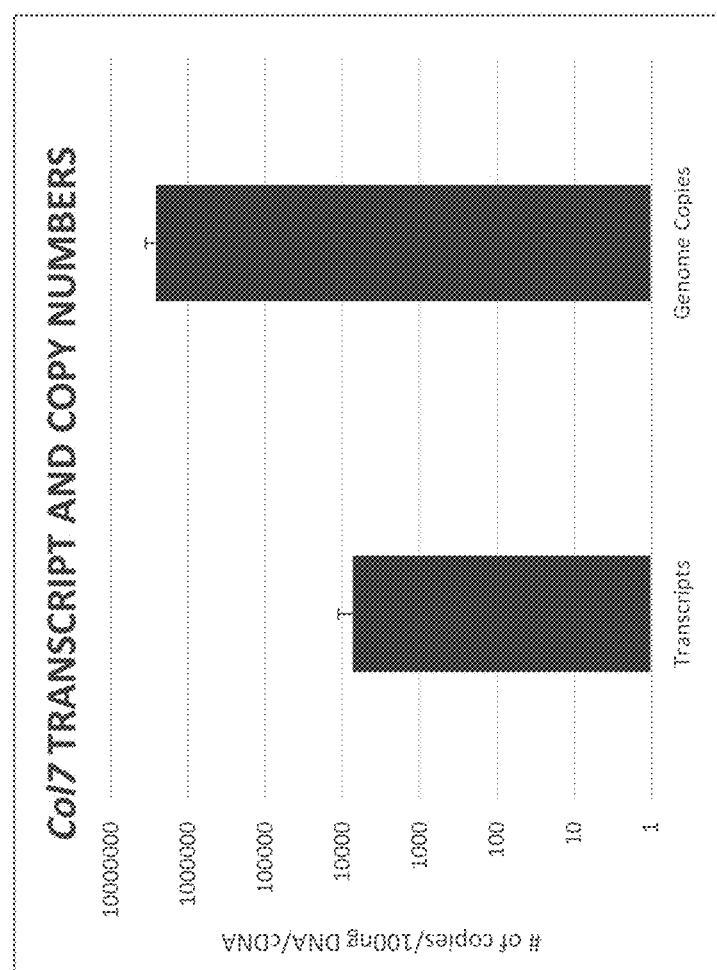
FIG. 11 shows the quantification of viral genome copy number and human Col7 transcript levels in tissue isolated from KB103-infected mice.
Figure 12:
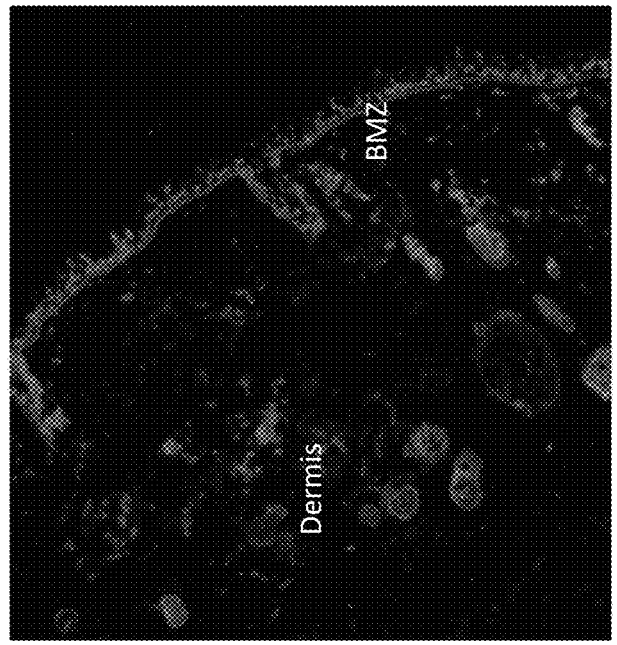
FIG. 12 shows human Col7 protein expression in dermal tissue from KB103-infected mice by immunofluorescence, including the initiation of human Col7 deposition at the basement membrane zone (BMZ).

To test the ability of KB103 to successfully deliver and express human Col7 protein in vivo, mice were intradermally administered the KB103 virus. Viral genome copy number in infected mouse tissue was assessed, and delivery of high levels (>1,000,000 viral genome copies/100 ng mouse DNA) of the KB103 viral genome was observed in the mice (FIG. 11). Next, the ability of the ability of the virus to express human Col7 in vivo was examined. Quantification of human Col7 transcripts in KB103-infected mice were measured and assessed compared to expression of a control mouse housekeeping gene. High levels of human Col7 transcript were observed in the infected mouse tissue (FIG. 11), suggesting that the delivered viral genomes were capable of successfully expressing their human gene cargo. Finally, the ability of KB103 to express Col7 protein was tested in the infected mice. Mouse dermal tissue was excised from mice after infection, and Col7 protein expression was assessed by immunohistochemical staining of the mouse tissue. High levels of human Col7 protein were detected after tissue staining (FIG. 12). Surprisingly, not only was human Col7 protein expressed from the KB103 virus in mouse dermis, but the initiation of deposition of human Col7 at the Basement Membrane Zone in KB103-infected mice was observed (FIG. 12). Without wishing to be bound by theory, this data suggests that: 1) the KB103 virus can successfully infect relevant tissue in vivo, delivering high genome copy numbers to these tissues tissue, 2) delivery of the KB103 virus to relevant tissue results in significant expression of the encoded human genes on this virus, and 3) KB103 not only successfully expresses human Col7 protein in vivo, but this protein is capable of beginning to organize (e.g. at the Basement Membrane Zone) in a way suggesting its ability to rescue endogenous Col7 defects in affected individuals.

The invention claimed is:

1. A method of delivering a human transgene to an eye of a subject, the method comprising administering to the eye of the subject a pharmaceutical composition comprising:
   a) a replication-defective herpes simplex virus type-1 (HSV-1) comprising a recombinant HSV-1 genome, wherein the recombinant HSV-1 genome comprises one or more polynucleotides comprising the human transgene; and
   b) a pharmaceutically acceptable carrier,
   wherein the pharmaceutical composition is administered topically or via injection to the eye of the subject,
   wherein the one or more polynucleotides comprising the human transgene are operably linked to a promoter suitable for transcription in a mammalian cell,
   wherein the subject has a disorder or disease of the eye associated with vision loss,
   wherein the recombinant HSV-1 genome comprises an inactivating mutation in one or both copies of the ICP4 HSV-1 gene, and
   wherein the recombinant HSV-1 genome comprises an inactivating mutation in the ICP22 HSV-1 gene.

2. The method of claim 1, wherein the injection is intravitreal injection.

3. The method of claim 1, wherein the replication-defective HSV-1 is suitable for delivering the one or more polynucleotides comprising the human transgene to one or more target cells of the eye of the subject.

4. The method of claim 1, wherein the inactivating mutation in one or both copies of the ICP4 HSV-1 gene is a deletion of at least a portion of the coding sequence of the ICP4 HSV-1 gene.

5. The method of claim 1, wherein the one or more polynucleotides comprising the human transgene is in one or both of the ICP4 viral gene loci.

6. The method of claim 1, wherein the inactivating mutation in the ICP22 HSV-1 gene is a deletion of at least a portion of the coding sequence of the ICP22 HSV-1 gene.

7. The method of claim 1, wherein the recombinant HSV-1 genome comprises an inactivating mutation in one or both copies of an ICP0 HSV-1 gene, an ICP27 HSV-1 gene, an ICP47 HSV-1 gene, a tk HSV-1 gene, an UL41 HSV-1 gene, or an UL55 HSV-1 gene.

8. The method of claim 1, wherein the subject is a human.

9. The method of claim 1, wherein the replication-defective HSV-1 has reduced cytotoxicity when compared to its wild-type counterpart.

10. The method of claim 1, wherein the inactivating mutation in the ICP22 HSV-1 gene is a deletion of at least a portion of the promoter region of the ICP22 HSV-1 gene.

11. A method of delivering a human transgene to an eye of a subject, the method comprising:
   providing a pharmaceutical composition comprising:
      a) a replication-defective HSV-1 comprising a recombinant HSV-1 genome, wherein the recombinant HSV-1 genome comprises one or more polynucleotides comprising the human transgene, wherein the one or more polynucleotides comprising the human transgene are operably linked to a promoter suitable for transcription in a mammalian cell,
      wherein the recombinant HSV-1 genome comprises an inactivating mutation in one or both copies of the ICP4 HSV-1 gene,
      wherein the replication-defective HSV-1 is suitable for delivering the one or more polynucleotides comprising the human transgene to the epidermis and/or dermis of the subject; and b) a pharmaceutically acceptable carrier; and administering the pharmaceutical composition topically or via injection to the eye of the subject that has a disorder or disease of the eye associated with vision loss.

12. The method of claim 11, wherein the injection is intravitreal injection.

13. The method of claim 11, wherein the replication-defective HSV-1 is suitable for delivering the one or more polynucleotides comprising the human transgene to one or more target cells of the eye of the subject.

14. The method of claim 11, wherein the inactivating mutation in one or both copies of the ICP4 HSV-1 gene is a deletion of at least a portion of the coding sequence of the ICP4 HSV-1 gene.

15. The method of claim 11, wherein the one or more polynucleotides comprising the human transgene is in one or both of the ICP4 viral gene loci.

16. The method of claim 11, wherein the recombinant HSV-1 genome comprises an inactivating mutation in the ICP22 HSV-1 gene.

17. The method of claim 16, wherein the inactivating mutation in the ICP22 HSV-1 gene is a deletion of at least a portion of the coding sequence of the ICP22 HSV-1 gene.

18. The method of claim 16, wherein the inactivating mutation in the ICP22 HSV-1 gene is a deletion of at least a portion of the promoter region of the ICP22 HSV-1 gene.

19. The method of claim 11, wherein the recombinant HSV-1 genome comprises an inactivating mutation in one or both copies of an ICP0 HSV-1 gene, an ICP22 HSV-1 gene, an ICP27 HSV-1 gene, an ICP47 HSV-1 gene, a tk HSV-1 gene, an UL41 HSV-1 gene, or an UL55 HSV-1 gene.

20. The method of claim 11, wherein the subject is a human.

21. The method of claim 11, wherein the replication-defective HSV-1 has reduced cytotoxicity when compared to its wild-type counterpart.

* * * * *

SEQUENCE LISTING

```
Sequence total quantity: 30
SEQ ID NO: 1            moltype = DNA  length = 8835
FEATURE                 Location/Qualifiers
source                  1..8835
                        mol_type = unassigned DNA
                        organism = Homo sapiens
SEQUENCE: 1
atgacgctgc ggcttctggt ggccgcgctc tgcgccggga tcctggcaga ggcgccccga   60
gtgcgagccc agcacaggga gagagtgacc tgcacgcgcc tttacgccgc tgacattgtg  120
ttcttactgg atggctcctc atccattggc cgcagcaatt tccgcgaggt ccgcagcttt  180
ctcgaagggc tggtgctgcc tttctctgga gcagccagtg cacagggtgt gcgctttgcc  240
acagtgcagt acagcgatga cccacggaca gagttcggcc tggatgcact tggctctggg  300
ggtgatgtga tccgcgccat ccgtgagctt agctacaagg ggggcaacac tcgcacaggg  360
gctgcaattc tccatgtggc tgaccatgtc ttcctgcccc agctggcccg acctggtgtc  420
cccaaggtct gcatcctgat cacagacggg aagtcccagg acctggtgga cacagctgcc  480
caaggctga aggggcaggg ggtcaagcta tttgctgtgg ggatcaagaa tgctgaccct  540
gaggagctga agcgagttgc ctcacagccc accagtgact tcttcttctt cgtcaatgac  600
ttcagcatct tgaggacact actgcccctc gtttccggga gagtgtgcac gactgctggt  660
ggcgtgcctg tgacccgacc tccggatgac tcgacctctg ctccacgaga cctggtgctg  720
tctgagccaa gcagccaatc cttgagagta cagtggacag cggccagtgg ccctgtgact  780
ggctacaagg tccagtacac tcctctgacg gggctgggac agccactgcc gagtgagcgg  840
caggaggtga acgtcccagc tggtgagacc agtgtgcggc tgcggggtct ccggccactg  900
accgagtacc aagtgactgt gattgccctc tacgccaaca gcatcgggga ggctgtgagc  960
gggacagctc ggaccactgc cctagaaggg ccggaactga ccatccagaa taccacagcc 1020
cacagcctcc tggtggcctg gcggagtgtg ccaggtgcca ctggctaccg tgtgacatgg 1080
cgggtcctca gtggtgggcc cacacagcag caggagctgg gccctgggca gggttcagtg 1140
ttgctgcgtg acttggagcc tggcacggac tatgaggtga ccgtgagcac cctatttggc 1200
cgcagtgtgg ggcccgccac ttccctgatg gctcgcactg acgcttctgt tgagcagacc 1260
ctgcgcccgg tcatcctggg ccccacatcc atcctccttt cctggaactt ggtgcctgag 1320
gcccgtggct accggttgga atggcggcgt gagactggct tggagccacc gcagaaggtg 1380
gtactgccct ctgatgtgac ccgctaccag ttggatgggc tgcagccggg cactgagtac 1440
cgcctcacac tctacactct gctggagggc cacgaggtgg ccaccccctgc aaccgtggtt 1500
cccactggac cagagctgcc tgtgagccct gtaacagacc tgcaagccac cgagctgccc 1560
gggcagcggg tgcgagtgtc ctggagccca gtccctggtg ccacccagta ccgcatcatt 1620
gtgcgcagca cccaggggt tgagcggacc ctggtgcttc ctgggagtca gacagcattc 1680
gacttggatg acgttcaggc tgggcttagc tacactgtgc gggtgtctgc tcgagtgggt 1740
ccccgtgagg gcagtgccag tgtcctcact gtccgccggg agccggaaac tccacttgct 1800
gttccagggc tgcgggttgt ggtgtcagat gcaacgcgag tgaggtggc ctggggaccc 1860
gtccctggag ccagtggatt tcggattagc tggagcacag gcagtggtcc ggagtccagc 1920
cagacactgc cccagactc tactgccaca gacatcacag ggctgcagcc tggaaccacc 1980
taccaggtgg ctgtgtcggt actgcgaggc agagaggagg gccctgctgc agtcatcgtg 2040
gctcgaacgg acccactggg cccagtgagg acggtccatg tgactcaggc cagcagctca 2100
tctgtcacca ttacctggac cagggttcct ggcgccacag gatacagggt ttcctggcac 2160
tcagcccacg gcccagagaa atcccagttg gtttctgggg aggccacggt ggctgagctg 2220
gatgactgg agccagatac tgagtatacg gtgcatgtga gggcccatgt ggctggcgtg 2280
gatgggcccc ctgcctctgt ggttgtgagg actgccctg agcctgtggg tcgtgtgtcg 2340
aggctgcaga tcctcaatgc ttccagcgac gttctacgga tcacctgggt aggggtcact 2400
ggagccacag cttacagact ggcctggggc cggagtgaag gcggccccat gaggcaccag 2460
```

```
atactcccag gaaacacaga ctctgcagag atccggggtc tcgaaggtgg agtcagctac   2520
tcagtgcgag tgactgcact tgtcgggggac cgcgagggca cacctgtctc cattgttgtc   2580
actacgccgc ctgaggctcc gccagccctg gggacgcttc acgtggtgca gcgcggggag   2640
cactcgctga ggctgcgctg ggagccggtg cccagagcgc agggcttcct tctgcactgg   2700
caacctgagg gtgccagga acagtcccgg gtcctgggcc ccagctgcag cagctatcac   2760
ctggacgggc tggagccagc gacacagtac cgcgtgaggc tgagtgtcct agggccagct   2820
ggagaagggc cctctgcaga ggtgactgcg cgcactgagt cacctcgtgt tccaagcatt   2880
gaactacgtg tggtggacac ctcgatcgac tcggtgactt tggcctggac tccagtgtcc   2940
agggcatcca gctacatcct atcctggcgg ccactccagag gccctggcca ggaagtgcct   3000
gggtccccgc agacacttcc agggatctca agctcccagc gggtgacagg gctagagcct   3060
ggcgtctctt acatcttctc cctgacgcct gtcctggatg gtgtgcgggg tcctgaggca   3120
tctgtcacac agacgccagt gtgccccgt ggcctggcgg atgtggtgtt cctaccacat   3180
gccactcaag acaatgctca ccgtgcgagg ctacgagga gggtcctgga gcgtctggtg   3240
tggcacttg ggcctcttgg gccacaggca gttcaggttg gcctgctgtc ttacagtcat   3300
cggccctccc cactgttccc actgaatggc tcccatgacc ttggcattat cttgcaaagg   3360
atccgtgaca tgcccctacat ggacccaagt gggaacaacc tgggcacagc cgtggtcaca   3420
gctcacagat acatgttggc accagatgct cctgggcgcc gccagcacgt accagggggtg   3480
atggttctgc tagtggatga acccttgaga gtgacatat tcagccccat ccgtgaggcc   3540
caggcttctg ggcttaatgt ggtgatgttg ggaatggctg agcggaccc agagcagctg   3600
cgtcgcttgg cgccgggtat ggactctgtc cagaccttct tcgccgtgga tgatgggcca   3660
agcctggacc aggcagtcag tggtctggcc acagccctgt gtcaggcatc cttcactact   3720
cagccccggc cagagccctg cccagtgtat tgtccaaagg gccagaaggg ggaacctgga   3780
gagatgggcc tgagaggaca agttgggcct cctggcgacc ctggcctccc gggcaggacc   3840
ggtgctcccg gccccaggg gcccctgga agtgccactg ccaagggcga gaggggcttc   3900
cctggagcag atgggcgtcc aggcagccct ggccgcgccg ggaatcctgg acccctgga   3960
gcccctggcc taaagggctc tccaggggttg cctggccctc gtggggaccg ggagagcga   4020
ggacctcgag gcccaaaggg ggagccgggg gctcccggac aagtcatcgg aggtgaagga   4080
cctgggcttc ctgggcggaa aggggaccct ggaccatcgg gccccctgg acctcgtgga   4140
ccactgggg acccaggacc ccgtggcccc cagggcttc ctggaacagc catgaagggt   4200
gacaaaggcg atcgtgggga gcggggttcc cctggaccag gtgaaggtgg cattgctcct   4260
ggggagcctg ggctgccggg tcttcccgga agccctggac cccaaggccc gttggcccc   4320
cctggaaaga aggagaaaa aggtgactct gaggatggac ctccaggcct cccaggacaa   4380
cctgggtctc cgggtgagca gggcccacgg ggacctcctg gagctattgg ccccaaaggt   4440
gaccggggct ttccagggcc cctgggtgag gctggagaga agggcgaacg tggacccca   4500
ggcccagcgg gatcccgggg gctgccaggg gttgctggac gtcctggage caagggtcct   4560
gaagggccac caggacccac tggccgcaa ggagagaagg gggagcctgg tcgccctggg   4620
gaccctgcag tggtgggacc tgctgttgct ggacccaaag gagaaagggg agatgtgggg   4680
cccgctgggc ccagaggagc taccggagtc caaggggaac ggggccccacc cggcttggtt   4740
cttcctggag accctggccc caagggagac cctggagacc gggtcccat tggccttact   4800
ggcagagcag gaccccagg tgactcaggg cctcctggag agaagggaga ccctgggcgg   4860
cctgccccc caggacctgt tggccccga ggacgagatg tgaagttgg agagaaaggt   4920
gacgagggtc ctccggggtga cccggggtttg ctggaaaaag caggcgagcg tggccttcgg   4980
ggggcacctg gagttcgggg gcctgtgggt gaaaagggag accagggaga tcctggagag   5040
gatgacgaa atgcagccc tggatcatct ggacccaagg gtgaccgtgg ggagccgggt   5100
cccccaggac ccccgggacg gctggtagac acaggacctg gagccagaga aagggagag   5160
cctgggggacc gcggacaaga gggtcctcga gggcccaagg gtgatcctgg cctcctgga   5220
gcccctgggg aaaggggcat tgaagggttt cggggaccct gcccacaaga ggggaccca   5280
ggtgtccgag gcccagcagg agaaaagggt gaccgggggtc ccctgggct ggatggccgg   5340
agcggactgg atgggaaacc aggagccgct gggccctctg gccgaatgg tgctgcaggc   5400
aaagctgggg acccagggag agacgggctt ccaggcctcc gtgagaaca gggcctccct   5460
ggccctctg gtcccctgg attaccggga aagccaggcg aggatgcaa acctggcgtc   5520
aatgaaaaaa acgagaacc tgggaccct ggagaagacg ggaggaaggg agagaaaagga   5580
gattcaggcg cctctgggag agaaggtcgt gatggcccca agggtgagcg tggagctcct   5640
ggtatccttg gaccccaggg gcctccaggc ctcccagggc cagtgggccc tcctggccag   5700
ggttttcctg gtgtcccagg aggcacgggc cccaaggtg accgtgggga gactggatcc   5760
aaaggggagc agggcctccc tggagagcgt ggcctgcgag gagagcctgg aagtgtgccg   5820
aatgtggatc ggttgctgga aactgctggc atcaaggcat ctgccctgcg ggagatcgtg   5880
gagacctggg atgagagctc tggtagcttc ctgcctgtgc ccgaacgcgc tcgaggcccc   5940
aagggggact caggcgaaca gggcccccca ggcaaggagg gcccatcgg cttttcctgga   6000
gaacgcggcg tgaagggcga ccgtggagac cctggccgag aggggccacc tggtctgcga   6060
cttggggaga ggggcccccc cgggccttcc ggccttgccg gggagcctgg aaagcctggt   6120
attcccgggc tcccaggcag ggctggggt gtggagagg caggaaggcc aggagagagg   6180
ggagaacggg gagagaagg agaacgtgga gaacagggca gagatggccc tcctggactc   6240
cctggacccc ctgggccccc cggaccccct gggccaaggg tgtctgtgga tgagccgacag   6300
cctggactct ctggagaaca gggcccccct ggactcaagg tgctaaggg ggagccgggc   6360
agcaatggtg accaaggtcc caaggagac agggtgtgc aggcatcaa aggagaccgg   6420
ggagagcctg gaccgagggg tcaggacggc aacccgggtc taccaggaga gcgtggtatg   6480
gctgggcctg aagggaagcc gggtctgcag ggtccaagag gccccctgg cccagtgggt   6540
gtcatggag accctggacc acctggtgcc ccgggtcttg ccggccctca aggaccccaa   6600
ggaccttctg gcctgaaggg ggagcctgga gagacaggac ctccaggacg gggcctgact   6660
ggacctactg gagctgtggg acttcctgga ccccccggcc cttcaggcct tgtgggtcca   6720
cagggtctc caggttttgcc tggacaagtg ggggagacag ggaagccggg agccccaggt   6780
cgagatggtg ccagtggaaa agatggagac agagggagcc ctggtgtgcc agggtcacca   6840
ggtctgtcgg ccctcgtcgg ccataagga gaacgtggca ccgggggcc cctggacag   6900
gctgtggtcg ggctcccctgg agcaaaggga gagaagggaa ccctggagg ccttgctgga   6960
gacctggtgg gtgagccggg agccaaaggt gaccgggaac tgccaggcc gcgaggcgag   7020
aagggtgaag ctgccgtgc aggggagcc ggagacctg gggaagatgg tcagaaaggg   7080
gctccaggac ccaaaggttt caaggggtgac ccaggagtcg gggtcccggg ctcccctggg   7140
cctcctggcc ctccaggtgt gaagggagat ctgggcctcc ctgccctgcc cggtgctcct   7200
```

```
ggtgttgttg ggttcccggg tcagacaggc cctcgaggag agatgggtca gccaggccct    7260
agtggagagc ggggtctggc aggcccccca gggagagaag gaatcccagg acccctgggg    7320
ccacctggac caccggggtc agtgggacca cctgggccct ctggactcaa aggagacaag    7380
ggagaccctg gagtagggct gcctgggccc cgaggcgagc gtggggagcc aggcatccgg    7440
ggtgaagatg gccgcccggg ccaggaggga ccccgagaca tcacggggcc ccctggcagc    7500
aggggagagc gtggggagaa gggtgatgtt gggagtgcag gactaaaggg tgacaaggga    7560
gactcagctg tgatcctggg gcctccaggc cacaggggtg ccaaggggga catgggtgaa    7620
cgagggcctc ggggcttgga tggtgacaaa ggacctcggg gagacaatgg ggaccctggt    7680
gacaagggca gcaagggaga gcctggtgac aagggctcaa ccgggttgcc aggactgcgt    7740
ggactcctgg gaccccaggg tcaacctggt gcagcaggga tccctggtga cccgggatcc    7800
ccaggaaagg atggagtgcc tggtatccga ggagaaaaag gagatgttgg cttcatgggt    7860
ccccggggcc tcaagggtga acggggagtg aagggagcct gtggccttga tggagagaag    7920
ggagacaagg gagaagctgg tccccaggc cgccccgggc tggcaggaca caaaggagag    7980
atggggagc ctggtgtgcc ggggcagtcg ggggcccctg gcaaggaggg cctgatcggt    8040
cccaagggtg accgaggctt tgacgggcag ccaggcccca agggtgacca gggcgagaaa    8100
ggggagcggg gaaccccagg aattgggggc ttcccaggcc ccagtggaaa tgatggctct    8160
gctggtcccc caggggccacc tggcagtgtt ggtcccagag gccccgaagg acttcagggc    8220
cagaagggtg agcgaggtcc cccggagag agagtgttgg gggctcctgg ggtccctgga    8280
gctcctggcg agagagggga gcaggggcgg ccagggcctg ccggtcctcg aggcgagaag    8340
ggagaagctg cactgacgga ggatgacatc cggggctttg tgcgccaaga gatgagtcag    8400
cactgtgcct gccagggcca gttcatcgca tctggatcac gaccctccc tagttatgct    8460
gcagacactg ccggctccca gctccatgct gtgcctgtgc tccgcgtctc tcatgcagag    8520
gaggaagagc gggtaccccc tgaggatgat gagtactctg aatactccga gtattctgtg    8580
gaggagtacc aggaccctga agtccttgg gatagtgatg accctgttc cctgccactg    8640
gatgagggct cctgcactgc ctacaccctg cgctggtacc atcgggctgt gacaggcagc    8700
acagaggcct gtcacccttt tgtctatggt ggctgtggag gaatgccaa ccgttttggg    8760
acccgtgagg cctgcgagcg ccgctgccca ccccgggtgg tccagagcca ggggacaggt    8820
actgcccagg actga                                                    8835
```

SEQ ID NO: 2             moltype = AA   length = 2944
FEATURE                  Location/Qualifiers
source                   1..2944
                          mol_type = protein
                          organism = Homo sapiens
SEQUENCE: 2

```
MTLRLLVAAL CAGILAEAPR VRAQHRERVT CTRLYAADIV FLLDGSSSIG RSNFREVRSF    60
LEGLVLPFSG AASAQGVRFA TVQYSDDPRT EFGLDALGSG GDVIRAIREL SYKGGNTRTG   120
AAILHVADHV FLPQLARPGV PKVCILITDG KSQDLVDTAA QRLKGQGVKL FAVGIKNADP   180
EELKRVASQP TSDFFFFVND FSILRTLLPL VSRRVCTTAG GVPVTRPPDD STSAPRDLVL   240
SEPSSQSLRV QWTAASGPVT GYKVQYTPLT GLGQPLPSER QEVNVPAGET SVRLRGLRPL   300
TEYQVTVIAL YANSIGEAVS GTARTTALEG PELTIQNTTA HSLLVAWRSV PGATGYRVTW   360
RVLSGGPTQQ QELGPGQGSV LLRDLEPGTD YEVTVSTLFG RSVGPATSLM ARTDASVEQT   420
LRPVILGPTS ILLSWNLVPE ARGYRLEWRR ETGLEPPQKV VLPSDVTRYQ LDGLQPGTEY   480
RLTLYTLLEG HEVATPATVV PTGPELPVSP VTDLQATELP GQRVRVSWSP VPGATQYRII   540
VRSTQGVERT LVLPGSQTAF DLDDVQAGLS YTVRVSARVG PREGSASVLT VRREPETPLA   600
VPGLRVVVSD ATRVRVAWGP VPGASGFRIS WSTGSGPESS QTLPPDSTAT DITGLQPGTT   660
YQVAVSVLRG REEGPAAVIV ARTDPLGPVR TVHVTQASVS SVTITWTRVP GATGYRVSWH   720
SAHGPEKSQL VSGEATVAEL DGLEPDTEYT VHVRAHVAGV DGPPASVVVR TAPEPVGRVS   780
RLQILNASSD VLRITWVGVT GATAYRLAWG RSEGGPMRHQ ILPGNTDSAE IRGLEGGVSY   840
SVRVTALVGD REGTPVSIVV TTPPEAPPAL GTLHVVQRGE HSLRLRWEPV PRAQGFLLHW   900
QPEGGQEQSR VLGPELSSYH LDGLEPATQY RVRLSVLGPA GEGPSAEVTA RTESPRVPSI   960
ELRVVDTSID SVTLAWTPVS RASSYILSWR PLRGPGQEVP GSPQTLPGIS SSQRVTGLEP  1020
GVSYIFSLTP VLDGVRGPEA SVTQTPVCPR GLADVVFLPH ATQDNAHRAE ATRRVLERLV  1080
LALGPLGPQA VQVGLLSYSH RPSPLFPLNG SHDLGIILQR IRDMPYMDPS GNNLGTAVVT  1140
AHRYMLAPDA PGRRQHVPGV MVLLVDEPLR GDIFSPIREA QASGLNVVML GMAGADPEQL  1200
RRLAPGMDSV QTFFAVDDGP SLDQAVSGLA TALCQASFTT QPRPEPCVY CPKGQKGEPG  1260
EMGLRGQVGP PGDPGLPGRT GAPGQGPPGS SATAKGERGF PGADGRPGSP GRAGNPGTPG  1320
APGLKGSPGL PGRGDPGER GPRGPKGEPG APGQVIGGEG PGLPGRKGDP GPSGPPGPRG  1380
PLGDPGPRGP PGLPGTAMKG DKGDRGERGP PGPGEGGIAP GEPGLPGLPG SPGPQGPVGP  1440
PGKKGEKGDS EDGAPGLPGQ PGSPGEQGPR GPPGAIGPKG DRGFPGPLGE AGEKGERGPP  1500
GPAGSRGLPG VAGRPGAKGP EGPPGPTGRQ GEKGEPGRPG DPAVVGPAVA GPKGEKGDVG  1560
PAGPRGATGV QGERGPPGLV LPGDPGPKGD PGDRGPIGLT GRAGPPGDSG PPGEKGDPGR  1620
PGPPGPVGPR GRDGEVGEKG DEGPPGDPGL PGKAGERGLR GAPGVRGPVG EKGDQGDPGE  1680
DGRNGSPGSS GPKGDRGEPG PPGPPGRLVD TGPGAREKGE PGDRGQEGPR GPKGDPGLPG  1740
APGERGIEGF RGPPGPQGDP GVRGPAGEKG DRGPPGLDGR SGLDGKPGAA GPSGPNGAAG  1800
KAGDPGRDGL PGLRGEQGLP GPSGPPGLPG KPGEDGKPGL NGKNGEPGDP GEDGRKGEKG  1860
DSGASGREGR DGPKGERGAP GILGPQGPPG LPGPVGPPGQ GFPGVPGGTG PKGDRGETGS  1920
KGEQGLPGER GLRGEPGSVP NVDRLLETAG IKASALREIV ETWDESSGSF LPVPERRRGP  1980
KGDSGEQGPP GKEGPIGFPG ERGLKGDRGD PGPQGPPGLA LGERGPPGPS GLAGEPGKPG  2040
IPGLPGRAGG VGEAGRPGER GERGEKGERG EQGRDGPPGL PGTPGPPGPP GPKVSVDEPG  2100
PGLSGEQGPP GLKGAKGEPG SNGDQGPKGD RGVPGIKGDR GEPGPRGQDG NPGLPGERGM  2160
AGPEGKPGLQ GPRGPPGPVG GHGDPGPPGA PGLAGPAGPQ GPSGLKGEPG ETGPPGRGLT  2220
GPTGAVGLPG PPGPSGLVGP QGSPGLPGQV GETGKPGAPG RDGASGKDGD RGSPGVPGSP  2280
GLPGPVGPKG EPGPTGAPGQ AVVGLPGAKG EKGAPGGLAG DLVGEPGAKG DRGLPGPRGE  2340
KGEAGRAGEP GDPGEDGQKG APGPKGFKGD PGVGVPGSPG PPGPPGVKGD LGLPGLPGAP  2400
GVVGFPGQTG PRGEMGQPGP SGERGLAGPP GREGIPGPLG PPGPPGSVGP PGASGLKGDK  2460
GDPGVGLPGP RGERGEPGIR GEDGRPGQEG PRGLTGPPGS RGERGEKGDV GSAGLKGDKG  2520
DSAVILGPPG PRGAKGDMGE RGPRGLDGDK GPRGDNGDPG DKGSKGEPGD KGSAGLPGLR  2580
GLLGPQGQPG AAGIPGDPGS PGKDGVPGIR GEKGDVGFMG PRGLKGERGV KGACGLDGEK  2640
```

```
GDKGEAGPPG RPGLAGHKGE MGEPGVPGQS GAPGKEGLIG PKGDRGFDGQ PGPKGDQGEK    2700
GERGRTPGIGG FPGPSGNDGS AGPPGPPGSV GPRGPEGLQG QKGERGPPGE RVVGAPGVPG    2760
APGERGEQGR PGPAGPRGEK GEAALTEDDI RGFVRQEMSQ HCACQGQFIA SGSRPLPSYA    2820
ADTAGSQLHA VPVLRVSHAE EERVPPEDD  EYSEYSEYSV EEYQDPEAPW DSDDPCSLPL    2880
DEGSCTAYTL RWYHRAVTGS TEACHPFVYG GCGGNANRFG TREACERRCP PRVVQSQGTG    2940
TAQD                                                                2944

SEQ ID NO: 3            moltype = DNA  length = 2217
FEATURE                 Location/Qualifiers
source                  1..2217
                        mol_type = unassigned DNA
                        organism = Homo sapiens
SEQUENCE: 3
atgacctcct cggggcctgg accccggttc ctgctgctgc tgccgctgct gctgccccct      60
gcggcctcag cctccgaccg gccccggggc cgagacccgg tcaacccaga gaagctgctg     120
gtgatcactg tggccacagc tgaaaccgag gggtacctgc gtttcctgcg ctctgcggag     180
ttcttcaact acactgtgcg gaccctgggc ctggagaggt agtggcgagg gggtgatgtg     240
gctcgaacag ttggtggagg acagaaggtc cggtggttaa gaaggaaat  ggagaaatac     300
gctgaccggg aggatatgat catcatgttt gtggatagca cgacgtgat  tctggccggc     360
agccccacag agctgctgaa gaagttcgtc cagagtggca gccgcctgct cttctctgca     420
gagagcttct gctggcccga gtgggggctg gcggagcagt accctgaggt gggcacgggg     480
aagcgcttcc tcaattctgg tggattcatc ggttttgcca ccaccatcca ccaaatcgtg     540
cgccagtgga gtacaagga  tgatgacgac gaccagctgt tctacacacg gctctacctg     600
gacccaggac tgagggagaa actcagcctt aatctggatc ataagtctcg gatctttcag     660
aacctcaacg gggctttaga tgaagtggtt ttaaagtttg atcggaaccg tgtgcgtatc     720
cggaacgtgg cctacgacac gctcccccatt gtggtccata gaaacggttc cactaagctg     780
cagctcaact acctgggaaa ctacgtcccc aatggctgga ctcctgaggg aggctgtggc     840
ttctgcaacc aggaccggag gacactcccg gggggcagc  ctccccccg  ggtgtttctg     900
gccgtgtttg tggaacagcc tactccgttt ctgccccgct tcctgcagcg gctgctactc     960
ctggactatc cccccgacag ggtcacccct ttcctgcaca acaacgaggt cttccatgaa    1020
ccccacatcg ctgactcctg gccgcagctc caggaccact tctcagctgt gaagctcgtg    1080
gggccggagg aggctctgag cccaggcgag gccaggaca  tggccatgga cctgtgtcgg    1140
caggaccccg agtgtgagtt ctacttcagc ctggacgccg acgctgtcct caccaacctg    1200
cagaccctgc gtatcctcat tgaggagaac aggaaggtga tcgcccccat gctgtcccgc    1260
cacggcaagc tgtggtccaa cttctggggc gccctgagcc ccgatgagta ctacgcccgc    1320
tccgaggact acgtggagct ggtgcagcgg aagcgagtgg gtgtgtggaa tgtaccatac    1380
atctcccagg cctatgtgat ccggggtgat ccctgcgga tggagctgcc ccagagggat    1440
gtgttctcgg gcagtgacac agaccgggac atggccttct gtaagagctt cgagacaag    1500
ggcatcttcc tccatctgag caatcagcat gaatttgcc  ggctcctggc cacttccaga    1560
tacgacacgg agcacctgca ccccgacctc tggcagatct tcgacaaccc cgtcgactgg    1620
aaggagcagt acatccacga gaactacagc cgggccctgg aaggggaagg aatcgtggag    1680
cagccatgcc cggacgtgta ctggttccca ctgctgtcag aacaaatgtg tgatgagctg    1740
gtggcagaga tggagcacta cggccagtgg tcaggcgggc ggcatgagga ttcaaggctg    1800
gctggaggct acgagaatgt gccccaccgtg gacatccaca tgaagcaggt ggggtacgag    1860
gaccagtggc tgcagctgct gcggacgtat gtgggcccca tgaccgagag cctgtttccc    1920
ggttaccaca ccaaggcgcg ggcggtgatg aactttgtgg ttcgctaccg gccagacgag    1980
cagccgctct tgcggccaca ccacgactca tccaccttca ccctcaacgt tgccctcaac    2040
cacaagggcc tggactatga gggaggtggc tgccgcttcc tgcgctacga ctgtgtgatc    2100
tcctccccga ggaagggctg ggcactcctg caccccggcc gcctcaccca ctaccacgag    2160
gggctgccaa cgacctgggg cacacgctac atcatggtgt cctttgtcga ccccctga      2217

SEQ ID NO: 4            moltype = AA   length = 738
FEATURE                 Location/Qualifiers
source                  1..738
                        mol_type = protein
                        organism = Homo sapiens
SEQUENCE: 4
MTSSGPGPRF LLLLPLLLPP AASASDRPRG RDPVNPEKLL VITVATAETE GYLRFLRSAE     60
FFNYTVRTLG LGEEWRGGDV ARTVGGGQKV RWLKKEMEKY ADREDMIIMF VDSYDVILAG    120
SPTELLKKFV QSGSRLLFSA ESFCWPEWGL AEQYPEVGTG KRFLNSGGFI GFATTIHQIV    180
RQWKYKDDDD DQLFYTRLYL DPGLREKLSL NLDHKSRIFQ NLNGALDEVV LKFDRNRVRI    240
RNVAYDTLPI VVHGNGPTKL QLNYLGNYVP NGWTPEGGCG FCNQDRRTLP GGQPPPRVFL    300
AVFVEQPTPF LPRFLQRLLL LDYPPDRVTL FLHNNEVFHE PHIADSWPQL QDHFSAVKLV    360
GPEEALSPGE ARDMAMDLCR QDPECEFYFS LDADAVLTNL QTLRILIEEN RKVIAPMLSR    420
HGKLWSNFWG ALSPDEYYAR SEDYVELVQR KRVGVWNVPY ISQAYVIRGD TLRMELPQRD    480
VFSGSDTDPD MAFCKSFRDK GIFLHLSNQH EFGRLLATSR YDTEHLHPDL WQIFDNPVDW    540
KEQYIHENYS RALEGEGIVE QPCPDVYWFP LLSEQMCDEL VAEMEHYGQW SGGRHEDSRL    600
AGGYENVPTV DIHMKQVGYE DQWLQLLRTY VGPMTESLFP GYHTKARAVM NFVVRYRPDE    660
QPSLRPHHDS STFTLNVALN HKGLDYEGGG CRFLRYDCVI SSPRKGWALL HPGRLTHYHE    720
GLPTTWGTRY IMVSFVDP                                                  738

SEQ ID NO: 5            moltype = DNA   length = 75
FEATURE                 Location/Qualifiers
misc_feature            1..75
                        note = Synthetic Construct
source                  1..75
                        mol_type = other DNA
                        organism = synthetic construct
SEQUENCE: 5
```

```
agggccaaga ggggcagcgg cgagggcagg ggcagcctgc tgacctgcgg cgacgtggag    60
gagaaccccg gcccc                                                     75

SEQ ID NO: 6              moltype = AA  length = 25
FEATURE                   Location/Qualifiers
REGION                    1..25
                          note = Synthetic Construct
source                    1..25
                          mol_type = protein
                          organism = synthetic construct
SEQUENCE: 6
RAKRGSGEGR GSLLTCGDVE ENPGP                                          25

SEQ ID NO: 7              moltype = DNA  length = 66
FEATURE                   Location/Qualifiers
misc_feature              1..66
                          note = Synthetic Construct
source                    1..66
                          mol_type = other DNA
                          organism = synthetic construct
SEQUENCE: 7
ggaagcggag ctactaactt cagcctgctg aagcaggctg gagacgtgga ggagaaccct    60
ggacct                                                               66

SEQ ID NO: 8              moltype = AA  length = 22
FEATURE                   Location/Qualifiers
REGION                    1..22
                          note = Synthetic Construct
source                    1..22
                          mol_type = protein
                          organism = synthetic construct
SEQUENCE: 8
GSGATNFSLL KQAGDVEENP GP                                             22

SEQ ID NO: 9              moltype = DNA  length = 69
FEATURE                   Location/Qualifiers
misc_feature              1..69
                          note = Synthetic Construct
source                    1..69
                          mol_type = other DNA
                          organism = synthetic construct
SEQUENCE: 9
ggaagcggac agtgtactaa ttatgctctc ttgaaattgg ctggagatgt tgagagcaac    60
cctggacct                                                            69

SEQ ID NO: 10             moltype = AA  length = 23
FEATURE                   Location/Qualifiers
REGION                    1..23
                          note = Synthetic Construct
source                    1..23
                          mol_type = protein
                          organism = synthetic construct
SEQUENCE: 10
GSGQCTNYAL LKLAGDVESN PGP                                            23

SEQ ID NO: 11             moltype = DNA  length = 75
FEATURE                   Location/Qualifiers
misc_feature              1..75
                          note = Synthetic Construct
source                    1..75
                          mol_type = other DNA
                          organism = synthetic construct
SEQUENCE: 11
ggaagcggag tgaaacagac tttgaatttt gaccttctca gttggcggg agacgtggag    60
tccaaccctg gacct                                                     75

SEQ ID NO: 12             moltype = AA  length = 25
FEATURE                   Location/Qualifiers
REGION                    1..25
                          note = Synthetic Construct
source                    1..25
                          mol_type = protein
                          organism = synthetic construct
SEQUENCE: 12
GSGVKQTLNF DLLKLAGDVE SNPGP                                          25

SEQ ID NO: 13             moltype = DNA  length = 11121
FEATURE                   Location/Qualifiers
misc_feature              1..11121
```

```
                  note = Synthetic Construct
source            1..11121
                  mol_type = other DNA
                  organism = synthetic construct
SEQUENCE: 13
atgacgctgc ggcttctggt ggccgcgctc tgcgccggga tcctggcaga ggcgccccga    60
gtgcgagccc agcacaggga gagagtgacc tgcacgcgcc tttacgccgc tgacattgtg   120
ttcttactgg atggctcctc atccattggc cgcagcaatt ccgcgaggt  ccgcagcttt   180
ctcgaagggc tggtgctgcc tttctctgga gcagccagtg cacagggtgt gcgctttgcc   240
acagtgcagt acagcgatga cccgacggac gagttcggcc tggatgcact tggctctggg   300
ggtgatgtga tccgcgccat ccgtgagctt agctacaagg ggggcaacac tcgcacaggg   360
gctgcaattc tccatgtggc tgaccatgtc ttcctgcccc agctggcccg acctggtgtc   420
cccaaggtct gcatcctgat cacagacggg aagtcccagg acctggtgga cacagctgcc   480
caaaggctga aggggcaggg ggtcaagcta tttgctgtgg ggatcaagaa tgctgaccct   540
gaggagctga agcgagttgc ctcacagccc accagtgact tcttcttctt cgtcaatgac   600
ttcagcatct tgaggacact actgcccctc gtttcccgga gagtgtgcac gactgctggt   660
ggcgtgcctg tgacccgacc tccggatgac tcgacctctg ctccacgaga cctggtgctg   720
tctgagccaa gcagccaatc cttgagagta cagtggacag cggccagtgg ccctgtgact   780
ggctacaagg tccagtacac tcctctgacg gggctgggac agccactgcc gagtgagcgg   840
caggaggtga acgtcccagc tggtgagacc agtgtgcggc tgcggggtct ccggccactg   900
accgagtacc aagtgactgt gattgccctc tacgccaaca gcatcgggga ggctgtgagc   960
gggacagctc ggaccactgc cctagaaggg ccggaactga ccatccagaa taccacagcc  1020
cacagcctcc tggtggcctg gcggagtgtg ccaggtgcca ctggctaccg tgtgacatgg  1080
cgggtcctca gtggtgggcc cacacagcag caggagctgg gccctgggca gggttcagtg  1140
ttgctgcgtg acttggagcc tggcacggac tatgaggtga ccgtgagcac cctatttggc  1200
cgcagtgtgg ggcccgccac ttccctgatg gctcgcactg acgcttctgt tgagcagacc  1260
ctgcgcccgg tcatcctggg ccccacatcc atcctccttt cctggaactt ggtgcctgag  1320
gcccgtggct accggttgga atggcggcgt gagactggct tggagccacc gcagaaggtg  1380
gtactgcccc tgatgtgacc cgctaccagt tggatgggc  tgcagccggg cactgagtac  1440
cgcctcacac tctacactct gctggagggc acgaggtgg  ccacccctgc aaccgtggtt  1500
cccactggac cagagctgcc tgtgagccct gtaacagacc tgcaagccac cgagctgccc  1560
gggcagcggg tgcgagtgtc ctggagccca gtccctggtg ccaccagta  ccgcatcatt  1620
gtgcgcagca cccaggggt  tgagcggacc ctggtgcttc ctgggagtca gacagcattc  1680
gacttggatg acgttcaggc tgggcttagc tacactgtgc gggtgtctgc tcgagtgggt  1740
ccccgtgggg gcagtgccag tgtcctcact gtccgcgggg agcggaaac  tccacttgct  1800
gttccagggc tgcgggttgt ggtgtcagat gcaacgcgag tgaggtggc  ctggggaccc  1860
gtccctggag ccagtggatt tcggattagc tggagcacag gcagtggtcc ggagtccagc  1920
cagacactgc ccccagactc tactgccaca gacatcacag ggctgcagcc tggaaccacc  1980
taccaggtgg ctgtgtcggt actgcgaggc agagaggagg gcctgctgc  agtcatcgtg  2040
gctcgaacgg acccactggg cccagtgagg acgtccatg  tgactcaggc cagcagctca  2100
tctgtcacca ttacctggac cagggttcct ggcgccacag gatacaggt  ttcctggcac  2160
tcagcccacg gcccagagaa atcccagttg gtttctgggg aggccacggt ggctgagctg  2220
gatggactgg agccagatac tgagtatacg gtgcatgtga gggcccatgt gctggcgttg  2280
gatgggcccc ctgcctctgt ggttgtgagg actgccccg  agcctgtggg tcgtgtgtcg  2340
aggctgcaga tcctcaatgc ttccagcgac gttctacgga tcacctgggt aggggtcact  2400
ggagccacag cttacagact ggcctggggc cggagtgaag gcgccccat  gaggcaccag  2460
atactcccag gaaacacaga tctctgcagag atccggggtc tcgaaggtgg agtcagctac  2520
tcagtgcgag tgactgcact tgtcggggac cgcgagggca cacctgtctc cattgttgtc  2580
actacgccgc ctgaggctcc gccagccctg gggacgcttc acgtggtgca gcgcggggag  2640
cactcgctga ggctgcgctg ggagccggtg cccagagcgc agggcttcct tctgcactgg  2700
caacctgagg gtggccagga acagtcccgg gtcctgggc  ccgagctcag cagctatcag  2760
ctggacgggc tggagccagc gacacagtac cgcgtgagg  tgagtgtcct aggggccagt  2820
ggagaagggc cctctgcaga ggtgactgcg cgcactgagt cacctcgtgt tccaagcatt  2880
gaactacgtg tggtggacac ctcgatcgac tcggtgactt tggcctggac tccagtgtcc  2940
agggcatcca gctacatcct atcctggcgg ccactcagga cccctggcca ggaagtgcct  3000
gggtccccgc agacacttcc agggatctca agctcccagc gggtgacagg gctagagcct  3060
ggcgtctctt acatcttctc cctgacgcct gtcctggatg gtgtgcgggg tcctgaggca  3120
tctgtcacac agacgccagt gtgccccgt  ggcctggcgg atgtggtgtt cctaccacat  3180
gccactcaag acaatgctca ccgtgcggag gctacgagga gggtcctgga gcgtctggtg  3240
ttggcacttg ggcctcttgg gccacaggca gttcaggttg gcctgctgtc ttacagtcat  3300
cggccctccc cactgttccc actgaatggc tcccatgacc ttggcattat cttgcaaagg  3360
atccgtgaca tgcctacat  ggacccaagt gggaacaacc tgggcacagc cgtggtcaca  3420
gctcacagat acatgttggc accagatgct cctgggcgcc gccagcacgt accagggtg   3480
atggttctgc tagtggataa accttgaga gtgacatat  tcagccccat ccgtgaggcc  3540
caggcttctg ggcttaatgt ggtgatgttg gaatggctg  agcggacccc agagcagctg  3600
cgtcgcttgg cgccgggtat ggactctgtc cagaccttct tcgccgtgga tgatgggcca  3660
agcctggacc aggcagtcag tggtctggcc acagccctgt gtcaggcatc cttcactact  3720
cagcccccggc cagagccctg cccagtgtat tgtccaaagg gccagaaggg ggaacctgga  3780
gagatggccc tgagaggaca agttgggcct cctggcgacc ctggcctccc ggcaggaacc  3840
ggtgctcccg gccccaggg  gcccctggag agtgccactg ccaagggcga gaggggcttc  3900
cctggagcag atgggcgtcc aggcagccct ggccgcccg  gaatcctgg  accctggag   3960
gcccctggcc taaagggctc tccagggttg cctggccctc gtgggaccc  gggagagcga  4020
ggacctcgag gcccaagggg ggagccgggg gctcccggac aagtcatcgg aggtgaagga  4080
cctggggcttc ctgggcggaa agggggacct ggaccatcgg gccccctgg  acctcgtgga  4140
ccactggggg acccaggacc ccgtggcccc caggggcttc ctgaacagc  catgaagggt  4200
gacaaaggcg atcgtgggga gcgggtccc  cctggaccag gtgaaggtgg cattgctcct  4260
ggggagcctg ggctgccggg tcttcccgga agccctggac ccaaggccc  gttggcccc   4320
cctgaaagaa aaggagaaaa aggtgactct gaggatggag ctccaggcct cccaggacaa  4380
cctgggtctc cgggtgagca gggcccacgg ggacctcctg gagctattgg ccccaaaggt  4440
```

```
gaccggggct tccagggcc cctgggtgag gctggagaga agggcgaacg tggaccccca  4500
ggcccagcgg gatcccgggg gctgccaggg gttgctggac gtcctggagc caagggtcct  4560
gaagggccac caggacccac tggccgccaa ggagagaagg gggagcctgg tcgccctggg  4620
gaccctgcag tggtgggacc tgctgttgct ggacccaaag gagaaaggg agatgtgggg  4680
cccgctgggc ccagaggagc taccggagtc caaggggaac ggcccacc cggcttggtt  4740
cttcctggag accctggccc caagggagac cctggagacc ggggtcccat tggcctact  4800
ggcagagcag gaccccagg tgactcaggg cctcctggag agaagggaga ccctgggcgg  4860
cctgccccc caggacctgt ggccccga ggacgagatg tgtgaagttgg agagaaaggt  4920
gacgagggtc ctccgggtga cccgggtttg cctggaaaag caggcgagcg tggccttcgg  4980
ggggcacctg gagttcgggg gcctgtgggt gaaaaggag accagggaga tcctggagag  5040
gatgacgaa atggcagccc tggatcatct ggacccaagg gtgaccgtgg ggagccgggt  5100
cccccaggac ccccgggacg gctggtagac acaggacctg gagccagaga aagggggag  5160
cctgggggacc gcggacaaga gggtcctcga gggcccaagg gtgatcctgg cctcctgga  5220
gcccctgggg aaaggggcat tgaagggttt cggggaccca caggccccaca gggggacca  5280
ggtgtccgag gcccagcagg agaaaagggt gacccggggtc cccctgggct ggatggccga  5340
agcggactgg atgggaaacc aggagccgct gggcctctg gccgaatgg tgctgcaggc  5400
aaagctgggg acccagggag agcgggcttt ccaggcctcc gtgagaaca gggcctcct  5460
ggcccctctg gtccccctgg attaccggga aagccaggcg aggatggcaa acctggctcg  5520
aatgaaaaaa acgagaacc tgggggaccct ggagaagacg ggaggaaggg agagaaagga  5580
gattcaggcg cctctgggag agaaggtcgt gatggcccca agggtgagcg tggagctcct  5640
ggtatccttg gaccccaggg gcctccaggc ctcccagggc cagtgggccc tcctggccag  5700
ggttttcctg gtgtcccagg aggcacggc cccaaggtg accggggca gactggatcc  5760
aaaggggagc agggcctccc tggagagcgt ggcctgcgag gagagcctgg aagtgtgccg  5820
aatgtggatc ggttgctgga aactgctgga atcaaggcat ctgccctgcg ggagatcgtg  5880
gagacctggg atgagagctc tggtagcttc ctgcctgtgc ccgaacgcg tcgaggcccc  5940
aagggggact caggcgaaca gggccccca ggcaaggagg gcccatcgg cttctcggg  6000
gaacgcgggc tgaagggccga ccgtggagac cctggcccctc agggggccacc tggtctggcc  6060
cttgggggaga gggccccc cgggccttcc ggccttgccg ggagcctgg aaagcctggt  6120
attcccggc tccaggcag ggctggggt gtgggagagg caggaaggcc aggagagagg  6180
ggagaacggg gagagaaagg agaacgtgga gaacaggca agatggcc tcctggactc  6240
cctgaaccc ctgggccccc cggaccccct ggcccaagg tgtctgtgga tgagccaggt  6300
cctggactct ctggagaaca gggacccct ggactcaagg gtgctaaggg ggagccgggc  6360
agcaatggtg accaaggtcc caaggagac aggggtgtgc caggcatcaa aggagaccga  6420
ggagagcctg gaccgagggg tcaggacggc aacccgggtc taccaggaga gcgtggtatg  6480
gctgggcctg aagggaaagcc gggtctgcag gtccaagag gcccccctgg cccagtgggt  6540
ggtcatggag accctggacc acctggtgcc ccgggtcttg ctggccctgc aggaccccaa  6600
ggaccttctg gcctgaaggg ggagcctgga gagacaggac ctcaggacg gggcctgact  6660
ggacctactg gagctgtggg acttcctgga cccccggcc cttcaggcct tgtgggtcca  6720
caggggtctc caggtttgcc tggacaagtg ggggagacag ggaagccggg agccccaggt  6780
cgagatggtc ccagtggaaa agatggagac agagggagcc ctggtgtgcc agggtcacca  6840
ggtctgcctg gccctgtcgg acctaaagga gaacctggcc ccacggggc ccctggacag  6900
gctgtggtcg ggctccctgg agcaaaggga gagaaggag cccctggagg ccttgctgga  6960
gacctggtg gtgagccgga agccaaaggt gaccgaggac tgccaggcgc gcgaggcgag  7020
aagggtgaag ctggccgtgc aggggagccc ggagaccctg gggaagatgg tcagaaaggg  7080
gctccaggac ccaaaggttt caagggtgac ccaggagtcg gggtcccggg ctcccctggg  7140
cctcctggcc ctccaggtgt gaaggagat ctgggcctcc ctggcctgcc cggtgctcct  7200
ggtgttgttg ggttcccggg tcagacaggc cctcgaggag agatgggtca gccaggccct  7260
agtggagagc ggggtctggc aggccccca gggagagaag gaatcccagg accccctgggg  7320
ccacctggac caccggggtc agtgggacca cctgggcct ctggactcaa aggagacaag  7380
ggagaccctg gagtagggct gcctgggccc cgaggcgagc gtggggagcc aggcatccgg  7440
ggtgaagatg gccgccccgg ccaggaggga ccccaggagc tcacgggggcc cctggctgga  7500
aggggagagc gtggggagaa gggtgatgtt gggagtgcag gactaaaggg tgacaaggga  7560
gactcagctg tgatcctggg gcctccaggc ccacggggtg ccaagggga catgggtgaa  7620
cgagggcctc ggggcttgga tggtgacaaa ggacctcggg gagacaatgg ggaccctggt  7680
gacaagggca gcaagggaga gcctggtgac aagggctcag ccgggttgcc aggactgcgt  7740
ggactcctgg gacccagggg tcaacctggt gcagcaggga tccctggtga cccgggatcc  7800
ccaggaaagg atggagtgcc tggtatccga ggagaaaaag gagatgttgg cttcatgggt  7860
ccccggggcc tcaagggtga acggggagtg aaggagcct gtggcttga tggagagaag  7920
ggagacaagg gagaagctgg tccccaggc cgccccgggc tggcaggaca caaaggagag  7980
atgggtgaca ctggtgtgcc gggccagtcg ggggccctgg gcaaggaggg cctgatcggt  8040
cccaagggtg accgaggctt tgacgggcag ccaggcccca gggtgaccca gggcgagaaa  8100
ggggagcggg gaacccagg aattgggggc ttcccaggcc ccagtggaaa tgatggctct  8160
gctggtccc caggccacc tggcagtgtt ggtcccagag gccccgaagg acttcagggc  8220
cagaagggtg agcgagtggcc cccggagag agagtgcgg gggctcctgg ggtccctgga  8280
gctcctggg agagaggga gcaggggcgg ccagggcctg ccgtcctcg aggcgagaag  8340
ggagaagctg cactgacgga ggatgacatc cggggctttg tgcgccaaga gatgagcag  8400
cactgtgcct gccagggcca gttcatcgca tctggatcac gaccctccc tagttatgct  8460
gcagacactg ccggctccca gtccatgct gtgcctgtgc tccgcgtctc tcatgcgag  8520
gaggaaggg ggtactctg taggatgat gagtactctg aatactccga gtattctgga  8580
gaggagtacc aggaccctga agctccttgg gatagtgatg accctgttc cctgccactg  8640
gatgagggct cctgcactgc ctacaccctg cgctggtacc atgggctgt gacaggcagc  8700
acagaggcct gtcaccctt tgtctatggt ggctgtggag gaatgccaa ccgttttggg  8760
acccgtgagg cctgcgagcg ccgctgccca ccccgggtg tccagagcca gggacaggt  8820
actgccagg acagggccaa gaggggcagc ggcgagggca gccagcgct gctgacctga  8880
ggcgacgtgg aggagaaccc cggcccacc tcctcgggc ctggacccg gttcctgctg  8940
ctgctgccgc tgctgctgcc ccctcgcgcc tcagcctccg accggcccg ggccgagac  9000
ccggtcaacc cagagaagct gctggtgatc actgtggcca cagctgaaac cgaggggtac  9060
ctgcgttttc tgcgctctgc ggagttcttc aactacactg tgcggaccct gggcctggga  9120
gaggagtggc gaggggggga tgtggctcga acagttggtg gaggacagaa ggtccggtgg  9180
```

```
ttaaagaagg aaatggagaa atacgctgac cgggaggata tgatcatcat gtttgtggat  9240
agctacgacg tgattctggc cggcagcccc acagagctgc tgaagaagtt cgtccagagt  9300
ggcagccgcc tgctcttctc tgcagagagc ttctgctggc ccgagtgggg gctggcggag  9360
cagtaccctg aggtgggcac ggggaagcgc ttcctcaatt ctggtggatt catccggttt  9420
gccaccacca tccaccaaat cgtgccacag tggaagtaca aggatgatga cgacgaccag  9480
ctgttctaca cacggctcta cctggaccca ggactgaggg agaaactcag ccttaatctg  9540
gatcataagt ctcggatctt tcagaacctc aacggggctt tagatgaagt ggttttaaag  9600
tttgatcgga accgtgtgcg tatccggaac gtggcctacg acacgctccc cattgtggtc  9660
catggaaacg gtcccactaa gctgcagctc aactacctgg ggaggacact ccccaatggc  9720
tggactcctg agggaggctg tggcttctgc aaccaggacc ggaggacact cccggggagg  9780
cagcctcccc ccgggtgtt tctggccgtg tttgtggaac agcctactcc gtttctgccc  9840
cgcttcctgc agcggctgct actcctggac tatcccccg acagggtcac ccttttcctg  9900
cacaacaacg aggtcttcca tgaacccac atcgctgact cctggccgca gctccaggac  9960
cacttctcag ctgtgaagct cgtggggccg gaggaggctc tgagcccagg cgaggccagg 10020
gacatggcca tggacctgtg tcggcaggac cccgagtgtg agttctactt cagcctggac 10080
gccgacgctg tcctccaccaa cctgcagacc ctgcgtatcc tcattgagga gaacaggaag 10140
gtgatcgccc ccatgctgtc ccgccacggc aagctgtggt ccaacttctg gggcgccctg 10200
agccccgatg agtactacgc ccgctccgag gactacgtgg agctggtgca gcggaagcga 10260
gtgggtgtgt ggaatgtacc atacatctcc caggcctatg tgatccgggg tgataccctg 10320
cggatggagc tgccccagag ggatgtgttc tcgggcagtg acacagaccc ggacatggcc 10380
ttctgtaaga gctttcgaga caagggcatc ttcctccatc tgagcaatca gcatgaattt 10440
ggccggctcc tggccacttc cagatacgac acggagcacc tgcacccga cctctggcag 10500
atcttcgaca accccgtcga ctggaaggag cagtacatcc acgagaacta cagccgggcc 10560
ctggaagggg aaggaatcgt ggagcagcca tgcccggacg tgtactggtt cccactgctg 10620
tcagaacaaa tgtgtgatga gctggtggca gagatggagc actacggcca gtggtcaggc 10680
ggccggcatg aggattcaag gctgctggga ggctacgaga atgtgcccac cgtggacatc 10740
cacatgaagc aggtggggta cggaggaccag tggctgcagc tgctgcggac gtatgtgggc 10800
cccatgaccg agagcctgtt tcccggttac cacaccaagg cgcgggcggt gatgaacttt 10860
gtggttcgct accggccaga cgagcagccg tctctgcggc cacaccacga ctcatccacc 10920
ttcaccctca acgttgccct caaccacaag ggcctgacct atgagggagg tggctgccgc 10980
ttcctgcgct acgactgtgt gatctcctcc ccgaggaagg gctgggcact cctgcacccc 11040
ggccgcctca cccactacca cgaggggctg ccaacgacct ggggcacacg ctacatcatg 11100
gtgtcctttg tcgacccctg a                                            11121
```

| | |
|---|---|
| SEQ ID NO: 14 | moltype = AA length = 3706 |
| FEATURE | Location/Qualifiers |
| REGION | 1..3706 |
| | note = Synthetic Construct |
| source | 1..3706 |
| | mol_type = protein |
| | organism = synthetic construct |

```
SEQUENCE: 14
MTLRLLVAAL CAGILAEAPR VRAQHRERVT CTRLYAADIV FLLDGSSSIG RSNFREVRSF   60
LEGLVLPFSG AASAQGVRFA TVQYSDDPRT EFGLDALGSG GDVIRAIREL SYKGGNTRTG  120
AAILHVADHV FLPQLARPGV PKVCILITDG KSQDLVDTAA QRLKGQGVKL FAVGIKNADP  180
EELKRVASQP TSDFFFFVND FSILRTLLPL VSRRVCTTAG GVPVTRPPDD STSAPRDLVL  240
SEPSSQSLRV QWTAASGPVT GYKVQYTPLT GLGQPLPSER QEVNVPAGET SVRLRGLRPL  300
TEYQVTVIAL YANSIGEAVS GTARTTALEG PELTIQNTTA HSLLVAWRSV PGATGYRVTW  360
RVLSGGPTQQ QELGPGQGSV LLRDLEPGTD YEVTVSTLFG RSVGPATSLM ARTDASVEQT  420
LRPVILGPTS ILLSWNLVPE ARGYRLEWRR ETGLEPPQKV VLPSDVTRYQ LDGLQPGTEY  480
RLTLYTLLEG HEVATPATVV PTGPELPVSP VTDLQATELP GQRVRVSWSP VPGATQYRII  540
VRSTQGVERT LVLPGSQTAF DLDDVQAGLS YTVRVSARVG PREGSASVLT VRREPETPLA  600
VPGLRVVVSD ATRVRVAWGP VPGASGFRIS WSTGSGPESS QTLPPDSTAT DITGLQPGTT  660
YQVAVSVLRG REEGPAAVIV ARTDPLGPVR TVHVTQASSS SVTITWTRVP GATGYRVSWH  720
SAHGPEKSQL VSGEATVAEL DGLEPDTEYT VHVRAHVAGV DGPPASVVVR TAPEPVGRVS  780
RLQILNASSD VLRITWVGVT GATAYRLAWG RSEGGPMRHQ ILPGNTDSAE IRGLEGGVSY  840
SVRVTALVGD REGTPVSIVV TTPPEAPPAL GTLHVVQRGE HSLRLRWEPV PRAQGFLLHW  900
QPEGGQEQSR VLGPELSSYH LDGLEPATQY RVRLSVLGPA GEGPSAEVTA RTESPRVPSI  960
ELRVVDTSID SVTLAWTPVS RASSYILSWR PLRGRPGQVG GSPQTLPGIS SSQRVTGLEP 1020
GVSYIFSLTP VLDGVRGPEA SVTQTPVCPR GLADVVFLPH ATQDNAHRAE ATRRVLERLV 1080
LALGPLGPQA VQVGLLSYSH RPSPLFPLNG SHDLGIILQR IRDMPYMDPS GNNLGTAVVT 1140
AHRYMLAPDA PGRRQHVPGV MVLLVDEPLR GDIFSPIREA QASGLNVVML GMAGADPEQL 1200
RRLAPGMDSV QTFFAVDDGP SLDQAVSGLA TALCQASFTT QPRPEPCPVY CPKGQKGEPG 1260
EMGLRGQVGP PGDPGLPGRT GAPGPQGPPG SATAKGERGF PGADGRPGSP GRAGNPGTPG 1320
APGLKGSPGL PGPRGDPGER GPRGPKGEPG APGQVIGGEG PGLPGRKGDP GSGPPGPRG 1380
PLGDPGPRGP PGLPGTAMKG DKGDRGERGP PGPGEGGIAP GEPGLPGLPG SPGPQGPVGP 1440
PGKKGEKGDS EDGAPGLPGQ PGSPGEQGPR GPPGAIGPKG DRGFPGPLGE AGEKGERGPP 1500
GPAGSRGLPG VAGRPGAKGP EGPPGPTGRQ GEKGEPGRPG DPAVVGPAVA GPKGEKGDVG 1560
PAGPRGATGV QGERGPPGLV LPGDPGPKGD PGDRGPIGLT GRAGPPGDSG PPGEKGDPGR 1620
PGPPGPVGPR GRDGEVGEKG DEGPPGDPGL PGKAGERGLR GAPGVRGPVG EKGDQGDPGE 1680
DGRNGSPGSS GPKGDRGEPG PPGPPGRLVD TGPGAREKGE PGDRGQEGPR GPKGDPGLPG 1740
APGERGIEGF RGPPGPQGDP GVRGPAGEKG DRGPPGLDGR SGLDGKPGAA GPSGPNGAAG 1800
KAGDPGRDGL PGLRGEQGLP GPSGPPGLPG PGEDGKPGL NGKNGEPGDP GEDGRKGEKG 1860
DSGASGREGR DGPKGERGAP GILGPQGPPG LPGPVGPPGQ GFPGVPGGTG PKGDRGETGS 1920
KGEQGLPGER GLRGEPGSVP NVDRLLETAG IKASALREIV ETWDESSGSF LPVPERRRGP 1980
KGDSGEQGPP GKEGPIGFPG ERGLKGDRGD PGPQGPPGLA LGERGPPGPS GLAGEPGKPG 2040
IPGLPGRAGG VGEAGRPGER GERGEKGERG EQGRDGPPGL PGTPGPPGPP GPKVSVDEPG 2100
PGLSGEQGPP GLKGAKGEPG SNGDQGPKGD RGVPGIKGDR GEPGPRGQDG NPGLPGERGM 2160
AGPEGKPGLQ GPRGPPGPVG GHGDPGPPGA PGLAGPAGPQ GPSGLKGEPG ETGPPGRGLT 2220
```

```
GPTGAVGLPG PPGPSGLVGP QGSPGLPGQV GETGKPGAPG RDGASGKDGD RGSPGVPGSP  2280
GLPGPVGPKG EPGPTGAPGQ AVVGLPGAKG EKGAPGGLAG DLVGEPGAKG DRGLPGPRGE  2340
KGEAGRAGEP GDPGEDGQKG APGPKGFKGD PGVGVPGSPG PPGPPGVKGD LGLPGLPGAP  2400
GVVGFPGQTG PRGEMGQPGP SGERGLAGPP GREGIPGPLG PPGPPGSVGP PGASGLKGDK  2460
GDPGVGLPGP RGERGEPGIR GEDGRPGQEG PRGLTGPGPG RGERGEKGDV GSAGLKGDKG  2520
DSAVILGPPG PRGAKGDMGE RGPRGLDGDK GPRGDNGDPG DKGSKGEPGD KGSAGLPGLR  2580
GLLGPQGQPG AAGIPGDPGS PGKDGVPGIR GEKGDVGFMG PRGLKGERGV KGACGLDGEK  2640
GDKGEAGPPG RPGLAGHKGE MGEPGVPGQS GAPGKEGLIG PKGDRGFDGQ PGPKGDQGEK  2700
GERGTPGIGG FPGPSGNDGS AGPPGPPGSV GPRGPEGLQG QKGERGPPGE RVVGAPGVPG  2760
APGERGEQGR PGPAGPRGEK GEAALTEDDI RGFVRQEMSQ HCACQGQFIA SGSRPLPSYA  2820
ADTAGSQLHA VPVLRVSHAE EERVPPEDD EYSEYSEYSV EEYQDPEAPW DSDDPCSLPL  2880
DEGSCTAYTL RWYHRAVTGS TEACHPFVYG GCGGNANRFG TREACERRCP PRVVQSQGTG  2940
TAQDRAKRGS GEGRGSLLTC GDVEENPGPT SSGPGPRFLL LLPLLLPPAA SASDRPRGRD  3000
PVNPEKLLVI TVATAETEGY LRFLRSAEFF NYTVRTLGLG EEWRGGDVAR TVGGGQKVRW  3060
LKKEMEKYAD REDMIIMFVD SYDVILAGSP TELLKKFVQS GSRLLFSAES FCWPEWGLAE  3120
QYPEVGTGKR FLNSGGFIGF ATTIHQIVRQ WKYKDDDDDQ LFYTRLYLDP GLREKLSLNL  3180
DHKSRIFQNL NGALDEVVLK FDRNRVRIRN VAYDTLPIVV HGNGPTKLQL NYLGNYVPNG  3240
WTPEGGCGFC NQDRRTLPGG QPPPRVFLAV FVEQPTPFLP RFLQRLLLLD YPPDRVTLFL  3300
HNNEVFHEPH IADSWPQLQD HFSAVKLVGP EEALSPGEAR DMAMDLCRQD PECEFYFSLD  3360
ADAVLTNLQT LRILIEENRK VIAPMLSRHG KLWSNFWGAL SPDEYYARSE DYVELVQRKR  3420
VGVWNVPYIS QAYVIRGDTL RMELPQRDVF SGSDTDPDMA FCKSFRDKGI FLHLSNQHEF  3480
GRLLATSRYD TEHLHPDLWQ IFDNPVDWKE QYIHENYSRA LEGEIVEQP CPDVWFPLL  3540
SEQMCDELVA EMEHYGQWSG GRHEDSRLAG GYENVPTVDI HMKQVGYEDQ WLQLLRTYVG  3600
PMTESLFPGY HTKARAVMNF VVRYRPDEQP SLRPHHDSST FTLNVALNHK GLDYEGGGCR  3660
FLRYDCVISS PRKGWALLHP GRLTHYHEGL PTTWGTRYIM VSFVDP            3706

SEQ ID NO: 15          moltype = DNA  length = 11121
FEATURE                Location/Qualifiers
misc_feature           1..11121
                       note = Synthetic Construct
source                 1..11121
                       mol_type = other DNA
                       organism = synthetic construct
SEQUENCE: 15
atgacctcct cggggcctgg accccggttc ctgctgctgc tgccgctgct gctgccccct    60
gcggcctcag cctccgaccg gccccggggc cgagacccgg tcaacccaga gaagctgctg   120
gtgatcactg tggccacagc tgaaaccgag gggtacctgc gtttcctgcg ctctgcggag   180
ttcttcaact acactgtgcg gaccctgggc ctgggagagg agtggcgagg gggtgatgtg   240
gctcgacagg ttggtggagg acagaaggtc cggtggttaa agaaggaaat ggagaaatac   300
gctgaccggg aggatatgat catcatgttt gtggatagca cgacgtgat tctggccggc   360
agccccacag agctgctgaa gaagttcgtc cagagtggca gccgcctgct cttctctgca   420
gagagcttct gctggcccga gtggggcctg gcggagcagt accctgaggt gggcacgggg   480
aagcgcttcc tcaattctgg tggattcatc ggttttgcca ccaccatcca ccaaatcgtt   540
cgccagtgga agtacaagga tgatgacgac gaccagctgt tctacacacg gctctacctg   600
gacccaggac tgagggagaa actcagcctt aatctggatc ataagtctcg gatctttcag   660
aacctcaacg gggctttaga tgaagtggtt ttaaagtttg atcggaaccg tgtgcgtatc   720
cggaacgtgg cctacgacac gctccccatt gtggtccatg gaaacggtcc cactaagctg   780
cagctcaact acctgggaaa ctacgtcccc aatggctgga ctcctgaggg aggctgtggc   840
ttctgcaacc aggaccggag gacactcccg ggggggcagc ctccccccg ggtgtttctg   900
gccgtgtttt ggaacagcc tactccgttt ctgcccccgct cctgcagcg gctgctactc   960
ctggactatc cccccgacag ggtcaccctt ttcctcatgca acaacgaggt cttccatgga  1020
ccccacatcg ctgactcctg gccgcagctc caggaccact tctcagctgt gaagctcgtg  1080
gggccggagg aggctctgag cccaggcgag gccagggaca tggccatgga cctgtgtcgg  1140
caggaccccg agtgtgagtt ctacttcagc ctggacgccg acgctgtcct caccaacctg  1200
cagaccctgc gtatcctcat tgaggagaac aggaaggtga tcgccccat gctgtcccgc  1260
cacggcaagc tgtggtccaa cttctggggc gccctgagcc cgatgagta ctacgcccgc  1320
tccgaggact acgtggagct ggtgcagcgg aagcgagtgg gtgtgtggaa tgtaccatac  1380
atctcccagg cctatgtgat ccggggtgat accctgcgga tggagctgcc ccagagggat  1440
gtgttctcgg gcagtgacac agacccggac atggcctttct gtaagagctt tcgagacaag  1500
ggcatcttcc tccatctgag caatcagcat gaatttggcc ggctcctggc cacttccaga  1560
tacgacacgg agcacctgca ccccgacctc tggcagatct tcgacaaccc cgtcgactgg  1620
aaggagcagt acatccacga gaactacagc cgggccctgg aaggggaagg aatcgtggag  1680
cagccatgcc cggacgtgta ctggttccca ctgctgtcag aacaaatgtg tgatgagctg  1740
gtggcagaga tggagcacta cggccagtgg tcaggcggc ggcatgagga ttcaaggctg  1800
gctggaggct acgagaatgt gcccaccgtg gacatccaca tgaagcaggt ggggtacgag  1860
gaccagtggc tgcagctgct gcggacgtat gtgggcccca tgaccgagag cctgtttccc  1920
ggttaccaca ccaaggcgcg ggcggtgatg aactttgtgg ttcgctaccg gccagacgag  1980
cagccgtctc tgcggccaca ccacgactca tccaccttca ccctcaacgt tgccctcaac  2040
cacaagggcc tggactatga gggaggtggc tgccgcttcc tgcgctacga ctgtgtgatc  2100
tcctccccga ggaagggctg ggcactcctg caccccggcc gcctcaccca ctaccacgag  2160
gggctgccaa cgacctgggg cacacgctac atcatggtgt cctttgtcga ccccagggcc  2220
aagaggggca gcggcagggg caggggcagc ctgctgacct gcggcgacgt ggaggagaac  2280
cccggcccca cgctgcggct tctggtggcc gcgctctgcg ccgggatcct ggcagaggcg  2340
ccccggcgga gccccagca caggagaga gtgcccagca gccgccttta ccgccgctga  2400
attgtgttct tactgatgg ctcctcatcc attggccgca gcaatttccg cgaggtccgc  2460
agctttctcg aagggctggt gctgcctttc tctggagcag ccagtgcaca gggtgtgcgc  2520
tttgccacag tgcagtacag cgatgaccca cggacagagt tcggcctgga tgcacttggc  2580
tctgggggta atgtgatccg cgccatccgt gagcttagct acaagggggg caacactcgc  2640
acaggggctg caattctcca tgtggctgac catgtcttcc tgcccagct ggcccgacct  2700
```

```
ggtgtcccca aggtctgcat cctgatcaca gacgggaagt cccaggacct ggtggacaca  2760
gctgcccaaa ggctgaaggg gcaggggggtc aagctatttg ctgtggggat caagaatgct  2820
gaccctgagg agctgaagcg agttgcctca cagcccacca gtgacttctt cttcttcgtc  2880
aatgacttca gcatcttgag gacactactg ccccctcgttt cccggagagt gtgcacgact  2940
gctggtggcg tgcctgtgac ccgacctccg gatgactcga cctctgctcc acgagacctg  3000
gtgctgtctg agccaagcag ccaatccttg agagtacagt ggacagcggc cagtggccct  3060
gtgactggct acaaggtcca gtacactcct ctgacggggc tgggacagcc actgccgagt  3120
gagcggcagg aggtgaacgt cccagctggt gagaccagtg tgcggctgcg gggtctccgg  3180
ccactgaccg agtaccaagt gactgtgatt gccctctacg ccaacagcat cggggaggct  3240
gtgagcggga cagctcggac cactgcccta gaagggccag aactgaccat ccagaataac  3300
acagcccaca gcctcctggt ggcctggcgg agtgtgccag gtgccactgg ctaccgtgtg  3360
acatggcggt tcctcagtgg tgggcccaca cagcagcagg agctgggccc tgggcagggt  3420
tcagtgttgc tgcgtgactt ggagcctggc acggactatg aggtgaccgt gagcacccta  3480
tttggccgca gtgtgggggcc cgccacttcc ctgatgagctg gcactgacgc ttctgttgag  3540
cagaccctgc gcccggtcat cctgggcccc acatccatcc tcctttcctg gaacttggtg  3600
cctgaggccc gtggctaccg gttggaatgg cggcgtgaga ctggcttgga gccaccgcag  3660
aaggtggtac tgccctctga tgtgacccgc taccagttgg atgggctgca gccgggcact  3720
gagtaccgcc tcacactcta cactctgctg gagggccacg aggtggccac ccctgcaacc  3780
gtggttccca ctggaccaga gctgcctgtg agccctgtaa cagacctgca agccaccgag  3840
ctgcccgggc agcgggtgcg agtgtcctgg agccagtcc ctggtgccac ccagtaccgc  3900
atcattgtgc gcagcaccca ggggggttgag cggaccctgg tgcttcctgg gagtcagaca  3960
gcattcgact tggatgacgt tcaggctggg cttagctaca ctgtgcgggt gtctgctcga  4020
gtggggtcccc gtgagggcag tgccagtgtc ctcactgtcc gccggagcc ggaaaactcca  4080
cttgctgttc cagggctgcg ggttgtggtg tcagatgcaa cgcgagtgag ggtggcctgg  4140
ggacccgtcc ctggagccag tggatttcgg attagctgga gcacaggcag tggtccggaa  4200
tccagccaga cactgcccccc agactctact gccacagaca tcacagggct gcagcctgca  4260
accacctacc aggtggctgt gtcggtactg cgaggcagag aggaggggccc tgctgcagtc  4320
atcgtggctc gaacgaccc actgggccca gtgaggacgg tccatgtgac tcaggccagc  4380
agctcatctg tcaccattac ctggaccagg gttcctggcg ccacaggata cagggtttcc  4440
tggcactcag cccacgggcc agagaaatcc cagttggttt ctggggaggc caggtggct  4500
gagctggatg gactgagcc agatactgag tatacggtgc atgtgagggc ccatgtggct  4560
ggcgtggatg ggccccctgc ctctgtggtt gtgaggactg cccctgagcc tgtgggtcgt  4620
gtgtcgaggc tgcagatcct caatgcttcc agcgacgttc tacggatcac ctgggtaggg  4680
gtcactggag ccacagctta cagactggcc tggggccgga gtgaaggcgg ccccatgagg  4740
caccagatac tcccaggaaa cacagactct gcagagatcc gggtctcgga aggtggagtc  4800
agctactcag tgcgagtgac tgcacttgtc ggggaccgcg agggcacacc tgtctccatt  4860
gttgtcacta cgccgcctga ggctccgcca gccctgggga cgcttcacgt ggtgcagcgc  4920
ggggagcact cgctgaggct gcgctgggag ccggtgccca gagcgcaggg cttccttctg  4980
cactgcaaac ctgagggtgg ccaggaacag tcccggcccc tgggcccga gctcagcagc  5040
tatcacctgg acgggctgga gccagcgaca cagtaccgcg tgaggctgag tgtcctaggg  5100
ccagctggag aagggccctc tgcagaggtg actgcgcgca ctgagtcacc tcgtgttcca  5160
agcattgaac tacgtgtggt ggacacctcg atcgactcgg tgactttggc ctggactcca  5220
gtgtccaggg catccagcta catcctatcc tggcggccac tcagaggccc tggccaggaa  5280
gtgcctgggt ccccgcagac acttccaggg atctcaagct cccagcgggt gacagggcta  5340
gagcctggcg tctcttacat cttctcccctg acgcctgtcc tggatggtgt gcggggtcct  5400
gaggcatctg tcacacagac gccagtgtgc ccccgtggcc tggcggatgt ggtgttccta  5460
cccacatgcca ctcaagacaa tgctcaccgt gcggaggcta cgaggaggt cctgagcgt  5520
ctggtgttgg cacttgggcc tcttgggcca caggcagttc aggttgggcct gctgtcttac  5580
agtcatcggc cctccccact gttcccactg aatggctccc atgaccttgg cattatcttg  5640
caaaggatcc gtgacatgcc ctacatggac ccaagtggga acaacctggg cacagccgtg  5700
gtcacagctc acagatacat gttggcacca gatgctcctg ggcgccgcca gcacgtacca  5760
ggggtgatgg ttctgctagt ggatgaaccc ttgagaggtg acatattcag ccccatccgt  5820
gaggcccagg cttctgggct taatgtggta atgttgggaa tggctggagc ggacccagag  5880
cagctgcgtc gcttggcgcc gggtatggac tctgtccaga ccttcttcgc cgtggatgat  5940
gggccaagcc tggaccaggc agtcagtggt ctggccacag ccctgtgtca ggcatccttc  6000
actactcagc cccggccaga gccctgccca gtgtattgtc caaagggcca gaaggggggaa  6060
cctggagaga tgggcctgag aggacaagtt gggcctcctg gcgaccctgg cctcccgggc  6120
aggaccggtg ctcccggccc ccaggggccc cctggaagtg ccactgccaa gggcgagagg  6180
ggcttccctg gagcagatgg gcgtccaggc agccctggcc gcgccgggaa tcctgggacc  6240
cctggagccc ctggcctaaa gggctctcca gggttgcctg gccctcgtgg ggacccggga  6300
gagcgaggac ctcgaggccc aaaggggggag ccggggggctc ccggacaagt catcggaggt  6360
gaaggacctg ggcttcctgg gcggaaaggg gaccctggac catcgggccc cctggacct  6420
cgtggaccac tggggggaccc aggaccccgt ggccccccag ggcttcctgg aacagccatg  6480
aagggtgaca aaggcgatcg tggggagcgg ggtccccctg gaccaggtga aggtggcatt  6540
gctcctgggg agcctgggct gccggtgctctt cccggaagcc ctggaccccag gccccgtt  6600
ggccccctg gaaagaaagg agaaaaggt gactctgagg atggagctcc aggcctccca  6660
ggacaacctg ggtctccggg tgagcagggc ccacgggac ctcctggagc tattggcccc  6720
aaaggtgacc gggggctttcc agggccctg ggtgaggctg gagagaaggg cgaacgtgga  6780
ccccaggcc cagcgggatc ccgggggctg ccaggggttg ctggacgtg tggagccaag  6840
ggtcctgaag ggccaccagg acccactggc cgccaagga gaaggggga gcctggtcgc  6900
cctgggggacc ctgcagtggt gggacctgct gttgctggac ccaaaggaga aagggagat  6960
gtgggggccc ctgggcccag aggagctacc ggagtccaag ggaacgggg cccacccggc  7020
ttggttcttc ctggagaccc tggccccaag ggagaccctg gagaccggg tcccattggc  7080
cttactggca gagcaggacc ccaggtcga tcagggcctc ctggagaga gggagaccct  7140
gggcggcctg gcccccagg acctgttggc cccggaggac gagatggtga agttggagag  7200
aaaggtgacg agggtcctcc gggtgaccg gtttgcctg gaaaagcagg cgagcgtgggc  7260
cttcggggg cacctggagt tcggggggcct gtgggtgaaa agggagacca gggagatcct  7320
ggagaggatg gacgaaatgg cagccctgga tcatctggac ccaagggtga ccgtggggag  7380
ccgggtcccc caggaccccc gggacggctg gtagacacag gacctggagc cagagagaag  7440
```

-continued

```
ggagagcctg gggaccgcgg acaagagggt cctcgagggc ccaagggtga tcctggcctc   7500
cctggagccc ctggggaaag gggcattgaa gggtttcggg gacccccagg cccacagggg   7560
gacccaggtg tccgaggccc agcaggagaa aaggggtgacc gggtccccc tgggctggat   7620
ggccggagcg gactggatgg gaaaccagga gccgctgggc cctctgggcc gaatggtgct   7680
gcaggcaaag ctggggaccc agggagagaac gggcttccag gcctccgtgg agaacagggc   7740
ctccctggcc cctctggtcc ccctggatta ccgggaaagc caggcgagga tggcaaacct   7800
ggcctgaatg gaaaaaacgg agaacctggg gaccctggag aagacgggag aagggagag   7860
aaaggagatt caggcgcctc tgggagagaa ggtcgtgatg gccccaaggg tgagcgtgga   7920
gctcctggta tccttggacc ccaggggcct ccaggcctcc cagggccagt gggccctcct   7980
ggccagggtt ttcctggtgt cccaggggagc acgggcccca agggtgaccg tggggagact   8040
ggatccaaag gggagcaggg cctccctgga gagcgtggcc tgcgaggaga gcctggaagt   8100
gtgccgaatg tggatcggtt gctggaaact gctggcatca aggcatctgc cctgcgggag   8160
atcgtggaga cctgggatga gagctctggt agcttcctgc ctgtgcccga acggcgtcga   8220
ggccccaagg gggactcagg cgaacagggc ccccaggca aggagggccc catcggcttt   8280
cctggagaac gcgggctgaa gggcgaccgt ggagaccctg gcctcagggg gccacctggt   8340
ctggcccttg gggagagggg cccccccggg ccttccggcc ttgccgggga gcctggaaag   8400
cctggtattc ccgggctccc aggcagggct gggggtgtgg gagaggcagg aaggccagga   8460
gagagggag aacgggaga gaaaggacaga cgtggagaac agggcagaga tggccctcct   8520
ggactccctg gaacccctgg gcccccccgga cccctggcc ccaaggtgtc tgtggatgag   8580
ccaggtcctg gactctctgg agaacaggga cccctggac tcaagggtgc taaggggag   8640
ccgggcagca atggtgacca aggtcccaaa ggagacaggg tgtgccagg catcaaagga   8700
gaccgggag agcctggacc gagggggtcag gacggcaacc cgggtctacc aggagagcgt   8760
ggtatggctg ggcctgaagg gaagccgggt ctgcaggtc caagaggccc ccctggccca   8820
gtgggtggtc atggagaccc tggaccacct ggtgccccgg gtcttgctgg ccctgcagga   8880
cccccaagac cttctggcct gaagggggag cctggagaga caggacctcc aggacggggc   8940
ctgactggac ctactggagc tgtgggactt cctggaccc ccggcccctt aggccttggg   9000
ggtccacagg ggtctccagg tttgcctgga caagtggggg agacaggga gccgggagcc   9060
ccaggtcgaga atggtgccag tggaaaagat ggagacagag ggagccctgg tgtgccaggg   9120
tcaccaggtc tgcctggccc tgtcggacct aaaggagaac ctggccccac gggggcccct   9180
ggacaggctg tggtcgggct ccctggagca aagggagaa aggagcccc tggaggcctt   9240
gctggagacc tggtgggtga gccgggagcc aaaggtgacc aggagctgcc agggccgcga   9300
ggcgagaagg tgaagctgg ccgtgcaggg gagcccggag accctgggga agatggtcag   9360
aaaggggctc caggacccaa aggttcaag ggtgacccag gagtcgggt cccgggctcc   9420
cctggggctc ctggcctcc agtgtgaag ggagatctgg gcctccctgg cctgcccgt   9480
gctcctggtg ttgttgggtt cccgggtcag acaggccctc gaggagagat gggtcagcca   9540
ggccctagtg gagagcgggg tctggcaggc ccccaggga gaaggaat cccaggaccc   9600
ctggggccac ctgggaccacc ggggtcagtg ggaccacctg gggcctctgg actcaaagga   9660
gacaaggag accctggagt agggctgcct gggccccgag gcgagcgtgg ggagccaggc   9720
atccgggtg aagatggccg ccccggccag gagggaccc gaggactcac gggccccct   9780
ggcagcaggg gagagcgtgg ggagaagggt gatgttggga gtgcaggact aaaggggtgac   9840
aagggagact cagctgtgat cctggggcct ccaggcccac gggtgccaa ggggacatg   9900
ggtgaacgag ggcctcgggg cttggatggt gacaaaggac ctcggggaga caatggggac   9960
cctggtgaca agggcagcaa ggagagcct ggtgacaagg gctcagccgg gttgccagga  10020
ctgcgtggac tcctgggacc ccagggtcaa cctggtgcag cagggatccc tggtgacccg  10080
ggatccccag gaaaggatgg agtgcctggt atccgaggag aaaaaggaga tgttggcttc  10140
atgggtcccc ggggcctcaa gggtgaacgg ggagtgaagg gagcctgtgg ccttgatgga  10200
gagaaggaga caagggaga agctggtccc ccaggccgc ccgggctggc aggacacaaa  10260
ggagagatgg gggagcctgg tgtgccgggc cagtcgggg ccctggcaa ggagggcctg  10320
atcggtccca agggtgaccg aggctttgac gggcagccag gccccaaggg tgaccaggc  10380
gagaaagggg agcggggaac cccaggaatt ggggcttcc caggcccag tggaaatgat  10440
ggctctgctg gtccccagg gccacctggc agtgttggtc ccagaggccc cgaaggactt  10500
cagggccaga agggtgagcg aggtccccc ggagagagag tggtgggggc cctgggtc   10560
cctggagctc ctggcgagag agggagcag gggcggccag gcctgccgg tcctcgagcc  10620
gagaaggag aagctgcact gacggaggat gacatccggg gctttgtgcg ccaagagatg  10680
agtcgcact gtgcctgcca gggccagttc atcgcatctg gatcacgacc cctccctagt  10740
tatgctgcag acactgccgg ctcccagctc catgctgtgc ctgtgctccg cgtctctcat  10800
gcagaggagg aagagcgggt accccctgag gatgatgagt actctgaata ctccgagtat  10860
tctgtggagg agtaccagga ccctgaagct ccttgggata tgatgaccc ctgttccctg  10920
ccactggatg agggctcctg cactgcctac acctgcgct ggtaccatcg ggctgtgaca  10980
ggcagcacag aggcctgtca ccctttgtc tatgctgct gtgagggaa tgccaaccgt  11040
tttgggaccc gtgaggcctg cgagcgccgc tgcccaccc gggtggtcca gagccagggg  11100
acaggtactg cccaggactg a                                          11121
```

```
SEQ ID NO: 16           moltype = AA   length = 3706
FEATURE                 Location/Qualifiers
REGION                  1..3706
                        note = Synthetic Construct
source                  1..3706
                        mol_type = protein
                        organism = synthetic construct
SEQUENCE: 16
MTSSGPGPRF LLLLPLLLPP AASASDRPRG RDPVNPEKLL VITVATAETE GYLRFLRSAE    60
FFNYTVRTLG LGEEWRGGDV ARTVGGGQKV RWLKKEMEKY ADREDMIIMF VDSYDVILAG   120
SPTELLKKFV QSGSRLLFSA ESFCWPEWGL AEQYPEVGTG KRFLNSGGFI GFATTIHQIV   180
RQWKYKDDDD DQLFYTRLYL DPGLREKLSL NLDHKSRIFQ NLNGALDEVV LKFDRNRVRI   240
RNVAYDTLPI VVHGNGPTKL QLNYLGNYVP NGWTPEGGCG FCNQDRRTLP GGQPPPRVFL   300
AVFVEQPTPF LPRFLQRLLL LDYPPDRVTL FLHNNEVFHE PHIADSWPQL QDHFSAVKLV   360
GPEEALSPGE ARDMAMDLCR QDPECEFYFS LDADAVLTNL QTLRILIEEN RKVIAPMLSR   420
HGKLWSNFWG ALSPDEYYAR SEDYVELVQR KRVGWNVPY ISQAYVIRGD TLRMELPQRD   480
```

-continued

```
VFSGSDTDPD MAFCKSFRDK GIFLHLSNQH EFGRLLATSR YDTEHLHPDL WQIFDNPVDW   540
KEQYIHENYS RALEGEGIVE QPCPDVYWFP LLSEQMCDEL VAEMEHYGQW SGGRHEDSRL   600
AGGYENVPTV DIHMKQVGYE DQWLQLLRTY VGPMTESLFP GYHTKARAVM NFVVRYRPDE   660
QPSLRPHHDS STFTLNVALN HKGLDYEGGG CRFLRYDCVI SSPRKGWALL HPGRLTHYHE   720
GLPTTWGTRY IMVSFVDPRA KRGSGEGRGS LLTCGDVEEN PGPTLRLLVA ALCAGILAEA   780
PRVRAQHRER VTCTRLYAAD IVFLLDGSSS IGRSNFREVR SFLEGLVLPF SGAASAQGVR   840
FATVQYSDDP RTEFGLDALG SGGDVIRAIR ELSYKGGNTR TGAAILHVAD HVFLPQLARP   900
GVPKVCILIT DGKSQDLVDT AAQRLKGQGV KLFAVGIKNA DPEELKRVAS QPTSDFFFFV   960
NDFSILRTLL PLVSRRVCTT AGGVPVTRPP DDSTSAPRDL VLSEPSSQSL RVQWTAASGP  1020
VTGYKVQYTP LTGLGQPLPS ERQEVNVPAG ETSVRLRGLR PLTEYQVTVI ALYANSIGEA  1080
VSGTARTTAL EGPELTIQNT TAHSLLVAWR SVPGATGYRV TWRVLSGGPT QQQELGPGQG  1140
SVLLRDLEPG TDYEVTVSTL FGRSVGPATS LMARTDASVE QTLRPVILGP TSILLSWNLV  1200
PEARGYRLEW RRETGLEPPQ KVVLPSDVTR YQLDGLQPGT EYRLTLYTLL EGHEVATPAT  1260
VVPTGPELPV SPVTDLQATE LPGQRVRVSW SPVPGATQYR IIVRSTQGVE RTLVLPGSQT  1320
AFDLDDVQAG LSYTVRVSAR VGPREGSASV LTVRREPETP LAVPGLRVVV SDATRVRVAW  1380
GPVPGASGFR ISWSTGSGPE SSQTLPPDST ATDITGLQPG TTYQVAVSVL RGREEGPAAV  1440
IVARTDPLGP VRTVHVTQAS SSSVTITWTR VPGATGYRVS WHSAHGPEKS QLVSGEATVA  1500
ELDGLEPDTE YTVHVRAHVA GVDGPPASVV VRTAPEPVGR VSRLQILNAS SDVLRITWVG  1560
VTGATAYRLA WGRSEGGPMR HQILPGNTDS AEIRGLEGGV SYSVRVTALV GDREGTPVSI  1620
VVTTPPEAPP ALGTLHVVQR GEHSLRLRWE PVPRAQGFLL HWQPEGGQEQ SRVLGPELSS  1680
YHLDGLEPAT QYRVRLSVLG PAGEGPSAEV TARTESPRVP SIELRVVDTS IDSVTLAWTP  1740
VSRASSYILS WRPLRGPGQE VPGSPQTLPG ISSSQRVTGL EPGVSYIFSL TPVLDGVRGP  1800
EASVTQTPVC PRGLADVVFL PHATQDNAHR AEATRRVLER LVLALGPLGP QAVQVGLLSY  1860
SHRPSPLFPL NGSHDLGIIL QRIRDMPYMD PSGNNLGTAV VTAHRYMLAP DAPGRRQHVP  1920
GVMVLLVDEP LRGDIFSPIR EAQASGLNVV MLGMAGADPE QLRRLAPGMD SVQTFFAVDD  1980
GPSLDQAVSG LATALCQASF TTQPRPEPCP VYCPKGQKGE PGEMGLRGQV GPPGDPGLPG  2040
RTGAPGPQGP PGSATAKGER GFPGADGRPG SPGRAGNPGT PGAPGLKGSP GLPGPRGDPG  2100
ERGPRGPKGE PGAPGQVIGG EGPGLPGRKG DPGPSGPPGP RGPLGDPGPR GPPGLPGTAM  2160
KGDKGDRGER GPPGPGEGGI APGEPGLPGL PGSPGPQGPV GPPGKKGEKG DSEDGAPGLP  2220
GQPGSPGEQG PRGPPGAIGP KGDRGFPGPL GEAGEKGERG PPGPAGSRGL PGVAGRPGAK  2280
GPEGPPGPTG RQGEKGEPGR PGDPAVVGPA VAGPKGEKGD VGPAGPRGAT GVQGERGPPG  2340
LVLPGDPGPK GDPGDRGPIG LTGRAGPPGD SGPPGEKGDP GRPGPPGPVG PRGRDGEVGE  2400
KGDEGPPGDP GLPGKAGERG LRGAPGVRGP VGEKGDQGDP GEDGRNGSPG SSGPKGDRGE  2460
PGPPGPPGRL VDTGPGAREK GEPGDRGQEG PRGPKGDPGL PGAPGERGIE GFRGPPGPGG  2520
DPGVRGPAGE KGDRGPPGLD GRSGLDGKPG AAGPSGPNGA AGKAGDPGRD GLPGLRGEQG  2580
LPGPSGPPGL PGKPGEDGKP GLNGKNGEPG DPGEDGRKGE KGDSGASGRE GRDGPGKGERG  2640
APGILGPQGP PGLPGPVGPP GQGFPGVPGG TGPKGDRGET GSKGEQGLPG ERGLRGEPGS  2700
VPNVDRLLET AGIKASALRE IVETWDESSG SFLPVPERRR GPKGDSGEQG PPGKEGPLGP  2760
PGERGLKGDR GDPGPQGPPG LALGERGPPG PSGLAGEPGK PGIPGLPGRA GGVGEAGRPG  2820
ERGERGEKGE RGEQGRDGPP GLPGTPGPPG PPGPKVSVDE PGPGLSGEQG PPGLKGAKGE  2880
PGSNGDQGPK GDRGVPGIKG DRGEPGPRGQ DGNPGLPGER GMAPGEGKPG LQGPRGPPGP  2940
VGGHGDPGPP GAPGLAGPAG PQGPSGLKGE PGETGPPGRG LTGPTGAVGL PGPPGPSGLV  3000
GPQGSPGLPG QVGETGKPGA PGRDGASGKD GDRGSPGVPG SPGLPGPVGP KGEPGPTGAP  3060
GQAVVGLPGA KGEKGAPGGL AGDLVGEPGA KGDRGLPGPR GEKGEAGRAG EPGDPGEDGQ  3120
KGAPGPKGFK GDPGVGVPGS PGPPGPPGVK GDLGLPGLPG APGVVGFPGQ TGPRGEMGQP  3180
GPSGERGLAG PPGREGIPGP LGPPGPPGSV GPPGASGLKG DKGDPGVGLP GPRGERGEPG  3240
IRGEDGRPGQ EGPRGLTGPP GSRGERGEKG DVGSAGLKGD KGDSAVILGP PGPRGAKGDM  3300
GERGPRGLDG DKGPRGDNGD PGDKGSKGEP GDKGSAGLPG LRGLLGPGQG PGAAGIPGDP  3360
GSPGKDGVPG IRGEKGDVGF MGPRGLKGER GVKGACGLDG EKGDKGEAGP PGRPGLAGHK  3420
GEMGEPGVPG QSGAPGKEGL IGPKGDRGFD GQPGPKGDQG EKGERGTPGI GGFPGPGSND  3480
GSAGPPGPEG SVGPRGPEGL QGQKGERGPF GERVVGAPGV PGAPGERGEQ GRPGPAGPRG  3540
EKGEAALTED DIRGFVRQEM SQHCACQGQF IASGSRPLPS YAADTAGSQL HAVPVLRVSH  3600
AEEEERVPPE DDEYSEYSEY SVEEYQDPEA PWDSDDPCSL PLDEGSCTAY TLRWYHRAVT  3660
GSTEACHPFV YGGCGGNANR FGTREACERR CPPRVVQSQG TGTAQD                3706

SEQ ID NO: 17         moltype = DNA   length = 11112
FEATURE               Location/Qualifiers
misc_feature          1..11112
                      note = Synthetic Construct
source                1..11112
                      mol_type = other DNA
                      organism = synthetic construct
SEQUENCE: 17
atgacgctgc ggcttctggt ggccgcgctc tgcgccggga tcctggcaga ggcgccccga    60
gtgcagcccc agcacaggga gagagtgacc tgcacgcgcc tttacgccgc tgacattgtg   120
ttcttactgg atggctcctc atccattggc cgcagcaatt tccgcgaggt ccgcagcttt   180
ctcgaagggc tggtgctgcc tttctctgga gcagccagtg cacagggtgt gcgctttgcc   240
acagtgcagt acagcgatga cccacggaca gagttcgggc tggatgcact ggctctgggg   300
ggtgatgtga tccgcgccat ccgtgagctt agctacaagg ggggcaacac tcgcacaggg   360
gctgcaattc tccatgtggc tgaccatgtc ttcctgcccc agctggcccg acctggtgtc   420
cccaaggtct gcatcctgat cacagacggg aagtcccagg acctggtgga cacagctgcc   480
caaaggctga aggggcaggg ggtcaagcta tttgctgtgg ggatcaagaa tgctgaccct   540
gaggagctga agcgagttgc ctcacagccc accagtgact tcttcttctt cgtcaatgac   600
ttcagcatct tgaggacact actgccccct gtttcccgga aagtgtgcac cactgcaggt   660
ggcgtgcctg tgacccgacc tccgatgac tcgacctctg ctccacgaga cctggtgctg   720
tctgagccaa gcagccaatc cttgagagta cagtggacag cggccagtgg ccctgtgact   780
ggctacaagg tccagtacac tcctctgacg gggctgggac agccactgcc gagtgagcgg   840
caggaggtga acgtcccagc tggtgagacc agtgtgcgc tgcggggtct ccggccactg   900
accgagtacc aagtgactgt gattgccctc tacgccaaca gcatcgggga ggctgtgagc   960
```

```
gggacagctc ggaccactgc cctagaaggg ccggaactga ccatccagaa taccacagcc    1020
cacagcctcc tggtggcctg gcggagtgtg ccaggtgcca ctggctaccg tgtgacatgg    1080
cgggtcctca gtggtgggcc cacacagcag caggagctgg gccctgggca gggttcagtg    1140
ttgctgcgtg acttggagcc tggcacggac tatgaggtga ccgtgagcac cctatttggc    1200
cgcagtgtgg ggcccgccac ttccctgatg gctcgcactg acgcttctgt tgagcagacc    1260
ctgcgcccgg tcatcctggg ccccacatcc atcctccttt cctgaacttg ggtgcctgag    1320
gcccgtggct accggttgga atggcggcgt gagactggct tggagccacc gcagaaggtg    1380
gtactgccct ctgatgtgac ccgctaccag ttggatgggc tgcagccggg cactgagtac    1440
cgcctcacac tctacactct gctggagggc cacgaggtgg ccaccctgc aaccgtggtt    1500
cccactggac cagagctgcc tgtgagccct gtaacagacc tgcaagccac cgagctgccc    1560
gggcagcggg tgcgagtgtc ctggagccca gtccctggtg ccacccagta ccgcatcatt    1620
gtgcgcagca cccagggggt tgagcggacc ctggtgcttc ctgggagtca gacagcattc    1680
gacttggatg acgttcaggc tgggcttagc tacactgtgg ggtgtctgc tcgagtgggt    1740
ccccgtgggg gcagtgccag tgtcctcact gtccgccggg agccggaaac tccacttgct    1800
gttcagggc tgcgggttgt ggtgtcagat gcaacgcgag tgaggtggc ctggggaccc    1860
gtccctggag ccagtggatt tcggattagc tggagcacag gcagtggtcc ggagtccagc    1920
cagacactgc ccccagactc tactgccaca gacatcacag gctgcagcc tggaaccacc    1980
taccaggtgg ctgtgtcggt actgcgaggc agagaggagg gccctgctgc agtcatcgtg    2040
gctcgaacgg acccactggg cccagtgagg acgtccatg tgactcaggc cagcagctca    2100
tctgtcacca ttacctggac cagggttcct ggcgccacag gatacagggt ttcctggcac    2160
tcagcccacg cccagagaa atcccagttg gtttctgggg aggccacggt ggctgagctg    2220
gatggactgg agcagatac tgagtatacg gtgcatgtga gggcccatgt ggctggcgtg    2280
gatgggcccc ctgcctctgt ggttgtgagg actgccctg agcctgtggg tcgtgtgtcg    2340
aggctgcaga tcctcaatgc ttccagcgac gttctacgga tcacctgggt agggtcact    2400
ggagccacag cttacagact ggcctggggc cggagtgaag gcggcccat gaggcaccag    2460
atactcccag gaaacacaga ctctgcagag atccgggtc tcgaaggtgg agtcagctac    2520
tcagtgcgag tgactgcact tgtcggggac cgcgagggca cacctgtctc cattgttgtc    2580
actacgccgc ctgaggctcc gccagccctg gggacgcttc acgtggtgca gcgcggggag    2640
cactcgctga ggctgcgctg ggagccggtc ccagagcgc agggcttcct tctgcactgg    2700
caacctgagg gtggccagga acagtcccgg gtcctgggga ccgagctcag cagctatcac    2760
ctggacgggc tggagccagc gacacagtac cgcgtgagc tgagtgtcct agggccagct    2820
ggagaagggc cctctgcaga ggtgactgcg cgcactgagt cacctcgtgt tccaagcatt    2880
gaactacgtg tggtggacac ctcgatcgac tcggtgactt tggcctggac tccagtgtcc    2940
agggcatcca gctacatcct atcctggcgg ccactccagag gccctggcca ggaagtgcct    3000
gggtccccgc agacacttcc agggatctca agctcccagc gggtgacagg gctagagcct    3060
ggcgtctctt acatcttctc cctgacgcct gtcctggatg gtgtgcgggg tcctgaggca    3120
tctgtcacac agacgccagt gtgccccgt ggctggcgg atgtggtgtt cctaccacat    3180
gccactcaag acaatgctca ccgtgcgag gctacgagga gggtcctgga gcgtctggtg    3240
ttggcacttg ggcctcttgg gccacaggca gttcaggttg gcctgctgtc ttacagtcat    3300
cggccctccc cactgttccc actgaatggc tcccatgacc ttggcattat cttgcaaagt    3360
atccgtgaca tgcccctacat ggaccccaagt gggaacaacc tggcacagc cgtggtcaca    3420
gctcacagat acatgttggc accagatgct cctgggcgcc gcagcacgt accagggggtg    3480
atggttctgc tagtggatga acccttgaga gtgacatat tcagccccat ccgtgaggcc    3540
caggcttctg ggcttaatgt ggtgatgttg gaatggctg gagcggaccc agagcagctg    3600
cgtcgcttgg cgcgggtat ggactctgtc cagaccttct tcgccgtgga tgatgggcca    3660
agcctggacc aggcagtcag tggtctggcc acagccctgt gtcaggcatc cttcactact    3720
cagcccccgc cagagccctg cccagtgtat tgtccaaagg gccagaaggg ggaacctgga    3780
gagatgggcc tgagaggaca agttgggcct cctggcgacc ctggcctccc gggcaggacc    3840
ggtgctcccg gccccagggg gcccccctgga agtgccactg ccaagggcga gaggggcttc    3900
cctggagcag atgggcgtcc aggcagccct ggccgcgccg ggaatcctgg gaccccctgga    3960
gccccctggcc taaagggctc tccaggggttg cctggccctg gtggggaccc gggagagcga    4020
ggacctcgag gcccaaaggg ggagccgggg gctcccggac aagtcatcgg aggtgaagga    4080
cctgggcttc ctgggcggaa agggaccct ggaccatcgg gccccctgg acctcgtgga    4140
ccactgggg acccaggacc ccgtggcccc cagggcttcc tgaacagc catgaagggt    4200
gacaaaggga atcgtgggga gcgggtccc cctggaccag gtgaaggtgg cattgctcct    4260
ggggagcctg ggctgccggg tcttcccgga agccctggac cccaaggccc cgttggcccc    4320
cctggaaaga aggagaaaa aggtgactct gaggatggag ctccaggcct cccaggacaa    4380
cctgggtctc cgggtgagca gggcccacgg ggacctcctg gagctattgg ccccaaaggt    4440
gaccggggct ttccaggggc cctggtgag gctggagaga agggcgaacg tggacccca    4500
gggccagcgg gatcccgggg gctgccaggg gttgctggac gtcctggaac caagggtcct    4560
gaagggccac caggacccac tggccgcaa ggagagaaggt gggagcctgg tcgccctggg    4620
gaccctgcag tggtgggacc tgctgttgct ggacccaaag gagaaaaggg agatgtgggg    4680
cccgctgggc ccagaggagc taccggagtc caagggaac ggggcccacc cggcttggtt    4740
cttcctggag accctggccc caagggagac cctggagacc ggggtcccat tggccttact    4800
ggcagagcag gaccccagg tgactcaggg cctcctggag agaagggaga ccctgggcgg    4860
cctgccccc caggacctgt tggccccga ggacgagatg tgaagttgga agagaaaggt    4920
gacgagggtc ctccgggtga cccgggtttg cctgaaaaag caggcgagcg tggccttcgg    4980
ggggcacctg gagttcgggg gcctgtgggt gaaaaaggag accagggaga tcctggagag    5040
gatgacgaaa atggcagccc tggatcatct ggaccaaggg tgaccgtgg ggagccgggt    5100
cccccaggac cccggggacg gctggtagac acaggacctg gagcccagaga agggaaag    5160
cctgggacc ccggacaaga gggtcctcga gggcccaagg gtgatcctgg cctccctgga    5220
gcccctgggg aaaggggcat tgaagggttt cggggacccc caggcccaca ggggacccca    5280
ggtgtccgag gccagcgagg agaaaaggt gaccggggtc cccctgggct ggatggccgg    5340
agcggactgg atgggaaac aggagccgct gggcctcgg ggccgaatgg tgctgcagg    5400
aaagctgggg accagggag agacggggctt ccaggcctcc gtggagaaca gggcctccct    5460
ggcccctctg gtccctggga attaccggga aagccaggcg aggatggcaa acctggcctg    5520
aatgaaaaaa acgagaaacc tggggaccct ggagaagacg gaggaaggg agagaaagga    5580
gattcaggcg cctctgggag agaaggtcgt gatggcccca agggtgagcg tggagctcct    5640
ggtatccttg gaccccaggg gcctccaggc ctcccagggc cagtgggccc tcctggccag    5700
```

```
ggttttcctg gtgtcccagg aggcacgggc cccaagggtg accgtgggga gactggatcc    5760
aaaggggagc agggcctccc tggagagcgt ggcctgcgag gagagcctgg aagtgtgccg    5820
aatgtggatc ggttgctgga aactgctggc atcaaggcat ctgccctgcg ggagatcgtg    5880
gagacctggg atgagagctc tggtagcttc ctgcctgtgc ccgaacgcgc tcgaggcccc    5940
aaggggact caggcgaaca gggcccccca ggcaaggagg gcccatcgg ctttcctgga      6000
gaacgcgggc tgaagggcga ccgtggagac cctggccctc aggggccacc tggtctggcc    6060
cttggggaga ggggccccc cgggccttcc ggccttgccg gggagcctgg aaagcctggt     6120
attcccgggc tcccaggcag ggctgggggt gtgggagagg caggaaggcc aggagagagg    6180
ggagaacggg gagagaaagg agaacgtgga gaacgggca gagatggccc tcctggactc     6240
cctggaaccc ctgggccccc cggaccccct ggcccaagg tgtctgtgga tgagccaggt     6300
cctggactct ctggagaaca gggaccccct ggactcaagg gtgctaaggg ggagccgggc    6360
agcaatggtg accaaggtcc caaggagac agggtgtgc caggcatcaa aggagaccgg      6420
ggagagcctg gaccgagggg tcaggacggc aacccgggtc taccaggaga gcgtggtatg    6480
gctgggcctg aagggaagcc gggtctgcag ggtccaagag gccccctgg cccagtgggt     6540
ggtcatggag accctggacc acctggtgcc ccgggtcttg ctggccctgc aggaccccaa    6600
ggaccttctg gcctgaaggg ggagcctgga gagacaggac ctccaggacg gggcctgact    6660
ggacctactg gagctgtggg acttcctgga ccccccggcc cttcaggcct tgtgggtcca    6720
caggggtctc caggtttgcc tggacaagtg ggggagacag ggaagccggg agccccaggt    6780
cgagatggtg ccagtggaaa agatggagac agagggagcc ctggtgtgcc agggtcacca    6840
ggtctgcctg gcctgtcgg acctaaagga gaacctggcc ccacggggc ccctggacag      6900
gctgtggtcg ggctccctgg agcaaaggga gagaaggag cccctggagg ccttgctgga     6960
gacctggtgg gtgagccggga agccaaaggt gaccgaggac tgccagggcc gcgaggcgag   7020
aagggtgaag ctggccgtgc aggggagccc ggagaccctg ggaagatggg tcagaaaggg   7080
gctccaggac ccaaaggttt caagggtgac ccaggagtcg gggtcccggg ctcccctggg   7140
cctcctggcc ctccaggtgt gaaggagat ctgggcctcc ctggcctgcc cggtgctcct    7200
ggtgttgttg ggttcccggg tcagacaggc cctcgaggag agatggtca gccaggccct    7260
agtggagagc ggggtctggc aggcccccca gggagagaag gaatcccagg accccctggg    7320
ccacctggac caccgggtc agtgggacca cctgggcct ctggactcaa aggagacaag     7380
ggagaccctg gagtagggct gcctgggccc cgaggcgagc gtggggagcc aggcatccgg    7440
ggtgaagtg gccgcccggg ccaggaggga cccccagaga tcacggggcc ccctggcagg    7500
agggagagc gtggggagaa gggtgatgtt gggagtgcag gactaaaggg tgacaaggga    7560
gactcagctg tgatcctggg gcctccaggc ccacggggtg ccaaggggga catgggtgaa    7620
cgagggcctc ggggcttgga tggtgacaaa ggacctcggg gagacaatgg ggaccctggt    7680
gacaagggca gcaagggaga gcctggtgac aagggctcag ccgggttgcc aggactgcgt    7740
ggactcctgg gaccccaggg tcaacctggt gcagcaggga tccctggtga cccgggatcc    7800
ccaggaaagg atggagtgcc tggtatccga ggagaaaaag gagatgttgg cttcatgggt    7860
ccccgggggc tcaagggtga acgggagtg aaggagcct gtggccttga tggagagaag    7920
ggagacaagg gagaagctgg tccccaggc cgccccggc tggcaggaca caaaggagag    7980
atggggagc ctggtgtgcc gggccagtcg ggggccctc gcaaggaggg cctgatcggt    8040
cccaagggtg accgaggctt tgacgggcag ccaggcccca agggtgacca gggcgagaaa    8100
ggggagcggg gaaccccagg aattgggggc ttcccaggcc ccagtggaaa tgatggctct    8160
gctggtcccc cagggccacc tggcagtgtt ggtcccagag gccccgaagg acttcagggc    8220
cagaagggta gcgaggtcc ccccggagag agagtggga gggctcctgg ggtccctgga    8280
gctcctggcg agagaggga gcaggggcgg ccagggcctg ccgtcctcg aggcgagaag   8340
ggagaagctg cactgacgga ggatgacatc cggggcttg tgcgcaaga gatgagtcag    8400
cactgtgcct gccaggggca gttcatcgca tctggatcac gaccccctcc tagttatgct    8460
gcagacactg ccggctccca gctccatgct gtgcctgtgc tccgcgtctc tcatgcagag    8520
gaggaagagc gggtacccc tgaggatgat gagtactctg aatactccga gtattctgtg    8580
gaggagtacc aggaccctga agctccttgg gatagtgatg acccctgttc cctgccactg    8640
gatgagggct cctgcactgc ctacaccctg cgctggtacc atcgggctgt gacaggcagc    8700
acagagagtt gtcaccctt tgtctatggt ggctgtggga gaatgccaa ccgttttggg    8760
acccgtgagg cctgcgagcg ccgctgccca ccccgggtgg tccagagcca ggggacaggt    8820
actgcccagg acggaagcgg agctactaac ttcagcctgc tgaagcaggc tggagacgtg    8880
gaggagaacc ctggacctac ctcctcgggg cctggacccc ggttcctgct gctgctgccg    8940
ctgctgctgc ccctgcggc ctcagcctcc gaccggcccc gggccgaga cccggtcaac    9000
ccagagaagc tgctggtgat cactgtggcc acagctgaaa ccgaggggta cctgcgtttc    9060
ctgcgctctg cggagttctt caactacact gtgcggaccc tgggcctggg agaggagtgg    9120
cgaggggggtg atgtggctcg aacagttggt ggaggacaga aggtccggtg gttaaagaag    9180
gaaatggaga aatacgctga ccgggaggat atgatcatca tgtttgtgga tagctacgac    9240
gtgattctgg ccggcagccc cacagacgtg tgtgaagagt tcgtccagag tggcagccgc    9300
ctgctcttct ctgcagagag cttctgctgg cccgagtggg ggctggcgga gcagtaccct    9360
gaggtgggca cggggaagcg cttcctcaat tctggtggat tcatccggttt tgccaccacc    9420
atccaccaaa tcgtgcgcca gtggaagtac aaggatgatg acgacgacca gctgttctac    9480
acacgctct acctggaccc aggactgagg gagaaactca gccttaatct ggatcataag    9540
tctcggatct ttcagaacct caacgggct ttagatgaag tggttttaaa gtttgatcgg    9600
aaccgtgtgc gtatccggaa cgtggcctac gacacgctcc ccattgtggt ccatggaaac    9660
ggtcccacta agctgcagct caactacctg gaaactacg tccccaatgg ctggactcct    9720
gagggaggct gtggcttctg caaccaggac cggaggacac tcccggggg gcagcctccc    9780
cccgggtct ttctggccgt gtttgtggaa cagcctactc cgtttgtacc tgccttcctg    9840
cagcggctgc tactcctgga ctatcccccc gacagggtca ccctttcct gcacaacaac    9900
gaggtcttcc atgaaccca catcgctgac tcctggccgc agtccagga ccacttctca    9960
gctgtgaagc tcgtggggcc ggaggaggct ctgagcccag cgaggccag ggacatggcc    10020
atggacctgt gtcggcagga cccgagtgt gagttctact tcagcctgga cgccgacgct    10080
gtcctcacca acctgcagac cctgcgtatc ctcattgagg agaacaggaa ggtgatcgcc    10140
cccatgctgt ccccgcacgg caagctgtgg tccaacttct ggggcgccct gagcccgat     10200
gagtactacg ccccgctcga ggactacgtg gagctggtgc agcggaagcg agtgggtgtg    10260
tggaatgtac catacatctc ccaggcctat gtgatccggg gtgataccct gcggatggag    10320
ctgccccaga gggatgtgtt ctcggcagt gacacagacc cggacatggc cttctgtaag    10380
agctttcgag acaagggcat cttcctccat ctgagcaatc agcatgaatt tggccggctc    10440
```

```
ctggccactt ccagatacga cacggagcac ctgcacccct acctctggca gatcttcgac    10500
aaccccgtcg actggaagga gcagtacatc cacgagaact acagccgggc cctggaaggg    10560
gaaggaatcg tggagcagcc atgcccggac gtgtactggt tcccactgct gtcagaacaa    10620
atgtgtgatg agctggtggc agagatggag cactacggcc agtggtcagg cggccggcat    10680
gaggattcaa ggctggctgg aggctacgga aatgtgccca ccgtggacat ccacatgaag    10740
caggtggggt acgaggacca gtggctgcag ctgctgcgga cgtatgtggg ccccatgacc    10800
gagagcctgt tcccggttta ccacaccaag gcgcgggcgg tgatgaactt tgtggttcgc    10860
taccggccag acgagcagcc gtctctgcgg ccacaccacg actcatccac cttcaccctc    10920
aacgttgccc tcaaccacaa gggcctggac tatgaggag gtggctgccg cttcctgcgc      10980
tacgactgtg tgatctcctc cccgaggaag ggctgggcac tcctgcaccc cggccgcctc    11040
acccactacc acgaggggct gccaacgacc tggggcacac gctacatcat ggtgtccttt    11100
gtcgacccct ga                                                         11112

SEQ ID NO: 18        moltype = AA   length = 3703
FEATURE              Location/Qualifiers
REGION               1..3703
                     note = Synthetic Construct
source               1..3703
                     mol_type = protein
                     organism = synthetic construct
SEQUENCE: 18
MTLRLLVAAL CAGILAEAPR VRAQHRERVT CTRLYAADIV FLLDGSSSIG RSNFREVRSF      60
LEGLVLPFSG AASAQGVRFA TVQYSDDPRT EFGLDALGSG GDVIRAIREL SYKGGNTRTG     120
AAILHVADHV FLPQLARPGV PKVCILITDG KSQDLVDTAA QRLKGQGVKL FAVGIKNADP     180
EELKRVASQP TSDFFFFVND FSILRTLLPL VSRRVCTTAG GVPVTRPPDD STSAPRDLVL     240
SEPSSQSLRV QWTAASGPVT GYKVQYTPLT GLGQPLPSER QEVMVPAGET SVRLRGLRPL     300
TEYQVTVIAL YANSIGEAVS GTARTTALEG PELTIQNTTA HSLLVAWRSV PGATGYRVTW     360
RVLSGGPTQQ QELGPGQGSV LLRDLEPGTD YEVTVSTLFG RSVGPATSLM ARTDASVEQT     420
LRPVILGPTS ILLSWNLVPE ARGYRLEWRR ETGLEPPQKV VLPSDVTRYQ LDGLQPGTEY     480
RLTLYTLLEG HEVATPATVV PTGPELPVSP VTDLQATELP GQRVRVSWSP VPGATQYRII     540
VRSTQGVERT LVLPGSQTAF DLDDVQAGLS YTVRVSARVG PREGSASVLT VRREPETPLA     600
VPGLRVVVSD ATRVRVAWGP VPGASGFRIS WSTGSGPESS QTLPPDSTAT DITGLQPGTT     660
YQVAVSVLRG REEGPAAVIV ARTDPLGPVR TVHVTQASSS SVTITWTRVP GATGYRVSWH     720
SAHGPEKSQL VSGEATVAEL DGLEPDTEYT VHVRAHVAGV DGPPASVVVR TAPEPVGRVS     780
RLQILNASSD VLRITWVGVT GATAYRLAWG RSEGGPMRHQ ILPGNTDSAE IRGLEGGVSY     840
SVRVTALVGD REGTPVSIVV TTPPEAPPAL GTLHVVQRGE HSLRLRWEPV PRAQGFLLHW     900
QPEGGQEQSR VLGPELSSYH LDGLEPATQY RVRLSVLGPA GEGPSAEVTA RTESPRVPSI     960
ELRVVDTSID SVTLAWTPVS RASSYILSWR PLRGRPGQEV GSPQTLPGIS SSQRVTGLEP    1020
GVSYIFSLTP VLDGVRGPEA SVTQTPVCPR GLADVVFLPH ATQDNAHRAE ATRRVLERLV    1080
LALGPLGPQA VQVGLLSYSH RPSPLFPLNG SHDLGIILQR IRDMPYMDPS GNNLGTAVVT    1140
AHRYMLAPDA PGRRQHVPGV MVLLVDEPLR GDIFSPIREA QASGLNVVML GMAGADPEQL    1200
RRLAPGMDSV QTFFAVDDGP SLDQAVSGLA TALCQASFTT QPRPEPCPVY CPKGQKGEPG    1260
EMGLRGQVGP PGDPGPGLGR TGAPGPQGPPG SATAKGERGF PGADGRPGSP GRAGNPGPPG    1320
APGLKGSPGL PGPRGDPGER GPRGPKGEPG APGQVIGGEG PGLPGRKGDP GPSGPPGPRG    1380
PLGDPGPRGP PGLPGTAMKG DKGDRGERGP PGPGEGGIAP GEPGLPGLPG SPGPQGPVGP    1440
PGKKGEKGDS EDGAPGLPGQ PGSPGEQGPR GPPGAIGPKG DRGFPGPLGE AGEKGERGPP    1500
GPAGSRGLPG VAGRPGAKGP EGPPGPTGRQ GEKGEPGRPG DPAVVGPAVA PGKGEKGPVG    1560
PAGPRGATGV QGERGPPGLV LPGDPGPKGD PGDRGPIGLT GRAGPPGDSG PPGEKGDPGR    1620
PGPPGPVGPR GRDGEVGEKG DEGPPGDPGL PGKAGERGLR GAPGVRGPVG EKGDQGDPGE    1680
DGRNGSPGSS GPKGDRGEPG PPGPPGRLVD TGPGAREKGE PGDRGQEGPR GPKGDPGLPG    1740
APGERGIEGF RGPPGPQGDP GVRGPAGEKG DRGPPGLDGR SGLDGKPGAA GPSGPNGAAG    1800
KAGDPGRDGL PGLRGEQGLP GPSGPPGLPG KPGEDGKPGL NGKNGEPGDP GEDGRKGEKG    1860
DSGASGREGR DGPKGERGAP GILGPQGPPG LPGPVGPPGQ GFPGVPGGTG PKGDRGETGS    1920
KGEQGLPGER GLRGEPGSVP NVDRLLETAG IKASALREIV ETWDESSGSF LPVPERRRGP    1980
KGDSGEQGPP GKEGPIGFPG ERGLKGDRGD PGPQGPPGLA LGERPPGPS GLAGEPGKPG    2040
IPGLPGRAGG VGEAGRPGER GERGEKGERG EQGRDGPPGL PGTPGPPGPP GPKVSVDEPG    2100
PGLSGEQGPP GLKGAKGEPG SNGDQGPKGD RGVPGIKGDR GEPGPRGQDG NPGLPGERGM    2160
AGPEGKPGLQ GPRGPPGPVG GHGDPGPPGA PGLAGPAGPQ GPSGLKGEPG ETGPPGRGLT    2220
GPTGAVGLPG PPGPSGLVGP QGSPGLPGQV GETGKPGAPG RDGASGKDGD RGSPGVPGSP    2280
GLPGPVGPKG EPGPTGAPGQ AVVGLPGAKG EKGAPGGLAG DLVGEPGAKG DRGLPGPRGE    2340
KGEAGRAGEP GDPGEDGQKG APGPKGFKGD PGVGVPGSPG PPGPPGVKGD LGLPGLPGAP    2400
GVVGFPGQTG PRGEMGQPGP SGERGLAGPP GREGIPGPLG PPGPPGSVGP PGASGLKGDK    2460
GDPGVGLPGP RGERGEPGIR GEDGRPGQEG PRGLTGPPGS RGERGEKGDV GSAGLKGDKG    2520
DSAVILGPPG PRGAKGDMGE RGPRGLDGDK GPRGDNGDPG DKGSKGEPGD KGSAGLPGLR    2580
GLLGPQGQPG AAGIPGDPGS PGKDGVPGIR GEKGDVGFMG PRGLKGERGV KGACGLDGEK    2640
GDKGEAGPPG RPGLAGHKGE MGEPGVPGQS GAPGKEGLIG PKGDRGFDGQ PGPKGDQGEK    2700
GERGTPGIGG FPGPSGNDGS AGPPGPPGSV GRPGPEGLQG QKGERGPPGE RVVGAPGVPG    2760
APGERGEQGR PGPAGPRGEK GEAALTEDDI RGFVRQEMSQ HCACQGQFIA SGSRPLPSYA    2820
ADTAGSQLHA VPVLRVSHAE EEERVPPEDD EYSEYSEYSV EEYQDPEAPW DSDDPCSLPL    2880
DEGSCTAYTL RWYHRAVTGS TEACHPFVYG GCGGNANRFG TREACERRCP PRVVQSQGTG    2940
TAQDGSGATN FSLLKQAGDV EENPGPTSSG PGPRFLLLLP LLLPPAASAS DRPRGRDPVN    3000
PEKLLVITVA TAETEGYLRF LRSAEFFNYT VRTLGLGEEW RGGDVARTVG GGQKVRWLKK    3060
EMEKYADRED MIIMFVDSYD VILAGSPTEL LKKFVQSGSR LLFSAESFCW PEWGLAEQYP    3120
EVGTGKRFLN SGGFIGFATT IHQIVRQWKY KDDDDDQLFY TRLYLDPGLR EKLSLNLDHK    3180
SRIFQNLNGA LDEVVLKFDR NRVRIRNVAY DTLPIVVHGN GPTKLQLNYL GNYVPNGWTP    3240
EGGCGFCNQD RRTLPGGQPP PRVFLAVFVE QPTPFLPRFL QRLLLLDYPP DRVTLFLHNN    3300
EVFHEPHIAD SWPQLQDHFS AVKLVGPEEA LSPGEARDMA MDLCRQDPEC EFYFSLDADA    3360
VLTNLQTLRI LIEENRKVIA PMLSRHGKLW SNFWGALSPD EYYARSEDYV ELVQRKRVGV    3420
WNVPYISQAY VIRGDTLRME LPQRDVFSGS DTDPDMAFCK SFRDKGIFLH LSNQHEFGRL    3480
```

| | | | | | | |
|---|---|---|---|---|---|---|
| LATSRYDTEH | LHPDLWQIFD | NPVDWKEQYI | HENYSRALEG | EGIVEQPCPD | VYWFPLLSEQ | 3540 |
| MCDELVAEME | HYGQWSGGRH | EDSRLAGGYE | NVPTVDIHMK | QVGYEDQWLQ | LLRTYVGPMT | 3600 |
| ESLFPGYHTK | ARAVMNFVVR | YRPDEQPSLR | PHHDSSTFTL | NVALNHKGLD | YEGGGCRFLR | 3660 |
| YDCVISSPRK | GWALLHPGRL | THYHEGLPTT | WGTRYIMVSF | VDP | | 3703 |

```
SEQ ID NO: 19        moltype = DNA   length = 11112
FEATURE              Location/Qualifiers
misc_feature         1..11112
                     note = Synthetic Construct
source               1..11112
                     mol_type = other DNA
                     organism = synthetic construct
SEQUENCE: 19
atgacctcct cggggcctgg accccggttc ctgctgctgc tgccgctgct gctgccccct   60
gcggcctcag cctccgaccg gccccggggc cgagacccgg tcaacccaga gaagctgctg  120
gtgatcactg tggccacagc tgaaaccgag gggtacctgc gtttcctgcg ctctgcggag  180
ttcttcaact acactgtgcg gaccctgggc ctgggagagg agtggcgagg gggtgatgtg  240
gctcgaacag ttggtggagg acagaaggtc cggtggttaa gaaggaaat ggagaaatac   300
gctgaccggg aggatatgat catcatgttt gtggatagct acgacgtgat tctggccggc  360
agccccacag agctgctgaa gaagttcgtc cagagtggca gccgcctgct cttctctgca  420
gagagcttct gctggcccga gtgggggctg gcggagcagt accctgaggt gggcacgggg  480
aagcgcttcc tcaattctgg tggattcatc ggttttgtca ccaccatcca ccaaatcgtg  540
cgccagtgga agtacaagga tgatgacgac gaccagctgt tctacacacg gctctacctg  600
gacccaggac tgaggagaa actcagcctt aatctggatc ataagtctcg gatctttcag  660
aacctcaacg gggctttaga tgaagtggtt ttaaagtttg atcggaaccg tgtgcgtatc  720
cggaactgtg cctacgacac gctccccatt gtggtccatg gaaacggtcc cactaagctg  780
cagctcaact acctgggaaa actacgtccc aatggctgga ctcctgaggg aggctgtggc  840
ttctgcaacc aggaccggag gacactcccg gggggcagc ctcccccccg ggtgtttctg   900
gccgtgtttt tggaacagcc tactccgttt ctgccccgct tcctgcagcg gctgctactc  960
ctggactatc cccccgacag ggtcacccttt tcctgcaca acaacgaggt cttccatgaa 1020
ccccacatcg ctgactcctg gccgcagctc caggaccact tctcagctgt gaagctcgtg 1080
gggccggagg aggctctgag cccaggcgag gccaggggaca tggccatgga cctgtgtcgg 1140
caggaccccg agtgtgagtt ctacttcagc ctggacgccg acgctgtcct caccaacctg 1200
cagaccctgc gtatcctcat tgaggagaac aggaaggtga tcgcccccat gctgtccccgc 1260
cacggcaagc tgtggtccaa cttctgggc gccctgagcc cgatgagta ctacgcccgc  1320
tccgaggact acgtggagct ggtgcagcgg aagcgagtgg gtgtgtggaa tgtaccatac 1380
atctcccagg cctatgtgat ccggggtgat ccctgcgga tggagctgcc ccagagggat 1440
gtgttctcgg gcagtgacac agacccggac atggccttct gtaagagctt tcgagacaag 1500
ggcatcttcc tccatctgag caatcagcat gaatttgaca ggctcctgcc cacttccaga 1560
tacgacacgg agcacctgca cccgacctc tggcagatct tcgacaaccc cgtcgactgg 1620
aaggagcagt acatccacga gaactacagc cgggccctgg aaggggaagg aatcgtggag 1680
cagccatgcc cggacgtgta ctggttccca ctgctgtcag aacaaatgtg tgatgagctg 1740
gtggcagaga tggagcacta cggccagtgg tcaggcggcc ggcatgagga ttcaaggctg 1800
gctggaggct acgagaatgt gcccaccgtg gacatccaca tgaagcaggt ggggtacgag 1860
gaccagtggc tgcagctgct gcggacgtat gtggggcccca tgaccgagag cctgtttccc 1920
ggttaccaca ccaaggcgcg gcggtgatg aactttgtgg ttcgctaccg gccagacgag 1980
cagccgctcc tgcggccaca ccacgactca tccaccttca ccctcaacgt tgccctcaac 2040
cacaagggcc tggactatga gggaggtggc tgccgcttcc tgcgctacga ctgtgtgatc 2100
tcctccccga ggaagggctg ggcactcctg caccccggcc gcctcaccca ctaccacgag 2160
gggctgccaa cgacctgggg cacacgctac atcatggtgt cctttgtcga ccccggaagc 2220
ggagctacta acttcagcct gctgaagcag gctggagacg tggaggagaa ccctggacct 2280
acgctgcggc ttctggtggc cgcgctctgc gccgggatcc tggcagaggc gccccgagtg 2340
cgagcccagc acagggagag agtgacctgc acgcgccttt acgccgctga cattgtgttc 2400
ttactggatg gctcctcatc cattggccgc agcaatttcc gcgaggtccg cagctttctc 2460
gaagggctgg tgctgccttt ctctggagca gccagtgcac agggtgtgcg ctttgccaca 2520
gtgcagtaca gcgatgaccc acggacagag ttcggcctgg atgcacttgg ctctcggggt 2580
gatgtgatcc gcgccatccg tgagcttagc tacaagggggg gcaacactcg cacaggggct 2640
gcaattctcc atgtggctga ccatgtcttc ctgcccccagc tggcccgacc tggtgtcccc 2700
aaggtctgca tcctgatcac agacggggaag tcccaggacc tggtggacac agctgcccaa 2760
aggctgaagg ggcagggggt caagtgtattt gctgtgggga tcaagaatgc tgaccctgag 2820
gagctgaagc gagttgcctc acagcccacc agtgacttct tcttcttcgt caatgacttc 2880
agcatcttga ggacactact gccccctcgtt tccggagag tgtgcacgac tgctggtggc 2940
gtgcctgtga cccgacctcc ggatgactcg acctctgctc cacgagacct ggtgctgtct 3000
gagccaagca gccaatcctt gagagtacag tggacagcca cagtggccc tgtgactggc 3060
tacaaggtcc agtacactcc tctgacgggg ctgggacagc cactgccgag tgagcggcag 3120
gaggtgaacg tcccagctgg tgagaccagt gtgcggctgc ggggtctccg gccactgacc 3180
gagtaccaag tgactgtgat tgccctctac gccaacagca tcgggaggc tgtgagcggg 3240
acagctcgga ccactgccct agaagggccg gaactgctca tccagaatac cacagcccac 3300
agcctcctgg tggcctgcg gagtgtgcca ggtgccactg ctaccgtgt gacatgggg  3360
gtcctcagtg gtgggcccac acagcagcag gagctgggcc ctgggcaggg ttcagtgttg 3420
ctgcgtgact tggagcctgg cacggactat gaggtgaccg tgagcaccct atttggccgc 3480
agtgtggggc cgccacttc cctgatggct cgcactgacg cttctgttga gcagaccctg 3540
cgcccggtca tcctgggccc cacatccatc ctccttcct ggaacttggt gcctgaggcc 3600
cgtggctacc ggttgaatg gcgccgtgag actggctggg agcaccggca gaaggtggta 3660
ctgcctctcg atgtgacccg ctaccagttg gatgggctgc agcccgggcac tgagtaccgc 3720
ctcacactct acactctgct ggagggccac gaggtggcca cctgcaac cgtggttccc 3780
actgaccag agctgctgt gagccctgta acagacctgc aagccaccga gctgccccggg 3840
cagcggggtg gagtgtcctg gagcccagtc cctggtgcca cccagtaccg catcattgtg 3900
cgcagcaccc aggggttga gcggaccctg gtgcttcctg ggagtcagac agcattcgac 3960
```

-continued

```
ttggatgacg ttcaggctgg gcttagctac actgtgcggg tgtctgctcg agtgggtccc   4020
cgtgagggca gtgccagtgt cctcactgtc cgccggagc  cggaaactcc acttgctgtt   4080
ccagggctgc gggttgtggt gtcagatgca acgcgagtga gggtggcctg ggaccegtc    4140
cctggagcca gtggatttcg gattagctgg agcacaggca gtggtccgga gtccagccag   4200
acactgcccc cagactctac tgccacagac atcacgggc  tgcagcctgg aaccacctac   4260
caggtggctg tgtcggtact gcgaggcaga gaggagggcc ctgctgcagt catcgtggct   4320
cgaacgacc  cactgggccc agtgaggacg tccatgtga  ctcaggccag cagctcatct   4380
gtcaccatta cctggaccag ggttcctggc gccacaggat acagggtttc ctggcactca   4440
gcccacgcc  cagagaaatc ccagttggtt tctggggagg ccacggtggc tgagctggat   4500
ggactggagc cagatactga gtatacggtg catgtgaggg cccatgtggc tggcgtggat   4560
gggcccctg  cctctgtggt tgtgaggact gcccctgagc ctgtgggtcg tgtgtcgagg   4620
ctgcagatcc tcaatgcttc cagcgacgtt ctacggatca cctgggtagg ggtcactgga   4680
gccacagctt acagactggc ctggggccgg agtgaaggcg ccccatgag  gcaccagata   4740
ctcccaggaa acacagactc tgcagagatc cggggtctcg aaggtggagt cagctactca   4800
gtgcgagtga ctgcacttgt cggggaccgc gagggcacac ctgtctccat tgttgtcact   4860
acgccgcctg aggctccgcc agccctgggg acgcttcacg tggtgcagcg cggggagcac   4920
tcgctgaggc tgcgctggga gccggtgccc agagcgcagg cttccttct  gcactggcaa   4980
cctgagggtg gccaggaaca gtcccggctc ctgggggccg agtcagcag  ctatcacctg   5040
gacgggctgg agccagcgac acagtaccgc gtgaggctga gtgtcctagg ccagctggaa   5100
gaagggcct  ctgcagaggt gactgcgcgc actgagtcac ctcgtgttcc aagcattgaa   5160
ctacgtgtgg tggacacctc gatcgactcg gtgactttgg cctggactcc agtgtccagg   5220
gcatccagct acatcctatc ctggcggcca ctcagagcc  tggccagga  agtgcctggg   5280
tccccgcaga cacttccagg gatctcaagc tcccagcggg tgacagggct agagcctggc   5340
gtctcttaca tcttctccct gacgcctgtc ctggatggtg tgcggggtcc tgaggcatct   5400
gtcacacaga cgccagtgtg ccccgtggc  ctggcggatg tggtgttcct accacatgcc   5460
actcaagaca atgctcaccg tgcggaggct acgaggaggg tcctgagcg  tctggttgttg  5520
gcacttgggc ctcttgggcc acaggcagtt caggttggcc tgctgtctta cagtcatcgg   5580
ccctccccac tgttcccact gaatggctcc catgaccttg gcattatctt gcaaaggatc   5640
cgtgacatgc cctacatgga cccaagtggg aacaacctgg gcacagccgt ggtcacagct   5700
cacagataca tgttggcacc agatgctcct gggcgccgcc agcacgtacc agggggtgatg  5760
gttctgctag tggatgaacc cttgagaggt gacatattca gccccatccg tgaggcccaa   5820
gcttctgggc ttaatgtggt gatgttggga atggctggag cggacccaga gcagctgcgt   5880
cgcttggcgc cgggtatgga ctctgtccag accttcttcg ccgtggatga tgggccaagc   5940
ctggaccagg cagtcagtgg tctggccaca gccctgtgtc aggcatcctt cactactcag   6000
ccccggccag agcctgccc  agtgtattgt ccaaagggcc agaagggga  acctggagag   6060
atgggcctga gggacaagt  tgggcctcct ggcgaccctg gctcccggg  caggaccggt   6120
gctcccggcc ccagggggcc ccctggaagt gccactgcca agggcgagag gggcttccct   6180
ggagcagatg ggcgtccagg cagccctggc cgcgccggga atcctgggac ccctggagcc   6240
cctggcctaa agggctctcc agggttgcct ggcctccgtg ggaccggg   agagcgagga   6300
cctcgaggcc caaaggggga gccggggct  cccggacaag tcatcggagg tgaaggacct   6360
gggcttcctg gcggaaaagg ggaccctgga ccatcgggcc ccctggacc  tcgtggacca   6420
ctgggggacc caggaccccg tggcccccca gggcttcctg gaacagccat gaagggtgac   6480
aaaggcgatc gtggggagcg gggtccccca ggaccagggca aggtggcat  tgctcctggg   6540
gagcctgggc tgccgggtct tcccggaagc cctggacccc aaggcccgt  tggcccccct   6600
ggaaagaaag gagaaaaagg tgactctgag gatggagctc caggcctccc aggacaacct   6660
gggtctccgg gtgagcaggg cccacgggga cctcctggag ctattggccc caaaggtgac   6720
cgggcttttc caggggcccct gggtgaggct ggagagaagg gcgaacgtgg acccccaggc   6780
ccagcgggat cccgggggct gccagggtt  gctggacgtc ctggagccaa gggtcctgaa   6840
gggccaccag gacccactgg ccgccaagga gagaagggg  agcctggtcg ccctggggac   6900
cctgcagtgg tgggacctgc tgttgctgga cccaaaggag aaaagggaga gtgggggccc   6960
gctgaggccca gaggagctac cggagtccaa ggggaacggg gcccaccegg cttggttctt   7020
cctggagacc ctggccccaa gggagaccct ggagaccggg gtccattgg  ccttactggc   7080
agacaggac  cccaggtga  ctcagggcct ctggagaga  agggagaccc tgggcggcct   7140
ggccccccag gacctgttgg ccccgaggac gagatggtg  aagttggaga gaaaggtgac   7200
ggagtcctc  cgggtgaccc gggttttgcct ggaaaagcag gcgagcgtgg ccttcggggg   7260
gcacctggag ttcggggggcc tgtgggtgaa agggagacc  agggagatcc tggagaggat   7320
ggacgaaatg gcagccctgg atcatctgga cccaagggtg accgtgggga gccgggtccc   7380
ccaggacccc cgggacggct ggtagacaca ggacctggag ccagagagaa gggagagcct   7440
ggggaccgcg gacaagaggg tcctcgaggg cccaagggtg atcctggcct ccctggagca   7500
cctggggaaa ggggcatga  aggggttcgg ggaccccccca gcccacaggg ggacccaggt   7560
gtccgaggcc cagcaggaga aaagggtgac cgggtccccc ctgggctgga tggccggagc   7620
ggactggatg ggaaccagg  agccgctggg ccctctgggc gaatggtgc  tgcaggcaaa   7680
gctgggacc  caggagaga  cgggcttcca ggcctccgtg gagaacaggg cctccctggc   7740
ccctctggtc cccctggatt accgggaaag ccaggcgagg atggcaaacc tggcgaat    7800
ggaaaaaacg gagaacctgg ggaccctgga gaagacgggg ggaagggaga gaaggagat    7860
tcaggcgcct ctgggagaga aggtcgtgat ggccccaagg gtgagcgtgg agctcctggt   7920
atccttggac cccaggggcc tccaggcctc caggggccag tggccctcc  tggccagggt   7980
tttcctggtg tccaggagg  cacgggcccc aagggtgacc gtggggagac tggagtccaaa  8040
ggggagcagg gcctccctgg agagcgtggc ctgcagggga agctggaag  tgtgccaagg   8100
gtggatcggt tgctgaaaac tgctggcatc aaggcatctg ccctgcggga gatcgtggag   8160
acctgggatg agagctctgg tagcttcctg cctgtgcccg aacggcgtcg aggccccaag   8220
ggggactcag gcgaacaggg ccccccaggc aaggagggcc ccatcggctt tcctggaaa    8280
cgcgggctga agggcgaccg tggagaccct ggcctcaggg gcacctggg  tctggccctt   8340
ggggagaggg gcccttccgg gccttcggga agctggaaa  gctcggtatt   8400
cccgggctcc caggcaggggc tggggtgtg  ggagaggcag gaaggccagg agagagggga   8460
gaacgggag  agaaggaga  acgtggagaa caggcagag  atggccctcc tggactccct   8520
ggaaccctg  ggcccccgg  accccctggc cccaaggtgt ctgtgatga  gccaggtcct   8580
ggactctctg gagaacaggg acccctgga  ctcaagggtg ctaaggggga gccgggcagc   8640
aatggtgacc aaggtcccaa aggagacagg ggtgtgccag gcatcaaagg agaccgggga   8700
```

```
gagcctggac cgaggggtca ggacggcaac ccgggtctac caggagagcg tggtatggct  8760
gggcctgaag ggaagccggg tctgcagggt ccaagaggcc cccctggccc agtgggtggt  8820
catggagacc ctggaccacc tggtgccccg ggtcttgctg ccctgcagg accccaagga  8880
ccttctggcc tgaaggggga gcctggagag acaggacctc caggacgggg cctgactgga  8940
cctactggag ctgtgggact tcctggaccc cccggcctc caggccttgt gggtccacag  9000
gggtctccag gttttgcctgg acaagtgggg gagacaggga agccgggagc cccaggtcga  9060
gatggtgcca gtgaaaaga tggagacaga gggagccctg gtgtgccagg tcaccaggt  9120
ctgcctggcc ctgtcggacc taaaggagaa cctggcccca cggggcccc tggacaggct  9180
gtggtcgggc tccctggagc aaagggagag aagggagccc ctggaggcct tgctggagac  9240
ctggtggtg agccgggagc caaaggtgac cgaggactgc caggggccgcg aggcgagaag  9300
ggtgaagctg gccgtgcagg ggagcccgga gaccctgggg aagatggtca gaaaggggct  9360
ccaggaccca aaggtttcaa gggtgaccca ggagtcgggg tcccgggctc ccctgggcct  9420
cctggccctc caggtgtgaa gggagatctg ggcctcctg gcctgccgg tgctcctggt  9480
gttgttgggt tcccgggtca gacaggccct cgaggagaga tgggtcagcc aggccctagt  9540
ggagagcggg gtctgcagg ccccccaggg agagaaggaa tcccaggacc cctggggcca  9600
cctgaccac cggggtcagt gggaccacct gggggcctctg gactcaaagg agacaaggga  9660
gaccctggag taggggctgcc tgggccccga ggcgagcgtg gggagccagg catccgggt  9720
gaagatggcc gccccggcca ggagggaccc cgaggactca cggggccccc tggcagcagg  9780
ggagagcgtg gggagaaggg tgatgttggg agtgcaggac taaagggtga caagggagac  9840
tcagctgtga tcctggggcc tccaggccca cggggtgcca aggggagcat gggtgaacga  9900
gggcctcggg gcttggatgg tgacaaagga cctcggggag acaatgggga ccctggtgac  9960
aagggcagca aggagagcc tggtgacaag ggctcagcgg ggttgccagg actgcgtgga  10020
ctcctgggac cccagggtca acctggtgca gcagggatcc ctggtgaccc gggatccca  10080
ggaaaggatg gagtgcctgg tatccgagga gaaaagggag atgttggctt catgggtccc  10140
cgggggcctca agggtgaacg gggagtgaag ggagcctgtg gccttgatgg agagaaggga  10200
gacaagggag aagctggtcc cccaggccgc ccccgggctg cagacacaa aggagagatg  10260
ggggagcctg gtgtgccggg ccagtcgggg gcccctggca aggagggcct gatcggtccc  10320
aagggtgacc gaggctttga cgggcagcca ggccccaagg gtgaccaggg cgagaaaggg  10380
gagcggggaa ccccaggaat tggggctttc ccaggcccca gtgaaatga tggctctgct  10440
ggtcccccag ggccacctgg cagtgttggt cccagagggc tcgaaggact tcaggggcag  10500
aagggtgagc gaggtccccc cggagagaga gtggtggggg ctcctggggt ccctggagct  10560
cctggcgaga gaggggagca ggggcggcca gggcctgccg gtcctcgagg cgagaaggga  10620
gaagctgcac tgacggagga tgacatccgg ggctttgtgc ccaagagat gagtcagcac  10680
tgtgcctgcc agggccagtt catcgcatct ggatcacgac ccctccctag ttatgctgca  10740
gacactgccg gctcccagct ccatgctgtg cctgtgctcc gcgtctctca tgcagaggag  10800
gaagagcggg taccccctga ggatgatgag tactctgaat actccgagta ttctgtggag  10860
gagtaccagg accctgaagc tccttgggat agtgatgacc cctgttccct gccactggat  10920
gagggctcct gcactgccta cacctgcgc tggtaccatc gggctgtgac aggcagcaca  10980
gaggcctgtc acccttttgt ctatggtggc tgtggaggga atgccaacgc tttttgggacc  11040
cgtgaggcct gcgagcgccg ctgcccaccc cgggtggtcc agaccagggg acaggtact  11100
gcccaggact ga                                                     11112
SEQ ID NO: 20          moltype = AA    length = 3703
FEATURE                Location/Qualifiers
REGION                 1..3703
                       note = Synthetic Construct
source                 1..3703
                       mol_type = protein
                       organism = synthetic construct
SEQUENCE: 20
MTSSGPGPRF LLLLPLLLPP AASASDRPRG RDPVNPEKLL VITVATAETE GYLRFLRSAE   60
FFNYTVRTLG LGEEWRGGDV ARTVGGGQKV RWLKKEMEKY ADREDMIIMF VDSYDVILAG  120
SPTELLKKFV QSGSRLLFSA ESFCWPEWGL AEQYPEVGTG KRFLNSGGFI GFATTIHQIV  180
RQWKYKDDDD DQLFYTRLYL DPGLREKLSL NLDHKSRIFQ NLNGALDEVV LKFDRNRVRI  240
RNVAYDTLPI VVHGNGPTKL QLNYLGNYVP NGWTPEGGCG FCNQDRRTLP GGQPPPRVFL  300
AVFVEQPTPF LPRFLQRLLL LDYPPDRVTL FLHNNEVFHE PHIADSWPQL QDHFSAVKLV  360
GPEEALSPGE ARDMAMDLCR QDPECEFYFS LDDAVLTNL QTLRILIEEN RKVIAPMLSR  420
HGKLWSNFWG ALSPDEYYAR SEDYVELVQR KRVGVWNVPY ISQAYVIRGD TLRMELPQRD  480
VFSGSDTDPD MAFCKSFRDK GIFLHLSNQH EFGRLLATSR YDTEHLHPDL WQIFDNPVDW  540
KEQYIHENYS RALEGEGIVE QPCPDVWFP LLSEQMCDEL VAEMEHYGQW SGGRHEDSRL  600
AGGYENVPTV DIHMKQVGYE DQWLQLLRTY VGPMTESLFP GYHTKARAVM NFVVRYRPDE  660
QPSLRPHHDS STFTLNVALN HKGLDYEGGG CRFLRYDCVI SSPRKGWALL HPGRLTHYHE  720
GLPTTWGTRY IMVSFVDPGS GATNFSLLKQ AGDVEENPGP TLRLLVAALC AGILAEAPRV  780
RAQHRERVTC TRLYAADIVF LLDGSSSIGR SNFREVRSFL EGLVLPFSGA ASAQGVRFAT  840
VQYSDDPRTE FGLDALGSGG DVIRAIRELS YKGGNTRTGA AILHVADHVF LPQLARPGVP  900
KVCILITDGK SQDLVDTAAQ RLKGQGVKLF AVGIKNADPE ELKRVASQPT SDFFFFVNDF  960
SILRTLLPLV SRRVCTTAGG VPVTRPPDDS TSAPRDLVLS EPSSQSLRVQ WTAASGPVTG 1020
YKVQYTPLTG LGQPLPSERQ EVNVPAGETS VRLRGLRPLT VLYTVIALY ANSIGEAVSG 1080
TARTTALEGP ELTIQNTTAH SLLVAWRSVP GATGYRVTWR VLSGGPTQQQ ELGPGQGSVL 1140
LRDLEPGTDY EVTVSTLFGR SVGPATSLMA RTDASVEQTL RPVILGPTSI LLSWNLVPEA 1200
RGYRLEWRRE TGLEPPQKVV LPSDVTRYQL DGLQPGTEYR LTLYTLLEGH EVATPATVVP 1260
TGPELPVSPV TDLQATELPG QRVRVSWSPV PGATQYRIIV RSTQGVERTL VLPGSQTAFD 1320
LDDVQAGLSY TVRVSARVGP REGSASVLTV RREPETPLAV PGLRVVVSDA TRVRVAWGPV 1380
PGASGFRISW STGSGPESSQ TLPPDSTATD ITGLQPGTTY QVAVSVLRGR EEGPAAVIVA 1440
RTDPLGPVRT VHVTQASSSS VTITWTRVPG ATGYRVSWHS AHGPEKSQLV SGEATVAELD 1500
GLEPDTEYTV HVRAHVAGVD GPPASVVVRT APEPVGRVSR LQILNASSDV LRITWVGVTG 1560
ATAYRLAWGR SEGGPMRHQI LPGNTDSAEI RGLEGGVSYS VRVTALVGDR EGTPVSIVVT 1620
TPPEAPPALG TLHVVQRGEH SLRLRWEPVP RAQGFLLHWQ PEGGQESRV LGPELSSYHL 1680
DGLEPATQYR VRLSVLGPAG EGPSAEVTAR TESPRVPSIE LRVVDTSIDS VTLAWTPVSR 1740
```

```
ASSYILSWRP LRGPGQEVPG SPQTLPGISS SQRVTGLEPG VSYIFSLTPV LDGVRGPEAS   1800
VTQTPVCPRG LADVVFLPHA TQDNAHRAEA TRRVLERLVL ALGPLGPQAV QVGLLSYSHR   1860
PSPLFPLNGS HDLGIILQRI RDMPYMDPSG NNLGTAVVTA HRYMLAPDAP GRRQHVPGVM   1920
VLLVDEPLRG DIFSPIREAQ ASGLNVVMLG MAGADPEQLR RLAPGMDSVQ TFFAVDDGPS   1980
LDQAVSGLAT ALCQASFTTQ PRPEPCPVYC PKGQKGEPGE MGLRGQVGPP GDPGLPGRTG   2040
APGPQGPPGS ATAKGERGFP GADGRPGSPG RAGNPGTPGA PGLKGSPGLP GPRGDPGERG   2100
PRGPKGEPGA PGQVIGGEGP GLPGRKGDPG PSGPPGPRGP LGDPGPRGPP GLPGTAMKGD   2160
KGDRGERGPP GPGEGGIAPG EPGLPGLPGS PGPQGPVGPP GKKGEKGDSE DGAPGLPGQP   2220
GSPGEQGPRG PPGAIGPKGD RGFPGPLGEA GEKGERGPPG PAGSRGLPGV AGRPGAKGPE   2280
GPPGPTGRQG EKGEPGRPGD PAVVGPAVAG PKGEKGDVGP AGPRGATGVQ GERGPPGLVL   2340
PGDPGPKGDP GDRGPIGLTG RAGPPGDSGP PGEKGDPGRP GPPGPVGPRG RDGEVGEKGD   2400
EGPPGDPGLP GKAGERGLRG APGVRGPVGE KGDQGDPGED GRNGSPGSSG PKGDRGEPGP   2460
PGPPGRLVDT GPGAREKGEP GDRGQEGPRG PKGDPGLPGA PGERGIEGFR GPPGPQGDPG   2520
VRGPAGEKGD RGPPGLDGRS GLDGKPGAAG PSGPNGAAGK AGDPGRDGLP GLRGEQGLPG   2580
PSGPPGLPGK PGEDGKPGLN GKNGEPGDPG EDGRKGEKGD SGASGREGRD GPKGERGAPG   2640
ILGPQGPPGL PGPVGPPGQG FPGVPGGTGP KGDRGETGSK GEQGLPGERG LRGEPGSVPN   2700
VDRLLETAGI KASALREIVE TWDESSGSFL PVPERRRGKG GDSGEQGPPG KEGPIGFPGE   2760
RGLKGDRGDP GPQGPPGLAL GERGPPGPSG LAGEPGKPGI PGLPGRAGGV GEAGRPGERG   2820
ERGEKGERGE QGRDGPPGLP GTPGPPGPPG PKVSVDEPGP GLSGEQGPPG LKGAKGEPGS   2880
NGDQGPKGDR GVPGIKGDRG EPGPRGQDGN PGLPGERGMA GPEGKPGLQG PRGPPGPVGG   2940
HGDPGPPGAP GLAGPAGPQG PSGLKGEPGE TGPPGRGLTG PTGAVGLPGP PGPSGLVGPQ   3000
GSPGLPGQVG ETGKPGAPGR DGASGKDGDR GSPGVPGSPG PGVPGPKGE PGPTGAPGQA   3060
VVGLPGAKGE KGAPGGLAGD LVGEPGAKGD RGLPGPRGEK GEAGRAGEPG DPGEDGQKGA   3120
PGPKGFKGDP GVGVPGSPGP PGPPGVKGDL GLPGLPGAPG VVGFPGQTGP RGEMGQPGPS   3180
GERGLAGPPG REGIPGPLGP PGPPGSVGPP GASGLKGDKG DPGVGLPGPR GERGEPGIRG   3240
EDGRPGQEGP RGLTGPPGSR GERGEKGDVG SAGLKGDGLG SAVILGPPGP RGAKGDMGER   3300
GPRGLDGDKG PRGDNGDPGD KGSKGEPGDK GSAGLPGLRG LLGPQGQPGA AGIPGDPGSP   3360
GKDGVPGIRG EKGDVGFMGP RGLKGERGVK GACGLDGEKG DKGEAGPPGR PGLAGHKGEM   3420
GEPGVPGQSG APGKEGLIGP KGDRGFDGQP GPKGDQGEKG ERGTPGIGGF PGPSGNDGSA   3480
GPPGPPGSVG PRGPEGLQGQ KGERGPPGER VVGAPGVPGA PGERGEQGRP GPAGPRGEKG   3540
EAALTEDDIR GFVRQEMSQH CACQGQFIAS GSRPLPSYAA DTAGSQLHAV PVLRVSHAEE   3600
EERVPPEDDE YSEYSEYSVE EYQDPEAPWD SDDPCSLPLD EGSCTAYTLR WYHRAVTGST   3660
EACHPFVYGG CGGNANRFGT REACERRCPP RVVQSQGTGT AQD                    3703

SEQ ID NO: 21           moltype = DNA   length = 11115
FEATURE                 Location/Qualifiers
misc_feature            1..11115
                        note = Synthetic Construct
source                  1..11115
                        mol_type = other DNA
                        organism = synthetic construct
SEQUENCE: 21
atgacgctgc ggcttctggt ggccgcgctc tgcgccggga tcctggcaga ggcgccccga    60
gtgcgagccc agcacaggga gagtgacctg cacgcgcc tttacgccgc tgacattgtg   120
ttcttactgg atggctcctc atccattggc cgcagcaatt ccgcgaggt ccgcagcttt   180
ctcgaaggc tggtgctgcc tttctctgga gcagccagtg cacagggtgt gcgctttgcc   240
acagtgcagt acagcgatga cccacgggca gagttcggcc tggactgcat tggctctggg   300
ggtgatgtga tccgcgccat ccgtgagctt agctacaagg ggggcaacac tcgcacaggg   360
gctgcaattc tccatgtggc tgaccatgtc ttcctgcccc agctggccg acctggtgtc   420
cccaaggtct gcatcctgat cacagacggg aagtcccagg acctggtgga cacagctgcc   480
caaaggctga aggggcaggg ggtcaagcta tttgctgtgg ggatcaagaa tgctgaccct   540
gaggagctga agcgagttgc ctcacagccc accagtgact tcttcttctt cgtcaatgac   600
ttcagcatct tgaggacact actgccctc gtttcccgga gagtgtgcac gactgctggt   660
ggcgtgcctg tgacccgacc tccggatgac tcgacctctg ctccacgaga cctggtgctg   720
tctgagccaa gcagccaatc cttgagagta cagtggacac cggccagtgg ccctgtgact   780
ggctacaagg tccagtacac tcctctgacg gggctgggac agccactgcc gagtgagcgg   840
caggaggtga acgtcccagc tggtgagacc agtgtgcggc tgcggggtct ccggccactg   900
accgagtacc aagtgactgt gattgccctc tacgccaaca gcatcgggga ggctgtgagc   960
gggacagctc ggaccactgc cctagaaggg ccggaactga ccatccagaa taccacagcc  1020
cacgcctcc tggtgggcctg gcggagtgtg ccaggtgcca ctggctaccg tgtgacatgg  1080
cgggtcctca gtggtgggcc cacacagcag caggagctgg gccctgggca gggtcagtg  1140
ttgctgcgtg acttggagcc tggcacggac tatgaggtga ccgtgagcac cctatttggc  1200
cgcagtgtgg ggcccgccac ttccctgatg gctcgcactg acgcttctgt tgagcagacc  1260
ctgccccgg tcatcctggg ccccacatcc atcctccttt cctggaactt ggtgcctgag  1320
gcccgtggct accggttgga atggcggcgt gagactggct ggagccacc gcagaaggtg  1380
gtactgcccc tgatgtgac ccgctaccag ttggatgggc tgcagccggg cactgagtac  1440
cgcctccac tctacactct gctggagggc acgaggtgg ccaccctgc aaccgtggtt  1500
cccactggac cagagctgcc tgtgagacc gtaacagacc tgcaagtgca cgagctgccc  1560
gggcagtgg tgcgagtgtc ctggaagccca ccacccagta ccgcatcatt  1620
gtgcgcagca cccaggggt tgagcggacc ctggtgcttc ctgggagtca gacagcattc  1680
gacttggatg acgttcaggc tgggcttagc tacactgtgc gggtgtctgc tcagtgggt  1740
ccccgtgagg gcagtgccag tgtcctcact gtccgccggg agccgaaac tccacttgct  1800
gttcagggc tgcgggttgt ggtgtcagat gcaacgcgag tgagggtggc ctggggaccc  1860
gtccctggag ccagtggatt tcggattagc tgggaacga gagtgctca ggatccagc  1920
cagacactgc cccagactc tactgccaca gacatcacag gctgcagcc tggaaccacc  1980
taccaggtgc tgtgtcggt actgcgaggc agagaggag ccctgctgc agtcatcgtg  2040
gctcgaacgc acccactggg cccagtgagg acgtccatg tgactcaggc cagcagctca  2100
tctgtccaca ttacctggac cagggttcct ggcgccacag gatacaggt ttcctggcac  2160
tcagcccacg gcccagagaa atcccagttg gtttctgggg aggccacggt ggctgagctg  2220
```

```
gatggactgg agccagatac tgagtatacg gtgcatgtga gggcccatgt ggctggcgtg   2280
gatgggcccc ctgcctctgt ggttgtgagg actgccctg agcctgtggg tcgtgtgtcg    2340
aggctgcaga tcctcaatgc ttccagcgac gttctacgga tcacctgggt aggggtcact   2400
ggagccacag cttacagact ggcctggggc cggagtgaag gcggcccat gaggcaccag    2460
atactcccag gaaacacaga ctctgcagag atccgggtc tcgaaggtgg agtcagctac    2520
tcagtgcgag tgactgcact tgtcgggac cgcgagggca cacctgtctc cattgttgtc    2580
actacgccgc ctgaggctcc gccagccctg gggacgcttc acgtggtgca gcgcggggag   2640
cactcgctga ggctgcgctg ggagccggtg cccagagcgc agggcttcct tctgcactgg   2700
caacctgagg gtgccagga acagtccgg gtcctggggc ccagctcag cagctatcac     2760
ctggacgggc tggagccagc gacacagtac cgcgtgggc tgagtgtcct agggccagct   2820
ggagaagggc cctctgcaga ggtgactgcg cgcactgagt cacctcgtgt tccaagcatt   2880
gaactacgtg tggtggacac ctcgatcgac tcggtgactt tggcctggac tccagtgtcc   2940
agggcatcca gctacatcct atcctggcgg ccactcagag gccctggcca ggaagtgcct   3000
gggtcccccgc agacacttcc agggatctca agctcccagc gggtgacagg gctagagcct   3060
ggcgtctctt acatcttctc cctgacgcct gtcctggatg gtgtgcgggg tcctgaggca   3120
tctgtcacac agacgccagt gtgccccgt ggctggcgg atgtggtgtt cctaccacat    3180
gccactcaag acaatgctca ccgtgcgag gctacgagga gggtcctgga gcgtctggtg    3240
ttggcacttg ggcctcttgg gccacaggca gttcaggttg gcctgctgtc ttacagtcat   3300
cggccctccc cactgttccc actgaatggc tcccatgacc ttggcattat cttgcaaagg   3360
atccgtgaca tgccctacat ggacccaagt gggaacaacc tgggcacagc cgtggtcaca   3420
gctcacagat acatgttggc accagatgct cctgggcgcc gccagcacgt accagggtg    3480
atggttctgc tagtgcatga acccttgaga ggtgacatat tcagccccat ccgtgaggcc   3540
caggcttctg ggcttaatgt ggtgatgttg ggaatggctg gagcggaccc agagcagctg   3600
cgtcgcttgg cgccgggtat ggactctgtc cagaccttct tcgccgtgga tgatgggcca   3660
agcctggacc aggcagtcag tggtctggcc acagccctgt gtcaggcatc cttcactact   3720
cagccccggc cagagccctg cccagtgtat tgtccaaagg gccagaaggg ggaacctgga   3780
gagatgggcc tgagaggaca agttgggcct cctggcgacc ctggcctccc gggcaggacc   3840
ggtgctcccg gccccaggg gcccctgga agtgccactg ccaagggcga gaggggcttc    3900
cctggagcag atgggcgtcc aggcagccct ggccgcgccg gaatcctgg gaccctgga    3960
gcccctggcc taaagggctc tccagggttg cctggccctc gtggggaccc gggagagcga   4020
ggacctcgag gcccaaaggg ggagcggggc gctcccggac aagtcatcgg aggtgaagga   4080
cctgggcttc ctgggcggaa aggggaccct ggaccatcgg gccccctgg acctcgtgga   4140
ccactggggg acccaggacc ccgtggcccc cagggcttc ctggaacagc catgaagggt    4200
gacaaaggcg atcgtgggga gcgggtccc cctggaccag gtgaaggtgg cattgctcct    4260
ggggagcctg ggctgccggg tcttcccgga agccctggc cccaagggcc cgttggcccc   4320
cctggaaaga aggagaaaa aggtgactct gaggatggag ctccaggcct cccaggacaa   4380
cctgggtctc cgggtgagca gggcccacgg ggacctcctg gagctattgg ccccaaaggt   4440
gaccgggct ttccagggcc cctgggtgag gctggagaga agggcgaacg tggaccccca   4500
ggcccagcgg gatcccgggg gctgccaggg gttgctggac gtcctggagc caagggtcct   4560
gaagggccac caggacccac tggccgccaa ggagagaagg gggagcctgg tcgcccggg    4620
gaccctgcag tggtcgggacc tgctgttgct ggacccaaag gagaaagggg agatgtgggg   4680
cccgctgggc cagaggagc taccgagtc caagggaac ggggcccacc cggcttggtt      4740
cttcctggag acccctggccc caaggggac cctggagacc gggctcccat tggccttact   4800
ggcagagcag gaccccaggt gactcaggg cctcctggaga agggggaga cctgggcgg     4860
cctgccccc caggacctgt tggccccga ggacgagatg tgaagttgg agagaaaggt      4920
gacgagggtc ctcggggtga cccgggtttg cctgaaaaag caggcgagcg tggccttcgg   4980
ggggcacctg gagttcgggg gcctgtgggt gaaaaggag accagggaga tcctggagag   5040
gatggacgaa atgcagcccc tggatcatct ggacccaagg gtgaccgtgg ggagccggt    5100
cccccaggac ccccggacg gctggtagac acaggacctg gagccagaga aaggggagag    5160
cctggggacc gcggacaaga gggtcctcga gggcccaagg gtgatcctgg cctccctgga   5220
gccctggggg aaaggggcat tgaaggggtt cggggaccc caggcccaca ggggaccca     5280
ggtgtccgag gcccagcagg agaaaagggt gaccggggtc cccctgggct ggatggccgg   5340
agcggactgg atgggaaacc aggagccgct gggccctctg gccgaatgg tgctgcaggc   5400
aaagctggg acccagggag agacgggctt ccaggcctcc gtgagaaaca gggcctccct    5460
ggccctctg gtccccctgg attaccggga aagccaggcc aggatggca acctggcctg    5520
aatgaaaaa acggagaacc tggggacccct ggagaagacg ggaggaaggg agagaaagga   5580
gattcaggcg cctctgggag agaaggtcgt gatggcccca gggtgagcg tggagctcct   5640
ggtatccttg gaccccaggg gcctccaggc ctcccaggc cagtgggccc tcctggccag    5700
ggttttcctg gtgtcccagg aggcagggc cccaagggtg accgtgggga gactggatcc    5760
aaagggggagc agggcctccc tggagagcgt ggcctggac gagagccgg aagtgtgccg    5820
aatgtggatc ggttgctgga aactgctggc atcaaggcat ctgccctgcg ggagatcgtg   5880
gagacctggg atgagagctc tggtagcttc ctgcctgtgc ccgaacggc tcgaggcccc   5940
aagggggact caggcgaaca gggccccca ggcaaggagg gcccatcgg ctttcctgga     6000
gaaccgtggg tgaagggcga ccgtggagac cctggccctc aggggccac tggctgccca   6060
cttgggggaga gggccccccc cgggccttcc ggccttgccg gggagcctgg aaagcctggt   6120
attcccggc tcccaggcag gctgggggt gtggagaggg caggaagc aggagagagg      6180
ggagaacggc gagagaaagg agaacgtgga gaacaggca gagatggccc tcctggactc   6240
cctggaaccc ctgggccccc cggaccccct ggcccaagg tgtctgtgga tgagccaggt   6300
cctggactct ctggagaaca gtgaccccct ggactcaagg gtcaagg agggagccggc   6360
agcaatggtg accaaggtcc caaaggagac aggggtgtgc caggcatcaa aggagaccgg   6420
ggagagcctg gaccgagggg tcaggacggc aacccgggtc taccaggaga gcgtggtatg   6480
gctgggcctg aagggaagcc gggtctgcag gtccaagag ccccctggg ccagtgggt     6540
ggtcatggag accctggacc acctggtgcc ccgggtcttg ctggcctgc aggacccaa    6600
ggaccttctg gcctgaaggg ggagacagag acacagcagg gagccttgact ggccccagg   6660
ggacctactg gagctgtggg acttcctgga ccccccggcc cttcaggcct tgtgggtcca   6720
cagggctcc caggttgcc tggacaagtg ggggagacag ggagccggg agccccaggt     6780
cgagatggtc ccagtggaaa agatggagac agaggggagcc ctggtgtgcc agggtcacca   6840
ggtctgcctg gccctgtcgg acctaaagga gaacctggcc cacggggc ccctggacag    6900
gctgtggtcg ggctccctgg agcaaaggga gagaaggag ccctggagg ccttgctgga    6960
```

```
gacctggtgg gtgagccggg agccaaaggt gaccgaggac tgccaggcc gcgaggcgag    7020
aagggtgaag ctggccgtgc aggggagccc ggagaccctg gggaagatgg tcagaaaggg    7080
gctccaggac ccaaaggttt caagggtgac caggagtcg gggtcccggg ctcccctggg     7140
cctcctggcc ctccaggtgt gaaggagat ctgggcctcc ctggcctgcc cggtgctcct    7200
ggtgttgttg ggttcccggg tcagacaggc cctcgaggag agatgggtca gccaggcct    7260
agtggagagc ggggtctggc aggcccccca gggagagaag gaatcccagg accctggg     7320
ccacctggac caccggggtc agtgggacca cctgggcct ctggactcaa aggagacaag    7380
ggagaccctg gagtagggct gcctgggccc cgaggcgagc gtggggagcc aggcatccgg    7440
ggtgaagatg gccgccccgg ccaggaggga ccccgaggac tcacgggcc cctggcagc     7500
aggggagagc gtggggagaa gggtgatgtt gggagtgcag gactaaaggg tgacaaggga    7560
gactcagctg tgatcctggg gcctccaggc ccacggggtg ccaaggggga catgggtgaa    7620
cgagggcctc ggggcttgga tggtgacaaa ggacctcggg gagacaatgg ggaccctggt    7680
gacaagggca gcaagggaga gcctggtgac aagggctcag ccgggttgcc aggactgcgt    7740
ggactcctgg gaccccaggg tcaacctggt gcagcaggga tccctggtga cccgggatcc    7800
ccaggaaagg atggagtgcc tggtatccga ggagaaaaag gagatgttgg cttcatgggt    7860
ccccggggcc tcaagggtga acggggagtg aagggagcct gtggccttga tggagagaag    7920
ggagacaagg gagaagctgg tccccaggc cgccccgggc tggcaggaca caaggagag     7980
atggggagc ctggtgtgcc gggccagtcg ggggcccctg gcaaggaggg cctgatcggt    8040
cccaagggtg accgaggctt tgacgggcag ccaggcccca aggtgacca gggcgagaaa    8100
ggggagcggg gaaccccagg aattgggggc ttcccaggcc ccagtggaaa tgatggctct    8160
gctggtcccc cagggccacc tggcagtgtt ggtcccagag gccccaagg acttcagggc    8220
cagaagggta gcgaggtcc ccccggagag agagtggcc gggctcctgg ggtccctgga    8280
gctcctggcg agagaggga gcaggggcgg ccagggcctg ccggtcctcg aggcgagaag    8340
ggagaagctg cactgacgga ggatgacatc cggggcttg tgcgccaaga gatgagtcag    8400
cactgtgcct gccagggcca gttcatcgca tctggatcac gacccctccc tagttatgct    8460
gcagacactg ccggctccca gctccatgct gtgcctgtgc tccgcgtctc tcatgcagag    8520
gaggaagagc gggtaccccc tgaggatgat gagtactctg aatactccga gtattctgtg    8580
gaggagtacc aggaccctga agtccttgg gatagtgatg ccctgttc cctgccactg     8640
gatgagggct cctgcactgc ctacacctg cgctggtacc atcgggctgt gacaggcagc    8700
acagagcgct gtcacccttt tgtctatggt ggctgtggaa ggaatgccaa ccgttttggg    8760
acccgtgagg cctgcgagcg ccgctgccca ccccggggtgg tccagagcca ggggacaggt    8820
actgccagg acgaagcgg acagtgtact aattatgctc tcttgaaatt ggctggagat    8880
gttgagagca cccctggacc tacctcctcg gggcctggac cccggttcct gctgctgctg    8940
ccgctgctgc tgcccctgc ggcctcagcc tccgaccggc cccggggccg agaccggtc    9000
aacccagaga agctgctggt gatcactggt gccacacgtg aaaccgaggg gtacctgcgt    9060
ttcctgcgct ctgcggagtt cttcaactac actgtgcgga ccctgggcct gggagaggag    9120
tggcgagggg gtgatgtggc tcgaacagtt ggtggaggac agaaggtccg gtggttaaag    9180
aaggaaatgg agaaatacgc tgaccgggag gatatgatca tcatgtttgt ggatagctac    9240
gacgtgattc tggccggcag ccccacagag ctgctgaagg tcatctcca gagtggccgc    9300
cgcctgctct tctctgcaga gagcttctgc tggcccgagt gggggctggc ggagcagtac    9360
cctgaggtgg gcacggggaa gcgcttcctc aattctggtg gattcatcgg ttttgccacc    9420
accatccacc aaatcgtgcg ccagtggaag tacaaggatg atgacgacga ccagctgttc    9480
tacacacgtc tctacctgga cccaggacta gggagaaac tcagccttaa tctggatcat    9540
aagtctcgga tctttcagaa cctcaacggg gctttagatg aagtggtttt aaagttgat    9600
cggaaccgtg tgcgtatccg gaacgtggcc tacgacacgc tccccattgt ggtccatgga    9660
aacgtcccca ctaagctgca gctcaactac ctgggaaact acgtcccaa tggctggact    9720
cctgaggag gctgtggctt ctgcaaccag gaccggagga cactcccggg ggggcagcct    9780
cccccccggg tgtttctggc cgtgtttgtg aacagccta ctccgtttct gccccgcttc    9840
ctgcagcggc tgctactcct ggactatccc cccgacaggg tcacccttt cctgcacaac    9900
aacgaggtct ccatgaacc cacatcgct gactcctggc cgcagctcca ggaccacttc    9960
tcagctgtga agctcgtggg gccggaggag gctctgagcc caggcgaggc cagggacatg   10020
gccatggacc tgtgtcggca ggaccccgag tgtgagttct acttcagcct ggacgccgac   10080
gctgtcctca ccaacctgca gacctgcgt atcctcattg aggagaacag gaaggtgatc   10140
gcccccatgt gtcccgcca cggcaagctg tggtccaact tctggggcgc cctgagcccc   10200
gatgagtact acgcccgctc cgaggactac tgtggagcgg atgagggat gccagtggg     10260
gtgtggaatg taccatacat ctcccaggcc tatgtgatcc ggggtgatac cctgcgatg   10320
gagctgcccc agaggggatgt gttctcgggc agtgacacag acccggacat ggcctttgt   10380
aagagcttc gagacaaggg catcttcctc catctgagca atcagcatga atttggccgg   10440
ctcctggcca cttccagata cgacacggag cacctgcacc ccgacctgtg gcagatcttc   10500
gacaacccg tcgactggaa ggagcagtac atccacagga actacagccg ggccctggaa   10560
ggggaaggaa tcgtggagca gccatgcccg gacgtgtact ggttccacct gctgtcagaa   10620
caaatgtgtg atgagctggt ggcagagatg gagcactacg ccagtggtc aggcggccgg   10680
catgaggatt caaggctggc tggaggctac gagaatgtgc ccaccgtgga catccacatg   10740
aagcaggtgg ggtacgagga ccagtggctg cagctgctg gggccccatg                10800
accgagagcc tgtttcccgg ttaccacacc aaggcgcggg cggtgatgaa ctttgtggtt   10860
cgctaccggc cagacgagca gccgtctctg cggccacacc acgactcatc caccttcacc   10920
ctcaacgttg ccctcaacca caaggggctg gactatgagg gaggtggctg ccgcttcctg   10980
cgctacgact gtgtgatctc ctcccgagg aagggctggg cactcctgca ccccggccgc   11040
ctcacccact accacgaggg gctgccaacg acctgggcca cacgctacat catggtgtcc   11100
tttgtcgacc cctga                                                     11115

SEQ ID NO: 22        moltype = AA  length = 3704
FEATURE              Location/Qualifiers
REGION               1..3704
                     note = Synthetic Construct
source               1..3704
                     mol_type = protein
                     organism = synthetic construct
SEQUENCE: 22
```

| | | | | | | |
|---|---|---|---|---|---|---|
| MTLRLLVAAL | CAGILAEAPR | VRAQHRERVT | CTRLYAADIV | FLLDGSSSIG | RSNFREVRSF | 60 |
| LEGLVLPFSG | AASAQGVRFA | TVQYSDDPRT | EFGLDALGSG | GDVIRAIREL | SYKGGNTRTG | 120 |
| AAILHVADHV | FLPQLARPGV | PKVCILITDG | KSQDLVDTAA | QRLKGQGVKL | FAVGIKNADP | 180 |
| EELKRVASQP | TSDFFFFVND | FSILRTLLPL | VSRRVCTTAG | GVPVTRPPDD | STSAPRDLVL | 240 |
| SEPSSQSLRV | QWTAASGPVT | GYKVQYTPLT | GLGQPLPSER | QEVNVPAGET | SVRLRGLRPL | 300 |
| TEYQVTVIAL | YANSIGEAVS | GTARTTALEG | PELTIQNTTA | HSLLVAWRSV | PGATGYRVTW | 360 |
| RVLSGGPTQQ | QELGPGQGSV | LLRDLEPGTD | YEVTVSTLFG | RSVGPATSLM | ARTDASVEQT | 420 |
| LRPVILGPTS | ILLSWNLVPE | ARGYRLEWRR | ETGLEPPQKV | VLPSDVTRYQ | LDGLQPGTEY | 480 |
| RLTLYTLLEG | HEVATPATVV | PTGPELPVSP | VTDLQATELP | GQRVRVSWSP | VPGATQYRII | 540 |
| VRSTQGVERT | LVLPGSQTAF | DLDDVQAGLS | YTVRVSARVG | PREGSASVLT | VRREPETPLA | 600 |
| VPGLRVVVSD | ATRVRVAWGP | VPGASGFRIS | WSTGSGPESS | QTLPPDSTAT | DITGLQPGTT | 660 |
| YQVAVSVLRG | REEGPAAVIV | ARTDPLGPVR | TVHVTQASSS | SVTITWTRVP | GATGYRVSWH | 720 |
| SAHGPEKSQL | VSGEATVAEL | DGLEPDTEYT | VHVRAHVAGV | DGPPASVVVR | TAPEPVGRVS | 780 |
| RLQILNASSD | VLRITWVGVT | GATAYRLAWG | RSEGGPMRHQ | ILPGNTDSAE | IRGLEGGVSY | 840 |
| SVRVTALVGD | REGTPVSIVV | TTPPEAPPAL | GTLHVVQRGE | HSLRLRWEPV | PRAQGFLLHW | 900 |
| QPEGGQEQSR | VLGPELSSYH | LDGLEPATQY | RVRLSVLGPA | GEGPSAEVTA | RTESPRVPSI | 960 |
| ELRVVDTSID | SVTLAWTPVS | RASSYILSWR | PLRGPGQEVP | GSPQTLPGIS | SSQRVTGLEP | 1020 |
| GVSYIFSLTP | VLDGVRGPEA | SVTQTPVCPR | GLADVVFLPH | ATQDNAHRAE | ATRRVLERLV | 1080 |
| LALGPLGPQA | VQVGLLSYSH | RPSPLFPLNG | SHDLGIILQR | IRDMPYMDPS | GNNLGTAVVT | 1140 |
| AHRYMLAPDA | PGRRQHVPGV | MVLLVDEPLR | GDIFSPIREA | QASGLNVVML | GMAGADPEQL | 1200 |
| RRLAPGMDSV | QTFFAVDDGP | SLDQAVSGLA | TALCQASFTT | QPRPEPCPVY | CPKGQKGEPG | 1260 |
| EMGLRGVGP | PGDPGLPGRT | GAPGPQGPPG | SATAKGERGP | PGADGRPGSP | GRAGNPGTPG | 1320 |
| APGLKGSPGL | PGPRGDPGER | GPRGPKGEPG | APGQVIGGEG | PGLPGRKGDP | GPSGPPGPRG | 1380 |
| PLGDPGPRGP | PGLPGTAMKG | DKGDRGERGP | PGPGEGGIAP | GEPGLPGLPG | SPGPQGPVGP | 1440 |
| PGKKGEKGDS | EDGAPGLPGQ | PGSPGEQGPR | GPPGAIGPKG | DRGFPGPLGE | AGEKGERGPP | 1500 |
| GPAGSRGLPG | VAGRPGAKGP | EGPPGPTGRQ | GEKGEPGRPG | DPAVVGPAVA | GPKGEKGDVG | 1560 |
| PAGPRGATGV | QGERGPPGLV | LPGDPGPKGD | PGDRGPIGLT | GRAGPPGDSG | PPGEKGDPGR | 1620 |
| PGPPGPVGPR | GRDGEVGEKG | DEGPPGDPGL | PGKAGERGLR | GAPGVRGPVG | EKGDQGPGE | 1680 |
| DGRNGSPGSS | GPKGDRGEPG | PPGPPGRLVD | TGPGAREKGE | PGDRGQEGPR | GPKGDPGLPG | 1740 |
| APGERGIEGF | RGPPGPQGDP | GVRGPAGEKG | DRGPPGLDGR | SGLDGKPGAA | GPSGPNGAAG | 1800 |
| KAGDPGRDGL | PGLRGEQGLP | GPSGPPGLPG | KPGEDGKPGL | NGKNGEPGDP | GEDGRKGEKG | 1860 |
| DSGASGREGR | DGPKGERGAP | GILGPQGPPG | LPGPVGPPGQ | GFPGVPGGTG | PKGDRGETGS | 1920 |
| KGEQGLPGER | GLRGEPGSVP | NVDRLLETAG | IKASALREIV | ETWDESSGSF | LPVPERRRGP | 1980 |
| KGDSGEQGPP | GKEGPIGFPG | ERGLKGDRGD | PGPQGPPGLA | LGERGPPGPS | GLAGEPGKPG | 2040 |
| IPGLPGRAGG | VGEAGRPGER | GERGEKGERG | EQGRDGPPGL | PGTPGPPGPP | GPKVSVDEPG | 2100 |
| PGLSGEQGPP | GLKGAKGEPG | SNGDQGPKGD | RGVPGIKGDR | GEPGPRGQDG | NPGLPGERGM | 2160 |
| AGPEGKPGLQ | GPRGPPGPVG | GHGDPGPPGA | PGLAGPAGPQ | GPSGLKGEPG | ETGPPGRGLT | 2220 |
| GPTGAVGLPG | PPGPSGLVGP | QGSPGLPGQV | GETGKPGAPG | RDGASGKDGD | RGSPGVPGSP | 2280 |
| GLPGPVGPKG | EPGPTGAPGQ | AVVGLPGAKG | EKGAPGGLAG | DLVGEPGAKG | DRGLPGPRGE | 2340 |
| KGEAGRAGEP | GDPGEDGQKG | APGPKGFKGD | PGVGVPGSPG | PPGPPGVKGD | LGLPGLPGAP | 2400 |
| GVVGFPGQTG | PRGEMGQPGP | SGERGLAGPP | GREGIPGPLG | PPGPPGSVGP | PGASGLKGDK | 2460 |
| GDPGVGLPGP | RGERGEPGIR | GEDGRPGQEG | PRGLTGPPGS | RGERGEKGDV | GSAGLKGDKG | 2520 |
| DSAVILGPPG | PRGAKGDMGE | RGPRGLDGDK | GPRGDNGDPG | DKGSKGEPGD | KGSAGLPGLR | 2580 |
| GLLGPQGQPG | AAGIPGDPGS | PGKDGVPGIR | GEKGDVGFMG | PRGLKGERGV | KGACGLDGEK | 2640 |
| GDKGEAGPPG | RPGLAGHKGE | MGEPGVPGQS | GAPGKEGLIG | PKGDRGFDGQ | PGPKGDQGEK | 2700 |
| GERGTPGIGG | FPGPSGNDGS | AGPPGPPGSV | GPRGPEGLQG | QKGERGPPGE | RVVGAPGVPG | 2760 |
| APGERGPGR | PGPAGPRGEK | GEAALTEDDI | RGFVRQEMSQ | HCACQGQFIA | SGSRPLPSYA | 2820 |
| ADTAGSQLHA | VPVLRVSHAE | EEERVPPEDD | EYSEYSEYSV | EEYQDPEAPW | DSDDPCSLPL | 2880 |
| DEGSCTAYTL | RWYHRAVTGS | TEACHPFVYG | GCGGNANRFG | TREACERRCP | PRVVQSQGTG | 2940 |
| TAQDGSGQCT | NYALLKLAGD | VESNPGPTSS | GPGPRFLLLL | PLLLPPAASA | SDRPRGRDPV | 3000 |
| NPEKLLVITV | ATAETEGYLR | FLRSAEFFNY | TVRTLGLGEE | WRGGDVARTV | GGGQKVRWLK | 3060 |
| KEMEKYADRE | DMIIMFVDSY | DVILAGSPTE | LLKKFVQSGS | RLLFSAESFC | WPEWGLAEQY | 3120 |
| PEVGTGKRFL | NSGGFIGFAT | TIHQIVRQWK | YKDDDDDQLF | YTRLYLDPGL | REKLSLNLDH | 3180 |
| KSRIFQNLNG | ALDEVVLKFD | RNRVIRNVA | YDTLPIVVHG | NGPTKLQLNY | LGNYVPNGWT | 3240 |
| PEGGCGFCNQ | DRRTLPGGQP | PPRVPLAVFV | EQPTPFLPRF | LQRLLLLDYP | PDRVTLFLHN | 3300 |
| NEVFHEPHIA | DSWPQLQDHF | SAVKLVGPEE | ALSPGEARDM | AMDLCRQDPE | CEFYFSLDAD | 3360 |
| AVLTNLQTLR | ILIEENRKVI | APMLSRHGKL | WSNFWGALSP | DEYYARSEDY | VELVQRKRVG | 3420 |
| VWNVPYISQA | YVIRGDTLRM | ELPQRDVFSG | SDTDPDMAFC | KSFRDKGIFL | HLSNQHEFGR | 3480 |
| LLATSRYDTE | HLHPDLWQIF | DNPVDWKEQY | IHENYSRALE | GEGIVEQPCP | DVYWFPLLSE | 3540 |
| QMCDELVAEM | EHYGQWSGGR | HEDSRLAGGY | ENVPTVDIHM | KQVGYEDQWL | QLLRTYVGPM | 3600 |
| TESLFPGYHT | KARAVMNFVV | RYRPDEQPSL | RPHHDSSTFT | LNVALNHKGL | DYEGGGCRFL | 3660 |
| RYDCVISSPR | KGWALLHPGR | LTHYHEGLPT | TWGTRYIMVS | FVDP | | 3704 |

```
SEQ ID NO: 23         moltype = DNA  length = 11115
FEATURE               Location/Qualifiers
misc_feature          1..11115
                      note = Synthetic Construct
source                1..11115
                      mol_type = other DNA
                      organism = synthetic construct
SEQUENCE: 23
atgacctcct cggggcctgg accccggttc ctgctgctgc tgccgctgct gctgcccct      60
gcggcctcag cctccgaccg gccccggggc cgagacccgg tcaacccaga gaagctgctg    120
gtgatcactg tggccacagc tgaaaccgag gggtacctgc gtttcctgcg ctctgcggag    180
ttcttcaact acactgtgcg gaccctgggc ctgggagagg agtggcgagg ggtgatgtg     240
gctcgaacag ttggtggagg acagaaggtc cggtggttaa agaaggaaat ggagaaatac    300
gctgaccggg aggatatgat catcatgttt gtggatagct acgacgtgat tctgccggc     360
agccccacag agctgctgaa gaagttcgtc agagtggcag gccgcctgct cttctctgca    420
gagagcttct gctggcccga gtgggggctg gcggagcagt accctgaggt gggcacgggg    480
```

```
aagcgcttcc tcaattctgg tggattcatc ggttttgcca ccaccatcca ccaaatcgtg   540
cgccagtgga agtacaagga tgatgacgac gaccagctgt tctacacacg gctctacctg   600
gacccaggac tgagggagaa actcagcctt aatctggatc ataagtctcg gatctttcag   660
aacctcaacg gggctttaga tgaagtggtt ttaaagtttg atcggaaccg tgtgcgtatc   720
cggaacgtgg cctacgacac gctcccatt gtggtccatg gaaacggtcc cactaagctg   780
cagctcaact acctgggaaa ctacgtcccc aatggctgga ctcctgaggg aggctgtgcg   840
ttctgcaacc aggaccggag gacactcccg gggggcagc ctcccccccg ggtgtttctg   900
gccgtgtttg tggaacagcc tactccgttt ctgccccgct tcctgcagcg gctgctactc   960
ctggactatc cccccgacag ggtcacccctt ttcctgcaca acaacgaggt cttccatgaa  1020
ccccacatcg ctgactcctg gccgcagctc caggaccact tctcagctgt gaagctcgtg  1080
gggccggagg aggctctgag cccaggcgag gccaggggaca tggccatgga cctgtgtcgg  1140
caggaccccg agtgtgagtt ctacttcagc ctggacgccg acgctgtcct caccaacctg  1200
cagaccctgc gtatcctcat tgaggagaac aggaaggtga tcgccccccat gctgtcccgc  1260
cacggcaagc tgtggtccaa cttctggggc gcccctggcc ccgatgagta ctacgcccgc  1320
tccgaggact acgtggagct ggtgcagcgg aagcgagtgg gtgtgtggaa tgtaccatac  1380
atctcccagg cctatgtgat ccggggtgat accctgcgga tggagctgcc ccagagggat  1440
gtgttctcgg gcagtgacac agacccggac atggccttct gtaagagctt cgagacaag   1500
ggcatcttcc tccatctgag caatcagcat gaatttggcc ggctcctggc cacttccaga  1560
tacgacacgg agcacctgca ccccgacctc tggcagatct tcgacaaccc cgtcgactcg  1620
aaggagcagt acatccacga gaactacagc cgggccctgg aaggggaagg aatcgtggag  1680
cagccatgcc cggacgtgta ctggttccca ctgctgtcag aacaaatgtg tgatgagctg  1740
gtggcagaga tggagcacta cggccagtgg tcaggcgcgc agggaaggga ttcaaggcctg  1800
gctggaggct acgagaatgt gcccaccgtg gacatccaca tgaagcaggt gggggtacgag  1860
gaccagtggc tgcagctgct gcggacgtat gtggggccca tgaccgagag cctgtttccc  1920
ggttaccaca ccaaggcgcg gcggtgatg aactttgtgg ttcgctaccg gccagacgag  1980
cagccgctct tgcggccaca ccaacgactca tccaccttca ccctcaacgt tgccctcaac  2040
cacaagggcc tggactatga gggaggtggc tgccgcttcc tgcgctacga ctgtgtgatc  2100
tcctccccga ggaagggctg ggcactcctg caccccggcc gcctcaccca ctaccacgag  2160
gggctgccaa cgacctgggg cacacgctac atcatggtgt cctttgtcga ccccggaagc  2220
ggacagtgta ctaattatgc tctcttgaaa ttggctggag atgttgagag caaccctggg  2280
cctacgctgc ggcttctggt ggccgcgctc tgcgccagga tcctggcaga ggcgcccccga  2340
gtgcgagccc agcacaggga gagtgaccc tgcacgcgcc tttacgcgcg tgacattgtg  2400
ttcttactgg atggctcctc atccattggc cgcagcaatt tccgcgaggt ccgcagcttt  2460
ctcgaagggc tggtgctgcc tttctctgga gcagccagtg cacagggtgt gcgctttgcc  2520
acagtgcagt acagccgatga cccacgggaca gagttcggcc tggatgcact tggctctggg  2580
ggtgatgtga tccgcgccat ccgtgagctt agctacaagg ggggcaacac tcgcacaggg  2640
gctgcaattc tccatgtggc tgaccatgtc ttcctgcccc agctgcccg acctggtgtc  2700
cccaaggtct gcatcctgat cacagacggg aagtcccagg acctggtgga cacagctgcc  2760
caaaggctga aggggcaggg ggtcaagcta tttgctgtgg ggatcaagaa tgctgaccct  2820
gaggagctga agcgagttgc ctcacagccc accagtgact tcttcttctt cgtcaatgac  2880
ttcagcatct tgaggacact actgcccctc gtttcccgga gagtgtgcac gactgctggt  2940
ggcgtgcctg tgacccgacc tccggatgac tcgacctctg ctccacgaga cctggtgctg  3000
tctgagccaa gcagccaatc cttgagagta cagtggacac cggccagtgg ccctgtgact  3060
ggctacaagg tccagtacac tcctctgacg gggctgggac agccactgcc gagtgagcgg  3120
caggaggtga acgtcccagc tggtgagacc agtgtgcggc tgcggggtct ccggccactg  3180
accgagtacc aagtgactgt gattgccctc tacgccaaca gcatcgggga ggctgtgagc  3240
gggacagctc ggaccactgc cctagaaggg ccggaactga ccatccagaa taccacagcc  3300
cacagcctcc tggtggcctg gcggagtgtg ccaggtgcca ctggctaccg tgtgacatgg  3360
cgggtcctca gtggtgggcc cacacagcag caggagctgg gccctgggca gggttcagtg  3420
ttgctgcgtg acttggagcc tggcacggac tatgaggtga ccgtgagcac cctatttggc  3480
cgcagtgtgg ggcccgccac ttccctgatg gctcgcactg acgcttctgt tgagcagacc  3540
ctgcgcccgg tcatcctggg ccccacatcc atcctccttt cctggaactt ggtgcctgag  3600
gcccgtggct accggttgga atggcggcgt gagactggct tggagccacc gcagaaggtg  3660
gtactgccct ctgatgtgac ccgctaccag ttggatggc tgcagccggg cactgagtac  3720
cgcctcacac tctacactct gctggagggc cacgaggtgg cacccctgc aaccgtggtt  3780
cccactggac cagagctgcc tgtgagccct gtaacagacc tgcaagccac cgagctgccc  3840
gggcagcggg tgcgagtgtc ctggagccca gtccctggtg ccaccagta ccgcatcatt  3900
gtgcgcagca cccagggggt tgagcggacc ctggtgcttc tgggagtca gacagcattc  3960
gacttggatg acgttcaggc tggccttagc tacactgtgc gggtgtctgc tcgagtgggt  4020
ccccgtggag gcagtgccag tgtcctcact gtccgcgcag agccggaaac tccacttgct  4080
gttcagggc tgcgggttgt ggtgtcagat gcaacgcgag tgagggtggc ctggggaccc  4140
gtccctggag ccagtggatt tcggattagc tggagcacag gcagtggtcc ggagtccagc  4200
cagacactgc ccccagactc tactgccaca gacatcacag ggctgcagcc tggaaccacc  4260
taccaggtgg ctgtgtcggt actgcgaggc agagaggagg gcctgctgc agtcatcgtg  4320
gctcgaacgg acccactggg cccagtgagg acgtccatg tgactcaggc cagcagctca  4380
tctgtcacca ttacctggac cagggttcct ggcgccacag gatacagggt ttcctggcac  4440
tcagcccacg gcccagagaa atcccagttg gtttctgggg aggccacggt ggctgagctg  4500
gatggactgg agccagatac tgagtatacg gtgcatgtga gggcccatgt ggctggcgtg  4560
gatgggcccc ctgccctcgt ggttgtgagg actgccctg acgtggtgtcg tcgtgtgcg  4620
aggctgcaga tcctcaatgc ttccagcgac gttctacgga tcacctgggt aggggtcact  4680
ggagccacag cttacagact ggctggggc cggagtgaag gcggcccat gaggcaccag  4740
atactcccag gaaacacaga ctctgcagag atccggggtc tcgaaggtgg agtcagctac  4800
tcagtgcgag tgactgcact tgtcgggac cgcgagggca cacctgtctc cattgttgtc  4860
actacgctga ctgaggctcc gccagccctg acgtggtgca gcgcgggag cactcgctga  4920
cactcgctga ggctgcgctg ggagccggtg cccagagcgc agggcttcct tctgcactgg  4980
caacctgaga gtgccagga acagtcccgg gtcctgggc ccagctcag cagctatcac  5040
ctggacgggg tggagccagc gacacagtac cgcgtgaggc tgagtgtcct agggccagct  5100
ggagaagggc cctctgcaga ggtgactgcg cgcactgagt cacctcgtgt tccaagcatt  5160
gaactacgtg tggtggacac ctcgatcgac tcggtgactt tggcctggac tccagtgcc   5220
```

```
agggcatcca gctacatcct atcctggcgg ccactcagag gccctggcca ggaagtgcct   5280
gggtccccgc agacacttcc agggatctca agctcccagc gggtgacagg gctagagcct   5340
ggcgtctctt acatcttctc cctgacgcct gtcctggatg gtgtgcgggg tcctgaggca   5400
tctgtcacac agacgccagt gtgccccgt ggcctggcgg atgtggtgtt cctaccacat    5460
gccactcaag acaatgctca ccgtgcggag gctacgaggg gggtcctgga gcgtctggtg   5520
ttggcacttg ggcctcttgg gccacaggca gttcaggttg gcctgctgtc ttacagtcat   5580
cggccctccc cactgttccc actgaatggc tccatgacc ttggcattat cttgcaaagg    5640
atccgtgaca tgccctacat ggacccaagt gggaacaacc tgggcacagc cgtggtcaca   5700
gctcacagat acatgttggc accagatgct cctgggcgcc gccagcacgt accaggggtg   5760
atggttctgc tagtggatga acccttgaga ggtgacatat tcagccccat ccgtgaggcc   5820
caggcttctg ggcttaatgt ggtgatgttg ggaatggctg agcggaccc agagcagctg    5880
cgtcgcttgg cgccgggtat ggactctgtc cagaccttct tcgccgtgga tgatgggcca   5940
agcctggacc aggcagtcag tggtctggcc acagccctgt gtcaggcatc cttcactact   6000
cagccccggc cagagccctg cccagtgtat tgtccaaagg gccagaaggg ggaacctgga   6060
gagatgggcc tgagaggaca agttgggcct cctggcgacc ctggcctccc gggcaggacc   6120
ggtgctcccg gcccccaggg gcccctggaa gtgccactg ccaagggcga gaggggcttc    6180
cctggagcag atgggcgtcc aggcagccct ggccgcgccg ggaatcctgg gacccctgga   6240
gccctggcc taaagggctc tccagggttg cctgccctc gtggggaccc gggagagcga    6300
ggacctcgag gcccaaaggg ggagccgggg gctcccggac aagtcatcgg aggtgaagga   6360
cctgggcttc ctgggcggaa aggggaccct ggaccatcgg gccccctgg acctcgtgga    6420
ccactggggg acccaggacc ccgtggcccc cagggcttc ctggaacagc catgaagggt    6480
gacaaaggcg atcgtgggga gcggggtccc cctggaccag gtgaaggtgg cattgctcct   6540
ggggagcctg ggctgccggg tcttcccgga agccctggac cccaaggccc cgttggcccc   6600
cctgaaagaa aaggagaaaa aggtgactct gaggatggag ctccaggcct cccaggacaa   6660
cctgggtctc cgggtgagca gggcccacgg ggacctcctg gagctattgg ccccaaaggt   6720
gaccggggct ttccagggcc cctgggtgag gctggagaga agggcgaacg tggaccccca   6780
ggccagcgg gatccgggg gctgccaggg gttgctggac gtcctggagc caagggtcct    6840
gaagggccac caggacccac tggccgccaa ggagagaagg gggagcctgg tcgccctggg   6900
gaccctgcag tggtgggacc tgctgttgct ggacccaaag gagaaagggg agatgtgggg   6960
cccgctgggc ccagaggac taccggagtc caagggaag ccgccacc cggcttggtt       7020
cttcctggag accctggccc caagggagac cctggagacc gggtcccat tggcctttact  7080
ggcagagcag gaccccagg tgactcaggg cctcctggag agaagggaga ccctgggcgg    7140
cctgcccc caggacctgt tggccccga ggacgagatg tgaagttgg agagaaaggt       7200
gacgagggtc ctccgggtga cccgggtttg cctggaaaag caggcgagcg tggccttcgg   7260
ggggcacctg gagttcgggg gcctgtgggt gaaaagggag accagggaca tcctggagag   7320
gatgacgaa atgcagccc tggatcatct ggacccaagg gtgaccgtgg ggagccgggt     7380
cccccaggac ccccgggacg gctggtagac acaggacctg gagccagaga gaagggagag   7440
cctgggggacc gcggacaaga gggtcctcga gggccaagg gtgatcctgg cctccctgga    7500
gcccctgggg aaaggggcat tgaagggttt cggggaccca caggcccaca ggggagccca   7560
ggtgtccgag gccagcagg agaaaagggt gaccggggtc cctgggct ggatggccga      7620
agcggactga atgggaaacc aggagccgct gggccctctg gccgaatgg tgctgcaggc    7680
aaagctgggg acccagggag agacgggctt ccaggcctcc gtgagaaca gggcctcctt    7740
ggcccctctg gtccccctgg attaccggga aagccaggcg aggatgcca acctggcgtt    7800
aatgaaaaaa acgagaacc tgggaccct ggagaagacg ggaggaaggg agagaaagga    7860
gattcaggcg cctctgggag agaaggtcgt gatggcccca agggtgagcg tggagctcct   7920
ggtatccttg gaccccaggg gcctccaggc ctcccaggc cagtgggccc tcctggccag   7980
ggtttcctg gtgtcccagg aggcacgggc cccaagggtg accgtggga gactggatcc    8040
aaaggggagc agggcctccc tggagagcgt ggcctgcgag gagagcctgg aagtgtgccg   8100
aatgtggatc ggttgctgga aactgctggc atcaaggcat ctgccctgcg ggagatcgtg   8160
gagacctggg atgagagctc tggtagcttc ctgcctgtgc ccgaacgcgc tcgaggcccc   8220
aaggggact caggcgaaca gggccccca ggcaaggagg gcccatgg ctttcctgg       8280
gaacgcgggc tgaagggcga ccgtggagac cctggccctc aggggccacc tggtctggcc   8340
cttgggagaa gggccccccc cgggccttcc ggccttgccg gggagcctgg aaagcctggt   8400
attcccggc tccaggcag ggctgggggt gtgggagagg caggaaggcc aggagagagg    8460
ggagaacggg gagagaaagg agaacgtgga gaacagggca gagatggcc tcctggactc   8520
cctggaaccc ctgggccccc cggacccct ggcccaagg tgtctgtgga tgagcaggt     8580
cctggactct ctggagaaca gggacccct ggactcaagg gtgctaaggg ggagccgggc    8640
agcaatggtg accaaggtcc caaaggagac aggggtgtgc caggcatcaa aggagaccgg   8700
ggagagcctg gaccgagggg tcaggacggc aacccgggtc taccaggaga gcgtggtatg   8760
gctgggcctg aagggaagcc gggtctgcag ggtccaagag gccccctgg cccagtggga   8820
ggtcatggag acctggacc acctggtgcc ccggtcttg ctggccctgc aggacccaa     8880
ggaccttctg gcctgaaggg ggagcctgga gagacaggac ctccaggacg gggcctgact   8940
ggacctactg gagctgtggg acttcctgga ccccccggcc cttcaggcct tgtgggtcca   9000
caggggtctc caggtttgcc tggacaagtg ggggaacgg gggaagccgg agccccaggt   9060
cgagatggtc ccagtggaaa agatggagac agagggagcc tggtgtgcc agggtcacca   9120
ggtctgcctg gccctgtcgg acctaaagga gaacctggcc ccacgggggc ccctggacag   9180
gctgtggtcg ggctccctgg agcaaaggga gagaaggag ccctggagg ccttgctgga    9240
gacctggtgg gtgagccgg agccaaaggt gaccgaggac tgccagggcc gcgaggcgag   9300
aagggtgaag ctggccgtgc agggggaccc gagaccctgg gggaagatgg tcagaaaggg   9360
gctccaggac ccaaggtttt caagggtgac ccaggagtcg gggtcccggg ctcccctggg   9420
cctcctggcc ctccaggtgt gaaggagatt ctgggcctcc ctggcctgcc cggtgctcct   9480
ggtgttgttg ggttcccggg tcagacaggc cctcgaggag atgggtca gccaggccct    9540
agtggagagc gggggtctgg cagggccccca gggagagaag gaatccagg accccctggg   9600
ccacctggac caccggggtc agtggaaca cctggactca ggcaagacaag                 9660
ggagaccctg gagtagggct gcctgggccc cgaggcgagc gtgggagcc aggcatccgg     9720
ggtgaagatg gccgccccgg ccaggaggga ccccggaggc tcacggggcc cctggcagc    9780
aggggagagc gtgggagaa gggtgatgtt gggagtgcag gactaaaggg tgacaagga     9840
gactcagctg tgatcctggg gcctccaggc ccacggggtg ccaaggggga catgggtgaa   9900
cgagggcctc ggggcttgga tggtgacaaa ggacctcggg gagacaatgg ggaccctggt   9960
```

-continued

```
gacaagggca gcaagggaga gcctggtgac aagggctcag ccgggttgcc aggactgcgt    10020
ggactcctgg gacccagggg tcaacctggt gcagcaggga tccctggtga cccgggatcc    10080
ccaggaaagg atggagtgcc tggtatccga ggagaaaaag gagatgttgg cttcatgggt    10140
ccccggggc tcaagggtga acgggagtg aagggagcct gtggccttga tggagagaag    10200
ggagacaagg agaagctgg tcccccaggc cgccccaggc tggcaggaca caaaggagag    10260
atggggagc ctggtgtgcc gggccagtcg ggggcccctg gcaaggaggg cctgatcggt    10320
cccaagggtg accgaggctt tgacgggcag ccaggcccca agggtgacca gggcgagaaa    10380
ggggagcggg gaaccccagg aattggggc ttcccaggcc ccagtggaaa tgatggctct    10440
gctggtcccc cagggccacc tggcagtgtt ggtcccagag gccccgaagg acttcagggc    10500
cagaagggtg agcgaggtcc ccccggagag agagtggtgg gggctcctgg ggtccctgga    10560
gctcctggcg agagaggga gcaggggcgg ccagggcctg ccggtcctcg aggcgagaag    10620
ggagaagctg cactgacgga ggatgacatc cgggctttg tgcgccaaga gatgagtcag    10680
cactgtgcct gccagggcca gttcatcgca tctggatcac gaccctccc tagttatgct    10740
gcagacatgg ccggctccca gctccatgct gtgcctgtgc tccgcgtctc tcatgcagag    10800
gaggaagagc gggtaccccc tgaggatgat gagtactctg aatactccga gtattctgtg    10860
gaggagtacc aggaccctga agtccttgg gatagtgatg acccctgttc cctgccactg    10920
gatgagggct cctgcactgc ctacacctg cgctggtacc atcgggctgt gacaggcagc    10980
acagaggcct gtcacccttt tgtctatggt ggctgtggag ggaatgccaa ccgttttggg    11040
acccgtgagg cctgcgagcg ccgctgccca ccccgggtgg tccagagcca ggggacaggt    11100
actgcccagg actga                                                     11115
```

```
SEQ ID NO: 24           moltype = AA  length = 3704
FEATURE                 Location/Qualifiers
REGION                  1..3704
                        note = Synthetic Construct
source                  1..3704
                        mol_type = protein
                        organism = synthetic construct
SEQUENCE: 24
MTSSGPGPRF LLLLPLLLPP AASASDRPRG RDPVNPEKLL VITVATAETE GYLRFLRSAE     60
FFNYTVRTLG LGEEWRGGDV ARTVGGGQKV RWLKKEMEKY ADREDMIIMF VDSYDVILAG    120
SPTELLKKFV QSGSRLLFSA ESFCWPEWGL AEQYPEVGTG KRFLNSGGFI GPATTIHQIV    180
RQWKYKDDDD DQLFYTRLYL DPGLREKLSL NLDHKSRIFQ NLNGALDEVV LKFDRNRVRI    240
RNVAYDTLPI VVHGNGPTKL QLNYLGNYVP NGWTPEGGCG FCNQDRRTLP GGQPPPRVFL    300
AVFVEQPTPF LPRFLQRLLL LDYPPDRVTL FLHNNEVFHE PHIADSWPQL QDHFSAVKLV    360
GPEEALSPGE ARDMAMDLCR QDPECEFYFS LDDAAVLTNL QTLRILIEEN RKVIAPMLSR    420
HGKLWSNFWG ALSPDEYYAR SEDYVELVQR KRVGVWNVPY ISQAYVIRGD TLRMELPQRD    480
VFSGSDTDPD MAFCKSFRDK GIFLHLSNQH EFGRLLATSR YDTEHLHPDL WQIFDNPVDW    540
KEQYIHENYS RALEGEGIVE QPCPDVYWFP LLSEQMCDEL VAEMEHYGQW SGGRHEDSRL    600
AGGYENVPTV DIHMKQVGYE DQWLQLLRTY VGPMTESLFP GYHTKARAVM NFVVRYRPDE    660
QPSLRPHHDS STFTLNVALN HKGLDYEGGG CRFLRYDCVI SSPRKGWALL HPGRLTHYHE    720
GLPTTWGTRY IMVSFVDPGS GQCTNYALLK LAGDVESNPG PTLRLLVAAL CAGILAEAPR    780
VRAQHRERVT CTRLYAADIV FLLDGSSSIG RSNFREVRSF LEGLVLPFSG AASAQGVRFA    840
TVQYSDDPRT EFGLDALGSG GDVIRAIREL SYKGGNTRTG AAILHVADHV FLPQLARPGV    900
PKVCILITDG KSQDLVDTAA QRLKGQGVKL FAVGIKNADP EELKRVASQP TSDFFFFVND    960
FSILRTLLPL VSRRVCTTAG GVPVTRPPDD STSAPRDLVL SEPSSQSLRV QWTAASGPVT   1020
GYKVQYTPLT GLGQPLPSER QEVNVPAGET SVRLRGLRPL TEYQVTVIAL YANSIGEAVS   1080
GTARTTALEG PELTIQNTTA HSLLVAWRSV PGATGYRVTW RVLSGGPTQQ QELGPGQGSV   1140
LLRDLEPGTD YEVTVSTLFG RSVGPATSLM ARTDASVEQT LRPVILGPTS ILLSWNLVPE   1200
ARGYRLEWRR ETGLEPPQKV VLPSDVTRYQ LDGLQPGTEY RLTLYTLLEG HEVATPATVV   1260
PTGPELPVSP VTDLQATELP GQRVRVSWSP VPGATQYRII VRSTGQVERT LVLPGSQTAF   1320
DLDDVQAGLS YTVRVSARVG PREGSASVLT VRREPETPLA VPGLRVVVSD ATRVRVAWGP   1380
VPGASGFRIS WSTGSSGPESS QTLPPDSTAT DITGLQPGTT YQVAVSVLRG REEGPAAVIV   1440
ARTDPLGPVR TVHVTQASSS SVTITWTRVP GATGYRVSWH SAHGPEKSQL VSGEATVAEL   1500
DGLEPDTEYT VHVRAHVAGV DGPPASVVVR TAPEPVGRVS RLQILNASSD VLRITWVGVT   1560
GATAYRLAWG RSEGGPMRHQ ILPGNTDSAE IRGLEGGVSY SVRVTALVGD REGTPVSIVV   1620
TTPPEAPPAL GTLHVVQRGE HSLRLRWEPV PRAQGFLLHW QPEGGQEQSR VLGPELSSYH   1680
LDGLEPATQY RVRLSVLGPA GEGPSAEVTA RTESPRVPSI ELRVVDTSID SVTLAWTPVS   1740
RASSYILSWR PLRGPGQEVP GSPQTLPGIS SSQRVTGLEP GVSYIFSLTP VLDGVRGPEA   1800
SVTQTPVCPR GLADVVFLPH ATQDNAHRAE ATRRVLERLV LALGPLGPQA VQVGLLSYSH   1860
RPSPLFPLNG SHDLGIILQR IRDMPYMDPS GNNLGTAVVT AHRYMLAPDA PGRRQHVPGV   1920
MVLLVDEPLR GDIFSPIREA QASGLNVVML GMAGADPEQL RRLAPGMDSV QTFFAVDDGP   1980
SLDQAVSGLA TALCQASFTT QPRPEPCPVY CPKGQKGEPG MALRGQVGP PGDPGLPGRT   2040
GAPGPQGPPG SATAKGERGF PGADGRPGSP GRAGNPGTPG APGLKGSPGL PGPRGDPGER   2100
GPRGPKGEPG APGQVIGGEG PGLPGRKGDP GPSGPPGPRG PLGDPGPRGP PGLPGTAMKG   2160
DKGDRGERGP PGPGEGGIAP GEPGLPGLPS SPGPQGPVGP PGKKGEKGDS EDGAPGLPGQ   2220
PGSPGEQGPP GPPGAIGPKG DRGFPGPLGE AGEKGERGPP GPAGSRGLPG VAGRPGAKGP   2280
EGPPGPTGRQ GEKGPERGPG DPAVVGPAVA GPKGEKGPVG PAPRGATGV QGERGPGLV   2340
LPGDPGPKGD PGDRGPIGLT GRAGPPGDSG PPGEKGDPGR PGPPGPVGPR GRDGEVGEKG   2400
DEGPPGDPGL PGKAGERGLR GAPGVRGPVG EKGDQGDPGE DGRNGSPGSS GPKGDRGEPG   2460
PPGPPGRLVD TGPGAREKGE PGDRGQEGPR GPKGDPGLPG APGERGIEGF RGPPGPQGDP   2520
GVRGPAGEKG DRGPPGLDGR SGLDGKPGAA GPSGPNGAAG KAGDPGRDGL PGLRGEQGLP   2580
GPSGPPGLPG KPGEDGKPGL NGKNGEPGDP GEDGRSGREGR DGPKGERGAP   2640
GILGPQGPPG LPGPVGPPGQ GFPGVPGGTG PKGDRGETGS KGEQGLPGER GLRGEPGSVP   2700
NVDRLLETAG IKASALREIV ETWDESSGSF LPVPERRRGP KGDSGEQPP GKEGPIGFPG   2760
ERGLKGDRGD PGPQGPPGLA LGERGPPGPS GLAGEPGKPG IPGLPGRAGG VGEAGRPGER   2820
GERGEKGERG EQGRDGPPGL PGTPGPPGPP GPKVSVDEPG PGLSGEQGPP GLKGAKGEPG   2880
SNGDQGPKGD RGVPGIKGDR GEPGPRGQDG NPGLPGERGM AGPEGKPGLQ GPRGPPGPVG   2940
GHGDPGPPGA PGLAGPAGPQ GPSGLKGEPG ETGPPGRGLT GPTGAVGLPG PPGPSGLVGP   3000
```

| | | | | |
|---|---|---|---|---|
| QGSPGLPGQV | GETGKPGAPG | RDGASGKDGD | RGSPGVPGSP | GLPGPVGPKG | EPGPTGAPGQ | 3060 |
| AVVGLPGAKG | EKGAPGGLAG | DLVGEPGAKG | DRGLPGPRGE | KGEAGRAGEP | GDPGEDGQKG | 3120 |
| APGPKGFKGD | PGVGVPGSPG | PPGPPGVKGD | LGLPGLPGAP | GVVGFPGQTG | PRGEMGQPGP | 3180 |
| SGERGLAGPP | GREGIPGPLG | PPGPPGSVGP | PGASGLKGDK | GDPGVGLPGP | RGERGEPGIR | 3240 |
| GEDGRPGQEG | PRGLTGPPGS | RGERGEKGDV | GSAGLKGDKG | DSAVILGPPG | PRGAKGDMGE | 3300 |
| RGPRGLDGDK | GPRGDNGDPG | DKGSKGEPGD | KGSAGLPGLR | GLLGPQGQPG | AAGIPGDPGS | 3360 |
| PGKDGVPGIR | GEKGDVGFMG | PRGLKGERGV | KGACGLDGEK | GDKGEAGPPG | RPGLAGHKGE | 3420 |
| MGEPGVPGQS | GAPGKEGLIG | PKGDRGFDGQ | PGPKGDQGEK | GERGTPGIGG | FPGPSGNDGS | 3480 |
| AGPPGPPGSV | GPRGPEGLQG | QKGERGPPGE | RVVGAPGVPG | APGERGEQGR | PGPAGPRGEK | 3540 |
| GEAALTEDDI | RGFVRQEMSQ | HCACQGQFIA | SGSRPLPSYA | ADTAGSQLHA | VPVLRVSHAE | 3600 |
| EEERVPPEDD | EYSEYSEYSV | EEYQDPEAPW | DSDDPCSLPL | DEGSCTAYTL | RWYHRAVTGS | 3660 |
| TEACHPFVYG | GCGGNANRFG | TREACERRCP | PRVVQSQGTG | TAQD | | 3704 |

```
SEQ ID NO: 25          moltype = DNA   length = 11121
FEATURE                Location/Qualifiers
misc_feature           1..11121
                       note = Synthetic Construct
source                 1..11121
                       mol_type = other DNA
                       organism = synthetic construct
SEQUENCE: 25
atgacgctgc ggcttctggt ggccgcgctc tgcgccggga tcctggcaga ggcgccccga   60
gtgcgagccc agcacaggga gagagtgacc tgcacgcgcc tttacgccgc tgacattgtg  120
ttcttactgg atggctcctc atccattggc cgcagcaatt tccgcgaggt ccgcagcttt  180
ctcgaagggc tggtgctgcc tttctctgga gcagccagtg cacagggtgt gcgctttgcc  240
acagtgcagt acagcgatga cccacgtgga gagttcggcc tggctggcac ttggctctgg  300
ggtgatgtga tccgcgccat ccgtgagctt agctacaagg ggggcaacac tcgcacaggg  360
gctgcaattc tccatgtggc tgaccatgtc ttcctgcccc agctgcccg acctggtgtc  420
cccaaggtct gcatcctgat cacagacggg aagtcccagg acctggtgga cacagctgcc  480
caaaggctga aggggcaggg ggtcaagcta tttgctgtgg ggatcaagaa tgctgaccct  540
gaggagctga agcgagttgc ctcacagccc accagtgact tcttcttctt cgtcaatgac  600
ttcagcatct tgaggacact actgccctc gtttccga gagtgtgcac gactgctggt  660
ggcgtgcctg tgacccgacc tccggatgac tcgacctctg ctccacgaga cctggtgctg  720
tctgagccaa gcagccaatc cttgagagta cagtggacag cggccagtgg ccctgtgact  780
ggctacaagg tccagtacac tcctctgacg gggctgggac agccactgcc gagtgagcgg  840
caggaggtga acgtcccagc tggtgagacc agtgtgcggc tgcggggtct ccggccactg  900
accgagtacc aagtgactgt gattgccctc tacgccaaca gcatcgggga gctgtgagc  960
gggacagctc ggaccactgc cctagaaggg ccggaactga ccatccagaa taccacagcc 1020
cacagcctcc tggtggcctg gcggagtgtg ccaggtgcca ctggctaccg tgtgacatgg 1080
cgggtcctca gtggtgggcc cacacagcag caggagctgg gccctgggca gggttcagtg 1140
ttgctgcgtg acttggagcc tggcacggac tatgaggtga ccgtgagcac cctatttggc 1200
cgcagtgtgt ggcccgccac ttccctgatg gctcgcactg acgcttctgt tgagcagacc 1260
ctgcgccgg tcatcctggg ccccacatcc atcctccttt cctggaactt ggtgcctgag 1320
gcccgtggct accggttgga atggcggcgt gagactggct tggagccacc gcagaaggtg 1380
gtactgccct ctgatgtgac ccgctaccag ttggatgggc tgcagccggg cactgagtac 1440
cgcctcacac tctacactct gctggagggc acgaggtgg ccaccctgc aaccgtggtt 1500
cccactggac cagagctgcc tgtgagccct gtaacagacc cgagctgccc 1560
gggcagcggg tgcgagtgtc ctggagccca gtccctggtg ccaccccagta ccgcatcatt 1620
gtgcgcagca cccagggggt tgagcggacc ctggtgcttc tgggagtcag acagcattc 1680
gacttggatg acgttcaggc tgggcttagc tacactgtgc gggtgtctgc tcgagtgggt 1740
ccccgtgagg gcagtgccag tgtcctcact gtccgcccgg agccggaaac tccacttgct 1800
gttccagggc tgcgggttgt ggtgtcagat gcaacgcgag tgagggtggc ctggggaccc 1860
gtccctggag ccagtggatt tcggattagc tggagcacag gcagtggtcc ggagtccagc 1920
cagacactgc ccccagactc tactgccaca gacatcacag gctgcagcc tggaaccacc 1980
taccaggtgg ctgtgtcggt actgcgaggc agagaggagg gccctgctgc agtcatcgtg 2040
gctcgaacgg acccactggg cccagtgagg acgtccatg tgactcaggc cagcagctca 2100
tctgtcacca ttacctggac cagggttcct ggcgccacag gatacagggt tcctggcac 2160
tcagcccacg gcccagagaa atcccagttg gtttctgggg aggccacggt ggctgagctg 2220
gatggactgg agccagatac tgagtatacg gtgcatgtga gggccatgt ggctggcgtg 2280
gatgggcccc ctgcctctgt ggttgtgagg actgccctg agcctgtggg tcgtgtgtga 2340
aggctgcaga tcctcaatgc ttccagcgac gttcacgga tcacctgggt aggggtcact 2400
ggagccacac cttacagact ggcctgggc cggagtgaag cggcccat gaggcaccag 2460
atactcccag gaaacacaga ctctgcagag atccggggtc tcgaaggtgg agtcagctac 2520
tcagtgcgag tgactgcact tgtcggggac cgcgagggca caccctgtc cattgttgtc 2580
actacgccgc tgaggctcc gccagccctg gggacgcttc acgtggtgca gcgcggggag 2640
cactcgctga ggctgcgctg ggagccggtc ccagagcgc agggcttcct tctgcactgg 2700
caacctgagg gtgccaggga acagtcccgg gtcctgggg ccgagctcag cagctatcac 2760
ctggacgggc tggagccagc gacacagtac cgcgtgaggc tgagtgtcct agggccagct 2820
ggagaagggc cctcgcaga ggtgactgcg cgcactgact cacctcgtg tccaagcatt 2880
gaactacgtg tggtggacac ctcgatcgac tcgctgactt tggcctggac tccagtgtcc 2940
agggcatcca gctacatcct atctggcgg ccactcagga gcctggcca ggaagtgcct 3000
gggtccccgc agacacttcc agggatctca agctcccagc gggtgacagg ctagagcct 3060
ggcgtctctt acatctttctc cctgacgcct gtcctggatg tgtgcggggg tcctgaggca 3120
tctgtcacac agacgccagt gtgcccccgt ggcctgggcg atgtggttgtt cctaccacat 3180
gccactcaag acaatgctca ccgtgcgagc gctacgagga gggtcctgga gcgtctggtg 3240
ttggcacttg gcctcttgg gccacaggca gttcaggttg gctgctgtc ttacagtcat 3300
cggccctccc cactgttccc actgaatggc tcccatgacc ttggcattat cttgcaaagg 3360
atccgtgaca tgccctacat ggaccccaag gggaacaacc tgggcacagc cgtggtcaca 3420
gctcacagat acatgttggc accagatgct cctgggcgcc gccagcacgt accagggtg 3480
```

```
atggttctgc tagtggatga acccttgaga ggtgacatat tcagcccat ccgtgaggcc   3540
caggcttctg ggcttaatgt ggtgatgttg ggaatggctg gagcggaccc agagcagctg   3600
cgtcgcttgg cgccgggtat ggactctgtc cagaccttct tcgccgtgga tgatgggcca   3660
agcctggacc aggcagtcag tggtctggcc acagccctgt gtcaggcatc cttcactact   3720
cagcccggc cagagccctg cccagtgtat tgtccaaagg gccagaaggg ggaacctgga   3780
gagatgggcc tgagaggaca agttgggcct cctggcgacc ctggcctccc gggcaggacc   3840
ggtgctccg gccccaggg gcccctgga agtgccactg ccaagggcga gaggggcttc   3900
cctggagcag atgggcgtcc aggcagccct ggccgcgccg gaatcctgg accccctgga   3960
gccctggcc taaagggctc tccaggttg cctggcctc gtgggaccc gggagagcga   4020
ggacctcgag gcccaaaggg ggagccgggg gctcccggac aagtcatcgg aggtgaagga   4080
cctgggcttc ctgggcggaa aggggaccct ggaccatcgg gccccctgg acctcgtgga   4140
ccactgggg acccaggacc ccgtggcccc cagggcttc ctggaacagc catgaagggt   4200
gacaaaggcg atcgtgggga gcgggtccc cctggaccag gtgaaggtgg cattgctcct   4260
ggggagcctg ggctgccgg tcttcccgga agccctggc cccaaggccc cgttggcccc   4320
cctggaaaga aggagaaaa aggtgactct gaggatggag ctccaggcct cccaggacaa   4380
cctgggtctc cgggtgagca gggcccacgg ggacctcctg gagctattgg ccccaaaggt   4440
gaccggggct ttccagggcc cctgggtgag gctggagaga agggcgaacg tggaccccca   4500
ggcccagcgg gatcccgggg gctgccaggg gttgctggac gtcctggagc caagggtcct   4560
gaagggccac caggacccac tggccgccaa ggagagaagg gggagcctgg tcgccctggg   4620
gacccctgcag tggtcgggacc tgctgttgct ggacccaaag gagaaagggg agatgtgggg   4680
cccgctgggc ccagaggagc taccgagtc caaggggaac ggggcccacc cggcttggtt   4740
cttcctggag accctggccc caaggggagac cctggagacc cccat tggccttact   4800
ggcagagcag gaccccagg tgactcaggg cctcctggag agaaggaga cctgggcgg   4860
cctgcccc caggacctgt tggccccga ggacgagatg tgaagttgg agagaaaggt   4920
gacgagggtc ctccgggtga cccggtttg cctgaaaag caggcgagcg tggccttcgg   4980
ggggcacctg gagttcgggg gcctgtggt gaaaaggaga accaggaga tcctggagag   5040
gatgacgaa atggcagccc tggatcatct ggacccaagg gtgaccgtgg ggagccgggt   5100
cccccaggac cccgggacg gctggtagac acaggacctg gagccagaga agggagag   5160
cctggggacc gcggacaaga gggtcctcga gggcccaagg gtgatcctgg cctccctgga   5220
gcccctgggg aaaggggcat tgaaggggtt cggggaccc caggccaca ggggaccca   5280
ggtgtccgag gcccagcagg agaaaagggt gaccggggtc cccctgggct ggatggccga   5340
agcggactgg atgggaaacc aggagccgct gggccctctg gccgaatgg tgctgcaggc   5400
aaagctgggg acccagggag agacgggctt ccaggcctcc gtgagaaca gggcctccct   5460
ggccctctg gtcccctgg attacccgga aagccaggcg aggatggcaa acctggcctg   5520
aatgaaaaa acggagaacc tgggaccct ggagaagga cggagaaaga agagaaagga   5580
gattcaggcg cctctgggag agaaggtcgt gatggcccca agggtgagcg tggagctcct   5640
ggtatccttg gaccccaggg gcctccaggc ctcccaggg cagtgggcc tcctggccag   5700
ggttttcctg gtgtcccagg aggcacggc cccaagggtg accgtgggga gactggatcc   5760
aaagggggagc aggggctccc tggagagcgt ggcctgccgg gagagcctgg aagtgtgccg   5820
aatgtggatc ggttgctgga aactgctggc atcaaggcat ctgccctgcg ggagatcgtg   5880
gagacctggg atgagagctc tggtagcttc ctgcctgtgc ccgaacggcg tcgaggcccc   5940
aagggggact caggcgaaca gggccccca ggcaaggagg ccccatcgg ctttcctgga   6000
gaacgggc tgaagggca ccgtggagac cctggcctc aggggccac tggtctgccg   6060
cttggggaga ggggcccccc cgggccttcc ggccttgccg gggagcctgg aaagcctggt   6120
attcccggc tcccaggcag ggctgggggt gtggagagg caggaaggcc aggagagagg   6180
ggagaacggg gagagaaagg agaacgtgga gaacagggca gagatggccc tcctggactc   6240
cctggaaccc ctggggcccc cggaccccct ggcccccaga tgtctgtgga tgagccaggt   6300
cctggactct ctgagaacac gggaccccct ggactcaagg gtgctaaggg ggagccgggc   6360
agcaatggtg accaaggtcc caaggagac aggggtgtgc caggcatcaa aggagaccgg   6420
ggagagcctg gaccgagggg tcaggacgg aacccgggtc taccaggaga gcgtggtatg   6480
gctgggcgtg aagggaagcc gggtctgcag ggtcaagag gccccctgg cccagtgggt   6540
ggtcatggag accctggacc acctggtgcc ccgggtcttg ctggccctgc aggaccccaa   6600
ggaccttctg gcctgaaggg ggagcctgga gagacaggac ctcaggacg gggcctgact   6660
ggacctactg gagctgtggg acttcctgga cccccccggcc cttcaggcct tgtgggtcca   6720
caggggtctc caggttttgcc tggacaagtg ggggagacag ggaagccgga agccccaggt   6780
cgagatggtg ccagtggaaa agatggagac agagggagcc ctggtgtgcc agggtcacca   6840
ggtctgcctg gccctgtcgg acctaaagga gaacctggcc cacgggcc ccctggacag   6900
gctgtggtcg ggctccctgg agcaaaggga gagaagggag ccctggagg ccttgctgga   6960
gacctggtgg gtgagccggg agccaaaggt gaccggaggc tgcagggcc gcgaggcgag   7020
aagggtgaag ctggccgtgc agggggagccc ggagaccctg gggaagatgg tcagaagggg   7080
gctccaggac ccaaaggttt caaggtgac ccaggagtcg gggtcccggg ctcccctggg   7140
cctcctggcc ctccaggtgt gaaggagat ctgggcctcc ctggcctgcc cggtgctcct   7200
ggtgttgttg ggttcccggg tcagacaggc cctcggagga gatgggtca gccaggccct   7260
agtggagagc gggtctggc aggcccccca gggagagaag gaatcccagg tggccggggg   7320
ccacctggac caccgggtc agtgggacca cctgggccct ctggactcaa aggagacaag   7380
ggagaccctg gagtagggct gcctgggccc gaggcgagc gtgggagcc aggcatccgg   7440
ggtgaagatg gccgcccgg ccaggagga ccccgaggac tcacggggcc ccctggcagc   7500
aggggagagc gtgggagaa gggtgatgtt gggagtcag gactaaaggg tgacaaggga   7560
gactcagctg tgatcctggg gcctccaggc ccacgggtca ccaagggga catgggtgaa   7620
cgagggcctc ggggcttgga tggtgacaaa ggacctcggg gagacaatgg ggaccctggt   7680
gacaagggca gcaagggaga gcctggtgac aagggctcag ccgggttgcc aggactgcgt   7740
ggactcctgg gaccccaggg tcaacctggt gcagcaggga tcctggtga cccgggatcc   7800
ccaggaaagg atggagtgcc tggtatccga ggagaaaaag gagatgttgg cttcatgggt   7860
ccgggggcc tcaaggtga cgggggagtg aagggagcct gtggccttga tggagagaag   7920
ggagacaagg gagaagctgg tccccaggc gcccggggc tggcaggaca caaaggagag   7980
atggggagc ctggtgtgcc gggccagtcg ggggccctg gcaaggagg cctgatcggt   8040
cccaagggtg accgaggctt tgacgggcag ccaggcccca gggtgacca gggcgagaaa   8100
ggggagcggg gaaccccagg aattgggggc ttcccaggcc ccagtggaaa tgatggctct   8160
gctggtcccc caggccacc tggcagtgtt ggtcccagag gccccgaagg acttcagggc   8220
```

```
cagaaggtg   agcgaggtcc  ccccggagag  agagtggtgg  gggctcctgg  ggtccctgga   8280
gctcctggcg  agagagggga  gcaggggcg   ccagggcctg  ccggtcctcg  aggcagaaag   8340
ggagaagctg  cactgacgga  ggatgacatc  cggggctttg  tgcgccaaga  gatgagtcag   8400
cactgtgcct  gccagggcca  gttcatcgca  tctggatcac  gacccctccc  tagttatgct   8460
gcagcacctg  ccggctccca  gctccatgct  gtgcctgtgc  tccgcgtctc  tcatgcagag   8520
gaggaagagc  gggtaccccc  tgaggatgat  gagtactctg  aatactccga  gtattctgtg   8580
gaggagtacc  aggaccctga  agtccttggg  gatagtgatg  accccgtttc  cctgccactg   8640
gatgagggct  cctgcactgc  ctacaccctg  cgctggtacc  atcgggctgt  gacaggcagc   8700
acagaggcct  gtcaccctt   tgtctatggt  ggctgtggga  ggaatgccaa  ccgttttggg   8760
acccgtgagg  cctgcgagcg  ccgctgccca  cccgggtgg   tccagagcca  ggggacagtg   8820
actgcccagg  acgaagcgg   agtgaaacag  actttgaatt  ttgaccttct  caagttggcg   8880
ggagacgtgg  agtccaaccc  tggacctacc  tcctcggggc  ctggaccccg  gttcctgctg   8940
ctgctgccgc  tgctgctgcc  ccctgcggcc  tcagcctccg  accggcccg   gggccgagac   9000
ccggtcaacc  cagagaagct  gctggtgatc  actgtgaaac  cgaggggtac  cgaggggtac   9060
ctgcgtttcc  tgcgctctgc  ggagttcttc  aactacactg  tgcggaccct  gggcctggga   9120
gaggagtggc  gaggggggtga  tgtggctcga  acagttggtg  gaggacagaa  ggtccggtgg   9180
ttaaagaagg  aaatggagaa  atacgctgac  cgggaggata  tgatcatcat  gtttgtggat   9240
agctacgacg  tgattctggc  cggcagcccc  acagagctgc  tgaagaagtt  cgtccagagt   9300
ggcagccgcc  tgctcttctc  tgcagagagc  ttctgctggc  ccgagtgggg  gctggcggag   9360
cagtaccctg  aggtgggcac  ggggaagcgc  ttcctcaatt  ctggtggatt  catcggtttt   9420
gccaccacca  tccaccaaat  cgtgcgccag  tggaagtaca  aggatgatga  cgacgaccag   9480
ctgttctaca  cacggctcta  cctggaccca  ggactaggaa  agaaactcag  ccttaatctg   9540
gatcataagt  ctcggatctt  tcagaacctc  aacggggctt  tagatgaagt  ggttttaaag   9600
tttgatcgga  accgtgtgcg  tatccggaac  gtggcctacg  acacgctccc  cattgtggtc   9660
catggaaacg  tcccactaa   gctgcagctc  aactacctgg  gaaactacgt  ccccaatggc   9720
tggactcctg  agggaggctg  tggcttctgc  aaccaggacc  aggagacact  cccgggggg   9780
cagcctcccc  cccgggtgtt  tctgccgtg   tttgtggaac  agcctactcc  gtttctgccc   9840
cgcttcctgc  agcggctgct  actcctggac  tatcccccg   acagggtcac  cctttttcctg   9900
cacaacaacg  aggtcttcca  tgaacccac   atcgctgact  cctggccgca  gctccaggac   9960
cacttctcag  ctgtgaagct  cgtggggccg  gaggaggctc  tgagcccagg  cggaggccagg  10020
gacatggcca  tggacctgtg  tcggcaggac  cccgagtgtg  agttctactt  cagcctggac  10080
gccgacgctg  tcctcaccaa  cctgcagacc  ctgcgtatcc  tcattgagga  gaacaggaag  10140
gtgatcgccc  ccatgctgtc  ccgccacggc  aagctgtggt  ccaacttctg  gggcgccctg  10200
agccccgatg  agtactacgc  ccgctccgag  gactacgtgg  agctggtgca  gcggaagcga  10260
gtgggtgtgt  ggaatgtacc  atacatctcc  caggcctatg  tgatccggga  tgataccctg  10320
cggatggagc  tgcccagag   ggatgtgttc  tcgggcagtg  acacagaccc  ggacatggcc  10380
ttctgtaaga  gctttcgaga  caagggcatc  ttcctccatc  tgagcaatca  gcatgaattt  10440
ggccggctcc  tggccacttc  cagatacgac  acggagcacc  tgcaccccga  cctctggcag  10500
atcttcgaca  acccgtcga   ctggaaggag  cagtacatcc  acgagaacta  cagccgggcc  10560
ctggaagggg  aaggaatcgt  ggagcagcca  tgccccgacg  tgtactggtt  cccactgctg  10620
tcagaacaaa  tgtgtgatga  gctggtggca  gagatgagc   actacggcca  gtggtcaggc  10680
ggccggcatg  aggattcaag  gctggctgga  ggctacgaga  atgtgcccac  cgtggacatc  10740
cacatgaagc  aggtggggta  cgaggaccag  tggctgcggac  tgctgcggac  gtatgtgggc  10800
cccatgaccg  agagcctgtt  tccccggttac  cacaccaagg  cgcgggcggt  gatgaactt   10860
gtggttcgct  accggccaga  cgagcagccg  tctctgcggc  cacaccacga  ctcatcccac  10920
ttcaccctca  acgttgccct  caaccacaag  ggcctggact  atgagggagg  tggctgccgc  10980
ttcctgcgct  acgactgtgt  gatctcctcc  ccgaggaagg  gctgggcact  cctgcacccc  11040
ggccgcctca  cccactacca  cgaggggctg  ccaacgacct  ggggcacacg  ctacatcatg  11100
gtgtcctttg  tcgaccccctg  a                                              11121
```

SEQ ID NO: 26          moltype = AA   length = 3706
FEATURE                Location/Qualifiers
REGION                 1..3706
                       note = Synthetic Construct
source                 1..3706
                       mol_type = protein
                       organism = synthetic construct SEQUENCE: 26
```
MTLRLLVAAL  CAGILAEAPR  VRAQHRERVT  CTRLYAADIV  FLLDGSSSIG  RSNFREVRSF    60
LEGLVLPFSG  AASAQGVRFA  TVQYSDDPRT  EFGLDALGSG  GDVIRAIREL  SYKGGNTRTG   120
AAILHVADHV  FLPQLARPGV  PKVCILITDG  KSQDLVDTAA  QRLKGQGVKL  FAVGIKNADP   180
EELKRVASQP  TSDFFFFVND  FSILRTLLPL  VSRRVCTTAG  GVPVTRPPDD  STSAPRDLVL   240
SEPSSQSLRV  QWTAASGPVT  GYKVQYTPLT  GLGQPLPSER  QEVNVPAGET  SVRLRGLRPL   300
TEYQVTVIAL  YANSIGEAVS  GTARTTALEG  PELTIQNTTA  HSLLVAWRSV  PGATGYRVTW   360
RVLSGGPTQQ  QELGPGQGSV  LLRDLEPGTD  YEVTVSTLFG  RSVGPATSLM  ARTDASVEQT   420
LRPVILGPTS  ILLSWNLVPE  ARGYRLEWRR  ETGLEPPQKV  VLPSDVTRYQ  LDGLQPGTEY   480
RLTLYTLLEG  HEVATPATVV  PTGPELPVSP  VTDLQATELP  GQRVRVSWSP  VPGATQYRII   540
VRSTQVGVERT  LVLPGSQTAF  DLDDVQAGLS  YTVRVSARVG  PREGSASVLT  VRREPETPLA   600
VPGLRVVVSD  ATRVRVAWGP  VPGASGFRIS  WSTGSGPESS  QTLPPDSTAT  DITGLQPGTT   660
YQVAVSVLRG  REEGPAAVIV  ARTDPLGPVR  TVHVTQASSS  SVTITWTRVP  GATGYRVSWH   720
SAHGPEKSQL  VSGEATVAEL  DGLEPDTEYT  VHVRAHVAGV  DGPPASVVVR  TAPEPVGRVS   780
RLQILNASSD  VLRITWVGVT  GATAYRLAWG  RSEGGPMRHQ  ILPGNTDSAE  IRGLEGGVSY   840
SVRVTALVGD  REGTPVSIVV  TTPPEAPPAL  GTLHVVQRGE  HSLRLRWEPV  PRAQGFLLHW   900
QPEGGQEQSR  VLGPELSSYH  LDGLEPATQY  RVRLSVLGPA  GEGPSAEVTA  RTESPRVPSI   960
ELRVVDTSID  SVTLAWTPVS  RASSYILSWR  PLRGPGQEVP  GSPQTLPGIS  SSQRVTGLEP  1020
GVSYIFSLTP  VLDGVRGPEA  SVTQPVCPR   GLADVVFLPH  ATQDNAHRAE  ATRRVLERLV  1080
LALGPLGPQA  VQVGLLSYSH  RPSPLFPLNG  SHDLGIILQR  IRDMPYMDPS  GNNLGTAVVT  1140
AHRYMLAPDA  PGRRQHVPGV  MVLLVDEPLR  GDIFSPIREA  QASGLNVVML  GMAGADPEQL  1200
RRLAPGMDSV  QTFFAVDDGP  SLDQAVSGLA  TALCQASFTT  QPRPEPCPVY  CPKGQKGEPG  1260
```

```
EMGLRGQVGP PGDPGLPGRT GAPGPQGPPG SATAKGERGF PGADGRPGSP GRAGNPGTPG      1320
APGLKGSPGL PGPRGDPGER GPRGPKGEPG APGQVIGGEG PGLPGRKGDP GPSGPPGPRG      1380
PLGDPGPRGP PGLPGTAMKG DKGDRGERGP PGPGEGGIAP GEPGLPGLPG SPGPQGPVGP      1440
PGKKGEKGDS EDGAPGLPGQ PGSPGEQGPR GPPGAIGPKG DRGFPGPLGE AGEKGERGPP      1500
GPAGSRGLPG VAGRPGAKGP EGPPGPTGRQ GEKGEPGRPG DPAVVGPAVA GPKGEKGDVG      1560
PAGPRGATGV QGERGPPGLV LPGDPGPKGD PGDRGPIGLT GRAGPPGDSG PPGEKGDPGR      1620
PGPPGPVGPR GRDGEVGEKG DEGPPGDPGL PGKAGERGLR GAPGVRGPVG EKGDQGDPGE      1680
DGRNGSPGSS GPKGDRGEPG PPGPPGRLVD TGPGAREKGE PGDRGQEGPR GPKGDPGLPG      1740
APGERGIEGF RGPPGPQGDP GVRGPAGEKG DRGPPGLDGR SGLDGKPGAA GPSGPNGAAG      1800
KAGDPGRDGL PGLRGEQGLP GPSGPPGLPG KPGEDGKPGL NGKNGEPGDP GEDGRKGEKG      1860
DSGASGREGR DGPKGERGAP GILGPQGPPG LPGPVGPPGQ GFPGVPGGTG PKGDRGETGS      1920
KGEQGLPGER GLRGEPGSVP NVDRLLETAG IKASALREIV ETWDESSGSF LPVPERRRGP      1980
KGDSGEQGPP GKEGPIGFPG ERGLKGDRGD PGPQGPPGLA LGERGPPGPS GLAGEPGKPG      2040
IPGLPGRAGG VGEAGRPGER GERGEKGERG EQGRDGPPGL PGTPGPPGPP GPKVSVDEPG      2100
PGLSGEQGPP GLKGAKGEPG SNGDQGPKGD RGVPGIKGDR GEPGPRGQDG NPGLPGERGM      2160
AGPEGKPGLQ GPRGPPGPVG GHGDPGPPGA PGLAGPAGPQ GPSGLKGEPG ETGPPGRGLT      2220
GPTGAVGLPG PPGPSGLVGP QGSPGLPGQV GETGKPGAPG RDGASGKDGD RGSPGVPGSP      2280
GLPGPVGPKG EPGPTGAPGQ AVVGLPGAKG EKGAPGGLAG DLVGEPGAKG DRGLPGPRGE      2340
KGEAGRAGEP GDPGEDGQKG APGPKGFKGD PGVGVPGSPG PPGPPGVKGD LGLPGLPGAP      2400
GVVGFPGQTG PRGEMGQPGP SGERGLAGPP GREGIPGPLG PPGPPGSVGP PGASGLKGDK      2460
GDPGVGLPGP RGERGEPGIR GEDGRPGQEG PRGLTGPPGS RGERGEKGDV GSAGLKGDKG      2520
DSAVILGPPG PRGAKGDMGE RGPRGLDGDK GPRGDNGDPG DKGSKGEPGD KGSAGLPGLR      2580
GLLGPQGQPG AAGIPGDPGS PGKDGVPGIR GEKGDVGFMG PRGLKGERGV KGACGLDGEK      2640
GDKGEAGPPG RPGLAGHKGE MGEPGVPGQS GAPGKEGLIG PKGDRGFDGQ PGPKGDQGEK      2700
GERGTPGIGG FPGPSGNDGS AGPPGPPGSV GPRGPEGLQG QKGERGPPGE RVVGAPGVPG      2760
APGERGEQGR PGPAGPRGEK GEAALTEDDI RGFVRQEMSQ HCACQGQPFA SGSRPLPSYA      2820
ADTAGSQLHA VPVLRVSHAE EERVPPEDD EYSEYSEYSV EEYQDPEAPW DSDDPCSLPL      2880
DEGSCTAYTL RWYHRAVTGS TEACHPFVYG GCGGNANRFG TREACERRCP PRVVQSQGTG      2940
TAQDGSGVKQ TLNFDLLKLA GDVESNPGPT SSGPGPRFLL LLPLLLPPAA SASDRPRGRD      3000
PVNPEKLLVI TVATAETEGY LRFLRSAEFF NYTVRTLGLG EEWRGGDVAR TVGGGQKVRW      3060
LKKEMEKYAD REDMIIMFVD SYDVILAGSP TELLKKFVQS GSRLLFSAES FCWPEWGLAE      3120
QYPEVGTGKR FLNSGGFIGF ATTIHQIVRQ WKYKDDDDDQ LFYTRLYLDP GLREKLSLNL      3180
DHKSRIFQNL NGALDEVVLK FDRNRVRIRN VAYDTLPIVV HGNGPTKLQL NYLGNYVPNG      3240
WTPEGCGFC NQDRRTLPGG QPPPRVFLAV FVEQPTPFLP RFLQRLLLLD YPPDRVTLFL      3300
HNNEVFHEPH IADSWPQLQD HFSAVKLVGP EEALSPGEAR DMAMDLCRQD PECEFYFSLD      3360
ADAVLTNLQT LRILIEENRK VIAPMLSRHG KLWSNFWGAL SPDEYYARSE DYVELVQRKR      3420
VGVWNVPYIS QAYVIRGDTL RMELPQRDVF SGSDTDPDMA FCKSFRDKGI FLHLSNQHEF      3480
GRLLATSRYD TEHLHPDLWQ IFDNPVDWKE QYIHENYSRA LEGEIVEQP CPDVYWFPLL      3540
SEQMCDELVA EMEHYGQWSG GRHEDSRLAG GYENVPTVDI HMKQVGYEDQ WLQLLRTYVG      3600
PMTESLFPGY HTKARAVMNF VVRYRPDEQP SLRPHHDSST FTLNVALNHK GLDYEGGGCR      3660
FLRYDCVISS PRKGWALLHP GRLTHYHEGL PTTWGTRYIM VSFVDP                    3706

SEQ ID NO: 27           moltype = DNA  length = 11121
FEATURE                 Location/Qualifiers
misc_feature            1..11121
                        note = Synthetic Construct
source                  1..11121
                        mol_type = other DNA
                        organism = synthetic construct
SEQUENCE: 27
atgacctcct cggggcctgg accccggttc ctgctgctgc tgccgctgct gctgccccct      60
gcggcctcag cctccgaccg gccccggggc cgagacccgg tcaacccaga gaagctgctg     120
gtgatcactg tggccacagc tgaaaccgag gggtacctgc gtttcctgcg ctctgcggag     180
ttcttcaact acactgtgcg gaccctgggc ctggagagg agtggcgagg gggtgatgtg     240
gctcgaacag ttggtggagg acagaaggtc cggtggttaa agaaggaaat ggagaaatac     300
gctgaccggg aggatatgat catcatgttt gtggatagct acgacgtgat tctggccgga     360
agccccacag agctgctgaa gaagttcgtc cagagtggca gccgcctgct cttctctgca     420
gagagcttct gctggcccga gtggggggctg gcggagcagt accctgaggt gggcacgggg     480
aagcgcttcc tcaattctgg tggattcatc ggttttgcca ccaccatcca ccaaatcgtg     540
cgccagtgga agtacaagga tgatgacgac gaccagctgt tctacacacg gctctacctg     600
gacccaggac tgagggagaa actcagcctt aatctggatc ataagtcteg gatctttcag     660
aacctcaacg gggctttaga tgaagtggtt ttaaagtttg atcggaaccg tgtgcgtatc     720
cggaacgtgg cctacgacac gctccccatt gtggtccatg gaaacggtcc cactaagctg     780
cagctcaact acctgggaaa ctacgtcccc aatggctgaa ctcctgaggg aggctggtggc     840
ttctgcaacc aggaccggag gacactcccg gggggcagc ctcccccccg ggtgtttctg     900
gccgtgtttg tggaacagcc tactccgttt ctgcccgct tcctgcagcg gctgctactc     960
ctggactatc ccccgacag ggtcacccctt ttcctgcaca caacgaggt cttccatgaa    1020
ccccacatcg ctgactcctg gccgcagctc caggaccact tctccagtgt gaagctcgtg    1080
gggccggagg aggctctgag cccaggcgag gccagggaca tggccatgga cctgtgtcgg    1140
caggaccccg agtgtgagtt ctacttcagc ctggacgccg acgctgtcct caccaacctg    1200
cagaccctgc gtatcctcat tgaggagaac aggaaggtga tcgcccccat gctgtcccgc    1260
cacggcaagc tgtggtccaa cttctgggc gccctgagcc ccgatgagta ctacgcccgc    1320
tccgaggact acgtggagct ggtgcagcgg aagcgagtgg gtgtgtggaa tgtaccctac    1380
atctcccagg cctatgtgat ccgggggtgat accctgcgga ccagagggat    1440
gtgttctcgg gcagtgacac agacccggac atggccttct gtaagagctt cgagacaag    1500
ggcatcttcc tccatctgag caatcagcat gaatttggcc ggctcctggc cacttccaga    1560
tacgacacgg agcacctgca ccccgacctc tggcagatct tcgacaaccc cgtcgactgg    1620
aaggagcagt acatccacga gaactacagc cgggccctgg aaggggaagg aatcgtggag    1680
cagccatgcc cggacgtgta ctggttccca ctgctgtcag aacaaatgtg tgatgagctg    1740
```

```
gtggcagaga tggagcacta cggccagtgg tcaggcggcc ggcatgagga ttcaaggctg   1800
gctggaggct acgagaatgt gcccaccgtg gacatccaca tgaagcaggt ggggtacgag   1860
gaccagtggc tgcagctgct gcggacgtat gtgggcccca tgaccgagag cctgtttccc   1920
ggttaccaca ccaaggcgcg ggcggtgatg aactttgtgg ttcgctaccg gccagacgag   1980
cagccgctc tgccggccaca ccacgactca tccaccttca ccctcaacgt tgccctcaac   2040
cacaagggcc tggactatga gggaggtggc tgccgcttcc tgcgctacga ctgtgtgatc   2100
tcctccccga ggaagggctg ggcactcctg caccccggcc gcctcaccca ctaccacgag   2160
gggctgccaa cgacctgggg cacacgctac atcatggtgt cctttgtcga ccccggaagc   2220
ggagtgaaac agactttgaa ttttgacctt ctcaagttgg cgggagacgt ggagtccaac   2280
cctggaccta cgctgcggct tctggtggcc gcgctctgcg ccgggatcct ggcagaggcg   2340
ccccgagtgc gagcccagca cagggagaga gtgacctgca cgcgccttta cgccgctgac   2400
attgtgttct tactgatgg ctcctcatcc attggccgca gcaatttccg cgaggtccgc   2460
agctttctcg aagggctggt gctgcctttc tctggagcag ccagtgcaca gggtgtgcgc   2520
tttgccacag tgcagtacag cgatgaccca cggacagagt tcggcctgga tgcacttggg   2580
tctgggggtg atgtgatccg cgccatccgt gagcttagct acaaggggg caacactcgc   2640
acaggggctg caattctcca tgtggctgac catgtcttcc tgcccagct ggcccgacct   2700
ggtgtcccca aggtctgcat cctgatcaca gacgggaagt cccaggacct ggtggacaca   2760
gctgcccaaa ggctgaaggg gcaggggtc aagctatttg ctgtggggat caagaatgct   2820
gaccctgagg agctgaagcg agttgcctca cagcccacca gtgacttctt cttcttcgtc   2880
aatgacttca gcatcttgag gacactactg cccctcgttt cccggagagt gtgcacgact   2940
gctggtggcg tgcctgtgac ccgacctccg gatgactcga cctctgctcc acgagacctg   3000
gtgctgtctg agccaagcag ccaatccttg agagtacagt ggacagcgac cagtggccct   3060
gtgactggct acaaggtcca gtacactcct ctgacggggc tggacagcc actgccgagt   3120
gagcggcagg aggtaacgt cccagctggt gagaccagtg tgcggctgcg gggtctccgg   3180
ccactgaccg agtaccaagt gactgtgatt gccctctacg ccaacagcat cggggaggct   3240
gtgagcggga cagctcggac cactgcccta gaagggccga aactgaccat ccagaatacc   3300
acagcccaca gcctcctggt ggcctggcgg agtgtgccag gtgccactgg ctaccgtgtg   3360
acatggcggg tcctcagtgg tgggcccaca cagcagcagg agctgggccc tgggcagggt   3420
tcagtgttgc tgcgtgactt ggagcctggc acggactatg aggtgaccgt gagcaccta   3480
tttggccgca gtgtggggcc cgccacttcc ctgatgcgtc gcactgacgc ttctgttgag   3540
cagaccctgc gcccggtcat cctgggcccc acatccatcc tcctttcctg gaacttggtg   3600
cctgaggccc gtggctaccg gttggaatgg cggcgtgaga ctggcttgga gccaccgcag   3660
aaggtggtac tgccctctga tgtgacccgc taccagttgg atgggctgca gccgggcact   3720
gagtaccgcc tcacactcta cactctgctg gagggcacg aggtggccac cctgcaacc   3780
gtggttccca ctgaccaga gctgcctgtg agccctgtaa cagacctgca agccaccgag   3840
ctgcccgggc agcgggtgcg agtgtcctgg agccagtcc ctggtgccac ccagtaccgc   3900
atcattgtgc gcagcaccca gggggttgag cggaccctgg tgcttcctgg gagtcagaca   3960
gcattcgact tggatgacgt tcaggctggg cttagctaca ctgtgcgggt gtctgctcga   4020
gtgggtcccc gtgagggcag tgccagtgtc tccactgtcc gccgggagcc ggaaactcca   4080
cttgctgttc cagggctgcg ggttgtggtg tcagatgcaa cgcgagtgag ggtggcctga   4140
ggacccgtcc ctggagccag tggatttcgg attagctgga gcacaggcag tggtccggag   4200
tccagccaga cactgccccc agactctact gccacagaca tcacagggct gcagcctgga   4260
accacctacc aggtggctgt gtcggtactg cgaggcagga aggaggccc tgctgcactg   4320
atcgtggctc gaacgaccc actgggccca gtgaggacgg tccatgtgac tcaggccagc   4380
agctcatctg tcaccattac ctggaccagg gttcctggcg ccacaggata cagggttcc   4440
tggcactcag cccacggccc agagaaatcc cagttggttt ctggggaggc cacggtggct   4500
gagctggatg gactggagcc agatactgag tatacgggtgc atgtgagggc ccatgtggct   4560
ggcgtggatg ggcccccctgc ctctgtggtt gtgaggactg cccctgagcc tgtgggtcgt   4620
gtgtcgaggc tgcagatcct caatgcttcc agcgacgttc tacggatcac ctgggtaggg   4680
gtcactggag ccacagctta cagactggcc tgggccgga gtgaaggcgg ccccatgagg   4740
caccagatac tcccaggaaa cacagactct gcagagatcc gggtgtctcga aggtggagtc   4800
agctactcag tgcgagtgac tgcacttgtc ggggaccgcg agggcacacc tgtctccatt   4860
gttgtcacta cgccgcctga ggctccgcca gccctgggga cgcttcacgt ggtgcagcgc   4920
ggggagcact cgctgaggct gcgctgggag ccggtgccca gagcgcaggg cttccttctg   4980
cactggcaac ctgaggttgg ccaggaacag tcccgggccga gctcagcagc                5040
tatcacctgg acgggctgga gccagcgaca cagtaccgcg tgaggctgag tgtcctaggg   5100
ccagctggag aagggccctc tgcagaggtg actcgcgcca ctgagtcacc tcgtgttcca   5160
agcattgaac tacgtgtggt ggacacctcg atcgactcgg tgactttggc ctggactcca   5220
gtgtccaggg catccagcta catcctatcc tggcggccac tcagaggccc tggccaggaa   5280
gtgcctgggt ccccgcagac acttccaggg atctcaagct cccagcgggt gacagggcta   5340
gagcctggcg tctcttacat cttctcccctg acgcctgtcc tggatggtgt gcggggtcct   5400
gaggcatctg tcacacagac gccagtgtgc ccccgtggcc tggcggatgt ggtgttccta   5460
ccacatgcca ctcaagacaa tgctcaccgt gcggaggcta cgaggagggt cctggagcgt   5520
ctggtgttgg cacttgggcc tcttgggcca caggcagttc aggttggcct gctgtcttac   5580
agtcatcggc cctccccact gttcccactg aatggctccc atgaccttgg cattatcttg   5640
caaaggatcc gtgacatgcc ctacatggac ccaagtggga caacctggg cacagccgtg   5700
gtcacagctc acagatacat gttggcacca atgctcctg ggccgcgcca gcacgtacca   5760
ggggtgatgg ttctgctagt ggatgaacag ttgagaggtg acatattcag ccccatccgt   5820
gaggccagg cttctgggct taatgtggtg atgttgggaa tggctggagc ggacccagag   5880
cagctcgcgt cgcttggcgcc gggtatggac tctgtccaga ccttcttcgc cgtggatgat   5940
gggcaagcc tggaccaggc agtcagtggt ctggccacag ccctgtgtca gcatccttc   6000
actactcagc cccggccaga gcctgccca gtgtattgtc caaagggcca gaagggggaa   6060
cctgagagaa tgggcctgag aggacaagtt gggcctcctg gcgaccctgg cctcccgggc   6120
aggaccggtg ctcccgcccc ccagggccc cctggaagtg ccactgccaa gggcgaggg   6180
ggcttccctg gagcagatgg gcgtccaggc agccctggcc gcgccgggaa tcctggaccc   6240
cctggagccc ctgcctaaa gggctctcca ggttgcctg gccctcgtgg gacccggga   6300
gagcgaggac ctcgaggccc aaaggggag ccggggctc ccggacaagt catcggaggt   6360
gaaggacctg ggcttcctgg gcggaaaggg accctggac atcggggccc cctggaccct   6420
cgtggaccac tgggggaccc aggacccccgt ggccccccag ggcttcctgg aacagccatg   6480
```

```
aagggtgaca aaggcgatcg tggggagcgg ggtcccsctg gaccaggtga aggtggcatt    6540
gctcctgggg agcctgggct gccgggtctt cccggaagcc ctggacccca aggcccgtt     6600
ggcccccctg gaaagaaagg agaaaaaggt gactctgagg atggagctcc aggcctccca    6660
ggacaacctg ggtctccggg tgagcagggc ccacggggac ctcctggagc tattggcccc    6720
aaaggtgacc ggggctttcc agggcccctg ggtgaggctg gagagaaggg cgaacgtgga    6780
cccccaggcc cagcgggatc ccggggggctg ccagggggttg ctggacgtcc tggagccaag   6840
ggtcctgaag ggccaccagg acccactggc cgccaaggag agaagggggga gcctggtcgc    6900
cctgggggacc ctgcagtggt gggacctgct gttgctggac ccaaaggaga aaagggagat    6960
gtgggggcccg ctgggcccag aggagctacc ggagtccaag gggaacgggg cccacccggc    7020
ttggttcttc ctggagaccc tggccccaag ggagaccсctg ggagaccggg tcccattggc    7080
cttactggca gagcaggacc cccaggtgac tcagggcctc ctggagagaa gggagaccct     7140
gggcggcctg gccccccagg acctgttggc ccccgaggac gagatggtga agttggagag    7200
aaaggtgacg agggtcctcc gggtgacccg ggtttgcctg gaaaagcagg cgagcgtggc    7260
cttcgggctg cacctggagt tcgggggcct gtgggtgaaa agggagacca gggagatcct    7320
ggagaggatg gacgaaatgg cagccctgga tcatctggac ccaagggtga ccgtggggag    7380
ccgggtcccc caggaccccc gggacggctg gtagacacag gacctggagc cagagagaag    7440
ggagagcctg ggaccgcgg acaagagggt cctcgagggc ccaagggtga tcctggcctc     7500
cctgagccc ctgggggaaag gggcattgaa gggtttcggg gacccccagg cccacagggg     7560
gacccaggtg tccgaggccc agcaggagaa aagggtgacc ggggtccccc tgggctggat    7620
ggccggagcg gactgatgg gaaaccagga gccgctgggc cctctgggcc gaatggtgct     7680
gcaggcaaag ctgggggaccc agggagagac gggcttccag gcctccgtgg agaacagggc    7740
ctccсctggcc cctctggtcc ccctggatta ccgggaaagc caggcgagga tggcaaacct    7800
ggcctgaatg gaaaaaacgg agaacctggg gaccсctggag aagacgggag gaagggagag    7860
aaaggagatt caggcgcctc tgggagagaa ggtcgtgatg gccccaaggg tgagcgtgga    7920
gctcctggta tccttggacc ccaggggcct ccaggcctcc cagggccagt gggccctcct    7980
ggccaggggtt ttcctggtgt cccaggaggc acgggcссgca agggtgaссcc tgggggagact   8040
ggatccaaag gggagcaggg cctccсctgga gagcgtggcc tgcgaggaga gcctggaagt    8100
gtgccgaatg tggatcggtt gctggaaact gctggcatca aggcatctgc cctgcgggag    8160
atcgtgagaa cctgggatga gagctctggt agcttcctgc ctgtgcccga acggcgtcga    8220
ggccccaagg gggactcagg cgaacagggc cccccagga aggaggggccс catcggcttt    8280
cctggagaac gcgggctgaa ggccgaccgt ggagaccсctg gccсctcaggg gccacctggt    8340
ctggcccttg gggagagggg cccccccggg ccttccggcc ttgccggggga gcctggaaag    8400
cctggtattc ссggggctсcс aggcaggcct ggggggtgtgg gagaggcagg aaggccagga    8460
gagagggggag aacgggggaga gaaaggagaa cgtggagaac agggcagaga tggccctcct    8520
ggactсссctg gaacccctgg gcccccccga cccccctgcc ccaaggtgtc tgtgatgag    8580
ccaggtcctg gactctctgg agaacaggga cсcсcсtggac tcaagggtgc taaggggggag    8640
ccgggcagca atggtgacca aggtcсссaaa ggagacaggg gtgtgccagg catcaaagga    8700
gaccggggag agcctggacc gagggctcag gacggcaacc cgggtctacc aggagagcgt    8760
ggtatgcctg ggcctgaagg gaagcccggt ctgcagggtc caagaggccc ccctggccca    8820
gtgggtggtc atggagaccc tggaccacct ggtgccccgg gtcttgctgg ccctgcagga    8880
ccccaaggac cttctggcct gaaggggggag cctggagaga caggacctcc aggасgggggс    8940
ctgactggac ctactggagc tgtgggactt cctggacccc ccggcccttc aggccttgtg    9000
ggtccacagg ggtctccagg tttgcctgga caagtgggga agacaggggaa gccgggaccc    9060
ccaggtcgag atggtgccag tggaaaaagat ggagacagag ggagccctgg tgtgcccagg    9120
tcaccagggc tgcctggccc tgtcggacct aaaggagaac ctggccccac ggggggссcct    9180
ggacaggstg tggtcgggct ccctggacga aaggagaga agggagcccc tggaggcctt     9240
gctggagacc tggtgggtga gccgggaccc aaagtgacc gaggaccgca agggccgcca    9300
ggcgagaagg gtgaagctgg ccgtgcaggg gagcccggag accctgggga agtggtcag    9360
aaagggggстс caggacccaa aggtttcaag ggtgacccag gagtcggggt cccgggctcc    9420
cctgggcctc ctggccctcc agtgtgaag ggagatctgg gcctcctgg cctgcccggt    9480
gctcctggtg ttgttgggtt cccggttcag acaggccctc gaggagagat gggtcagcca    9540
ggccctagtg gagagcgggg tctggcaggc cccccaggga gaaggaat cccaggaccc    9600
ctggggccac ctggaccacc ggggtcagtc ggaccacctg gggcctctgg actcaaagga    9660
gacaaggggag accctggagt agggctgcct ggggcccgag cgagcgtgg ggagccaggc    9720
atccggggtg aagatggccg cccccggcca gagggacccc gaggactcac cgggccccct    9780
ggcagcaggg gagagcgtgg ggagaagggt gatgttggga gtgcaggact aaagggtgac    9840
aagggagact cagctgtgat cctgggccct ccaggcccac ggggtgccaa gggggacatg    9900
ggtgaacgag ggcctcgggg cttggatggt gacaaaggac ctcggggaga caatggggac    9960
cstgtgtcca aggggсagсaa gggagacct ggtgacaagg gctcagccgg gttgccagga    10020
ctgcgtggac tсctggggасc ccaggtcaa cctggtcga caggatccc tggtgacccg    10080
ggatccccag gaaaggatgg agтgccттggт atccgaggag aaaaaggaga tgttggcttc    10140
atgggtcccc ggggcctcaa gggtgaacgg ggagtgaagg gagcctgtgg ccttgatgga    10200
gagaagggag acaagggaga agctggtccc caggccgcc ccgggctggc aggacacaaa    10260
ggagagatgg gggagcctgg tgtgccggcc cagtcggggg ccctggcaa gggggcctg    10320
atcggtccca agggtgaccg aggctttgac gggcagccag gcccaagggg tgaccaggc    10380
gagaaagggg agcggggaac cccaggaatt gggggстттcс caggccccag tggaaatgat    10440
ggctctgctg gtccccaggc gccacctggc aгттgттggтс ccagaggccc cgaaggactt    10500
cagggccaga aggggтgagсg aggtcccccc ggagagagag tggtggggcc tcctgggctc    10560
ссstgggагсtс ctggcgagag aggggaccag ggcggcccag ggтссstcgagg    10620
gagaagggag aagctgcact gacgagcgat gacatccggg gctttgtccg ccaagagatg    10680
agtcagcact gtgcctgcca gggccaggtc atcgcatctg gatcacgacc cctccctagt    10740
tatgctgcag acactgccgg ctcccagctc catgctgtgc ctgtgctccg cgtctctcat    10800
gcagaggagg aagagcgggt accccctgag gatgatgagt actctgaata ctccgagtat    10860
tctgtgggag agtaccagga ccctgaagct ccttgggata gtgatgaccc ctgttccctg    10920
ccactgatg agggctcctg cactgcctac accctgcgct ggtaccatcg ggctgtgaca    10980
ggcagcacag aggcctgtca cccttttgtc tatgstggct gtgggaggaa tgccaaccgt    11040
tттggggaссc gtgaggcctg cgagcgccgc tgcccacccc gggтgтggсca gagccagggg    11100
acaggtactg cccaggactg a                                               11121
```

```
SEQ ID NO: 28            moltype = AA   length = 3706
FEATURE                  Location/Qualifiers
REGION                   1..3706
                         note = Synthetic Construct
source                   1..3706
                         mol_type = protein
                         organism = synthetic construct
SEQUENCE: 28
MTSSGPGPRF LLLLPLLLPP AASASDRPRG RDPVNPEKLL VITVATAETE GYLRFLRSAE  60
FFNYTVRTLG LGEEWRGGDV ARTVGGGQKV RWLKKEMEKY ADREDMIIMF VDSYDVILAG  120
SPTELLKKFV QSGSRLLFSA ESFCWPEWGL AEQYPEVGTG KRFLNSGGFI GPATTIHQIV  180
RQWKYKDDDD DQLFYTRLYL DPGLREKLSL NLDHKSRIFQ NLNGALDEVV LKFDRNRVRI  240
RNVAYDTLPI VVHGNGPTKL QLNYLGNYVP NGWTPEGGCG FCNQDRRTLP GGQPPPRVFL  300
AVFVEQPTPF LPRFLQRLLL LDYPPDRVTL FLHNNEVFHE PHIADSWPQL QDHFSAVKLV  360
GPEEALSPGE ARDMAMDLCR QDPECEFYFS LDADAVLTNL QTLRILIEEN RKVIAPMLSR  420
HGKLWSNFWG ALSPDEYYAR SEDYVELVQR KRVGVWNVPY ISQAYVIRGD TLRMELPQRD  480
VFSGSDTDPD MAFCKSFRDK GIFLHLSNQH EFGRLLATSR YDTEHLHPDL WQIFDNPVDW  540
KEQYIHENYS RALEGEGIVE QPCPDVYWFP LLSEQMCDEL VAEMEHYGQW SGGRHEDSRL  600
AGGYENVPTV DIHMKQVGYE DQWLQLLRTY VGPMTESLFP GYHTKARAVM NFVVRYRPDE  660
QPSLRPHHDS STFTLNVALN HKGLDYEGGG CRFLRYDCVI SSPRKGWALL HPGRLTHYHE  720
GLPTTWGTRY IMVSFVDPGS GVKQTLNFDL LKLAGDVESN PGPTLRLLVA ALCAGILAEA  780
PRVRAQHRER VTCTRLYAAD IVFLLDGSSS IGRSNFREVR SFLEGLVLPF SGAASAQGVR  840
FATVQYSDDP RTEFGLDALG SGGDVIRAIR ELSYKGGNTR TGAAILHVAD HVFLPQLARP  900
GVPKVCILIT DGKSQDLVDT AAQRLKGQGV KLFAVGIKNA DPEELKRVAS QPTSDFFFFV  960
NDFSILRTLL PLVSRRVCTT AGGVPVTRPP DDSTSAPRDL VLSEPSSQSL RVQWTAASGP  1020
VTGYKVQYTP LTGLGQPLPS ERQEVNVPAG ETSVRLRGLR PLTEYQVTVI ALYANSIGEA  1080
VSGTARTTAL EGPELTIQNT TAHSLLVAWR SVPGATGYRV TWRVLSGGPT QQQELGPGQG  1140
SVLLRDLEPG TDYEVTVSTL FGRSVGPATS LMARTDASVE QTLRPVILGP TSILLSWNLV  1200
PEARGYRLEW RRETGLEPPQ KVVLPSDVTR YQLDGLQPGT EYRLTYTLL EGHEVATPAT  1260
VVPTGPELPV SPVTDLQATE LPGQRVRVSW SPVPGATGYR IIVRSTQGVE RTLVLPGSQT  1320
AFDLDDVQAG LSYTVRVSAR VGPREGSASV LTVRREPETP LAVPGLRVVV SDATRVRVAW  1380
GPVPGASGFR ISWSTGSGPE SSQTLPPDST ATDITGLQPG TTYQVAVSVL RGREEGPAAV  1440
IVARTDPLGP VRTVHVTQAS SSSVTITWTR VPGATGYRVS WHSAHGPEKS QLVSGEATVA  1500
ELDGLEPDTE YTVHVRAHVA GVDGPPASVV VRTAPEPVGR VSRLQILNAS SDVLRITWVG  1560
VTGATAYRLA WGRSEGGPMR HQILPGNTDS AEIRGLEGGV SYSVRVTALV GDREGTPVSI  1620
VVTTPPEAPP ALGTLHVVQR GEHSLRLRWE PVPRAQGFLL HWQPEGGQEQ SRVLGPELSS  1680
YHLDGLEPAT QYRVRLSVLG PAGEGPSAEV TARTESPRVP SIELRVVDTS IDSVTLAWTP  1740
VSRASSYILS WRPLRGPGQE VPGSPQTLPG ISSSQRVTGL EPGVSYIFSL TPVLDGVRGP  1800
EASVTQTPVC PRGLADVVFL PHATQDNAHR AEATRRVLER LVLALGLPGP QAVQVGLLSY  1860
SHRPSPLFPL NGSHDLGIIL QRIRDMPYMD PSGNNLGTAV VTAHRYMLAP DAPGRRQHVP  1920
GVMVLLVDEP LRGDIFSPIR EAQASGLNVV MLGMAGADPE QLRRLAPGMD SVQTFFAVDD  1980
GPSLDQAVSG LATALCQASF TTQPRPEPCP VYCPKGQKGE PGEMGLRGQV GPPGDPGLPG  2040
RTGAPGPQGP PGSATAKGER GFPGADGRPG SPGRAGNPGT PGAPGLKGSP GLPGRPGDPG  2100
ERGRPGRPKGE PGAPGQVIGG EGPGLPGRKG DPGSGPPGP RGPLGDPGPR GPPGLPGTAM  2160
KGDKGDRGER GPPGPGEGGI APGEPGLPGL PGSPGPQGPV GPPGKKGEKG DSEDGAPGLP  2220
GQPGSPGEQG PRGPPGAIGP KGDRGFPGPL GEAGEKGERG PPGPAGSRGL PGVAGRPGAK  2280
GPEGPPGPTG RQGEKGEPGR PGDPAVVGPA VAGPKGEGKD VGPAGPRGAT GVQGERGPKG  2340
LVLPGDPGPK GDPGDRGPIG LTGRAGPPGD SGPPGEKGDP GRPGPPGPVG PRGRDGEVGE  2400
KGDEGPPGDP GLPGKAGERG LRGAPGVRGP VGEKGDQGDP GEDGRNGSPG SSGPKGDRGE  2460
PGPPGPPGRL VDTGPGAREK GEPGDRGQEG PRGPKGDPGL PGAPGERGIE GFRGPPGPQG  2520
DPGVRGPAGE KGDRGPPGLD GRSGLDGKPG AAGPSGPNGA AGKAGDPGRD GLPGLRGEQG  2580
LPGPSGPPGL PGKPGEDGKP GLNGKNGEPG DPGEDGRKGE KGDSGASGRE GRDGPKGERG  2640
APGILGPQGP PGLPGPVGPP GQGFPGVPGG TGPKGDRGET GSKGEQGLPG ERGLRGEPGS  2700
VPNVDRLLET AGIKASALRE IVETWDESSG SFLPVPERRR GPKGDSGEQG PPGKEGPIGF  2760
PGERGLKGDR GDPGPQGPPG LALGERGPPG PSGLAGEPGG PGIPGLPGRA GGVGEAGRPG  2820
ERGERGEKGE RGEQGRDGPP GLPGTPGPPG PPGPKVSVDE PGPGLSGEQG PPGLKGAKGE  2880
PGSNGDQGPK GDRGVPGIKG DRGEPGPRGQ DGNPGLPGER GMAPGEGKPG LQGPRGPPGP  2940
VGGHGDPGPP GAPGLAGPAG PQGPSGLKGE PGETGPPGRG LTGPTGAVGL PGPPGPSGLV  3000
GPQGSPGLPG QVGETGKPGA PGRDGASGKD GDRGSPGVPG GDRGSPGVPG KGEPGPTGAP  3060
GQAVVGLPGA KGEKGAPGGL AGDLVGEPGA KGDRGLPGPR GEKGEAGRAG EPGDPGEDGQ  3120
KGAPGPKGFK GDPGVGVPGS PGPPGPPGVK GDLGLPGLPG APGVVGFPGQ TGPRGEMGQP  3180
GPSGERGLAG PPGREGIPGP LGPPGPPGSV GPPGASGLKG DKGDPGVGLP GPRGERGEPG  3240
IRGEDGRPGQ EGPRGLTGPP GSRGERGEKG DVGSAGLKGD KGDSAVILGP KGPRGAKGDM  3300
GERGPRGLDG DKGPRGDNGD PGDKGSKGEP GDKGSAGLPG LRGLLGPGQG PGAAGIPGDP  3360
GSPGKDGVPG IRGEKGDVGF MGPRGLKGER GVKGACGLDG EKGDKGEAGP GRPGLAGHK  3420
GEMGEPGVPG QSGAPGKEGL IGPKGDRGFD GQPGPKGDQG EKGERGTPGI GGFPGPSGND  3480
GSAGPPGPPG SVGPRGPEGL QGQKGERGPP GERVVGAPGV PGAPGERGEQ GRPGPAGPRG  3540
EKGEAALTED DIRGFVRQEM SQHCACQGQF IASGSRPLPS YAADTAGSQL HAVPVLRVSH  3600
AEEEERVPPE DDEYSEYSEY SVEEYQDPEA PWDSDDPCSL PLDEGSCTAY TLRWYHRAVT  3660
GSTEACHPFV YGGCGGNANR FGTREACERR CPPRVVQSQG TGTAQD              3706

SEQ ID NO: 29            moltype = DNA   length = 1299
FEATURE                  Location/Qualifiers
source                   1..1299
                         mol_type = unassigned DNA
                         organism = Homo sapiens
SEQUENCE: 29
atgaccacct ccatccgcca gttcacctcc tccagctcca tcaagggctc ctccggcctg  60
gggggcggct cgtcccgcac ctcctgccgg ctgtctggcg gcctgggtgc cggctcctgc  120
```

```
aggctgggat ctgctggcgg cctgggcagc accctcgggg gtagcagcta ctccagctgc    180
tacagctttg gctctggtgg tggctatggc agcagctttg ggggtgttga tgggctgctg    240
gctggaggtg agaaggccac catgcagaac ctcaatgacc gcctggcctc ctacctggac    300
aaggtgcgtg ccctggagga ggccaacact gagctggagg tgaagatccg tgactggtac    360
cagaggcagg ccccggggcc cgcccgtgac tacagccagt actacaggac aattgaggag    420
ctgcagaaca agatcctcac agccaccgtg gacaatgcca acatcctgct acagattgac    480
aatgcccgtc tggctgctga tgacttccgc accaagtttg agacagagca ggccctgcgc    540
ctgagtgtgg aggccgacat caatggcctg cgcagggtgc tggatgagct gacccctggcc   600
agagccgacc tggagatgca gattgagaac ctcaaggagg agctggccta cctgaagaag    660
aaccacgagg aggagatgaa cgccctgcga ggccaggtgg gtggtgagat caatgtggag    720
atggacgctg ccccaggcgt ggacctgagc cgcatcctca acgagatgcg tgaccagtat    780
gagaagatgg cagagaagaa ccgcaaggat gccgaggatt ggttcttcag caagacagag    840
gaactgaacc gcgaggtggc caccaacagt gagctggtgc agagtggcaa gagtgagatc    900
tcggagctcc ggcgcaccat gcaggccttg gagatagagc tgcagtccca gctcagcatg    960
aaagcatccc tggagggcaa cctggcggag acagagaacc gctactgcgt gcagctgtcc   1020
cagatccagg ggctgattgg cagcgtggag gagcagctgg cccagcttcg ctgcgagatg   1080
gagcagcaga accaggaata caaaatcctg ctggatgtga agacgcggct ggagcaggag   1140
attgccacct accgccgcct gctggaggga gaggatgccc acctgactca gtacaagaaa   1200
gaaccggtga ccacccgtca ggtgcgtacc attgtggaag aggtccagga tggcaaggtc   1260
atctcctccc gcgagcaggt ccaccagacc acccgctga                          1299

SEQ ID NO: 30          moltype = AA  length = 432
FEATURE                Location/Qualifiers
source                 1..432
                       mol_type = protein
                       organism = Homo sapiens
SEQUENCE: 30
MTTSIRQFTS SSSIKGSSGL GGGSSRTSCR LSGGLGAGSC RLGSAGGLGS TLGGSSYSSC     60
YSFGSGGGYG SSFGGVDGLL AGGEKATMQN LNDRLASYLD KVRALEEANT ELEVKIRDWY    120
QRQAPGPARD YSQYYRTIEE LQNKILTATV DNANILLQID NARLAADDFR TKFETEQALR    180
LSVEADINGL RRVLDELTLA RADLEMQIEN LKEELAYLKK NHEEEMNALR GQVGGEINVE    240
MDAAPGVDLS RILNEMRDQY EKMAEKNRKD AEDWFFSKTE ELNREVATNS ELVQSGKSEI    300
SELRRTMQAL EIELQSQLSM KASLEGNLAE TENRYCVQLS QIQGLIGSVE EQLAQLRCEM    360
EQQNQEYKIL LDVKTRLEQE IATYRRLLEG EDAHLTQYKK EPVTTRQVRT IVEEVQDGKV    420
ISSREQVHQT TR                                                       432
```